US011466008B2

(12) United States Patent
Alam et al.

(10) Patent No.: US 11,466,008 B2
(45) Date of Patent: Oct. 11, 2022

(54) CO-CRYSTALS OF NEFLAMAPIMOD (VX-745)

(71) Applicant: EIP Pharma, LLC, Boston, MA (US)

(72) Inventors: John Jahangir Alam, Boston, MA (US); Jeffrey Douglas Wilson, Vero Beach, FL (US)

(73) Assignee: EIP Pharma, LLC, Boston, MA (US)

( * ) Notice: Subject to any disclaimer, the term of this patent is extended or adjusted under 35 U.S.C. 154(b) by 0 days.

(21) Appl. No.: 16/648,267

(22) PCT Filed: Sep. 18, 2018

(86) PCT No.: PCT/US2018/051558
§ 371 (c)(1),
(2) Date: Mar. 18, 2020

(87) PCT Pub. No.: WO2019/056003
PCT Pub. Date: Mar. 21, 2019

(65) Prior Publication Data
US 2020/0308176 A1 Oct. 1, 2020

Related U.S. Application Data

(60) Provisional application No. 62/559,944, filed on Sep. 18, 2017.

(51) Int. Cl.
A61K 31/5025 (2006.01)
C07D 487/04 (2006.01)
A61K 47/12 (2006.01)

(52) U.S. Cl.
CPC ............ C07D 487/04 (2013.01); A61K 47/12 (2013.01); C07B 2200/13 (2013.01)

(58) Field of Classification Search
CPC ........................ A61K 31/5025; C07D 487/04
USPC .......................................... 514/248; 544/236
See application file for complete search history.

(56) References Cited

U.S. PATENT DOCUMENTS

| | | | |
|---|---|---|---|
| 7,956,198 | B2 | 6/2011 | Sattigeri et al. |
| 8,304,413 | B2 | 11/2012 | Kossen et al. |
| 8,338,412 | B2 | 12/2012 | Bemis et al. |
| 8,697,627 | B2 | 4/2014 | Alam |
| 9,427,438 | B2 | 8/2016 | Alam |
| 9,427,439 | B1 | 8/2016 | Alam |
| 9,539,259 | B2 | 1/2017 | Zack et al. |
| 9,579,322 | B2 | 2/2017 | Alam |
| 10,420,770 | B2 | 9/2019 | Alam |
| 10,653,695 | B2 | 5/2020 | Alam et al. |
| 2003/0135957 | A1 | 7/2003 | Phinney |
| 2004/0204401 | A1 | 10/2004 | Migaly |
| 2005/0004167 | A1 | 1/2005 | Bora et al. |
| 2005/0203111 | A1 | 9/2005 | David |
| 2006/0193920 | A1 | 8/2006 | Bosch et al. |
| 2007/0232632 | A1 | 10/2007 | Lucking et al. |
| 2009/0203702 | A1 | 8/2009 | Bemis |
| 2012/0245188 | A1 | 9/2012 | Huentelman et al. |
| 2012/0289511 | A1 | 11/2012 | Alam |
| 2013/0059798 | A1 | 3/2013 | Bonny |
| 2014/0357638 | A1 | 12/2014 | Alam |
| 2016/0008364 | A1 | 1/2016 | Alam |
| 2016/0030431 | A1 | 2/2016 | Alam |
| 2019/0030035 | A1 | 1/2019 | Alam |
| 2019/0275045 | A1 | 9/2019 | Alam et al. |
| 2019/0381049 | A1 | 12/2019 | Alam |
| 2021/0077497 | A1 | 3/2021 | Alam |

FOREIGN PATENT DOCUMENTS

| | | |
|---|---|---|
| CN | 1244867 A | 2/2000 |
| CN | 103842362 A | 6/2014 |
| CN | 106659723 A | 5/2017 |
| JP | 2005-526785 A | 9/2005 |
| JP | 2007-528393 A | 10/2007 |
| JP | 2009-541483 A | 11/2009 |
| JP | 2014-513694 A | 6/2014 |
| WO | 98/27098 A1 | 6/1998 |
| WO | 03/080024 A2 | 10/2003 |
| WO | 2005/091891 A2 | 10/2005 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Extended European Search Report mailed Feb. 4, 2020, for Application No. EP 17786786.8 (E0602.70000EPOO).
International Search Report and Written Opinion dated Jul. 24, 2017, for Application No. PCT/US2017/029012.
International Preliminary Report on Patentability dated Nov. 1, 2018 for Application No. PCT/US2017/029012.
Extended European Search Report dated Oct. 27, 2017, for Application No. EP 15819113.0.
International Search Report and Written Opinion dated Nov. 6, 2015 for Application No. PCT/US2015/039539.

(Continued)

Primary Examiner — Douglas M Willis
(74) Attorney, Agent, or Firm — Wolf, Greenfield & Sacks, P.C.

(57) ABSTRACT

Provided herein are co-crystal forms comprising 5-(2,6-dichlorophenyl)-2-(2,4-difluorophenylthio)-6H-pyrimido[1,6-b]pyridazin-6-one (VX-745):

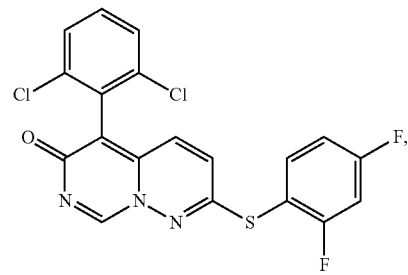

VX-745 and compositions thereof, useful as inhibitors of one or more protein kinases and which exhibit desirable characteristics for the same.

21 Claims, 133 Drawing Sheets

(56) References Cited

FOREIGN PATENT DOCUMENTS

| WO | 2008/002465 A2 | 1/2008 |
|----|----|----|
| WO | 2012/154814 A1 | 11/2012 |
| WO | 2014/145485 A2 | 9/2014 |
| WO | 2016/007616 A1 | 1/2016 |
| WO | 2017/185073 A1 | 10/2017 |
| WO | 2019/056003 A1 | 3/2019 |
| WO | 2019/155464 A1 | 8/2019 |
| WO | WO 2020/092107 A1 | 5/2020 |

OTHER PUBLICATIONS

International Preliminary Report on Patentability dated Jan. 19, 2017 for Application No. PCT/US2015/039539.
International Search Report and Written Opinion dated May 10, 2019 for Application No. PCT/US2019/021930.
International Preliminary Report on Patentability dated Sep. 24, 2020, for Application No. PCT/US2019/021930.
International Search Report and Written Opinion dated Dec. 12, 2018, for Application No. PCT/US2018/051558.
International Preliminary Report on Patentability dated Apr. 2, 2020, for Application No. PCT/US2018/051558.
Extended European Search Report dated Apr. 29, 2019, for Application No. EP 16860660.6.
International Search Report and Written Opinion dated Jan. 17, 2017, for Application No. PCT/US2016/058804.
International Preliminary Report on Patentability dated May 11, 2018, for Application No. PCT/US2016/058804.
International Search Report and Written Opinion for Application No. PCT/US2020/041736, dated Oct. 7, 2020.
Extended European Search Report dated Nov. 6, 2014, for Application No. EP 12782660.0.
Extended European Search Report dated Sep. 5, 2016, for Application No. EP 16169411.2.
International Search Report and Written Opinion dated Oct. 16, 2012 for Application No. PCT/US2012/037064.
International Preliminary Report on Patentability dated Nov. 21, 2013 for Application No. PCT/US2012/037064.
International Search Report and Written Opinion dated Dec. 15, 2020 for Application No. PCT/US2020/051439.
No Author Listed, Cognitive Effects of Oral p38 Alpha Kinase Inhibitor Neflamapimod in Dementia With LewyBodies (AscenD-LB). ClinicalTrials.gov. Jun. 28, 2019. https:J/clinicaltrials.gov/ct2/show/NCT04001517. retrieved on Sep. 25, 2020.
No Author Listed, Activase (Alteplase), Highlights of Prescribing Information, Genentech, Inc., 16 pages (2015).
Adamowicz et al., Hippocampal α-Synuclein in Dementia with Lewy Bodies Contributes to Memory Impairment and Is Consistent with Spread of Pathology. J Neurosci. Feb. 15, 2017;37(7):1675-1684. doi: 10.1523/JNEUROSCI.3047-16.2016. Epub Dec. 30, 2016.
Alam et al., Clinical Pharmacology Study of p38 alpha Map Kinase Inhibitor, Neflamapomid (VX-745), in Mild Cognitive Impairment (MCI) Due to Alzheimer's Disease (AD) or Mild AD. J Prev Alz Dis. Dec. 2016;3:277.
Alam et al., Neflamapimod: Clinical Phase 2b-Ready Oral Small Molecule Inhibitor of p38α to Reverse Synaptic Dysfunction in Early Alzheimer's Disease. J Prev Alzheimers Dis. 2017;4(4):273-278. doi: 10.14283/jpad.2017.41.
Alam, Selective Brain-Targeted Antagonism of p38 MAPKα Reduces Hippocampal IL-1β Levels and Improves Morris Water Maze Performance in Aged Rats. J Alzheimers Dis. 2015;48(1):219-27. doi: 10.3233/JAD-150277.
Alonso et al., Memory formation requires p38MAPK activity in the rat hippocampus. Neuroreport. Oct. 27, 2003;14(15):1989-92. doi: 10.1097/00001756-200310270-00022.
Arevalo-Rodriguez et al., Mini-Mental State Examination (MMSE) for the detection of Alzheimer's disease and other dementias in people with mild cognitive impairment (MCI). Cochrane Database Syst Rev. Mar. 5, 2015;2015(3):CD010783. doi: 10.1002/14651858.CD010783.pub2.
Arvidsson, et al., N-methyl-D-aspartate receptor-mediated increase of neurogenesis in adult rat dentate gyrus following stroke. Eur. J. Neurosci., 2001; 14(1):10-8 [Abstract Only].
Astolfi et al., p38alpha MAPK and Type I Inhibitors: Binding Site Analysis and Use of Target Ensembles in Virtual Screening. Molecules. 2015; 20(9):15842-61.
Azevedo et al., X-ray structure of p38α bound to TAK-715: comparison with three classic inhibitors. Acta Crystallogr. D Biol. Crystallogr. 2012; 68(Pt 8):1041-50.
Bach et al., The Role of CNI-1493 in the Function of Primary Microglia with Respect to Amyloid-β. J Alzheimers Dis. 2011;26(1):69-80. doi: 10.3233/JAD-2011-110179.
Bacher et al., CNI-1493 inhibits Aβ production, plaque formation, and cognitive deterioration in an animal model of Alzheimer's disease. J Exp Med. Jul. 7, 2008;205(7):1593-9. doi: 10.1084/jem.20060467. Epub Jun. 23, 2008.
Bachstetter et al., Attenuation of traumatic brain injury-induced cognitive impairment in mice by targeting increased cytokine levels with a small molecule experimental therapeutic. J Neuroinflammation. Apr. 10, 2015;12:69. doi: 10.1186/s12974-015-0289-5.
Bachstetter et al., Early stage drug treatment that normalizes proinflammatory cytokine production attenuates synaptic dysfunction in a mouse model that exhibits age-dependent progression of Alzheimer's disease-related pathology. J Neurosci. Jul. 25, 2012;32(30):10201-10. doi: 10.1523/JNEUROSCI.1496-12.2012.
Bachstetter et al., The p38α MAPK regulates microglial responsiveness to diffuse traumatic brain injury. J Neurosci. Apr. 3, 2013;33(14):6143-53. doi: 10.1523/JNEUROSCI.5399-12.2013.
Badger et al., Pharmacological profile of SB 203580, a selective inhibitor of cytokine suppressive binding protein/p38 kinase, in animal models of arthritis, bone resorption, endotoxin shock and immune function. J Pharmacol Exp Ther. 1996;279(3):1453-1461.
Bain et al., The selectivity of protein kinase inhibitors: a further update. Biochem J. Dec. 15, 2007;408(3):297-315. doi: 10.1042/BJ20070797.
Barone et al., SB 239063, a second-generation p38 mitogen-activated protein kinase inhibitor, reduces brain injury and neurological deficits in cerebral focal ischemia. J. Pharmacol. Exp. Ther. 2001;296(2):312-21.
Barrientos et al., Aging-related changes in neuroimmune-endocrine function: Implications for hippocampal-dependent cognition, Horm. Behav. 2012;62(3):219-227.
Barrientos et al., Time course of hippocampal IL-1 beta and memory consolidation impairments in aging rats following peripheral infection. Brain Behav Immun. Jan. 2009;23(1):46-54. doi: 10.1016/j.bbi.2008.07.002. Epub Jul. 11, 2008.
Bhaskar et al., Regulation of Tau Pathology by the Microglial Fractalkine Receptor. Neuron. 2010; 68:19-31.
Boehm et al., 1-substituted 4-aryl-5-pyridinylimidazoles: a new class of cytokine suppressive drugs with low 5-lipoxygenase and cyclooxygenase inhibitory potency. J Med Chem. 1996;39(20):3929-3937. doi:10.1021/jm960415o.
Boon et al., Non-Amnestic Alzheimer's Disease: A Possible Role for Neuroinflammation?. Alzheimers Dement. Jul. 2017;13(7) Supplemental:P1131 (1 page).
Brookmeyer et al., Forecasting the prevalence of preclinical and clinical Alzheimer's disease in the United States. Alzheimers Dement. Feb. 2018;14(2):121-129. doi: 10.1016/j.jalz.2017.10.009. Epub Dec. 7, 2017.
Brown et al., P38 MAP kinase inhibitors as potential therapeutics for the treatment of joint degeneration and pain associated with osteoarthritis. J Inflamm (Lond). Dec. 4, 2008;5:22. doi: 10.1186/1476-9255-5-22.
Burgess et al., The human hippocampus and spatial and episodic memory. Neuron. Aug. 15, 2002;35(4):625-41.
Caraccilo et al., Cognitive decline, dietary factors and gut-brain interactions. Mech Ageing Dev. Mar.-Apr. 2014;136-137:59-69. doi: 10.1016/j.mad.2013.11.011. Epub Dec. 12, 2013.

(56) References Cited

OTHER PUBLICATIONS

Castello et al., Moving beyond anti-amyloid therapy for the prevention and treatment of Alzheimer's disease. BMC Neurol. Sep. 2, 2014;14:169. doi: 10.1186/s12883-014-0169-0.

Chlan-Fourney et al., The increased density of p38 mitogen-activated protein kinase-immunoreactive microglia in the sensorimotor cortex of aged TgCRND8 mice is associated predominantly with smaller dense-core amyloid plaques. Eur J Neurosci. Apr. 2011;33(8):1433-44. doi: 10.1111/j.1460-9568.2010.07597.x. Epub Feb. 16, 2011.

Chollet, Pharmacologic approaches to cerebral aging and neuroplasticity: insights from the stroke model. Dialogues Clin Neurosci. Mar. 2013;15(1):67-76. doi: 10.31887/DCNS.2013.15.1/fchollet.

Chopra et al., Pharmacological profile of AW-814141, a novel, potent, selective and orally active inhibitor of p38 MAP kinase. Int Immunopharmacol. Apr. 2010;10(4):467-73. doi: 10.1016/j.intimp.2010.01.007. Epub Jan. 20, 2010.

Choudhury et al., Involvement of p38 MAPK in reactive astrogliosis induced by ischemic stroke. Brain Res. 2014; 1551:45-58.

Clark et al., Use of florbetapir-PET for imaging beta-amyloid pathology. JAMA. Jan. 19, 2011;305(3):275-83. doi: 10.1001/jama.2010.2008.

Clarkson et al., Reducing excessive GABA-mediated tonic inhibition promotes functional recovery after stroke. Nature. 2010; 468(7321):305-9.

Colie et al., Neuronal p38α mediates synaptic and cognitive dysfunction in an Alzheimer's mouse model by controlling β-amyloid production. Sci Rep. 2017;7:45306. Published Mar. 31, 2017. doi:10.1038/srep45306.

Correa et al., The Role of p38 MAPK and Its Substrates in Neuronal Plasticity and Neurodegenerative Disease. J Signal Transduct. 2012;2012:649079. doi: 10.1155/2012/649079. Epub Jun. 25, 2012.

Cortez et al., Aged dominant negative p38α MAPK mice are resistant to age-dependent decline in adult-neurogenesis and context discrimination fear conditioning. Behav Brain Res. 2017;322(Pt B):212-222. doi:10.1016/j.bbr.2016.10.023. Author Manuscript.

Coulthard et al., A broader view of dementia: multiple co-pathologies are the norm. Brain. Jul. 1, 2018;141(7):1894-1897. doi: 10.1093/brain/awy153.

Davis et al., Comprehensive analysis of kinase inhibitor selectivity. Nat Biotechnol. Oct. 30, 2011;29(11):1046-51. doi: 10.1038/nbt.1990.

Dong et al., Mmp-9, a potential target for cerebral ischemic treatment. Curr Neuropharmacol. Dec. 2009;7(4):269-75. doi: 10.2174/157015909790031157.

Duffy et al., The Discovery of VX-745: A Novel and Selective p38-alpha Kinase Inhibitor. ACS Med Chem Lett. Jul. 28, 2011;2(10):758-63. doi: 10.1021/ml2001455. eCollection Oct. 13, 2011.

Edwardson et al., Ischemic stroke prognosis in adults. UpToDate. Official Reprint. 2015. Topic 14086, Version 13.0. 14 pages, <www.uptodate.com>.

Fang et al., Synuclein impairs trafficking and signaling of BDNF in a mouse model of Parkinson's disease. Sci Rep. Jun. 20, 2017;7(1):3868. doi: 10.1038/s41598-017-04232-4.

Fang et al., Prions activate a p38 MAPK synaptotoxic signaling pathway. PLoS Pathog. Sep. 20, 2018;14(9):e1007283. doi: 10.1371/journal.ppat.1007283. eCollection Sep. 2018.

Ferman et al., Dementia with Lewy bodies. Neurol Clin. Aug. 2007;25(3):741-vii. doi:10.1016/j.ncl.2007.03.001.

Ferraccioli, Current Opinion in anti-inflammatory and immunomodulatory investigational drugs. Pharma Press. 2000; 2(1):74-77.

Fiore, Another Drug Moves Amyloid Without Clinical Effects—Study highlights amyloid-Alzheimer's 'disconnect'. MedPage Today. 2015. 4 pages.

Fujishiro et al., Depletion of cholinergic neurons in the nucleus of the medial septum and the vertical limb of the diagonal band in dementia with Lewy bodies. Acta Neuropathol. Feb. 2006;111(2):109-14. doi: 10.1007/S00401-005-0004-1. Epub Jan. 19, 2006.

Garcia-Alloza et al., Existing plaques and neuritic abnormalities in APP:PSI mice are not affected by administration of the gamma-secretase inhibitor LY-411575. Mol Neurodegener. May 6, 2009;4:19. doi: 10.1186/1750-1326-4-19.

Germann et al., P38 MAPK Signaling—A Robust Therapeutic Target for Rab5-Mediated Neurodegenerative Disease. Int J Mol Sci. Jul. 31, 2020;21(15):5485. doi: 10.3390/ijms21155485.

Gnanalingham et al., Motor and cognitive function in Lewy body dementia: comparison with Alzheimer's and Parkinson's diseases. J Neurol Neurosurg Psychiatry. Mar. 1997;62(3):243-52. doi: 10.1136/jnnp.62.3.243.

Godl et al., An efficient proteomics method to identify the cellular targets of protein kinase inhibitors. Proc Natl Acad Sci U S A. Dec. 23, 2003;100(26):15434-9. doi: 10.1073/pnas.2535024100. Epub Dec. 10, 2003.

Goldstein et al., Selective p38alpha inhibitors clinically evaluated for the treatment of chronic inflammatory disorders. J Med Chem. Mar. 25, 2010;53(6):2345-53. doi: 10.1021/jm9012906.

González-Gutiérrez et al., The Rab5-Rab11 Endosomal Pathway is Required for BDNF-Induced CREB Transcriptional Regulation in Hippocampal Neurons. J Neurosci. Oct. 14, 2020;40(42):8042-8054. doi: 10.1523/JNEUROSCI.2063-19.2020. Epub Sep. 14, 2020.

Graff-Radford, Alzheimer's and dementia: What's the difference? Mayo Clinic. https://www.mayoclinic.org/diseases-conditions/alzheimers-disease/expert-answers/alzheimers-and-dementia-whats-the-difference/faq-20396861. First available at least by Mar. 30, 2019.

Grupke et al., Understanding history, and not repeating it. Neuroprotection for acute ischemic stroke: from review to preview. Clin. Neurol. Neurosurg. 2015;129:1-9.

Haddad, VX-745 Vertex Pharmaceuticals. Curr Opin Investig Drugs. Aug. 2001;2(8):1070-6.

Hermann et al., Promoting neurological recovery in the post-acute stroke phase: benefits and challenges. Eur Neurol. 2014;72(5-6):317-25. doi: 10.1159/000365171. Epub Oct. 16, 2014.

Herrup, Reimagining Alzheimer's Disease—An Age-Based Hypothesis. J Neurosci. Dec. 15, 2010;30(50):16755-62. doi: 10.1523/JNEUROSCI.4521-10.2010.

Herrup, The case for rejecting the amyloid cascade hypothesis. Nat Neurosci. Jun. 2015;18(6):794-9. doi: 10.1038/nn.4017.

Hideshima et al., Targeting p38 MAPK inhibits multiple myeloma cell growth in the bone marrow milieu. Blood. 2003; 101(2):703-5.

Hoshino et al., Improvement of cognitive function in Alzheimer's disease model mice by genetic and pharmacological inhibition of the EP(4) receptor. J Neurochem. Mar. 2012;120(5):795-805. doi: 10.1111/j.1471-4159.2011.07567.x. Epub Jan. 23, 2012.

Hull et al., Pathways of Inflammatory Activation in Alzheimer's Disease: Potential Targets for Disease Modifying Drugs. Curr Med Chem. Jan. 2002;9(1):83-8. doi: 10.2174/0929867023371292.

Jack Jr et al., Dementia is not synonymous with Alzheimer's disease. Sci Transl Med. Dec. 11, 2019;11(522):eaav0511. doi: 10.1126/scitranslmed.aav0511.

Kalaria et al., Stroke and cognition. Curr Atheroscler Rep 2001;3:334-339. Doi: 10.1007/s11883-001-0028-5.

Karagianni et al., Pharmaceutical Cocrystals: New Solid Phase Modification Approaches for the Formulation of APIs. Pharmaceutics. 2018;10(1):18. Published Jan. 25, 2018. doi: 10.3390/pharmaceutics10010018.

Karran et al., The amyloid cascade hypothesis for Alzheimer's disease: an appraisal for the development of therapeutics. Nat Rev Drug Discov. Aug. 19, 2011;10(9):698-712. doi: 10.1038/nrd3505.

Kumar et al., p38 MAP kinases: key signalling molecules as therapeutic targets for inflammatory diseases. Nat. Rev. Drug Discov. 2003; 2(9):717-26.

Lachman et al., Natural History and Outcome in Systemic AA Amyloidosis Abstract Background. N Engl J Med. Jun. 7, 2007;356(23):2361-71. doi: 10.1056/NEJMoa070265.

Lawrence, Alzheimer's will be treated with 'cocktail' of drugs, predicts neuroscientist. The Pharmaceutical Journal. Jan. 2016;296(7885): 2 pages.

Lee et al., CX3CR1 Deficiency Alters Microglial Activation and Reduces Beta-Amyloid Deposition in Two Alzheimer's Disease

(56) References Cited

OTHER PUBLICATIONS

Mouse Models. Am J Pathol. Nov. 2010;177(5):2549-62. doi: 10.2353/ajpath.2010.100265. Epub Sep. 23, 2010.
Li et al., Soluble A-beta oligomers inhibit long-term potentiation through a mechanism involving excessive activation of extrasynaptic NR2B-containing NMDA receptors. J. Neurosci. 2011; 31(18):6627-38.
Lowenberg et al., Specific Inhibition of c-Raf Activity by Semapimod Induces Clinical Remission in Severe Crohn's Disease. J Immunol. Aug. 15, 2005;175(4):2293-300. doi: 10.4049/jimmunol.175.4.2293.
Maphis et al., Selective suppression of the α isoform of p38 MAPK rescues late-stage tau pathology. Alzheimers Res Ther. 2016;8(1):54. Published Dec. 15, 2016. doi:10.1186/s13195-016-0221-y.
Matousek et al., Chronic IL-1β-mediated neuroinflammation mitigates amyloid pathology in a mouse model of Alzheimer's disease without inducing overt neurodegeneration . J. Neuroimmune Pharmacol. 2012; 7(1): 156-164.
Mayer et al., p38 MAP kinase inhibitors: A future therapy for inflammatory diseases. Drug Discovery Today: Therapeutic Strategies. 2006; 3(1):49-54.
McAfoose et al., Evidence for cytokine model of cognitive function. Neurosci Biobehav Rev. Mar. 2009;33(3):355-66. doi: 10.1016/j.neubiorev.2008.10.005. Epub Oct. 18, 2008.
Merlini et al., Molecular mechanisms of amyloidosis. N Engl J Med. Aug. 7, 2003;349(6):583-96. doi: 10.1056/NEJMra023144.
Minoshima et al., Metabolic reduction in the posterior cingulate cortex in very early Alzheimer's disease. Ann. Neurol. 1997; 42(1):85-94.
Montalban et al., KR-003048, a potent, orally active inhibitor of p38 mitogen-activated protein kinase. Eur J Pharmacol. 2010;632(1-3):93-102. doi:10.1016/j.ejphar.2010.01.011.
Morris et al., Inconsistencies and controversies surrounding the amyloid hypothesis of Alzheimer's disease. Acta Neuropathol Commun. Sep. 18, 2014;2:135. doi: 10.1186/s40478-014-0135-5.
Munoz et al., A novel p38α MAPK inhibitor suppresses brain proinflammatory cytokine up-regulation and attenuates synaapic dysfunction and behavioral deficits in an Alzheimer's disease mouse model. Jour Neuroinflamm. 2007; 4(21): 1-14.
Munoz et al., Targeting p38 MAPK pathway for the treatment of Alzheimer's disease. Neuropharmacology. Mar. 2010;58(3):561-8. doi: 10.1016/j.neuropharm.2009.11.010. Epub Dec. 4, 2009.
Nava-Mesa et al., GABAergic neurotransmission and new strategies of neuromodulation to compensate synaptic dysfunction in early stages of Alzheimer's disease. Front Cell Neurosci. Jun. 25, 2014;8:167. doi: 10.3389/fncel.2014.00167. eCollection 2014.
Nixon, Endosome function and dysfunction in Alzheimer's disease and other neurodegenerative diseases, Neurobiol Aging. Mar. 1, 2005 ;26(3):373-82.
O'Callaghan et al., Beyond and below the cortex: the contribution of striatal dysfunction to cognition and behaviour in neurodegeneration. J Neurol Neurosurg Psychiatry. Apr. 2014;85(4):371-8. doi: 10.1136/jnnp-2012-304558. Epub Jul. 6, 2013.
Paik et al., Role of GABA plasticity in stroke recovery. Neural Regen Res. Dec. 1, 2014;9(23):2026-8. doi: 10.4103/1673-5374.147920.
Paul, Promising New Alzheimer's 'Drug' Halts Memory Loss, 'Drug' strikes newly identified target and could be used early in disease. Northwestern University News, 3 pages (2013) Online, last accessed Apr. 23, 2015 <http://www.northwestern.edu/newscenter/stories/2013/06/promising-new-alzheimers-drug-halts-memory-loss.html>.
Pensalfini et al., Endosomal Dysfunction Induced by Directly Overactivating Rab5 Recapitulates Prodromal and Neurodegenerative Features of Alzheimer's Disease. Cell Rep. Nov. 24, 2020;33(8):108420. doi: 10.1016/j.celrep.2020.108420.
Piao et al., Administration of the p38 MAPK inhibitor SB203580 affords brain protection with a wide therapeutic window against focal ischemic insult. J. Neurosci. Res. 2003; 73(4):537-44.

Power et al., Lewy Bodies and the Mechanisms of Neuronal Cell Death in Parkinson's Disease and Dementia with Lewy Bodies. Brain Pathol. Jan. 2017;27(1):3-12. doi: 10.1111/bpa.12344. Epub Jan. 18, 2016.
Qingwei et al., Cognitive frailty, a novel target for the prevention of elderly dependency. Ageing Res Rev. Mar. 2015;20:1-10. doi: 10.1016/j.arr.2014.12.004. Epub Dec. 30, 2014.
Rahimi et al., Prevalence of mixed pathologies in the aging brain. Alzheimers Res Ther. Nov. 21, 2014;6(9):82. doi: 10.1186/s13195-014-0082-1. eCollection 2014.
Reagan-Shaw et al., Dose translation from animal to human studies revisited. FASEB J. Mar. 2008;22(3):659-61. doi: 10.1096/fj.07-9574LSF. Epub Oct. 17, 2007.
Regan et al., Pyrazole Urea-Based Inhibitors of p38 MAP Kinase: From Lead Compound to Clinical Candidate. J Med Chem. Jul. 4, 2002;45(14):2994-3008. doi: 10.1021/jm020057r.
Richards et al., Neurodegenerative diseases have genetic hallmarks of autoinflammatory disease. Hum Mol Genet. Aug. 1, 2018;27(R2):R108-R118. doi: 10.1093/hmg/ddy139.
Roh, et al., Stealth attack: plaque-specific antibody allows for efficient Aβ removal without side effects. Neuron. Dec. 6, 2012;76(5):859-61. doi: 10.1016/j.neuron.2012.11.018.
Rojas et al., Functional assessment of four types of disintegrants and their effect on the spironolactone release properties. AAPS PharmSciTech. Dec. 2012;13(4):1054-62. doi: 10.1208/s12249-012-9835-y. Epub Aug. 17, 2012.
Roy et al., Targeting human central nervous system protein kinases: An isoform selective p38αMAPK inhibitor that attenuates disease progression in Alzheimer's disease mouse models. ACS Chem Neurosci. Apr. 15, 2015;6(4):666-80. doi: 10.1021/acschemneuro.5b00002. Epub Feb. 23, 2015.
Scheltens et al., Quantitative PET Study of the Effect of the p38a Kinase Inhibitor VX-745 on Brain Amyloid Plaque Load in Patients with Early Alzheimer's Disease. J Prev Alz Dis. Dec. 2016;3:272.
Schnöder et al., Deficiency of Neuronal p38α-MAPK Attenuates Amyloid Pathology in Alzheimer's Mouse and Cell Models through Facilitating Lysosomal Degradation of BACE1. J Biol Chem. Jan. 29, 2016;291(5):2067-79. doi: 10.1074/jbc.M1115.695916. Epub Dec. 9, 2015.
Stein et al., Chapter 29. The MAP Kinase Family: New "MAPs" for Signal Transduction Pathways and Novel Targets for Drug Discovery. Ann Rep Med Chem. 1996;31:289-98. doi:10.1016/S0065-7743(08)60468-6.
Teipel et al., Predictors of cognitive decline and treatment response in a clinical trial on suspected prodromal Alzheimer's disease. Neuropharmacology. Sep. 2016;108:128-35. doi: 10.1016/j.neuropharm.2016.02.005. Epub Feb. 10, 2016.
Terry, Eip Pharma Closes $20.5 to Fund Alzheimer's Studies. May 16, 2018. https:/Www.biospace.com/article/eip-phanna-closes-W-5-to-fund-alzheimer-s-studies. retrieved on Sep. 25, 2020.
Tse et al., Targeting pre-existing plaques in AD. Nature Reviews Drug Discovery. 2013; 12:100-101.
Ventriglia et al., Serum Brain-Derived Neurotrophic Factor Levels in Different Neurological Diseases. Biomed Res Int. 2013;2013:901082. doi: 10.1155/2013/901082. Epub Aug. 19, 2013.
Verkaar et al., Inhibition of Wnt/β-catenin signaling by p38 MAP kinase inhibitors is explained by cross-reactivity with casein kinase Iδ/ε. Chem Biol. Apr. 22, 2011;18(4):485-94. doi: 10.1016/j.chembiol.2011.01.015.
Villemagne et al., Longitudinal assessment of Aβ and cognition in aging and Alzheimer disease. Ann Neurol. Jan. 2011;69(1):181-92. doi: 10.1002/ana.22248.
Wadsworth et al., RWJ 67657, a Potent, Orally Active Inhibitor of p38 Mitogen-Activated Protein Kinase. J Pharmacol Exp Ther. Nov. 1999;291(2):680-7.
Wang et al., Memory deficits induced by inflammation are regulated by alpha5-subunit-containing GABAA receptors. Cell Rep. Sep. 27, 2012;2(3):488-96. doi: 10.1016/j.celrep.2012.08.022. Epub Sep. 20, 2012.
Watterson et al., Development of Novel In Vivo Chemical Probes to Address CNS Protein Kinase Involvement in Synaptic Dysfunction. PLoS One. Jun. 26, 2013;8(6):e66226. doi: 10.1371/journal.pone.0066226. Print 2013.

(56) References Cited

OTHER PUBLICATIONS

Weisman et al., A Double-Blind, Placebo-Controlled Trial of VX-745, an Oral p38 Mitogen Activated Protein Kinase (MAPK) Inhibitor, in Patients with Rheumatoid Arthritis (RA), Abstract FRI0018. European League Against Rheumatism (EULAR). 2002.
Wiesmann et al., Vascular aspects of cognitive impairment and dementia. J Cereb Blood Flow Metab. Nov. 2013;33(11):1696-706. doi: 10.1038/jcbfm.2013.159. Epub Sep. 11, 2013.
Wong et al., Activity-dependent BDNF release via endocytic pathways is regulated by synaptotagmin-6 and complexin. Proc Natl Acad Sci U S A. Aug. 11, 2015;112(32):E4475-84. doi: 10.1073/pnas.1511830112. Epub Jul. 27, 2015.
Wood, Could anti-amyloid-beta immunotherapy do more harm than good? Nat Rev Neurol. Jan. 2016;12(1):2. doi: 10.1038/nrneurol.2015.227. Epub Nov. 27, 2015.
Woodford et al., Cognitive assessment in the elderly: a review of clinical methods. QJM. Aug. 2007;100(8):469-84. doi: 10.1093/qjmed/hcm051. Epub Jun. 12, 2007.
Wu et al., Tonic inhibition in dentate gyrus impairs long-term potentiation and memory in an Alzheimer's disease model. Nat Commun. Jun. 13, 2014;5:4159. doi: 10.1038/ncomms5159.
Yadav et al., Co-crystals: a novel approach to modify physicochemical properties of active pharmaceutical ingredients. Indian J Pharm Sci. 2009;71(4):359-370. doi: 10.4103/0250-474X.57283.
Yang et al., Protective Effects of p38 MAPK Inhibitor SB202190 against Hippocampal Apoptosis and Spatial Learning and Memory Deficits in a Rat Model of Vascular Dementia. Biomed Res Int. 2013;2013:215798. doi: 10.1155/2013/215798. Epub Dec. 25, 2013.
Yasuda et al., p38 MAP kinase inhibitors as potential therapeutic drugs for neural diseases. Cent. Nerv. Syst. Agents Med. Chem. 2011; 11(1):45-59.
Zeman et al., Diagnosis of Dementia Using Nuclear Medicine Imagining Modalities, 12 Chapters on Nuclear Medicine, pp. 199-230 (2011).
Zhang et al., TCM Clinical Psychology. China Medical Science and Technology Press. pp. 219-237.
Zhu et al., CD45 Deficiency Drives Amyloid-$\beta$ Peptide Oligomers and Neuronal Loss in Alzheimer's Disease Mice. J Neurosci. Jan. 26, 2011;31(4):1355-65. doi: 10.1523/JNEUROSCI.3268-10.2011.
Zhu et al., CD45RB Is a Novel Molecular Therapeutic Target to Inhibit A$\beta$ Peptide-Induced Microglial MAPK Activation. PLoS One. May 14, 2008;3(5):e2135. doi: 10.1371/journal.pone.0002135.
No Author Listed, The Difference Between Lewy Body Dementia, Parkinson's Disease and Alzheimer's Disease. Davis Phinney Foundation. Mar. 8, 2018. 12 pages. https://davisphinneyfoundation.org/difference-lewy-body-dementia-parkinsons-disease-alzheimers-disease/ [last accessed Nov. 4, 2021].
U.S. Appl. No. 17/572,896, filed Nov. 11, 2021, Alam.
U.S. Appl. No. 17/761,703, filed Mar. 18, 2022, Alam et al.
International Preliminary Report on Patentability dated Jan. 27, 2022 for Application No. PCT/US2020/041736.
International Search Report and Written Opinion dated Feb. 7, 2022 for Application No. PCT/US2021/058360.
International Search Report and Written Opinion dated Feb. 7, 2022 for Application No. PCT/US2021/058361.
Aidem, "New Drug for Lewy Body Dementia Shows Promise", Oct. 30, 2020 (Oct. 30, 2020) retrieved on Jan. 10, 2022 from https://www.pacificneuroscienceinstitute.org/blog/clinicaltrials/new-drug-for-lewy-body-dementia-shows-promise.
Barras et al., Drug dosing in obese adults. Aust Prescr. Oct. 2017;40(5):189-193. doi: 10.18773/austprescr.2017.053. Epub Oct. 3, 2017.
Liu et al., Nucleus basalis of Meynert revisited: anatomy, history and differential involvement in Alzheimer's and Parkinson's disease. Acta Neuropathol. Apr. 2015;129(4):527-40. doi: 10.1007/s00401-015-1392-5. Epub Jan. 30, 2015.

* cited by examiner

FIGURE 3
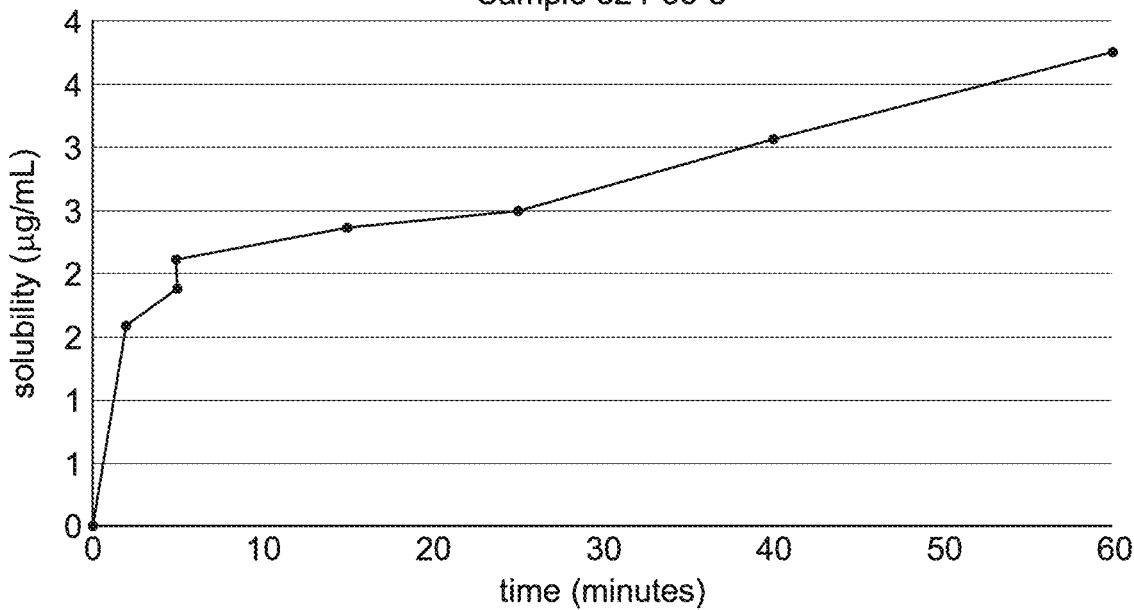
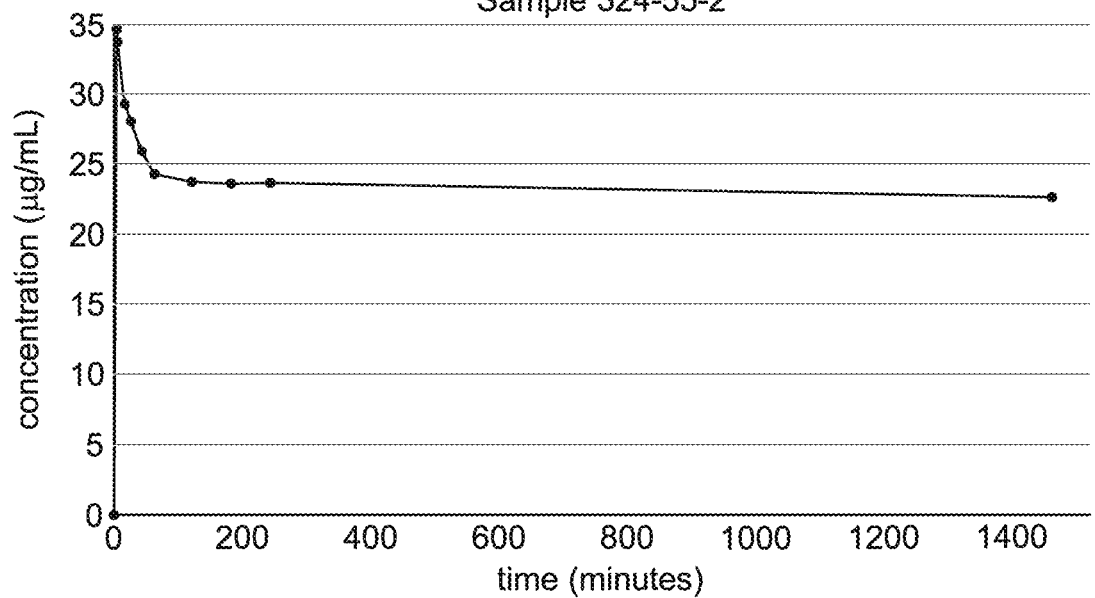
FIGURE 4

TGAKIN.143, sample 178-84-1
VX-745 gentisic acid cocrystal

TGAKIN.144, sample 182-37-1
VX-745 glutaric acid cocrystal

FIGURE 239A

| Sample No. | 178-7-1 | 178-7-2 | 178-7-3 | 178-7-4 | 178-7-5 | 178-7-6 |
|---|---|---|---|---|---|---|
| Coformer | acesulfame K | AcSA | ascorbic acid | adenine | adipic acid | 4-ABA |
| Solvent | MeOH | acetone | THF | MeOH | acetone | acetone |
| Result | CF + N | E + CF | E | B + CF + N | F + CF | E + CF |
| XRPD File | RX3464 | RX3449 | RX3455 | RX3461 | RX3450 | RX3454 |
| Sample No. | 178-7-7 | 178-7-8 | 178-7-9 | 178-7-10 | 178-7-11 | 178-7-12 |
| Coformer | ammonium chl. | arginine | L-ascorbic acid | asparagine | benzoic acid | betaine HCl |
| Solvent | MeOH | MeOH | MeOH | MeOH | acetone | MeOH |
| Result | B + CF | B | A + CF | B + N | E + F | B + CF |
| XRPD File | RX3453 | RX3477 | RX3448 | RX3457 | RX3452 | RX3462 |
| Sample No. | 178-7-13 | 178-7-14 | 178-7-15 | 178-8-1 | 178-8-2 | 178-8-3 |
| Coformer | caffeine | calcium chl. | camphoric acid | choline chloride | cinnamic acid | citric acid |
| Solvent | MeOH | MeOH | acetone | MeOH | THF | acetone |
| Result | B + CF | B | E + CF | B + N | F + CF | E + CF |
| XRPD File | RX3463 | RX3465 | RX3451 | RX3495 | RX3458 | RX3473 |
| Sample No. | 178-8-4 | 178-8-5 | 178-8-6 | 178-8-7 | 178-8-8 | 178-8-9 |
| Coformer | creatinine | cyclamic acid | cysteine | DHEA | ethyl maltol | ethyl paraben |
| Solvent | MeOH | MeOH | MeOH | acetone | THF | THF |
| Result | B + CF | B + CF | B | E + CF | E + CF | E + CF |
| XRPD File | RX3469 | RX3468 | RX3471 | RX3456 | RX3460 | RX3459 |
| Sample No. | 178-8-10 | 178-8-11 | 178-8-12 | 178-8-13 | 178-18-1 | 178-8-14 |
| Coformer | D-fructose | fumaric acid | gallic acid | gentisic acid | gentisic acid | glucosamine HCl |
| Solvent | MeOH | acetone | THF | ACN | ACN | MeOH |
| Result | B | E + CF | E + N | N | N | B + CF |
| XRPD File | RX3478 | RX3476 | RX3472 | RX3520 | RX3634 | RX3534 |
| Sample No. | 178-8-15 | 178-8-16 | 178-8-17 | 178-8-18 | 178-18-2 | 178-8-19 |
| Coformer | D-glucose | glutaric acid | glycine | glycolic acid | glycolic acid | hippuric acid |
| Solvent | MeOH | ACN | THF | ACN | ACN | acetone |
| Result | B + CF | N | E + CF | H | H | F + CF |
| XRPD File | RX3475 | RX3582 | RX3474 | RX3635 | RX3636 | RX3470 |
| Sample No. | 178-8-20 | 178-9-1 | 178-9-2 | 178-18-3 | 178-9-3 | 178-9-4 |
| Coformer | L-histidine | HBA | HNA | HNA | ketoglutaric acid | lactose |
| Solvent | MeOH | acetone | ACN | ACN | ACN | MeOH |
| Result | B + CF + N | E + CF | N | N | H | B + CF |
| XRPD File | RX3538 | RX3523 | RX3540 | RX3635 | RX3575 | RX3567 |
| Sample No. | 178-9-5 | 178-9-6 | 178-9-7 | 178-9-8 | 178-9-9 | 178-9-10 |
| Coformer | L-leucine | lithium chloride | L-lysine | maleic acid | L-malic acid | malonic acid |
| Solvent | MeOH | MeOH | MeOH | ACN | ACN | ACN |
| Result | B + CF | B + N | B | H | F + CF | H |
| XRPD File | RX3522 | RX3638 | RX3568 | RX3571 | RX3569 | RX3578 |

FIGURE 239B

| Sample No. | 178-9-11 | 178-9-12 | 178-9-13 | 178-9-14 | 178-9-15 | 178-9-16 |
|---|---|---|---|---|---|---|
| Coformer | maltol | mandelic acid | D-mannitol | meglumine | methyl paraben | nicotinamide |
| Solvent | acetone | THF | MeOH | MeOH | THF | acetone |
| Result | E + CF | E + CF | B + D + CF | B + CF | E + CF | E + CF |
| XRPD File | RX3491 | RX3494 | RX3573 | RX3505 | RX3521 | RX3492 |
| Sample No. | 178-9-17 | 178-9-18 | 178-9-19 | 178-9-20 | 178-10-1 | 178-10-2 |
| Coformer | nicotinic acid | oxalic acid | phenol | L-phenylalanine | L-proline | propyl gallate |
| Solvent | MeOH | acetone | acetone | MeOH | MeOH | acetone |
| Result | CF + N | E + CF + N | E + N | B + CF | CF + N | E + CF |
| XRPD File | RX3570 | RX3493 | RX3537 | RX3568 | RX3563 | RX3565 |
| Sample No. | 178-10-3 | 178-10-4 | 178-10-5 | 178-10-6 | 178-10-7 | 178-10-8 |
| Coformer | PGA | riboflavin | saccharin | salicylic acid | sebacic acid | L-serine |
| Solvent | acetone | ACN | MeOH | acetone | acetone | MeOH |
| Result | E | C + CF | B + CF + N | E + CF | E + CF | D + N |
| XRPD File | RX3562 | RX3577 | RX3546 | RX3544 | RX3545 | RX3541 |
| Sample No. | 178-10-9 | 178-10-10 | 178-10-11 | 178-10-12 | 178-18-4[b] | 178-10-13 |
| Coformer | sodium chloride | sorbic acid | sorbitol | succinic acid | succinic acid | sucralose |
| Solvent | MeOH | acetone | MeOH | ACN | ACN | MeOH |
| Result | B + D + CF | E + N | B + CF | H | H + CF | B |
| XRPD File | RX3564 | RX3574 | RX3539 | RX3547 | RX3623 | RX3583 |
| Sample No. | 178-10-14 | 178-10-15 | 178-10-16 | 178-64-3 | 182-38-1 | 178-10-17 |
| Coformer | sucrose | L-tartaric acid | thiamine HCl | thiamine HCl | thiamine HCl | L-threonine |
| Solvent | MeOH | ACN | MeOH | MeOH | MeOH | MeOH |
| Result | B + N | C + CF | N + CF | N + CF | B + CF | CF + N |
| XRPD File | RX3543 | RX3572 | RX3542 | RX4095 | RX4100 | RX3595 |
| Sample No. | 194-24-1 | 178-10-18 | 178-10-19 | 178-10-20 | 178-10-21 | 178-10-22 |
| Coformer | L-threonine | tris HCl | urea | L-valine | vanillic acid | vanillin |
| Solvent | MeOH | MeOH | MeOH | MeOH | acetone | acetone |
| Result | B + CF | B + CF | CF + N | B + CF | E + CF | E + CF |
| XRPD File | RX4212 | RX3598 | RX3606 | RX3608 | RX3590 | RX3592 |
| Sample No. | 178-10-23 | - | - | - | - | - |
| Coformer | zinc chloride | - | - | - | - | - |
| Solvent | acetone | - | - | - | - | - |
| Result | E + NC | - | - | - | - | - |
| XRPD File | RX3560 | - | - | - | - | - |

FIGURE 240A

| Sample No. | 178-12-1 | 178-12-2 | 178-12-3 | 178-12-4 | 178-12-5 | 178-12-6 |
|---|---|---|---|---|---|---|
| Coformer | acesulfame K | AcSA | aconitic acid | adenine | adipic acid | AmBa |
| Solvent | 2:1 MeOH; Hept | 2:1 acetone; hex | 2:1 THF; hex | 2:1 MeOH; Hept | 2:1 acetone; hex | 2:1 acetone; hex |
| Result | E + CF | E + CF | CF + N | E + CF | E + CF + N | F + CF + N |
| XRPD File | RX3583 | RX3586 | RX3609 | RX3607 | RX3594 | RX3587 |
| Sample No. | 178-12-7 | 178-12-8 | 178-12-9 | 178-12-10 | 178-12-11 | 178-12-12 |
| Coformer | ammonium chl. | L-ascorbic acid | asparagine | benzoic acid | betaine HCl | caffeine |
| Solvent | 2:1 MeOH; Hept | 2:1 MeOH; Hept | 2:1 MeOH; Hept | 2:1 acetone; hex | 2:1 MeOH; Hept | 2:1 MeOH; Hept |
| Result | E + CF | E + N | E + N | F + CF + N | E + CF + N | E + CF |
| XRPD File | RX3591 | RX3588 | RX3585 | RX3526 | RX3529 | RX3537 |
| Sample No. | 178-12-13 | 178-12-14 | 178-17-1 | 178-12-15 | 178-12-16 | 178-12-17 |
| Coformer | calcium chloride | camphoric acid | choline chloride | cinnamic acid | citric acid | creatinine |
| Solvent | 2:1 MeOH; Hept | 2:1 acetone; hex | 2:1 MeOH; Hept | 2:1 THF; hex | 2:1 acetone; hex | 2:1 MeOH; Hept |
| Result | N (some F?) | E + CF | E + CF + N | E + CF | E + CF | E + CF |
| XRPD File | RX3536 | RX3528 | RX3605 | RX3530 | RX3531 | RX3533 |
| Sample No. | 178-12-18 | 178-12-19 | 178-12-20 | 178-15-1 | 178-15-2 | 178-17-2 |
| Coformer | cyclamic acid | cysteine | DHEA | ethyl maltol | ethyl paraben | D-fructose |
| Solvent | 2:1 MeOH; Hept | 2:1 MeOH; Hept | 2:1 acetone; hex | 2:1 THF; hex | 2:1 THF; hex | 2:1 MeOH; Hept |
| Result | CF + N | E + CF | E + CF | E + CF | E + CF | E + CF |
| XRPD File | RX3532 | RX3534 | RX3525 | RX3581 | RX3619 | RX3613 |
| Sample No. | 178-17-3 | 178-15-3 | 178-24-1 | 178-19-3 | 178-17-4 | 178-33-1 |
| Coformer | fumaric acid | gallic acid | gentisic acid | glucosamine HCl | D-glucose | glutaric acid |
| Solvent | 2:1 acetone; hex | 2:1 THF; hex | 2:1 ACN; hex | 2:1 MeOH; Hept | 2:1 MeOH; Hept | 2:1 ACN; hex |
| Result | E + CF | E + CF | E + CF | E + CF | E + CF | E + CF |
| XRPD File | RX3628 | RX3615 | RX3622 | RX3611 | RX3626 | RX3625 |
| Sample No. | 178-15-4 | 178-24-2 | 178-15-5 | 178-19-5 | 178-19-4 | 178-24-3 |
| Coformer | glycine | glycolic acid | hippuric acid | L-histidine | HBA | HNA |
| Solvent | 2:1 THF; hex | 2:1 ACN; hex | 2:1 acetone; hex | 2:1 MeOH; Hept | 2:1 acetone; hex | 2:1 ACN; hex |
| Result | E + CF | E + CF | E + CF | E + CF | E + CF | CF + N |
| XRPD File | RX3587 | RX3624 | RX3584 | RX3632 | RX3620 | RX3529 |
| Sample No. | 178-26-1 | 178-26-2 | 178-19-6 | 178-26-3 | 178-26-4 | 178-26-5 |
| Coformer | ketoglutaric acid | lactose | L-leucine | L-lysine | maleic acid | L-malic acid |
| Solvent | 2:1 ACN; hex | 2:1 MeOH; Hept | 2:1 MeOH; Hept | 2:1 MeOH; Hept | 2:1 ACN; hex | 2:1 ACN; hex |
| Result | N | E + CF | E + CF | CF | E + CF | E + CF |
| XRPD File | RX3656 | RX3668 | RX3614 | RX3665 | RX3662 | RX3663 |
| Sample No. | 178-26-6 | 178-17-5 | 178-17-6 | 178-26-7 | 178-19-7 | 178-19-8 |
| Coformer | malonic acid | maltol | mandelic acid | D-mannitol | meglumine | methyl paraben |
| Solvent | 2:1 ACN; hex | 2:1 acetone; hex | 2:1 THF; hex | 2:1 MeOH; Hept | 2:1 MeOH; Hept | 2:1 THF; hex |
| Result | CF + N | E + CF | E + CF | E + CF | E + CF | E + CF |
| XRPD File | RX3664 | RX3618 | RX3627 | RX3669 | RX3610 | RX3633 |

FIGURE 240B

| Sample No | 178-17-7 | 178-26-8 | 178-17-8 | 178-33-2 | 178-27-4 | 178-27-5 |
|---|---|---|---|---|---|---|
| Coformer | nicotinamide | nicotinic acid | oxalic acid | phenol | L-phenylalanine | L-proline |
| Solvent | 2:1 acetone: hex | 2:1 MeOH: Hept | 2:1 acetone: hex | 2:1 acetone: hex | 2:1 MeOH: Hept | 2:1 MeOH: Hept |
| Result | E + CF | E + CF | CF | N | E + CF | E + CF |
| XRPD File | RX3612 | RX3667 | RX3617 | RX3833 | RX3674 | RX3671 |
| Sample No. | 178-27-6 | 178-27-7 | 178-33-3 | 178-22-1 | 178-22-2 | 178-22-3 |
| Coformer | propyl gallate | PGA | riboflavin | saccharin | salicylic acid | sebacic acid |
| Solvent | 2:1 acetone: hex | 2:1 acetone: hex | 2:1 ACN: hex | 2:1 MeOH: Hept | 2:1 acetone: hex | 2:1 acetone: hex |
| Result | E + CF | E + N | E + CF | E + CF | CF + N | E + CF |
| XRPD File | RX3831 | RX3672 | RX3832 | RX3641 | RX3639 | RX3630 |
| Sample No. | 178-22-4 | 178-27-1 | 178-27-2 | 178-22-5 | 178-24-4 | 178-37-1 |
| Coformer | L-serine | sodium chloride | sorbic acid | sorbitol | succinic acid | sucralose |
| Solvent | 2:1 MeOH: Hept | 2:1 MeOH: Hept | 2:1 acetone: hex | 2:1 MeOH: Hept | 2:1 ACN: hex | 2:1 MeOH: Hept |
| Result | E + CF + N | E + CF | E + CF | E + N | E + CF | E + CF |
| XRPD File | RX3637 | RX3675 | RX3670 | RX3640 | RX3625 | RX3834 |
| Sample No. | 178-22-6 | 178-27-3 | 178-22-7 | 178-27-8 | 178-32-1 | 178-33-4 |
| Coformer | sucrose | L-tartaric acid | thiamine HCl | L-threonine | tris HCl | urea |
| Solvent | 2:1 MeOH: Hept | 2:1 ACN: hex | 2:1 MeOH: Hept | 2:1 MeOH: Hept | 2:1 MeOH: Hept | 2:1 MeOH: Hept |
| Result | E + CF | E + CF | E | E + CF | E + CF | E + CF |
| XRPD File | RX3638 | RX3676 | RX3631 | RX3673 | RX3828 | RX3826 |
| Sample No | 178-33-5 | 178-32-2 | 178-32-3 | - | - | - |
| Coformer | L-valine | vanillic acid | vanillin | - | - | - |
| Solvent | 2:1 MeOH: Hept | 2:1 acetone: hex | 2:1 acetone: hex | - | - | - |
| Result | E + CF | E + CF | E + CF | - | - | - |
| XRPD File | RX3827 | RX3829 | RX3830 | - | - | - |

FIGURE 241

| Sample No | 178-13-1 | 178-19-1 | 178-19-2 | — | — | — |
|---|---|---|---|---|---|---|
| Coformer | alanine | lithium chloride | zinc chloride | — | — | — |
| Solvent | Water | acetone | acetone | — | — | — |
| Result | A+ CF | E | N | — | — | — |
| XRPD File | RX3502 | RX3579 | RX3616 | — | — | — |

CO-CRYSTALS OF NEFLAMAPIMOD (VX-745)

CROSS-REFERENCE TO RELATED APPLICATIONS

This application is a national stage filing under 35 U.S.C. § 371 of International Application PCT/US2018/051558, filed Sep. 18, 2018, which claims priority to and benefit of U.S. Provisional Patent Application No. 62/559,944, filed Sep. 18, 2017, the content of which is hereby incorporated by reference herein in its entirety.

BACKGROUND

Protein kinases are involved in various cellular responses to extracellular signals. A family of mitogen-activated protein kinases (MAPK) has been discovered. Members of this family are Ser/Thr kinases that activate their substrates by phosphorylation (Stein B. et. al., *Ann. Rep. Med. Chem.*, 31:289-98 (1996)). MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor CD14 and induced with LPS. Activation of p38 has been observed in cells stimulated by stresses, such as treatment of lipopolysaccharides (LPS), UV, anisomycin, or osmotic shock, and by cytokines, such as IL-1 and TNF.

p38, along with other MAPKs, has a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders.

In the brain, p38a regulates inflammation through its expression in microglia and astrocytes. Under stress and disease, p38a is also expressed in neurons, where its expression may contribute to the toxicity of amyloid-beta, inflammation, and tau to synapses. Consistent with that science, functional deficits are reversed with only 2 to 3 weeks of treatment with p38a selective small molecule kinase inhibitors in three central nervous system (CNS) animal models (APP/PS1, aged rats and hTau mice) in which cognitive deficits are induced by amyloid-beta, inflammation, or tau, respectively (Roy S M et al., *ACS Chem Neurosci.*, 6:666-680 (2015); Alam J J, *J Alzheimers Dis.*, 48:219-227 (2015); Maphis N et al., *Alzheimers Res Ther.*, 8:54 (2016)). Further, genetic reduction of neuronal p38a in Amyloid-Precursor-Protein (APP) overexpressing transgenic mice improves synaptic transmission and plasticity (i.e. prevents synaptic dysfunction), reduces memory loss, and reduces amyloid pathology (Colie S et al., *Sci Rep.*, 7:45306 (2017)). Moreover, genetically knocking down p38a in neurons protected mice from developing age-related hippocampal dysfunction and decline in neurogenesis (Cortez 1 et al. *Behav Brain Res.*, 322:212-222 (2017)). As a result, inhibition of p38 alpha kinase has potential in broad range of neurologic indications, as outlined in U.S. Pat. Nos. 9,427,439 and 9,579,322.

SUMMARY

There is a need to develop potent, p38-specific inhibitors with properties suitable for administration in pharmaceutical compositions for treating various conditions associated with p38 activation.

Neflamapimod or 5-(2,6-dichlorophenyl)-2-(2,4-difluorophenylthio)-6H-pyrimido[1,6-b]pyridazin-6-one (previously code named VX-745) is poorly water soluble and does not contain readily ionisable functional groups that allow salt formation. Thus, neflamapimod is not readily dissolved and presents certain challenges for formulations as well as bioavailability when administered to subjects.

Provided herein relate to novel co-crystals comprising neflamapimod or 5-(2,6-dichlorophenyl)-2-(2,4-difluorophenylthio)-6H-pyrimido[1,6-b]pyridazin-6-one (previously code named VX-745) and at least one coformer. These co-crystals can be used as inhibitors of one or more protein kinases and exhibit desirable characteristics for the same. In some embodiments, co-crystals described herein as well as pharmaceutical compositions comprising the same can be used to treat or lessen the severity of a variety of diseases or disorders that are associated with protein kinases.

One aspect provided herein relates to a solid form comprising VX-745 and at least one or more (e.g., 1, 2, 3, or more) distinct coformer species. In some embodiments, VX-745 and one or more coformer species form a co-crystal. In some embodiments, VX-745 and a single coformer species form a co-crystal.

In some embodiments, a coformer species present in a co-crystal is selected such that the co-crystal exhibits at least one or more of the following characteristics:

a) the solubility of the co-crystal is increased as compared with a free VX-745 (without incorporation of a coformer species);

b) the dose response, when the co-crystal is administered, is increased as compared with a free VX-745 (without incorporation of a coformer species);

c) the efficacy of the co-crystal is increased as compared with a free VX-745 (without incorporation of a coformer species);

d) the dissolution rate of the co-crystal is increased as compared with a free VX-745 (without incorporation of a coformer species);

e) the bioavailability of the co-crystal is increased as compared with a free VX-745 (without incorporation of a coformer species);

f) the stability of the co-crystal is increased as compared with a free VX-745 (without incorporation of a coformer species);

g) the hygroscopicity of the co-crystal is decreased as compared with a free VX-745 (without incorporation of a coformer species);

h) the form diversity of the co-crystal is decreased as compared with a free VX-745 (without incorporation of a coformer species); and i) the morphology of the co-crystal is modulated as compared with a free VX-745 (without incorporation of a coformer species).

Non-limiting examples of a coformer species include acesulfame potassium, trans-aconitic acid, adenine, adipic acid, 4-aminobenzoic acid, L-ascorbic acid, asparagine, benzoic acid, betaine HCl, calcium chloride, choline chloride, cyclamic acid, gallic acid, gentisic acid, glutaric acid, L-histidine, 1-hydroxy-2-naphthoic acid, ketoglutaric acid, lithium chloride, malonic acid, nicotinic acid, oxalic acid, phenol, L-proline, L-pyroglutamic acid, saccharin, salicylic acid, L-serine, sorbic acid, sorbitol, sucrose, L-threonine, urea, and zinc chloride. In some embodiments, the coformer species can be gentisic acid, nicotinic acid, phenol, glutaric acid, or zinc chloride.

In some embodiments, the molar ratio of VX-745 and one or more coformer species is in the range of about 5:1 to about 1:5. In some embodiments, the molar ratio of VX-745 and one or more coformer species is about 1:1.

In some embodiments, the molar ratio of VX-745 and a single coformer species is about 1:1, wherein the coformer species is gentisic acid, nicotinic acid, or zinc chloride.

In some embodiments, a co-crystal described herein is substantially free of impurities.

Methods for producing co-crystals are known in the art. For example, in some embodiments, a co-crystal of VX-745 can be formed by slow solvent evaporation, slurry crystallization, and/or milling (e.g., liquid-assisted milling).

Pharmaceutical compositions comprising a co-crystal described herein and a pharmaceutically acceptable carrier are also provided herein.

Another aspect provided herein relates to methods of inhibiting or reducing expression and/or activity of p38 MAPK in a patient. In some embodiments, methods comprise administering to a patient in need thereof a co-crystal (e.g., ones described herein) and/or a composition comprising the same.

Methods of treating a p38 MAPK-mediated disease in patients are also provided herein. Such methods comprise administering to patients in need thereof a co-crystal (e.g., ones described herein) and/or a composition comprising the same.

Additionally provided herein are methods for preparing a pharmaceutical composition comprising VX-745, which methods comprise at least one step of preparing, processing, or formulating a co-crystal as described herein.

BRIEF DESCRIPTION OF THE DRAWINGS

FIG. 3 shows a dissolution curve of a co-crystal comprising VX-745 and glutaric acid in FaSSIF.

FIG. 4 shows a dissolution curve of a co-crystal comprising VX-745 and zinc chloride in FaSSIF.

FIG. 239A shows results from stoichiometric slow evaporation experiments. XRPD results of the following samples no. 178-7-1 to 178-9-10 are shown in FIGS. 56-103 accordingly, as identified by XRPD filename. CF=coformer; N=new XRPD pattern; NC=non-crystalline. Experiments yielding XRPD patterns are outlined. The letters A, B, C, D, E, F, G, and H refers to polymorphs of VX-745.

FIG. 239B shows results from stoichiometric slow evaporation experiments. XRPD results of the following samples no. 178-9-11 to 178-10-23 are shown in FIGS. 104-140 accordingly, as identified by XRPD filename. CF=coformer; N=new XRPD pattern; NC=non-crystalline. Experiments yielding XRPD patterns are outlined. The letters A, B, C, D, E, F, G, and H refers to polymorphs of VX-745.

FIG. 240A shows results from stoichiometric slurry experiments. XRPD results of the following samples no. 178-12-1 to 178-19-8 are shown in FIGS. 141-188 accordingly, as identified by XRPD filename. CF=coformer; N=new XRPD pattern; NC=non-crystalline. Experiments yielding XRPD patterns are outlined. The letters A, B, C, D, E, F, G, and H refers to polymorphs of VX-745.

FIG. 240B shows results from stoichiometric slurry experiments. XRPD results of the following samples no. 178-17-7 to 178-32-3 are shown in FIGS. 189-215 accordingly, as identified by XRPD filename. CF=coformer; N=new XRPD pattern; NC=non-crystalline. Experiments yielding XRPD patterns are outlined. The letters A, B, C, D, E, F, G, and H refers to polymorphs of VX-745.

FIG. 241 shows results from stoichiometric milling experiments. XRPD results of the following samples no. 178-13-1 to 178-19-2 are shown in FIGS. 216-218 accordingly, as identified by XRPD filename. CF=coformer; N=new XRPD pattern; NC=non-crystalline. Experiments yielding XRPD patterns are outlined. The letters A, B, C, D, E, F, G, and H refers to polymorphs of VX-745.

CERTAIN DEFINITIONS

Figure 1:
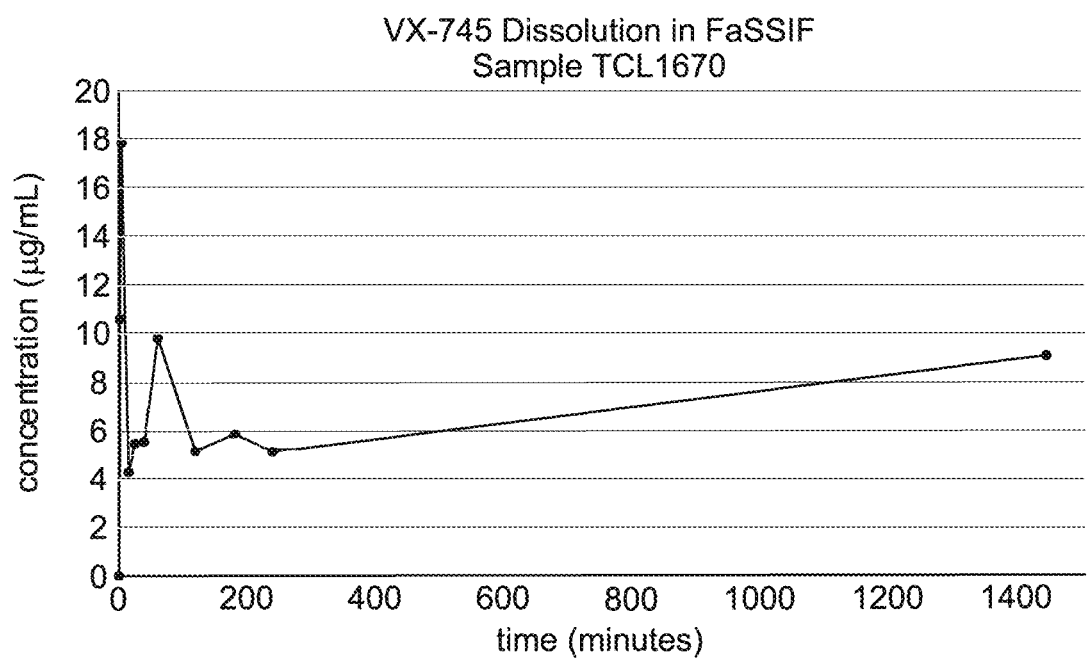
FIG. 1 shows a dissolution curve of free VX-745 in FaSSIF.
Figure 2:
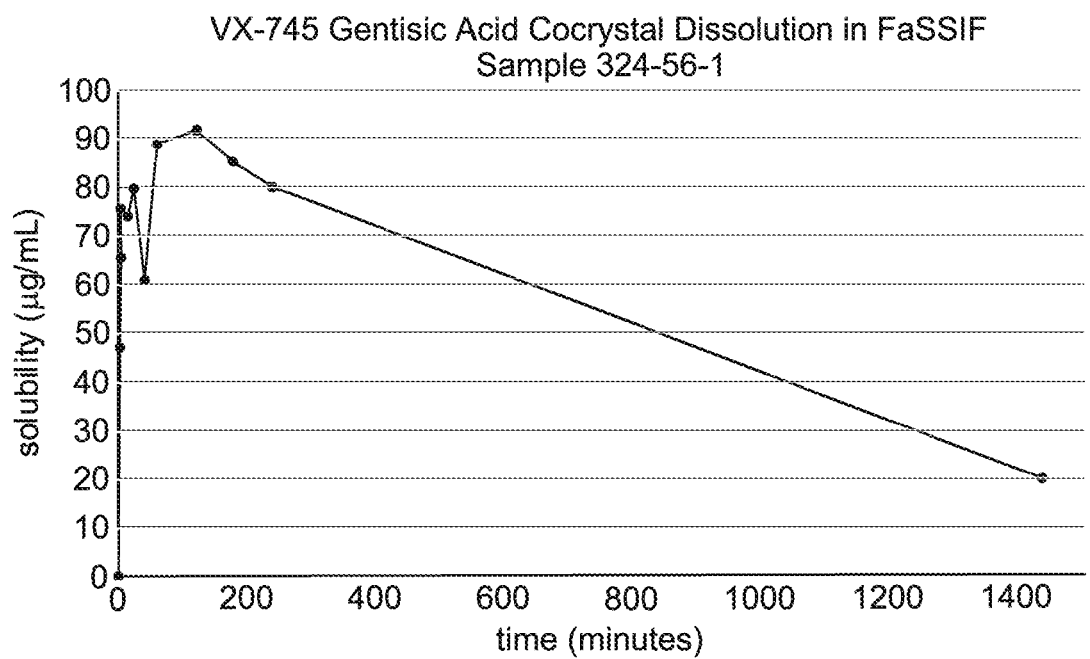
FIG. 2 shows a dissolution curve of a co-crystal comprising VX-745 and gentisic acid in FaSSIF.
Figure 5:
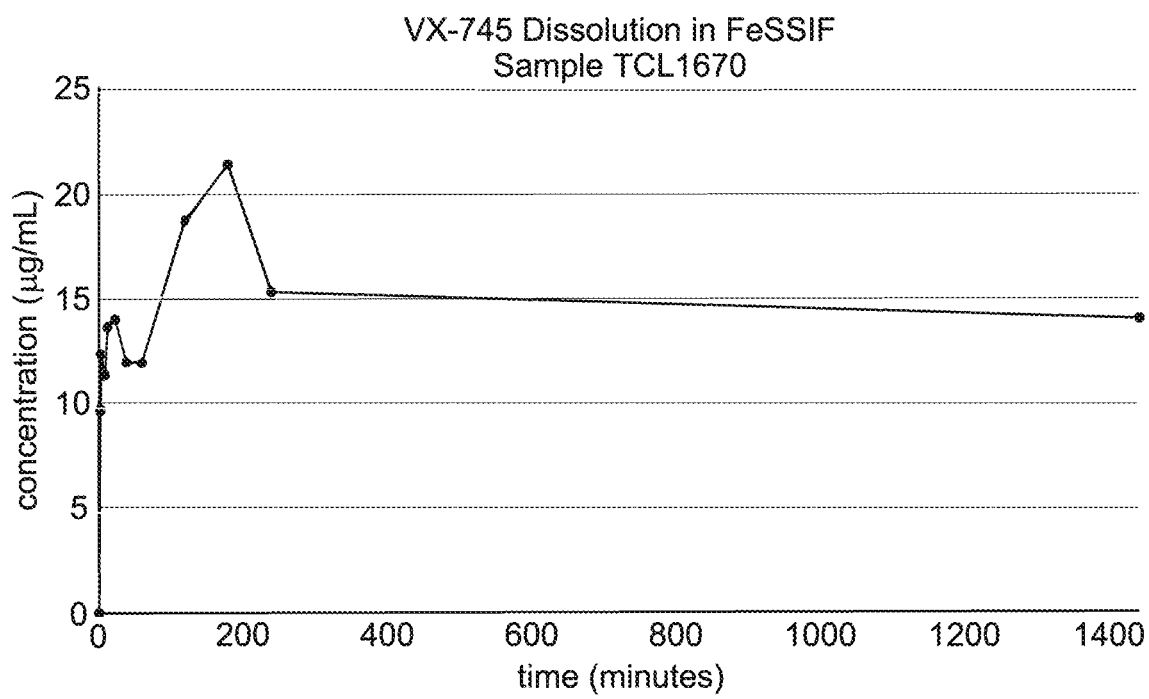
FIG. 5 shows a dissolution curve of free VX-745 in FeSSIF.
Figure 6:
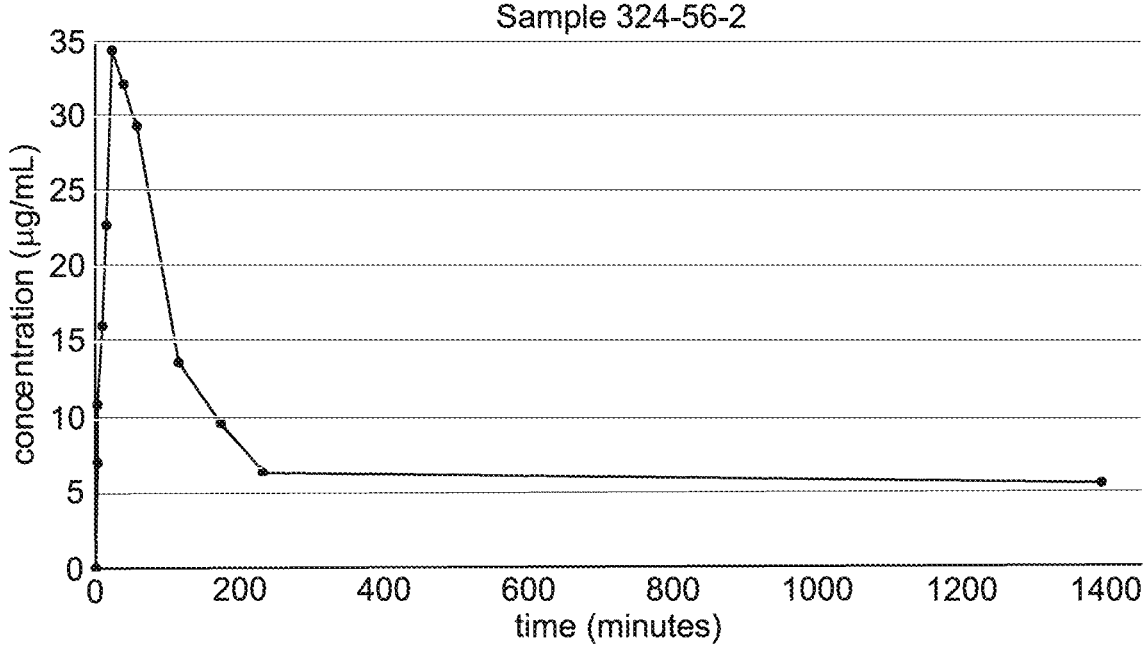
FIG. 6 shows a dissolution curve of a co-crystal comprising VX-745 and gentisic acid in FeSSIF.
Figure 7:
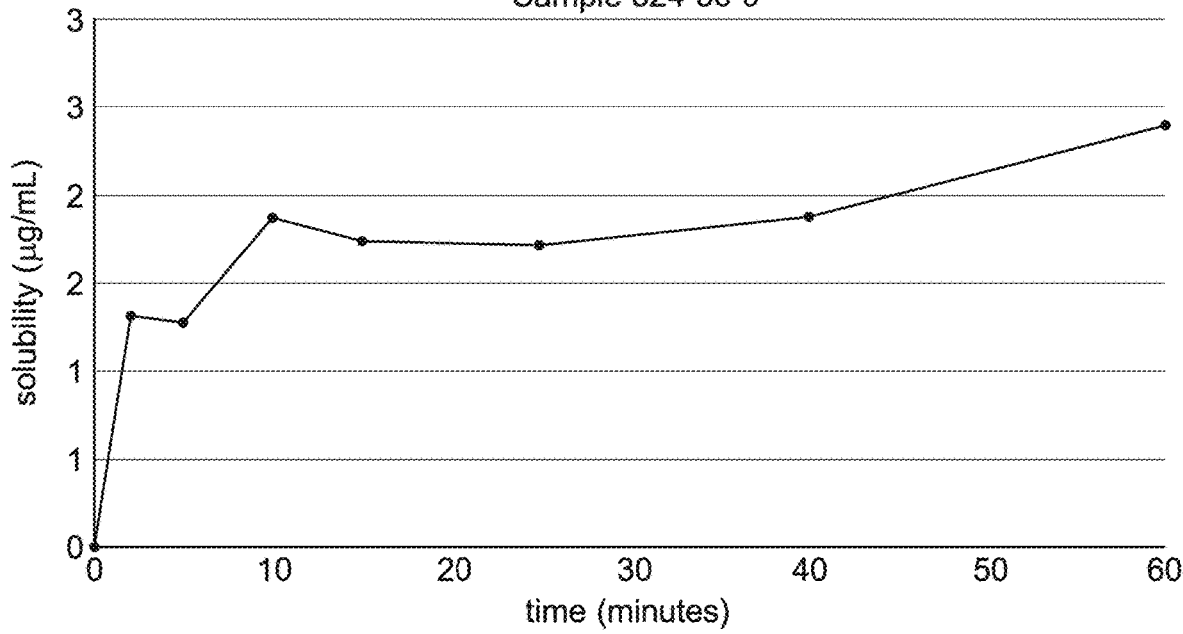
FIG. 7 shows a dissolution curve of a co-crystal comprising VX-745 and glutaric acid in FeSSIF.
Figure 8:
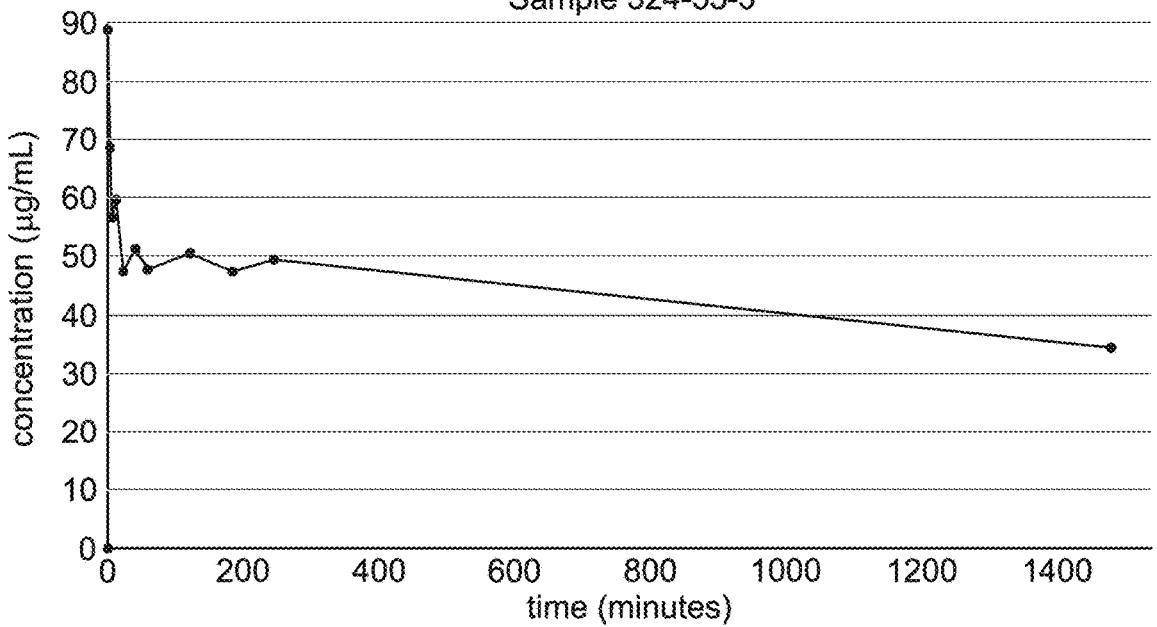
FIG. 8 shows a dissolution curve of a co-crystal comprising VX-745 and zinc chloride in FeSSIF.

Bioavailability: The term "bioavailability" as used herein refers to the fraction of an administered dose of a co-crystal of VX-745 that reaches the systemic circulation. By definition, when a pharmaceutically active ingredient (API) is administered intravenously, its bioavailability is 100%. However, when an API is administered via non-intravenous routes (such as orally), its bioavailability generally decreases (e.g., due to incomplete absorption and first-pass metabolism) or may vary from a subject to a subject. In some embodiments, the bioavailability of a co-crystal of VX-745 described herein is increased by, e.g., at least about 30% or more (including, e.g., at least about 40%, at least about 50%, at least about 60%, at least about 70%, at least about 80%, at least about 90%, at least about 95%, at least about 1.1-fold, at least about 2-fold, at least about 3-fold, at least about 4-fold, at least about 5-fold, or more), as compared to that of free VX-745 (without incorporation of any coformer species).

Co-crystal: As used herein, the term "co-crystal" refers to a solid which is a crystalline material comprising two or more different molecules, e.g., active pharmaceutical ingredient (API) and co-crystal formers ("co-formers"), in the same crystal lattice. The two or more different molecules, e.g., API and one or more coformers, are associated in a co-crystal lattice, typically by non-ionic or non-covalent bonds, e.g., hydrogen bonding, pi-stacking, and/or van der Waals interactions. In some embodiments, a co-crystal is a homogenous crystalline structure with a well-defined stoichiometric ratio. Unlike a single-component polymorph, which contains only one active pharmaceutical ingredient (API) in the crystal lattice, a co-crystal comprises an API and a coformer species (e.g., a neutral coformer species) in the crystal lattice. Unlike a salt where the components of a crystal lattice are in an ionized state, in some embodiments, components in a co-crystal lattice (e.g., with a defined stoichiometry) are in a neutral state and interact through non-ionic interactions. Thus, for example, while there is typically a proton transfer and ionization in salt formations, such need not appear in co-crystals. Those skilled in the art will appreciate that, in some embodiments, it may be possible that more than one polymorph may exist for a particular co-crystal. The term "polymorph", as is known in the art, refers to a particular crystal form of a relevant molecule (or molecules—e.g., API and one or more co-formers). As is known in the art, a particular molecule (or molecules) can often adopt a plurality of different crystal structures that have different arrangements (e.g., molecular packing, molecular orientation, and/or molecular conformation) of the molecules (e.g., API and coformer(s)) in the solid state but are otherwise identical in terms of chemical content. Polymorphs may have different physiochemical properties, e.g., chemical stability, mechanical properties, solubility, and/or dissolution rate.

Coformer: As herein, the terms "coformer" and "coformer species" are used interchangeably herein to refer to a co-crystal former. A coformer is molecule or compound that interacts with an API, e.g., VX-745, non-ionically or non-covalently in a crystal lattice. In some embodiments, a coformer is not a solvent or water. In some embodiments, a coformer is non-volatile. In some embodiments, a coformer is a second API that is distinct from a first API in a co-crystal.

Dissolution: As used herein, the term "dissolution" or "dissolution rate" describes changes in the solubility of a co-crystal of VX-745 in an aqueous solution or organic solvent over a period of time. The dissolution rate of a co-crystal of VX-745 described herein can be determined using any methods known in the art, e.g., as described in the Examples. In one embodiment, dissolution rate of a co-crystal of VX-745 can be measured using high-performance liquid chromatography. In some embodiments, the dissolution rate of a co-crystal of VX-745 described herein is increased by, e.g., at least about 30% or more (including, e.g., at least about 40%, at least about 50%, at least about 60%, at least about 70%, at least about 80%, at least about 90%, at least about 95%, at least about 1.1-fold, at least about 2-fold, at least about 3-fold, at least about 4-fold, at least about 5-fold, or more), as compared to that of free VX-745 (without incorporation of any coformer species).

Dose response: As used herein, the term "dose response" refers to the relationship between a dose or treatment regimen of a co-crystal of VX-745 or a composition comprising the same and its effect(s) on living cells, tissues, and/or subjects (e.g., humans) in one or more aspects (including, e.g., immune response, toxicity response, p38 inhibition, lessening of at least one or more symptoms associated with a p38-mediated disease or disorder). In some embodiments, the effect(s) of a certain dose of a co-crystal of VX-745 (e.g., ones described herein) or a composition comprising the same on living cells, tissues, and/or subjects (e.g., humans) in one or more aspects (including, e.g., immune response, toxicity response, p38 inhibition, lessening of at least one or more symptoms associated with a p38-mediated disease or disorder) is greater than that of a free VX-745 in the absence of coformer species administered at the same dose. For example, the dose response, when administered with a co-crystal of VX-745 or composition comprising the same, is increased by least about 30% or more (including, e.g., at least about 40%, at least about 50%, at least about 60%, at least about 70%, at least about 80%, at least about 90%, at least about 95%, at least about 1.1-fold, at least about 2-fold, at least about 3-fold, at least about 4-fold, at least about 5-fold, or more), as compared to that when a free VX-745 (without incorporation of a coformer species) is administered at the same dose.

Efficacy: As used herein, the term "efficacy" refers to the ability of a co-crystal of VX-745 or a composition comprising the same to produce a desirable effect (e.g., a therapeutic effect). In some embodiments, the ability of a co-crystal of VX-745 to inhibit or reduce p38 expression and/or activity is greater than that of a free VX-745 (without incorporation of a coformer species) when an equivalent molar amount of a co-crystal of VX-745 is used. For example, the efficacy of a co-crystal of VX-745 or composition comprising the same in inhibiting or reducing p38 expression and/or activity is increased by least about 30% or more (including, e.g., at least about 40%, at least about 50%, at least about 60%, at least about 70%, at least about 80%, at least about 90%, at least about 95%, at least about 1.1-fold, at least about 2-fold, at least about 3-fold, at least about 4-fold, at least about 5-fold, or more), as compared to that of a free VX-745 (without incorporation of a coformer species) when an equivalent molar amount of a molar amount of a co-crystal of VX-745 is used.

Figure 36:
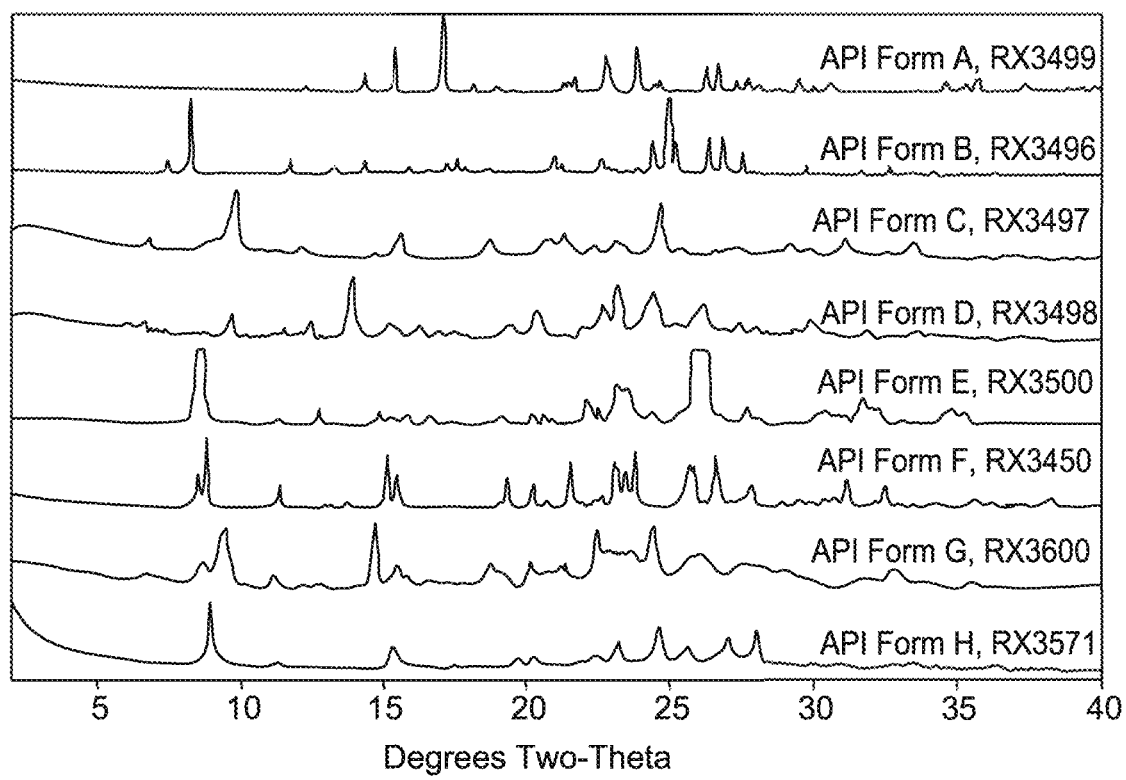
FIG. 36 shows XRPD patterns of VX-745 polymorphs, forms A through H.
Figure 37:
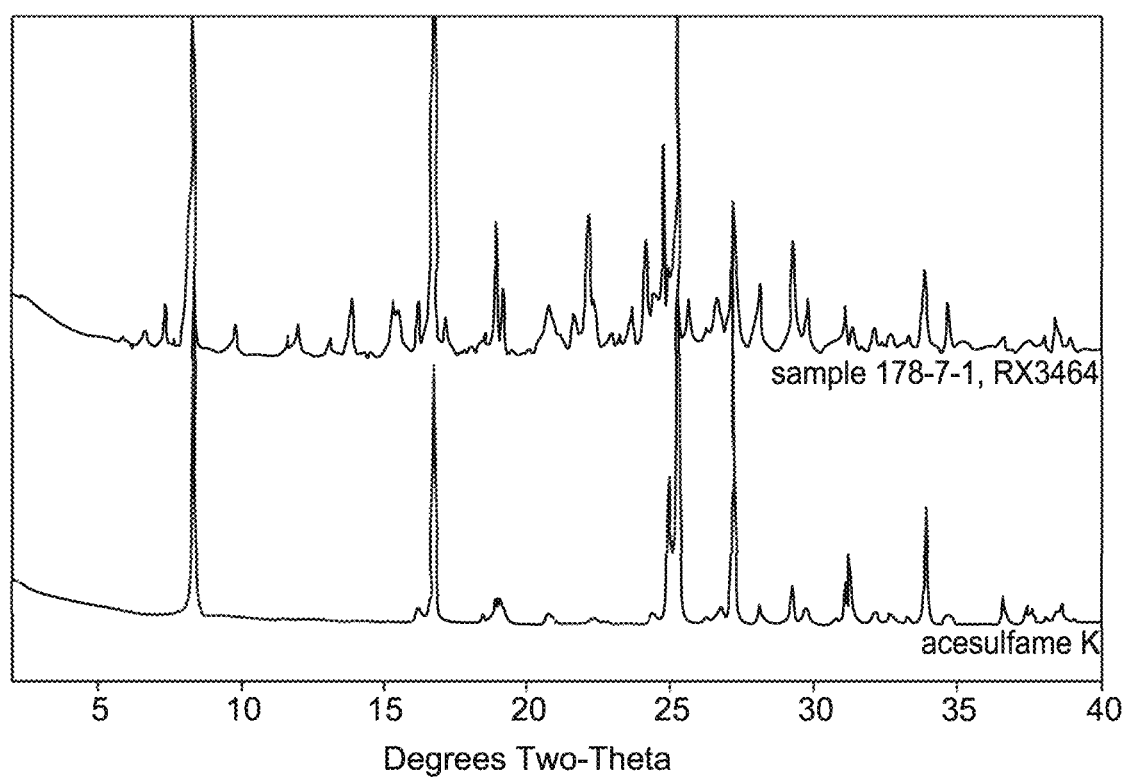
FIG. 37 shows XRPD patterns of (top) co-crystal comprising VX-745 and acesulfame potassium (top) and (bottom) coformer species alone (acesulfame potassium).
Figure 38:
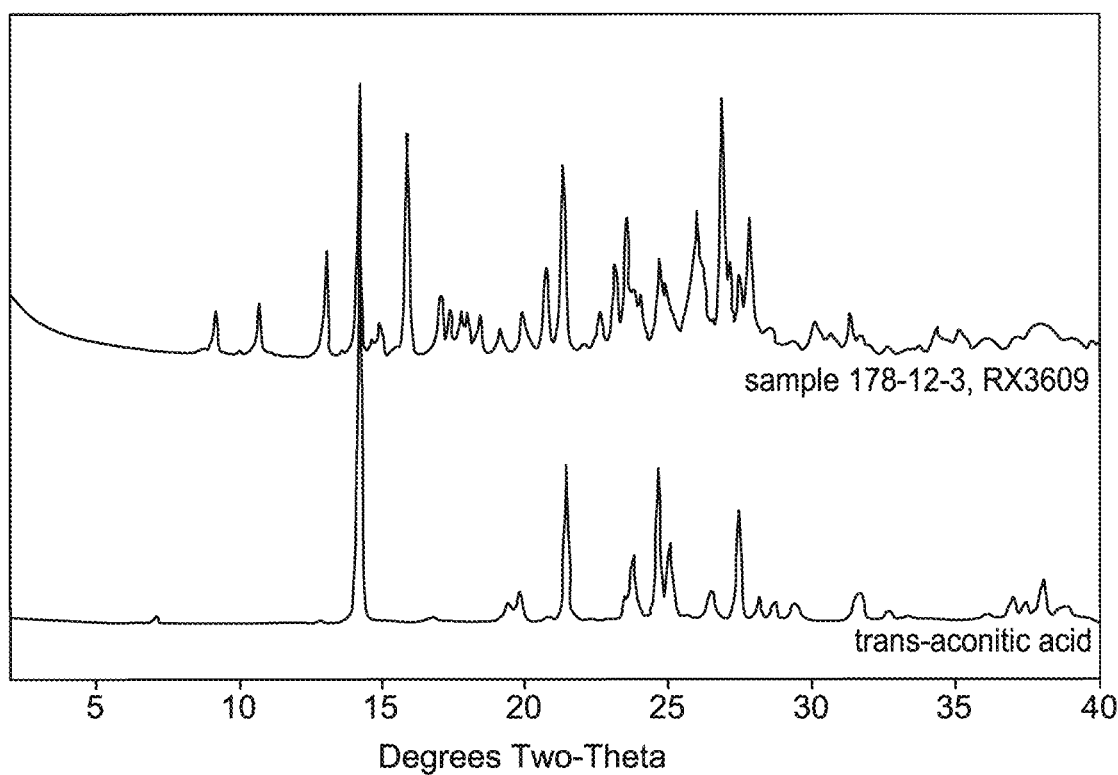
FIG. 38 shows XRPD patterns of (top) co-crystal comprising VX-745 and aconitic acid and (bottom) coformer species alone (aconitic acid).
Figure 39:
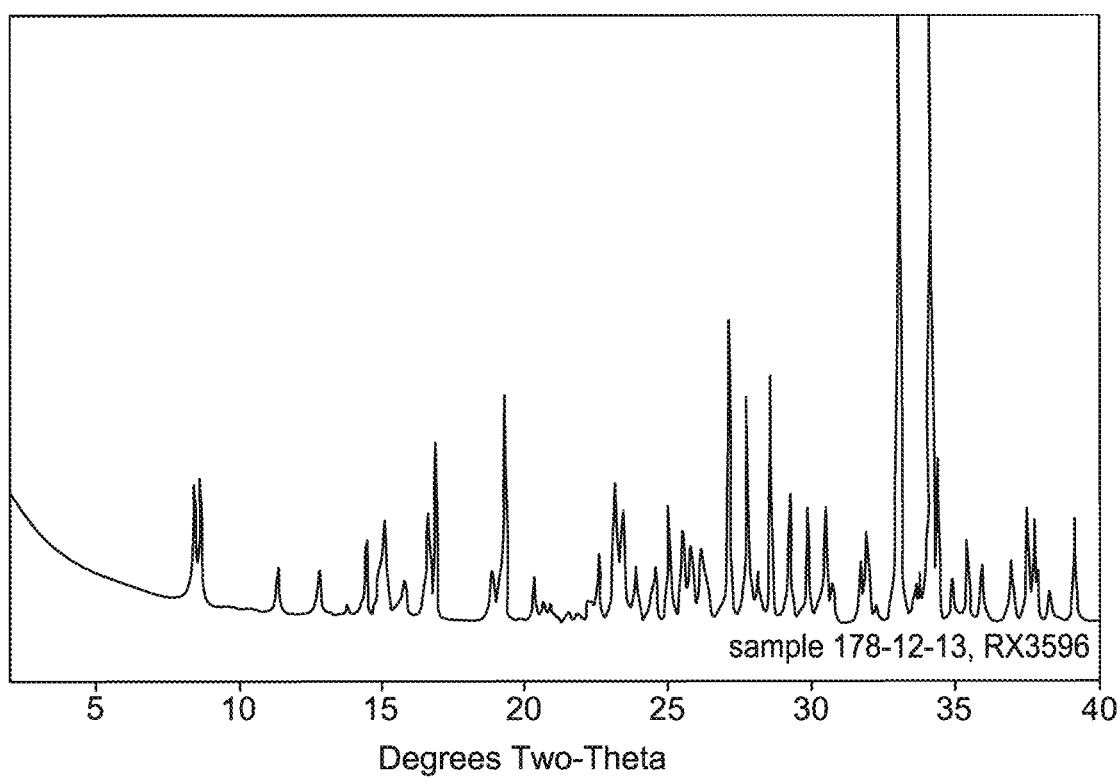
FIG. 39 shows XRPD pattern of co-crystal comprising VX-745 and calcium chloride.
Figure 40:
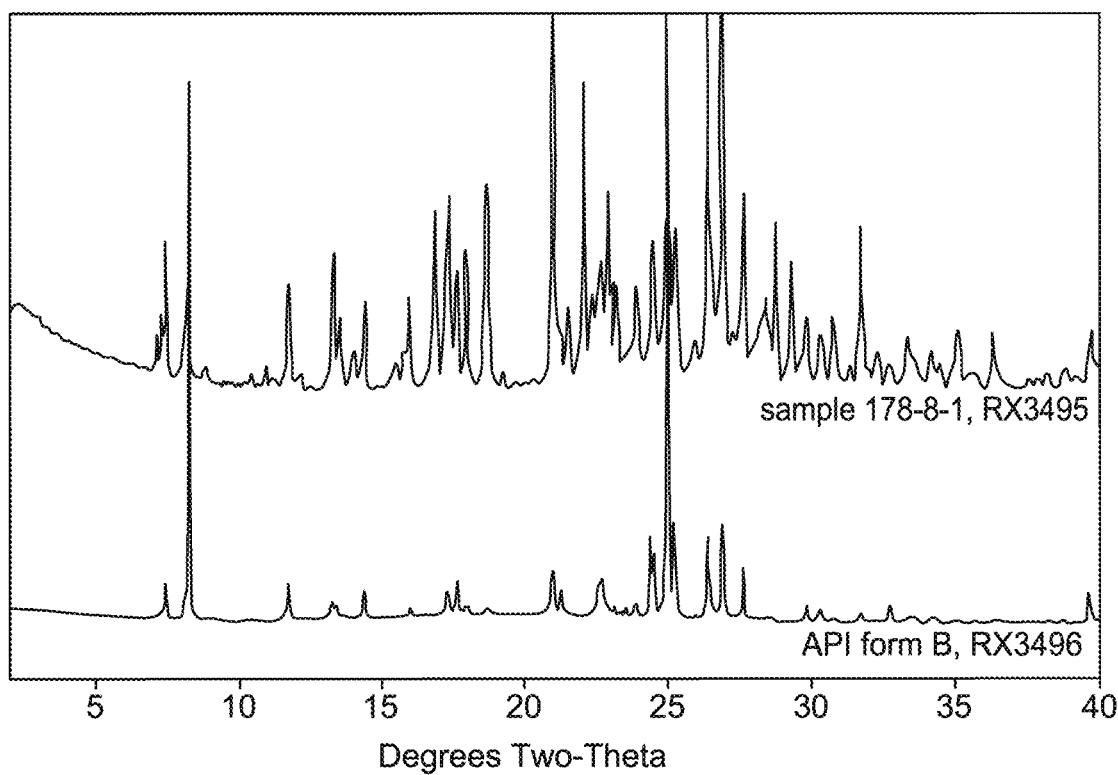
FIG. 40 shows XRPD patterns of (top) co-crystal comprising VX-745 and choline chloride and (bottom) polymorph form B of VX-745.
Figure 41:
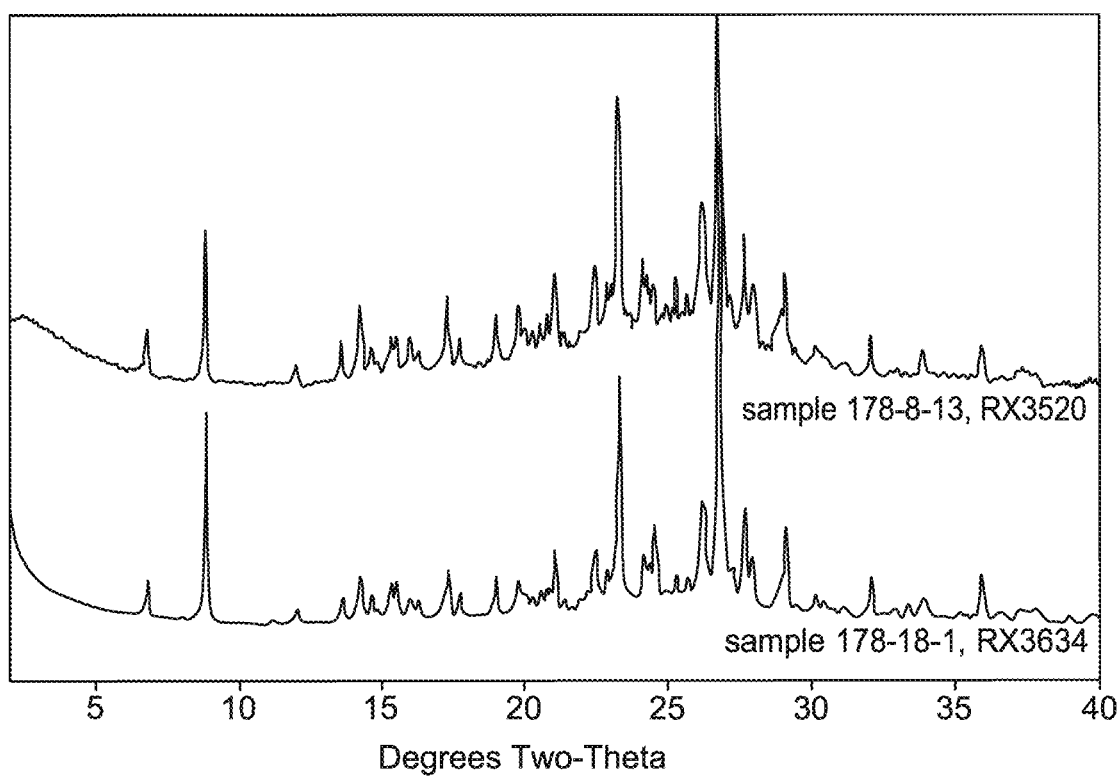
FIG. 41 shows XRPD patterns of co-crystals comprising VX-745 and gentisic acid (top and bottom).
Figure 42:
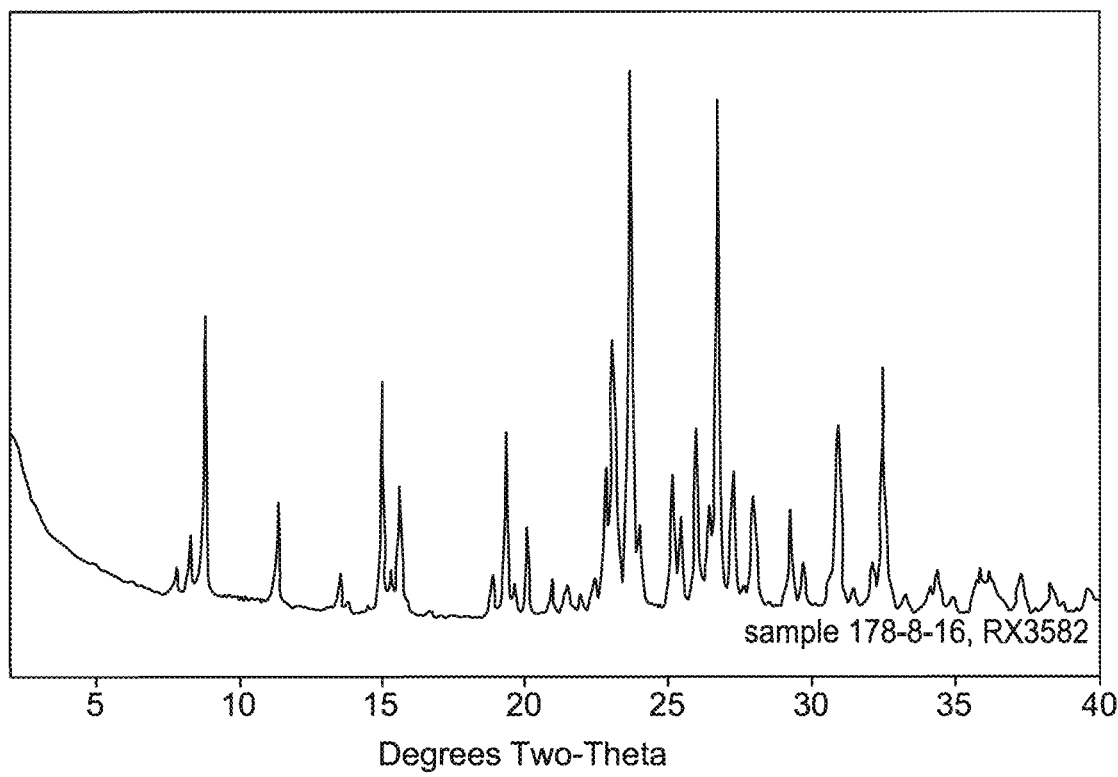
FIG. 42 shows XRPD pattern of co-crystal comprising VX-745 and glutaric acid.
Figure 43:
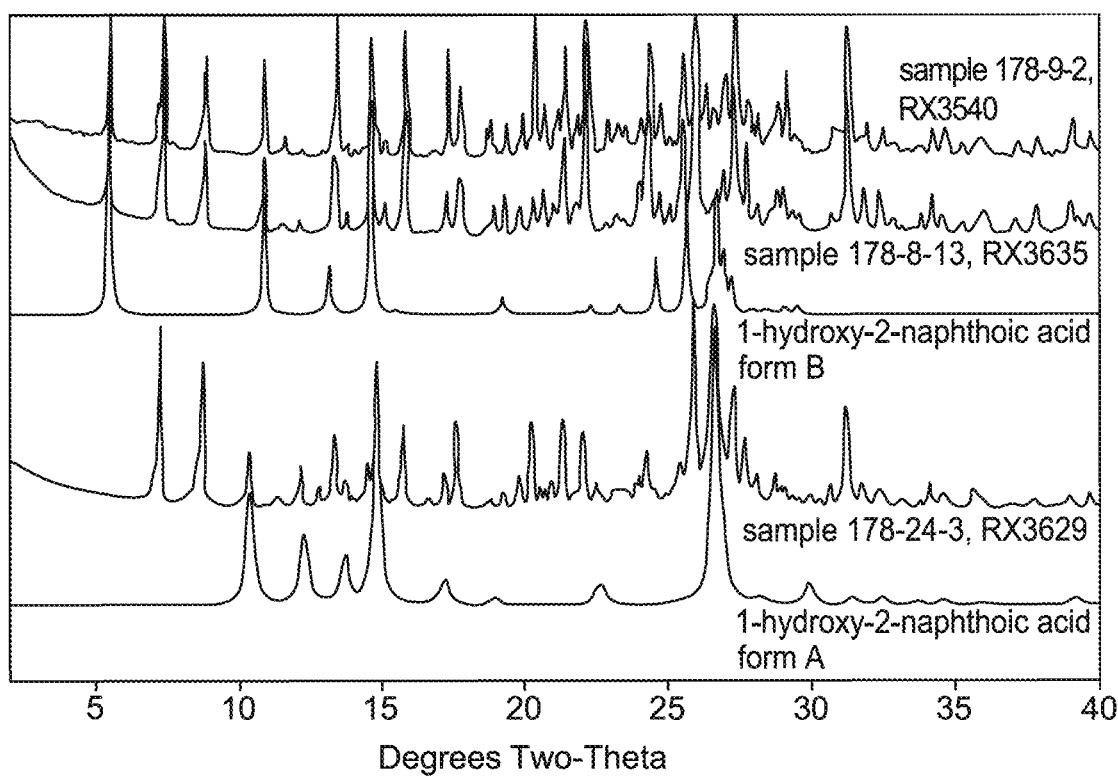
FIG. 43 shows XRPD patterns of co-crystals comprising VX-745 and 1-hydroxy-2-naphthioic acid (3 samples) overlaid with 1-hydroxy-2-naphthioic acid polymorphs A and B.
Figure 44:
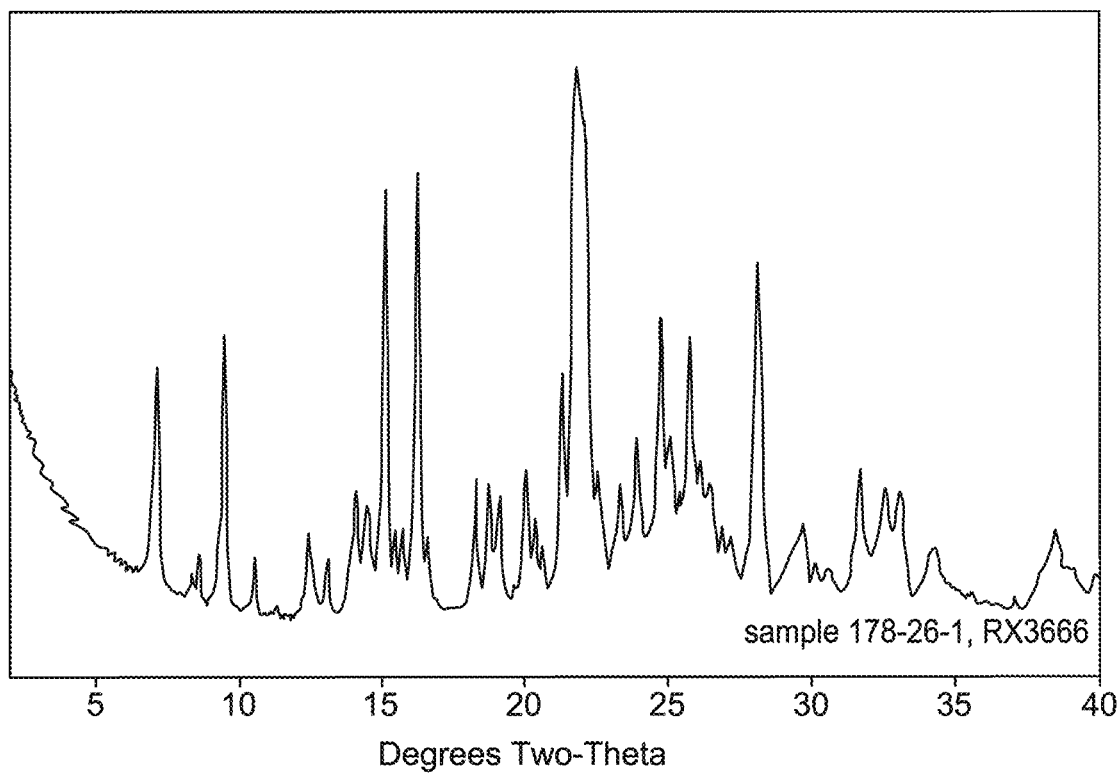
FIG. 44 shows XRPD pattern of co-crystal comprising VX-745 and ketoglutaric acid.
Figure 45:
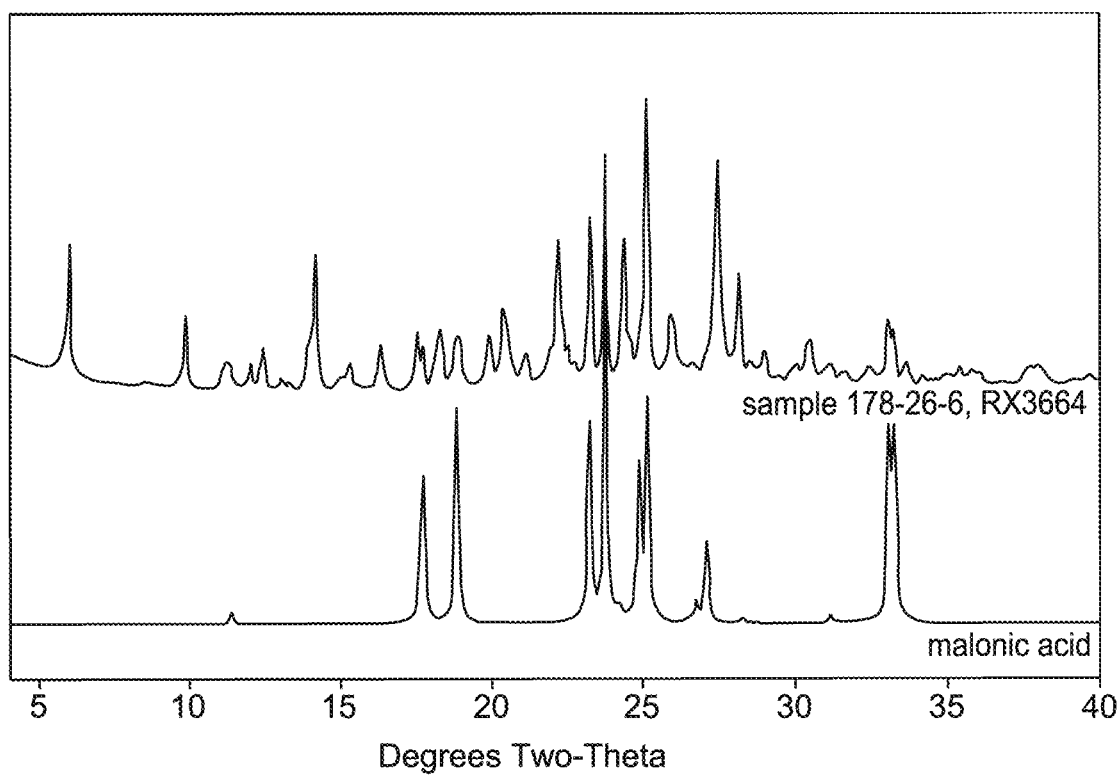
FIG. 45 shows XRPD patterns of (top) co-crystal comprising VX-745 and malonic acid and (bottom) coformer species alone (malonic acid).
Figure 46:
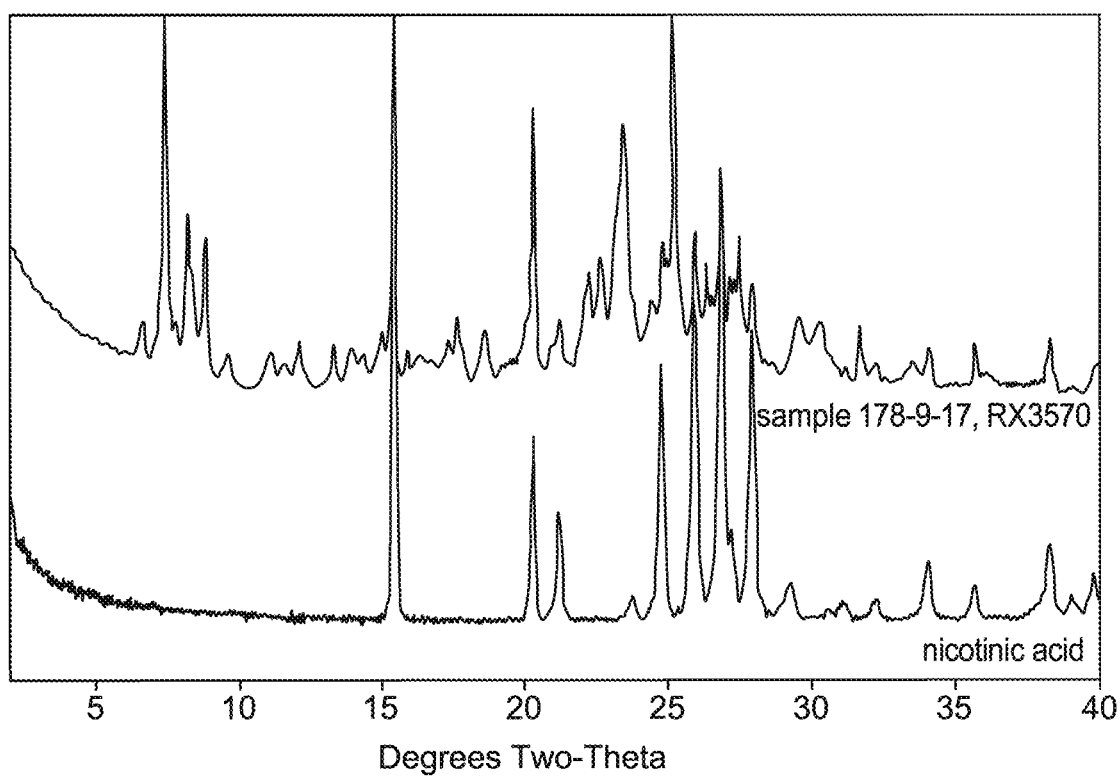
FIG. 46 shows XRPD patterns of (top) co-crystal comprising VX-745 and nicotinic acid and (bottom) coformer species alone (nicotinic acid).
Figure 47:
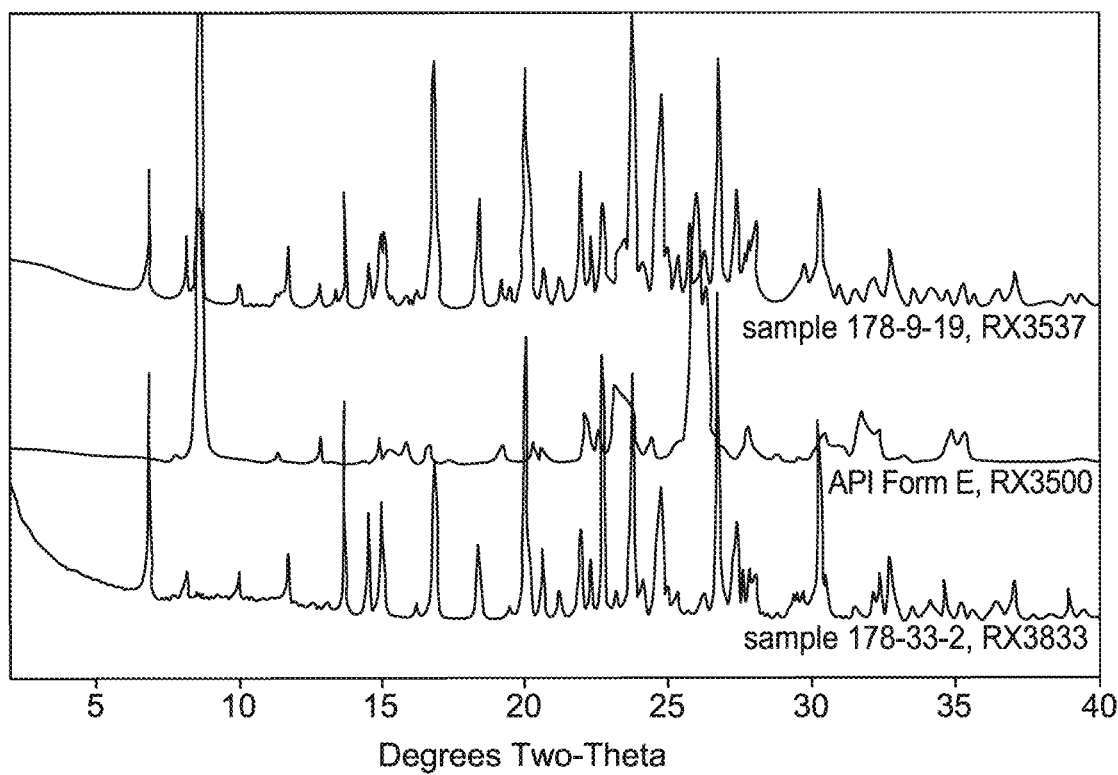
FIG. 47 shows XRPD patterns of (top) co-crystals comprising VX-745 and phenol (2 samples), overlaid with VX-745 polymorph Form E.
Figure 48:
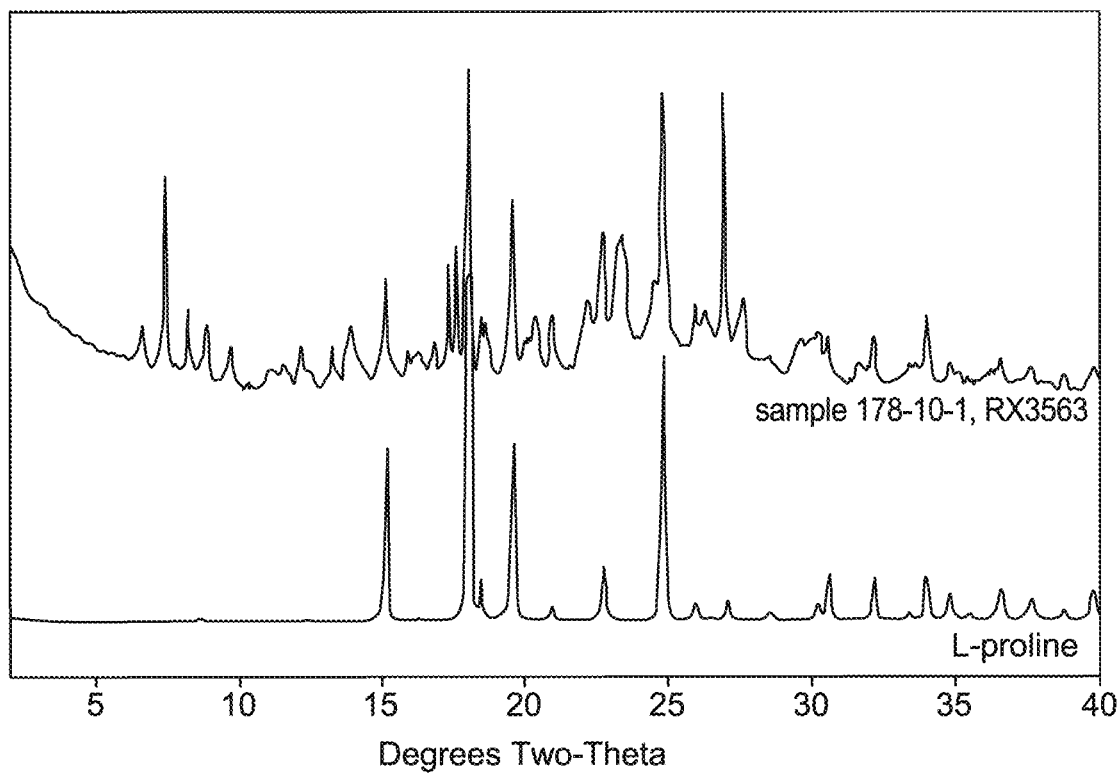
FIG. 48 shows XRPD patterns of (top) co-crystal comprising VX-745 and L-proline and (bottom) coformer species alone (L-proline).
Figure 49:
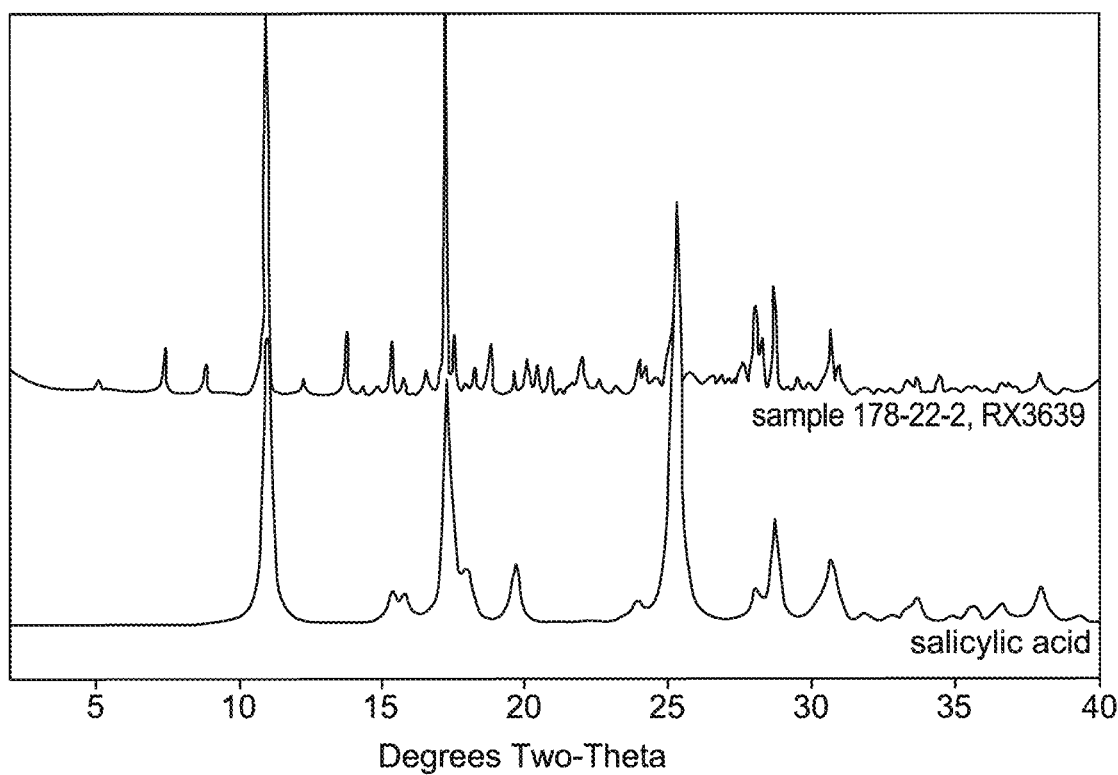
FIG. 49 shows XRPD patterns of (top) co-crystal comprising VX-745 and salicylic acid and (bottom) coformer species alone (salicylic acid).
Figure 50:
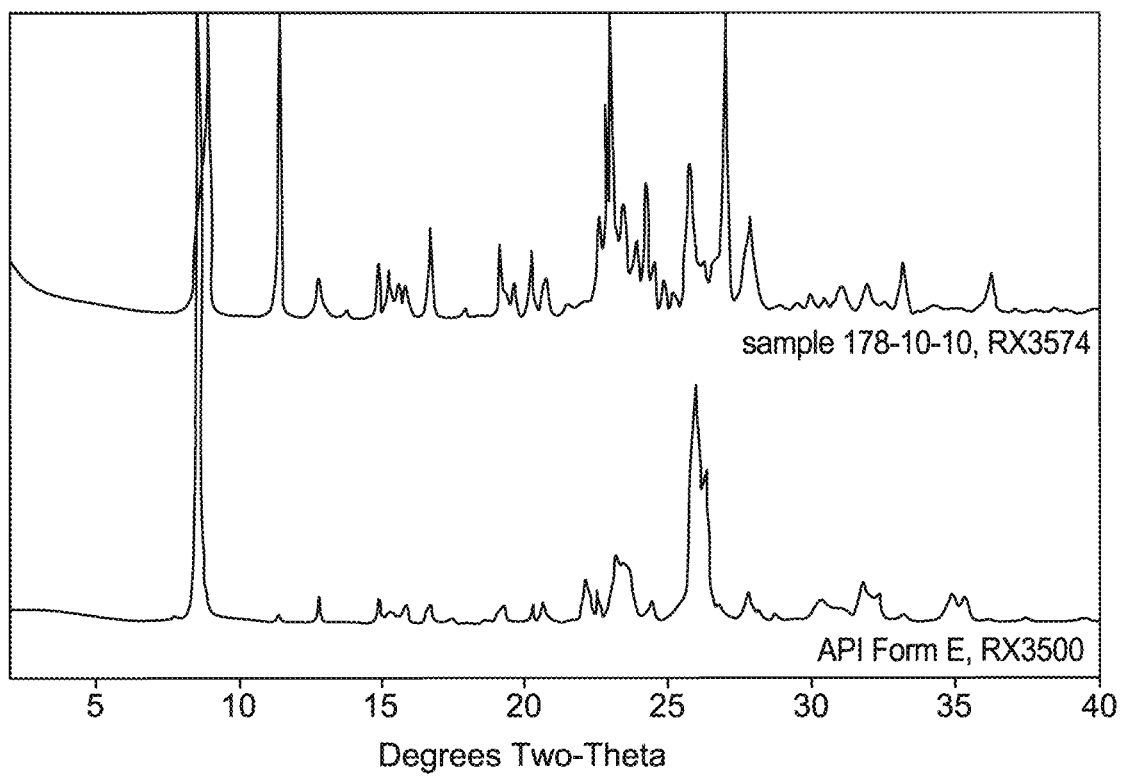
FIG. 50 shows XRPD patterns of (top) co-crystal comprising VX-745 and sorbic acid, overlaid with VX-745 polymorph Form E.
Figure 51:
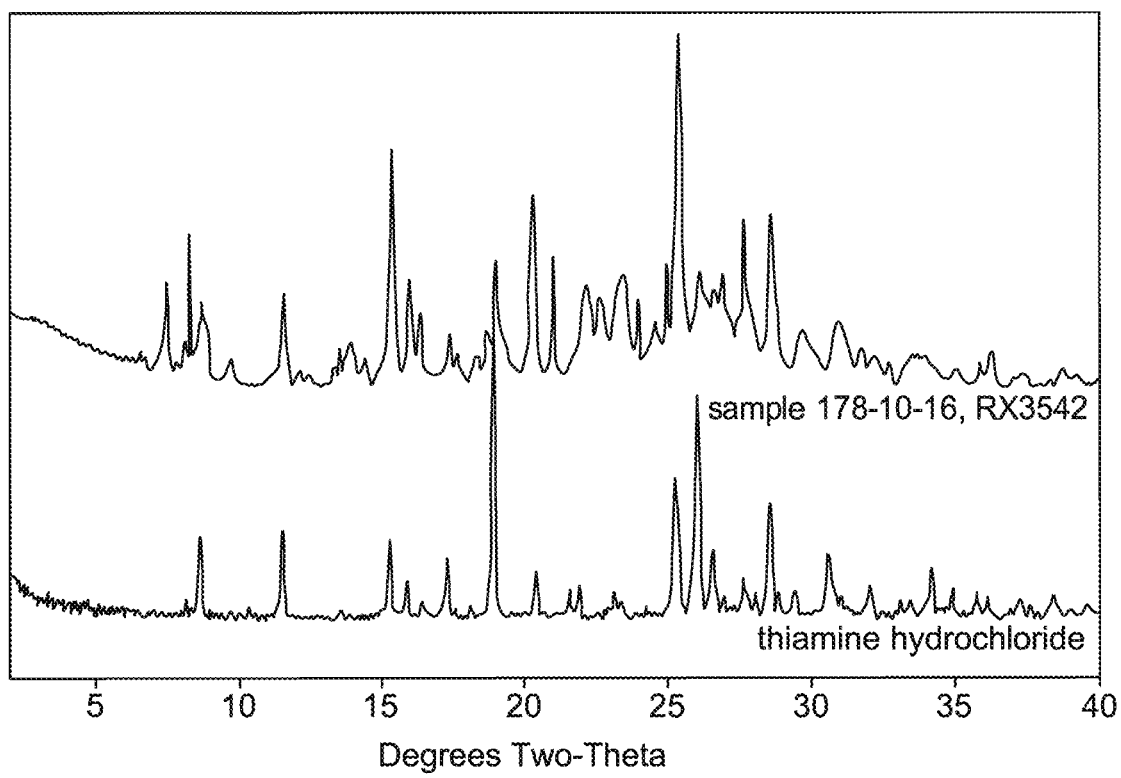
FIG. 51 shows XRPD patterns of (top) co-crystal comprising VX-745 and thiamine hydrochloride and (bottom) coformer species alone (thiamine hydrochloride).
Figure 52:
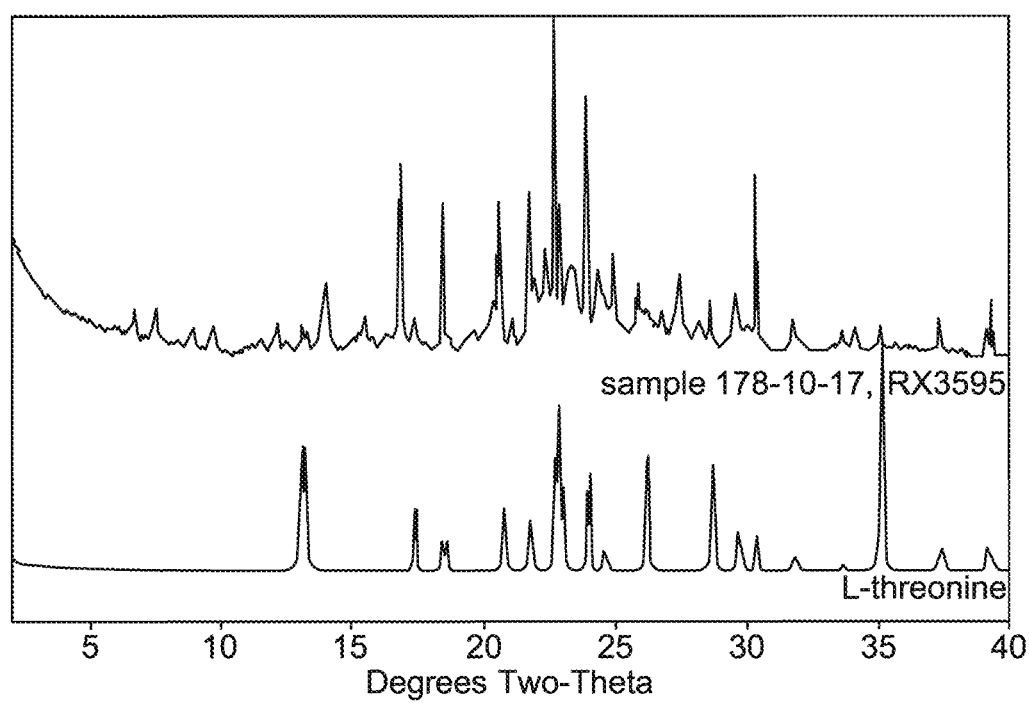
FIG. 52 shows XRPD patterns of (top) co-crystal comprising VX-745 and L-threonine and (bottom) coformer species alone (L-threonine).
Figure 53:
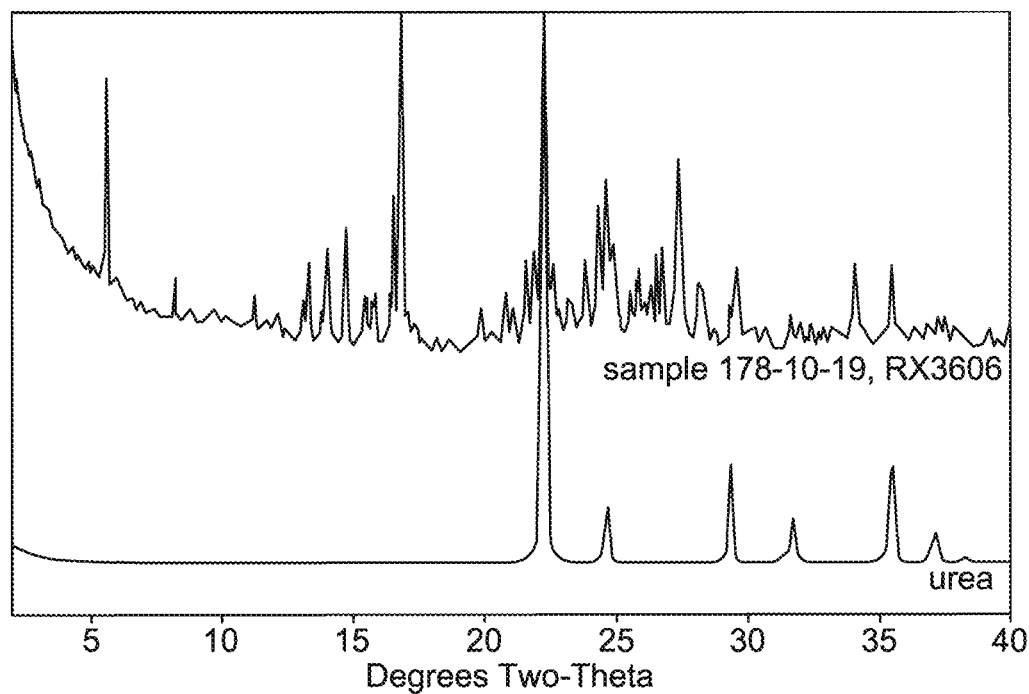
FIG. 53 shows XRPD patterns of (top) co-crystal comprising VX-745 and urea and (bottom) coformer species alone (urea).
Figure 54:
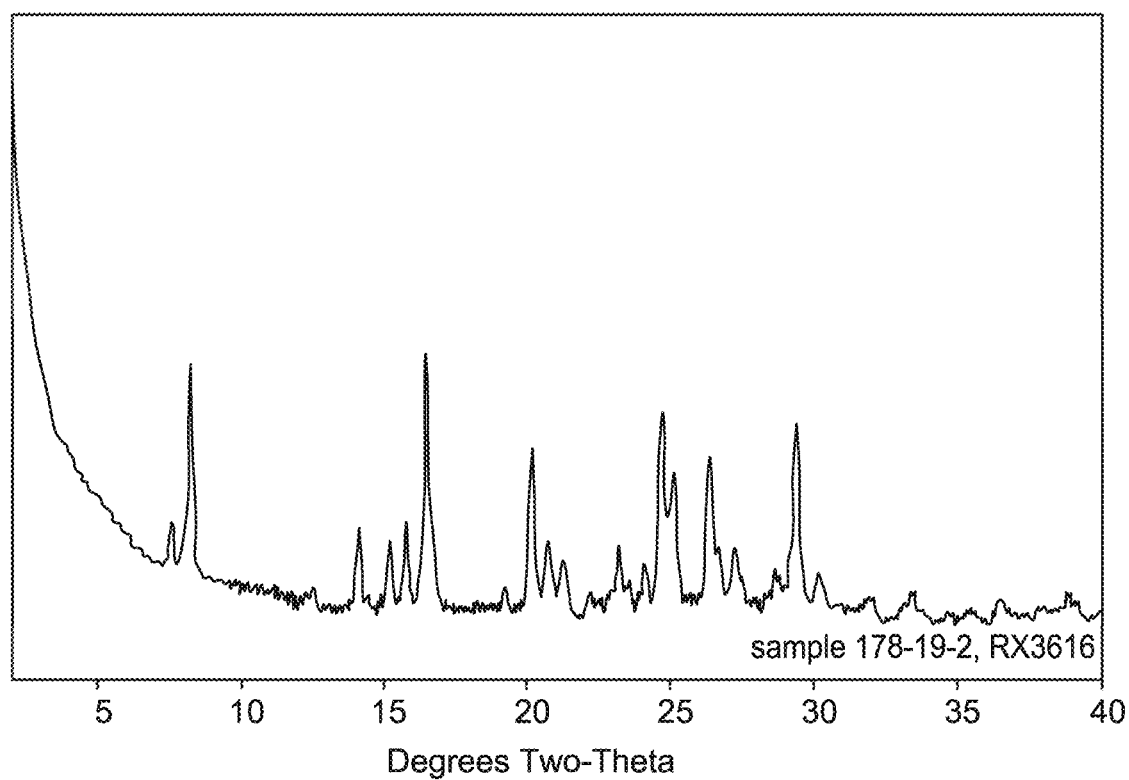
FIG. 54 shows XRPD patterns of (top) co-crystal comprising VX-745 and zinc chloride and (bottom) coformer species alone (zinc chloride).

Form diversity: As used herein, the term "form diversity" refers to the number of polymorphs observed with a crystalline compound. For example, while at least 8 polymorphs (as shown in FIG. 36) were observed for crystalline free VX-745 (without incorporation of a coformer species), fewer polymorphs may be observed when VX-745 forms a co-crystal with one or more coformer species described herein. In some embodiments, a co-crystal of VX-745 (e.g., ones described herein) is not polymorphic.

Hygroscopicity: The term "hygroscopicity" is used herein to describe the ability of a co-crystal of VX-745 to absorb or uptake water vapor or moisture from ambient air under a specified condition, e.g., at room temperature under atmospheric pressure. In some embodiments, the hygroscopicity of a co-crystal of VX-745 described herein is decreased by, e.g., at least about 10% or more (including, e.g., at least about 20%, at least about 30%, at least about 40%, at least about 50%, at least about 60%, at least about 70%, at least about 80%, at least about 90%, or more), as compared to that of free VX-745 (without incorporation of any coformer species). Methods for determining a compound's hygroscopicity are known in the art. For example, dynamic vapor sorption (DVS), e.g., as described herein, can be used to determine hygroscopicity of a co-crystal of VX-745 described herein.

Stability: The term "stability" as used herein refers to susceptibility of a co-crystal of VX-745 (e.g., ones described herein) to one or more conditions, including, e.g., humidity, high temperature, light, and/or hydrolysis. Thus, stability may encompass stability to moisture, thermal stability, photostability, and/or solution stability. In some embodiments, the stability of a co-crystal of VX-745 described herein (e.g., in one or more aspects as described above) is increased by, e.g., at least about 30% or more (including, e.g., at least about 40%, at least about 50%, at least about 60%, at least about 70%, at least about 80%, at least about 90%, at least about 95%, at least about 1.1-fold, at least about 2-fold, at least about 3-fold, at least about 4-fold, at least about 5-fold, or more), as compared to that of free VX-745 (without incorporation of any coformer species).

VX-745: As used herein, the term "VX-745" is 5-(2,6-dichlorophenyl)-2-(2,4-difluorophenylthio)-6H-pyrimido[1,6-b]pyridazin-6-one or neflamapimod, which is further discussed below. VX-745 is polymorphic. Powder X ray diffraction patterns of exemplary VX-745 polymorphs are shown in FIG. 36.

DETAILED DESCRIPTION OF EXEMPLARY EMBODIMENTS

U.S. Pat. No. 8,338,412, issued Dec. 25, 2012 ("the '412 patent," the entirety of which is hereby incorporated herein by reference), describes certain compounds which inhibit activity of p38, mitogen-activated protein kinases (MAPKs). Such compounds include VX-745:

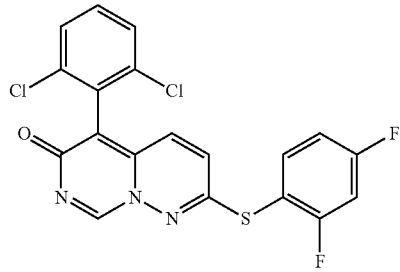

VX-745

VX-745 (5-(2,6-dichlorophenyl)-2-(2,4-difluorophenylthio)-6H-pyrimido[1,6-b]pyridazin-6-one) is a selective small-molecule inhibitor of p38 MAPK developed by Vertex Pharmaceuticals for the treatment of rheumatoid arthritis (RA). The inhibition of MAPK by VX-745 blocks the downstream synthesis of inflammatory cytokines TNF-α, IL-1β, and IL-6.

VX-745 is active in a variety of assays and therapeutic models demonstrating inhibition of p38 MAPK (in enzymatic and cellular assays). Notably, compound VX-745 was found to inhibit p38 MAPK in both in vitro and in vivo. Accordingly, VX-745 is useful for treating one or more disorders associated with p38 MAPK. However, VX-745 is poorly water-soluble and does not contain readily ionisable functional groups that allow salt formation.

It would be desirable to provide a co-crystal form of VX-745 that, as compared to VX-745 in its single-component solid form, imparts characteristics such as improved aqueous solubility, stability, dissolution rate, and ease of formulation. Accordingly, one aspect provided herein relates to a co-crystal form of VX-745.

According to one embodiment, a co-crystal of VX-745 comprises VX-745 and at least one suitable coformer, wherein:

each coformer is independently selected from acesulfame potassium, trans-aconitic acid, adenine, adipic acid, 4-aminobenzoic acid, L-ascorbic acid, asparagine, benzoic acid, betaine HCl, calcium chloride, choline chloride, cyclamic acid, gallic acid, gentisic acid, glutaric acid, L-histidine, 1-hydroxy-2-naphthoic acid, ketoglutaric acid, lithium chloride, malonic acid, nicotinic acid, oxalic acid, phenol, L-proline, L-pyroglutamic acid, saccharin, salicylic acid, L-serine, sorbic acid, sorbitol, sucrose, L-threonine, urea, or zinc chloride.

It will be appreciated by one of ordinary skill in the art that, typically, a coformer and VX-745 are non-covalently and non-ionically bonded to form a provided co-crystal. Suitable intermolecular interactions between a coformer and VX-745 forming a provided co-crystal include hydrogen-bonding, van der Waals forces, and pi-stacking, preferably hydrogen-bonding. In some embodiments, a coformer is a molecule or compound that is not covalently or ionically bonded to the VX-745 and crystallizes with the VX-745 such that the coformer molecules are integrated within the crystal matrix of the VX-745 thereby forming a provided co-crystal.

As defined above and described herein, each coformer is independently selected from acesulfame potassium, trans-aconitic acid, adenine, adipic acid, 4-aminobenzoic acid, L-ascorbic acid, asparagine, benzoic acid, betaine HCl, calcium chloride, choline chloride, cyclamic acid, gallic acid, gentisic acid, glutaric acid, L-histidine, 1-hydroxy-2-naphthoic acid, ketoglutaric acid, lithium chloride, malonic acid, nicotinic acid, oxalic acid, phenol, L-proline, L-pyroglutamic acid, saccharin, salicylic acid, L-serine, sorbic acid, sorbitol, sucrose, L-threonine, urea, or zinc chloride.

In some embodiments, the coformer is acesulfame potassium. In some embodiments, the coformer is trans-aconitic acid. In some embodiments, the coformer is adenine. In some embodiments, the coformer is adipic acid. In some embodiments, the coformer is 4-aminobenzoic acid. In some embodiments, the coformer is L-ascorbic acid. In some embodiments, the coformer is asparagine. In some embodiments, the coformer is benzoic acid. In some embodiments, the coformer is betaine HCl. In some embodiments, the coformer is calcium chloride. In some embodiments, the coformer is choline chloride. In some embodiments, the coformer is cyclamic acid. In some embodiments, the coformer is gallic acid. In some embodiments, the coformer is gentisic acid. In some embodiments, the coformer is glutaric acid. In some embodiments, the coformer is L-histidine. In some embodiments, the coformer is 1-hydroxy-2-naphthoic acid. In some embodiments, the coformer is ketoglutaric acid. In some embodiments, the coformer is lithium chloride. In some embodiments, the coformer is malonic acid. In some embodiments, the coformer is nicotinic acid. In some embodiments, the coformer is oxalic acid. In some embodiments, the coformer is phenol. In some embodiments, the coformer is L-proline. In some embodiments, the coformer is L-pyroglutamic acid. In some embodiments, the coformer is saccharin. In some embodiments, the coformer is salicylic acid. In some embodiments, the coformer is L-serine. In some embodiments, the coformer is sorbic acid. In some embodiments, the coformer is sorbitol. In some embodiments, the coformer is sucrose. In some embodiments, the coformer is L-threonine. In some embodiments, the coformer is urea. In some embodiments, the coformer is zinc chloride.

In some embodiments, a co-crystal provided herein comprises VX-745 and at least one or more (e.g., 1, 2, 3, or 4) distinct coformer species. In some embodiments, each coformer species present in a co-crystal can be independently selected from acesulfame potassium, trans-aconitic acid, adenine, adipic acid, 4-aminobenzoic acid, L-ascorbic acid, asparagine, benzoic acid, betaine HCl, calcium chloride, choline chloride, cyclamic acid, gallic acid, gentisic acid, glutaric acid, L-histidine, 1-hydroxy-2-naphthoic acid, ketoglutaric acid, lithium chloride, malonic acid, nicotinic acid, oxalic acid, phenol, L-proline, L-pyroglutamic acid, saccharin, salicylic acid, L-serine, sorbic acid, sorbitol, sucrose, L-threonine, urea, zinc chloride; conformer species described herein, and combinations thereof.

In some embodiments, a co-crystal comprises VX-745 and a single coformer species. In some embodiments where a single coformer species is present, the single coformer species is gentisic acid. In some embodiments where a single coformer species is present, the single coformer species is glutaric acid. In some embodiments where a single coformer species is present, the single coformer species is nicotinic acid. In some embodiments where a single coformer species is present, the single coformer species is phenol. In some embodiments where a single coformer species is present, the single coformer species is zinc chloride.

In some embodiments, a co-crystal comprises VX-745 and two distinct coformer species. For example, in some embodiments, the two distinct coformer species are glutaric acid and gentisic acid.

In some embodiments, a co-crystal comprises VX-745 and three distinct coformer species.

In some embodiments, a co-crystal comprises VX-745 and four distinct coformer species.

In some embodiments, a co-crystal provided herein is selected from those depicted in Table 1 below.

| Co-crystal Number | API | Coformer |
|---|---|---|
| CC-1 | VX-745 | acesulfame potassium |
| CC-2 | VX-745 | trans-aconitic acid |
| CC-3 | VX-745 | calcium chloride |
| CC-4 | VX-745 | choline chloride |
| CC-5 | VX-745 | gentisic acid |
| CC-6 | VX-745 | glutaric acid |
| CC-7 | VX-745 | 1-hydroxy-2-naphthoic acid |
| CC-8 | VX-745 | ketoglutaric acid |
| CC-9 | VX-745 | malonic acid |
| CC-10 | VX-745 | nicotinic acid |
| CC-11 | VX-745 | phenol |
| CC-12 | VX-745 | L-proline |
| CC-13 | VX-745 | salicylic acid |
| CC-14 | VX-745 | sorbic acid |
| CC-15 | VX-745 | thiamine hydrochloride |
| CC-16 | VX-745 | L-threonine |
| CC-17 | VX-745 | urea |
| CC-18 | VX-745 | zinc chloride |

In certain embodiments, a co-crystal comprises VX-745 and at least one or more coformer species, wherein the coformer species is selected such that the co-crystal exhibits at least one or more (e.g., 1, 2, 3, 4, or more) of the following characteristics:
  a) the solubility of the co-crystal is increased as compared to that of VX-745 in the absence of the coformer species; and/or
  b) the dose response of the co-crystal is increased as compared to that of VX-745 in the absence of the coformer species; and/or
  c) the efficacy of the co-crystal is increased as compared to that of VX-745 in the absence of the coformer species; and/or
  d) the dissolution of the co-crystal is increased as compared to that of VX-745 in the absence of the coformer species; and/or
  e) the bioavailability of the co-crystal is increased as compared to that of VX-745 in the absence of the coformer species; and/or
  f) the stability of the co-crystal is increased as compared to that of VX-745 in the absence of the coformer species; and/or
  g) the hygroscopicity of the co-crystal is decreased as compared to that of VX-745 in the absence of the coformer species; and/or
  h) the form diversity of the co-crystal is decreased as compared as compared to that of VX-745 in the absence of the coformer species; and/or
  i) the morphology of the co-crystal is modulated as compared to that of VX-745 in the absence of the coformer species.

In some embodiments, the solubility of a co-crystal described herein is increased by about 0.5-fold or higher as compared to that of VX-745 (e.g., in crystal form) in the absence of the coformer species. In some embodiments, the solubility of a co-crystal described herein is increased by about 1.0-fold as compared to that of VX-745 (e.g., in crystal form) in the absence of the coformer species. In some embodiments, the solubility of a co-crystal described herein is increased by about 1.5-fold as compared to that of VX-745 (e.g., in crystal form) in the absence of the coformer species. In some embodiments, the solubility of a co-crystal described herein is increased by about 2.0-fold as compared to that of VX-745 (e.g., in crystal form) in the absence of the coformer species. In some embodiments, the solubility of a co-crystal described herein is increased by about 2.5-fold as compared to that of VX-745 (e.g., in crystal form) in the absence of the coformer species In some embodiments, the solubility of a co-crystal described herein is increased by about 3.0-fold as compared to that of VX-745 (e.g., in crystal form) in the absence of the coformer species. In some embodiments, the solubility of a co-crystal described herein is increased by about 3.5-fold as compared to that of VX-745 (e.g., in crystal form) in the absence of the coformer species. In some embodiments, the solubility of a co-crystal described herein is increased by about 4.0-fold as compared to that of VX-745 (e.g., in crystal form) in the absence of the coformer species. In some embodiments, the solubility of a co-crystal described herein is increased by about 4.5-fold as compared to that of VX-745 (e.g., in crystal form) in the absence of the coformer species. In some embodiments, the solubility of a co-crystal described herein is increased by about 5.0-fold as compared to that of VX-745 (e.g., in crystal form) in the absence of the coformer species. In some embodiments, the solubility of a co-crystal described herein is increased by about 6.0-fold as compared to that of VX-745 (e.g., in crystal form) in the absence of the coformer species. In some embodiments, the solubility of a co-crystal described herein is increased by about 7.0-fold as compared to that of VX-745 (e.g., in crystal form) in the absence of the coformer species. In some embodiments, the solubility of a co-crystal described herein is increased by about 8.0-fold as compared to that of VX-745 (e.g., in crystal form) in the absence of the coformer species. In some embodiments, the solubility of a co-crystal described herein is increased by about 9.0-fold as compared to that of VX-745 (e.g., in crystal form) in the absence of the coformer species. In some embodiments, the solubility of a co-crystal described herein is increased by about 10.0-fold as compared to that of VX-745 (e.g., in crystal form) in the absence of the coformer species. In some embodiments, the solubility of a co-crystal described herein is increased by about 12.0-fold as compared to that of VX-745 (e.g., in crystal form) in the absence of the coformer species. In some embodiments, the solubility of a co-crystal described herein is increased by about 15.0-fold as compared to that of VX-745 (e.g., in crystal form) in the absence of the coformer species. In some embodiments, the solubility of a co-crystal described herein is increased by about 17.0-fold as compared to that of VX-745 (e.g., in crystal form) in the absence of the coformer species. In some embodiments, the solubility of a co-crystal described herein is increased by about 20.0-fold as compared to that of VX-745 (e.g., in crystal form) in the absence of the coformer species. In some embodiments, the solubility of a co-crystal described herein is increased by about more than 20.0-fold as compared to that of VX-745 (e.g., in crystal form) in the absence of the coformer species.

In some embodiments, the solubility of a co-crystal described herein is increased by about 0.5-fold to about 20.0-fold as compared to that of VX-745 (e.g., in crystal form) in the absence of the coformer species. In some embodiments, the solubility of a co-crystal described herein is increased by about 1.0-fold to about 20.0-fold as compared to that of VX-745 (e.g., in crystal form) in the absence of the coformer species. In some embodiments, the solubility of a co-crystal described herein is increased by about 1.0-fold to about 15.0-fold as compared to that of VX-745 (e.g., in crystal form) in the absence of the coformer species. In some embodiments, the solubility of a co-crystal described herein is increased by about 1.0-fold to about 10.0-fold as compared to that of VX-745 (e.g., in crystal form) in the absence of the coformer species. In some embodiments, the solubility of a co-crystal described herein is increased by about 1.0-fold to about 8.0-fold as compared to that of VX-745 (e.g., in crystal form) in the absence of the coformer species. In some embodiments, the solubility of a co-crystal described herein is increased by about 1.0-fold to about 6.0-fold as compared to that of VX-745 (e.g., in crystal form) in the absence of the coformer species. In some embodiments, the solubility of a co-crystal described herein is increased by about 1.0-fold to about 4.0-fold as compared to that of VX-745 (e.g., in crystal form) in the absence of the coformer species. In some embodiments, the solubility of a co-crystal described herein is increased by about 1.0-fold to about 2.0-fold as compared to that of VX-745 (e.g., in crystal form) in the absence of the coformer species. In some embodiments, the solubility of a co-crystal described herein is increased by about 2.0-fold to about 20.0-fold as compared to that of VX-745 (e.g., in crystal form) in the absence of the coformer species. In some embodiments, the solubility of a co-crystal described herein is increased by about 4.0-fold to about 20.0-fold as compared to that of VX-745 (e.g., in crystal form) in the absence of the coformer species. In some embodiments, the solubility of a co-crystal described herein is increased by about 6.0-fold to about 20.0-fold as compared to that of VX-745 (e.g., in crystal form) in the absence of the coformer species. In some embodiments, the solubility of a co-crystal described herein is increased by about 8.0-fold to about 20.0-fold as compared to that of VX-745 (e.g., in crystal form) in the absence of the coformer species. In some embodiments, the solubility of a co-crystal described herein is increased by about 10.0-fold to about 20.0-fold as compared to that of VX-745 (e.g., in crystal form) in the absence of the coformer species. In some embodiments, the solubility of a co-crystal described herein is increased by about 15.0-fold to about 20-fold as compared to that of VX-745 (e.g., in crystal form) in the absence of the coformer species.

In some embodiments, a co-crystal comprises VX-745 (e.g., in any polymorph) and any coformer as described above (e.g., in any tautomeric form).

In other embodiments, a co-crystal provided herein is substantially free of impurities. As used herein, the term "substantially free of impurities" means that a co-crystal contains no detectable amount of extraneous matter. Such extraneous matter may include excess coformer, excess API (e.g. VX-745), residual solvents, or any other impurities that may result from the preparation of, and/or isolation of, the co-crystal. Undesirable ions, polymeric molecules, or other substances present in API or solvent can also contribute to impurities. In certain embodiments, a co-crystal constitutes at least about 95% or more (e.g., at least about 96%, at least about 97%, at least about 98%, at least about 99%, at least about 99.5% or more) of initial total weight of components (e.g., VX-745, coformer(s), and/or solvent) used in preparation of the co-crystal. In certain embodiments, a co-crystal constitutes at least about 99% or more of initial total weight of components (e.g., VX-745, coformer(s), and/or solvent) used in preparation of the co-crystal.

According to one embodiment, a co-crystal is present in an amount of at least about 97, 97.5, 98.0, 98.5, 99, 99.5, or 99.8 weight percent where the percentages are based on the total weight of the initial composition for preparation of a co-crystal. In some embodiments, a co-crystal provided herein contains no more than about 3.0 area percent HPLC of total impurities (including, e.g., organic molecules, inorganic molecules, and trace metals) and, in certain embodiments, no more than about 1.5 area percent HPLC total impurities (including, e.g., organic molecules, inorganic molecules, and trace metals) relative to the total area of the HPLC chromatogram. In some embodiments, a co-crystal provided herein contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

In some embodiments, VX-745 and/or coformer(s) present in a co-crystal can be in tautomeric forms. For example, a co-crystal of VX-745 can be obtained with a coformer species that exists as tautomers. In some embodiments, structures of co-crystals depicted here are also intended to include compounds that differ only in the presence of one or more isotopically enriched atoms. For example, compounds (i.e., VX-745 and/or a coformer) having the present structure except for the replacement of hydrogen by deuterium or tritium, or the replacement of a carbon by a $^{13}$C- or $^{14}$C-enriched carbon are within the scope of this disclosure herein.

In certain embodiments, a provided co-crystal of VX-745 comprises VX-745 and one or more coformer species, wherein the molar ratio of VX-745 and total coformer species is within the range of about 10:1 to about 1:10. In certain embodiments, a provided co-crystal of VX-745 comprises VX-745 and one or more coformer species, wherein the molar ratio of VX-745 and total coformer species is within the range of about 5:1 to about 1:5. In certain embodiments, a provided co-crystal of VX-745 comprises VX-745 and one or more coformer species, wherein the molar ratio of VX-745 and total coformer species is within the range of about 2:1 to about 1:2. In certain embodiments, a provided co-crystal of VX-745 comprises VX-745 and one or more coformer species, wherein the molar ratio of VX-745 and total coformer species is within the range of about 1.5:1 to about 1:1.5.

In certain embodiments, a provided co-crystal of VX-745 comprises VX-745 and one or more coformer species, wherein the molar ratio of VX-745 and total coformer species is about 5:1. In certain embodiments, a provided co-crystal of VX-745 comprises VX-745 and one or more coformer species, wherein the molar ratio of VX-745 and total coformer species is about 2:1. In certain embodiments, a provided co-crystal of VX-745 comprises VX-745 and one or more coformer species, wherein the molar ratio of VX-745 and total coformer species is about 1.5:1. In certain embodiments, a provided co-crystal of VX-745 comprises VX-745 and one or more coformer species, wherein the molar ratio of VX-745 and total coformer species is about 1:1.

In certain embodiments, a provided co-crystal of VX-745 comprises VX-745 and one or more coformer species, wherein the molar ratio of VX-745 and total coformer species is about 1:5. In certain embodiments, a provided co-crystal of VX-745 comprises VX-745 and one or more coformer species, wherein the molar ratio of VX-745 and total coformer species is about 1:2. In certain embodiments, a provided co-crystal of VX-745 comprises VX-745 and one or more coformer species, wherein the molar ratio of VX-745 and total coformer species is about 1:1.5.

Solid Forms of Co-Crystals of VX-745:

In some embodiments, a co-crystal of VX-745 is a solvated co-crystal. As used herein, the term "solvate" or "solvated" refers to a co-crystal form with either a stoichiometric or non-stoichiometric amount of solvent molecules incorporated into the crystalline lattice of the co-crystal. When the solvent is water, a solvate is a hydrate, e.g., a co-crystal form with either a stoichiometric or non-stoichiometric amount of water molecules incorporated into the crystalline lattice of the co-crystal. Accordingly, another aspect described herein provides a composition comprising a co-crystal of VX-745 (e.g., ones described herein) and a solvent. In some embodiments, a co-crystal of VX-745 is dissolved in a solvent, which is then re-crystallized to form a co-crystal solvate or a co-crystal hydrate (if the solvent is water). Examples of a solvent include, but are not limited to acetone, acetonitrile, ethyl acetate, ethanol, isopropyl alcohol, methanol (MeOH), tetrahydrofuran (THF), water, and combinations thereof. In some embodiments, the solvent is or comprises acetone. In some embodiments, the solvent is or comprises acetonitrile. In some embodiments, the solvent is or comprises ethyl acetate. In some embodiments, the solvent is or comprises ethanol. In some embodiments, the solvent is or comprises isopropyl alcohol. In some embodiments, the solvent is or comprises methanol. In some embodiments, the solvent is or comprises tetrahydrofuran. In some embodiments, the solvent is or comprises water.

In some embodiments, a co-crystal of VX-745 is an anhydrous or non-solvated co-crystal. An anhydrous or non-solvated co-crystal describes a co-crystal form with no water or solvent molecules incorporated into the crystalline lattice of the co-crystal. It has been found that any co-crystal of VX-745 can exist in at least one distinct neat (e.g., anhydrous) crystal form, or polymorph.

In some embodiments, CC-5 (a co-crystal comprising VX-745 and gentisic acid) exhibits a melting point of about 136° C. In some embodiments, CC-5 has a stoichiometric ratio of VX-745 to gentisic acid of about 1:about 1, as evidenced by NMR. In some embodiments, CC-5 is a solvate. Methods for preparing CC-5 are described infra.

In some embodiments, CC-6 (a co-crystal comprising VX-745 and glutaric acid) exhibits a melting point of about 95° C. In some embodiments, CC-6 has a stoichiometric ratio of VX-745 to glutaric acid of about 1:about 1, as evidenced by NMR. In some embodiments, CC-6 is an anhydrate. Methods for preparing CC-6 are described infra.

In some embodiments, CC-18 (a co-crystal comprising VX-745 and zinc chloride) exhibits a melting point of about 189° C. In some embodiments, CC-18 has a stoichiometric ratio of VX-745 to zinc chloride of about 1:about 1, as evidenced by NMR. In some embodiments, CC-18 is a solvate. Methods for preparing CC-18 are described infra.

General Methods of Providing Co-Crystals of VX-745:

Those skilled in the art are aware of technologies for preparing VX-745, including as described in detail in the '412 patent, the disclosure of which is herein incorporated by reference.

A provided co-crystal of VX-745 is formed by combining VX-745 with at least one distinct coformer under a condition suitable to form a co-crystal thereof. In some embodiments, co-crystals of VX-745 can be formed by solvent-based and/or solid-based methods.

One aspect described herein relates to methods for preparing co-crystals of VX-745, comprising the steps of:

a) providing VX-745:

VX-745 b) combining VX-745 with at least one distinct coformer in a suitable solvent under a condition such that a co-crystal of VX-745 is formed; and c) optionally isolating the co-crystal of VX-745.

A suitable solvent may solubilize one or more of the reaction components, or, alternatively, the suitable solvent may facilitate the agitation of a suspension of one or more of the reaction components. Non-limiting examples of such suitable solvents include a protic solvent, a polar aprotic solvent, and mixtures thereof. In certain embodiments, suitable solvents include an ether, an ester, an alcohol, a ketone, or a mixture thereof. In certain embodiments, a suitable solvent is methanol, ethanol, isopropanol, or acetone wherein said solvent is anhydrous or in combination with water, hexane, or heptane. In other embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent comprises anhydrous ethanol. In some embodiments, a suitable solvent is methyl t-butyl ether (MTBE). In some embodiments, a suitable solvent comprises acetonitrile. In some embodiments, a suitable solvent comprises acetone.

In some embodiments, VX-745 and at least one distinct coformer are dissolved in a suitable solvent, e.g., a common solvent, with a suitable stoichiometric ratio, and then the solution undergoes solvent evaporation to form a co-crystal of VX-745. The selection of the solvent plays an important role in solubility. If the solubility of VX-745 and coformer(s) are not similar, then the component with the lower solubility will precipitate.

In some embodiments, a method for preparing a co-crystal of VX-745 comprises the steps of:

a) providing VX-745:

VX-745 b) combining VX-745 with a suitable solvent and optionally heating to form a solution thereof;

c) adding at least one distinct coformer to the solution of (h), after which the resulting mixture is caused to form a co-crystal of VX-745; and d) optionally isolating the co-crystal of VX-745.

As described generally above, VX-745 is dissolved in a suitable solvent (e.g., any solvent described herein), optionally with heating. In certain embodiments VX-745 is dissolved in a suitable solvent at about 50° C. to about 60° C. In other embodiments, VX-745 is dissolved in a suitable solvent at about 50° C. to about 55° C. In still other embodiments, VX-745 is dissolved in a suitable solvent at the boiling temperature of the solvent. In other embodiments, VX-745 is dissolved in a suitable solvent without heating.

In some embodiments, at least one distinct coformer species is added to a solution of VX-745 to form a suspension. In some embodiments, the resulting suspension can be stirred, filtered, and dried to form a co-crystal of VX-745.

In certain embodiments, a coformer species is added to VX-745 at a molar ratio or stoichiometric ratio of about 1:1 (coformer species: VX-745) to afford a co-crystal of VX-745. In other embodiments, a coformer species is added to VX-745 at a molar ratio or stoichiometric ratio of less than 1:1 (coformer species: VX-745) to afford a co-crystal of VX-745. In yet other embodiments, a coformer species is added to VX-745 at a molar ratio or stoichiometric ratio of greater than 1:1 (coformer species: VX-745) to afford a co-crystal of VX-745. In some embodiments, a coformer species is added to VX-745 at a molar ratio or stoichiometric ratio of about 0.9:1 to about 1.1:1 (coformer species: VX-745) to afford a co-crystal of VX-745. In another embodiment, a coformer species is added to VX-745 at a molar ratio or stoichiometric ratio of about 0.99:1 to about 1.01:1 (coformer species: VX-745) to afford a co-crystal of VX-745.

A suitable form of a coformer may be added to the mixture of VX-745 and a suitable solvent. For example, a coformer may be added in a solid form or as a solution or a suspension in a suitable solvent. The suitable solvent may be the same suitable solvent as that which is dissolves VX-745 or may be a different solvent. According to one embodiment, the coformer is added in a solid form. In certain embodiments, the coformer is combined with a suitable solvent prior to adding to VX-745. According to another embodiment, the coformer is added as a solution in a suitable solvent. In other embodiments, the suitable solvent in which the coformer is dissolved is a polar protic or polar aprotic solvent or mixtures thereof. Such solvents include water, alcohols, ethers, and ketones. Examples of such solvents include water, methanol, ethanol, isopropanol, acetone, tetrahydrofuran, dimethylformamide, dimethylsulfoxide, glyme, diglyme, methyl t-butyl ether, t-butanol, n-butanol, and acetonitrile, wherein said solvent is anhydrous or in combination with water, hexane, or heptane. In certain embodiments the suitable solvent is selected from those above and is anhydrous. In some embodiments, a coformer is dissolved in MTBE.

In some embodiments, methods for preparing co-crystals of VX-745 comprise steps of:

a) providing VX-745:

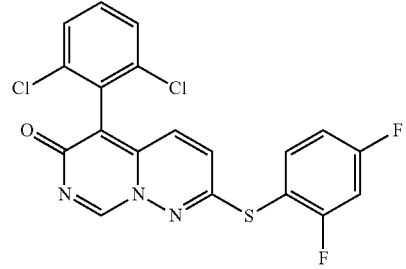

VX-745 b) combining solid materials of VX-745 and one or more coformer species, e.g., in a pre-determined stoichiometric or molar ratio (e.g., as described herein), to form a mixture;

c) grinding or milling the mixture of (b) to form a co-crystal of VX-745; and d) optionally isolating the co-crystal of VX-745.

In some embodiments, the grinding or milling can be performed in the absence of a solvent.

In some embodiments, the grinding or milling can be performed in the presence of a small amount of solvent (e.g., a few tenths of an equivalent of solvent per mole of the component).

In some embodiments, a provided co-crystal of VX-745 is achieved by slow evaporation of a solvent from a mixture comprising VX-745 and one or more coformer species dissolved in the solvent. In some embodiments, a provided co-crystal of VX-745 is prepared as described below, according to the Stoichiometric Slow Evaporation procedure. In other embodiments, a provided co-crystal of VX-745 is achieved by agitating the mixture. In some embodiments, a provided co-crystal of VX-745 is prepared as described below, according to the Stoichiometric Slurry procedure. In other embodiments, a provided co-crystal of VX-745 is prepared as described below, according to the Stoichiometric Wet Milling procedure.

In certain embodiments, the resulting mixture containing the co-crystal of VX-745 is cooled. In other embodiments, the mixture containing the co-crystal of VX-745 is cooled below 20° C.

In certain embodiments, the co-crystal of VX-745 precipitates from the mixture. In another embodiment, the co-crystal of VX-745 crystallizes from the mixture. In other embodiments, the co-crystal of VX-745 crystallizes from solution following seeding of the solution (e.g., adding crystals of the co-crystal of VX-745 to the solution).

Co-crystals of VX-745 can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent such as heptane, by cooling or by different combinations of these methods. Other methods for preparation of co-crystals, e.g., antisolvent addition, cooling crystallization, precipitation, and sonocrystallization, are known in the art and can be used to make co-crystals of VX-745 described herein. See, e.g., Yadav et al. "Co-crystals: A novel approach to modify physiochemical properties of active pharmaceutical ingredients" *Indian J Pharm Sci* (2009) 71: 359-370; and Karagianni et al. "Pharmaceutical co-crystals: New solid phase modification approaches for the formulation of APIs" *Pharmaceuticals* (2018) 10:18 (Review), the contents of each of which are incorporated herein by reference for the purpose described herein.

As described generally above, the co-crystal of VX-745 is optionally isolated. It will be appreciated that the co-crystal of VX-745 may be isolated by any suitable physical means known to one of ordinary skill in the art. In certain embodiments, solid co-crystals of VX-745, e.g., formed by solvent and solid based methods described herein, are separated from the supernatant by filtration or centrifugation. In some embodiments, solid co-crystals of VX-745, e.g., formed by solvent and/or solid based methods described herein, are separated from a reaction mixture by decanting the supernatant. In certain embodiments, isolated co-crystals of VX-745 are dried in air. In some embodiments, isolated co-crystals of VX-745 are dried under reduced pressure, optionally at elevated temperature.

Uses, Formulation and Administration

Pharmaceutically Acceptable Compositions

Another aspect described herein provides compositions comprising a co-crystal of VX-745 and a pharmaceutically acceptable carrier or vehicle. The amount of a co-crystal of VX-745 in compositions described herein is such that is effective to measurably inhibit p38 MAPK in a biological tissue or in a patient. In certain embodiments, a composition is formulated for administration to a patient in need of such a composition. In some embodiments, a composition is formulated for oral administration to a patient in need of such a composition.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, and polyethylene-polyoxypropylene-block polymers.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in an aqueous buffer, e.g., a saline buffer, or as a solution in a pharmaceutically acceptable solvent, e.g., 1,3-butanediol. Among the acceptable vehicles and solvents that may be employed are water, Ringer's solution and isotonic sodium chloride solution. In addition, sterile, fixed oils are conventionally employed as a solvent or suspending medium.

In some embodiments, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some embodiments, pharmaceutically acceptable compositions may be orally administered in any orally acceptable dosage form including, but not limited to, capsules, tablets, aqueous suspensions or solutions. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, pharmaceutically acceptable compositions described herein may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions described herein are formulated for oral administration. In some embodiments, pharmaceutically acceptable compositions described herein are formulated for parenteral administration.

Co-crystals of VX-745 described herein and compositions comprising the same may be combined with carrier materials to produce a composition in a single dosage form, which will vary depending upon the physical and/or medical condition of a subject to be treated, and/or a particular mode of administration. In certain embodiments, provided compositions are formulated such that a dosage of between 0.01-100 mg/kg body weight/day of a co-crystal of VX-745 can be administered to a patient in need of these compositions. In certain embodiments, provided compositions are formulated such that the amount of a co-crystal of VX-745 contained in a dosage is equivalent to the amount of free VX-745 (i.e., VX-745 without incorporation of solvent or water molecules or coformer species into the crystal structure of VX-745) known to be administered to a patient for treatment of a p38-associated disease or disorder.

It should also be understood that a specific dosage and treatment regimen for any particular patient can depend upon a variety of factors, including the activity of the specific compound employed, the age, body weight, general health, sex, diet, time of administration, rate of excretion, drug combination, and the judgment of the treating physician and the severity of the particular disease being treated. The amount of co-crystal of VX-745 in a composition can also depend upon the biochemical characteristics of the co-crystal.

Uses of Compounds and Pharmaceutically Acceptable Compositions

Co-crystals of VX-745 and compositions described herein are generally useful for inhibition of p38 MAPK.

The activity of co-crystals of VX-745 to inhibit p38 may be assayed by in vitro (e.g., in a cell line), or in vivo. In vitro assays include assays that determine inhibition of either the kinase activity or ATPase activity of activated p38. Alternate in vitro assays quantitate the ability of a co-crystal of VX-745 to bind to p38 and may be measured either by labelling (e.g., radiolabelling) a co-crystal of VX-745 prior to binding, isolating the co-crystal of VX-745/p38 complex and determining the amount of radio label bound, or by running a competition experiment where a co-crystal of VX-745 are incubated with p38 bound to known label ligands (e.g., radioligands).

Cell culture assays can be used to determine the inhibitory effect of co-crystals of VX-745 and/or compositions described herein by measuring the amounts of TNF, IL-1, IL-6 and/or IL-8 produced in whole blood or cell fractions thereof in cells treated with co-crystals of VX-745 and/or compositions described herein as compared to cells treated with negative controls or to cells treated without co-crystals of VX-745. Level of these cytokines may be determined through the use of commercially available ELISAs.

An exemplary in vivo assay useful for determining the inhibitory activity of co-crystals of VX-745 and/or compositions described herein is the suppression of hind paw edema in rats with *Mycobacterium butyricum*-induced adjuvant arthritis. This is described in J. C. Boehm et. al., *J Med. Chem.*, 39, pp. 3929-37 (1996), the disclosure of which is herein incorporated by reference. Co-crystals of VX-745 and/or compositions described herein may also be assayed in animal models of arthritis, bone resorption, endotoxin shock and immune function, as described in A. M. Badger et. al., *J. Pharmacol. Experimental Therapeutics*, 279, pp. 1453-61 (1996), the disclosure of which is herein incorporated by reference. Detailed conditions for assaying inhibitors of a p38 MAPK, or a mutant thereof, are set forth in detail in the '412 patent, as well as U.S. Pat. No. 8,697,627, issued Apr. 15, 2014 ("the '627 patent,") and can be used to assay the p38 MAPK inhibitory effect of co-crystals of VX-745 and/or compositions described herein.

A provided co-crystal of VX-745 is an inhibitor of p38 MAPK and therefore useful for treating one or more disorders associated with activity of p38 MAPK. Thus, another aspect described herein provides a method for treating a p38-mediated disorder comprising the step of administering to a patient in need thereof a co-crystal of VX-745, or pharmaceutically acceptable composition thereof.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Co-crystals of VX-745 and/or compositions described herein may be formulated into pharmaceutical compositions for administration to animals or humans. These pharmaceutical compositions, which comprise an amount of co-crystals of VX-745 (e.g., ones described herein) effective to treat or prevent a p38-mediated condition and a pharmaceutically acceptable carrier, also within the scope of the disclosures described herein.

The term "p38-mediated condition," as used herein means any disease or other deleterious condition in which p38 is known to play a role. This includes, for example, conditions which may be caused by IL-1, TNF, IL-6 or IL-8 overproduction. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxide synthase-2.

A further aspect provided herein relates to a method of treating or lessening the severity of one or more of the diseases or conditions associated with p38-MAPK, wherein said method comprises administering to a patient in need thereof a co-crystal of VX-745 or a composition comprising the same according to one or more embodiments described herein.

A provided co-crystal of VX-745 and compositions comprising the same may be administered using any amount and any route of administration effective for treating or lessening the severity of a p38-mediated disease. The exact amount required will vary from subject to subject, depending on the species, age, and general condition of the subject, the particular agent, its mode of administration, and the like. In some embodiments, a provided co-crystal of VX-745 and compositions described herein are formulated in dosage unit form for ease of administration and uniformity of dosage. The expression "dosage unit form" as used herein refers to a physically discrete unit of agent appropriate for the patient to be treated. It will be understood, however, that the total daily usage of co-crystals of VX-745 and/or compositions described herein will be decided by the attending physician within the scope of sound medical judgment. The specific effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions (e.g., ones described herein) may be administered to humans and other animals by any methods known in the art, including, e.g., orally, rectally, parenterally, intracisternally, intravaginally, intraperitoneally, topically (as by powders, ointments, or drops), bucally, as an oral or nasal spray, or the like, depending on the severity of a disease or disorder being treated. In certain embodiments, a co-crystal of VX-745 may be administered orally or parenterally at dosage levels of about 0.01 mg/kg to about 100 mg/kg or about 0.01 mg/kg to about 50 mg/kg, of subject body weight per day, one or more times a day, to obtain the desired therapeutic effect. In some embodiments, a co-crystal of VX-745 may be administered orally or parenterally at dosage levels of about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the co-crystal of VX-745, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided co-crystal of VX-745 (e.g., ones described herein), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microcapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing a co-crystal of VX-745 (e.g., ones described herein) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, a co-crystal of VX-745 is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

A provided co-crystal of VX-745 can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms a co-crystal of VX-745 (e.g., ones described herein) may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of co-crystals of VX-745 and/or compositions described herein include ointments, pastes, creams, lotions, gels, powders, solutions, sprays, inhalants or patches. A co-crystal of VX-745 is admixed under sterile conditions with a pharmaceutically acceptable carrier and any needed preservatives or buffers as may be required. Ophthalmic formulation, ear drops, and eye drops are also contemplated as being within the scope of the disclosures described herein. In some embodiments, co-crystals of VX-745 and/or compositions described herein may be formulated for use in transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Yet another aspect provided herein relates to methods of inhibiting protein kinase activity in a biological tissue comprising a step of contacting said biological tissue with a co-crystal of VX-745 (e.g., ones described herein) and/or a composition comprising the same.

In some embodiments, provided herein arc methods of inhibiting p38 MAPK, or a mutant thereof, activity in a biological tissue comprising a step of contacting said biological tissue with a co-crystal of VX-745, or a composition comprising said co-crystal. In certain embodiments, provided herein are methods of reducing amyloid plaques in biological tissue, the methods comprising a step of contacting said biological tissue with a co-crystal of VX-745, or a composition comprising said co-crystal.

Another embodiment provided herein relates to methods of inhibiting protein kinase activity in a patient comprising a step of administering to a patient a co-crystal of VX-745, or a composition comprising said compound.

According to another embodiment, provided herein are methods of inhibiting one or more of a p38 MAPK, or a mutant thereof, activity in a patient, the methods comprising a step of administering to a patient a co-crystal of VX-745, or a composition comprising said compound. In other embodiments, provided herein are methods for treating a disorder mediated by one or more of a p38 MAPK, or a mutant thereof, in a patient in need thereof, comprising the step of administering to said patient a co-crystal of VX-745 or a pharmaceutically acceptable composition thereof.

In some embodiments, provided herein are methods of preparing pharmaceutical compositions comprising VX-745, which methods comprise at least one step of preparing, processing, or formulating co-crystals as described herein.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, provided co-crystals are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

Synthesis of VX-745

VX-745 is prepared according to methods described in detail in the '412 patent; the disclosure of which is herein incorporated by reference.

X-Ray Powder Diffraction

The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits were used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku SmartLab is operated to give peak widths of 0.1 degrees 2-theta or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. The single-crystal, Si, low-background holder has a small circular recess (7 mm diameter and about 1 mm depth) that holds between 5 and 10 mg of powdered material. Each sample was analyzed from 2 to 40 degrees 2-theta using a continuous scan of 3 degrees 2-theta per minute with an effective step size of 0.02 degrees 2-theta.

Differential Scanning Calorimetry (DSC)

DSC analyses were carried out using a TA Instruments 2920 instrument. The instrument temperature calibration was performed using indium. The DSC cell was kept under a nitrogen purge of ~50 mL per minute during each analysis. Each sample was placed in a standard, crimped, aluminum pan and was heated from 20° C. to 350° C. at a rate of 10° C. per minute.

Thermogravimetric (TG) Analysis

The TG analysis was carried out using a TA Instruments Q50 instrument. The instrument balance was calibrated using class M weights and the temperature calibration was performed using alumel. For each analysis, the nitrogen purge at the balance was ~40 mL per minute, while the furnace was purged at ~60 mL per minute. Each sample was placed into a pre-tared platinum pan and heated from 20° C. to 350° C. at a rate of 10° C. per minute.

Dynamic Vapor Sorption Analysis

DVS analyses were carried out TA Instruments Q5000 Dynamic Vapor Sorption analyzer. The instrument was calibrated with standard weights and a sodium bromide standard for humidity. Samples were analysed at 25° C. with a maximum equilibration time of 60 minutes in 10% relative humidity (RH) steps from 5 to 95% RH (adsorption cycle) and from 95 to 5% RH (desorption cycle).

Raman Spectroscopy

Fourier transform (FT) Raman spectra were acquired on a Nicolet model 6700 spectrometer interfaced to a Nexus Raman accessory module. This instrument is configured with a Nd:YAG laser operating-at 1024 nm, a $CaF_2$ beam splitter, and a indium gallium arsenide detector. OMNIC 8.1 software was used for control of data acquisition and processing of the spectra. Samples were packed into a 3-inch glass NMR tube for analysis.

Nuclear Magnetic Resonance (NMR) Spectroscopy

The $^1H$ NMR spectra were acquired on a Bruker DRX-800 spectrometer located at the Chemistry Department of Purdue University. Samples were prepared by dissolving material in MeOH-$d_4$. The solutions were filtered and placed into individual 5-mm NMR tubes for subsequent spectral acquisition. The temperature controlled (296K) $^1H$ NMR spectra acquired on the DRX-800 utilized a 5-mm cryoprobe operating at an observing frequency of 800.13 MHz.

Stoichiometric Slow Evaporation Experiments

Stoichiometric slow evaporation experiments were carried out in glass vials. Each of the vials was charged with about 15 mg of VX-745 and an approximately equimolar amount of coformer. The contents were dissolved in a given solvent and placed in glass vials. The vials were covered with aluminium foil having three pinholes and allowed to evaporate at ambient. The resulting solids were analyzed by XRPD.

Stoichiometric Slurry Experiments

Stoichiometric slurry experiments were carried out in glass vials. Each of the vials was charged with about 15 mg of VX-745, an approximately equimolar amount of coformer, and approximately 500 µL of a saturated solution of both the VX-745 and the same coformer in the solvent used for that experiment. A magnetic stir bar was placed in each vial and the rack of vials was placed on a stir plate at room temperature for 2 days. The solids were isolated by centrifugation and analysed by XRPD.

Stoichiometric Wet Milling Experiments

For each experiment, A PEEK grinding cup was charged with about 15 mg of VX-745, an approximately equimolar amount of coformer, about 10 µL of either acetone or water, and one steel grinding ball. The cup was sealed and shaken on a Retsch mill for 20 min. The solid was removed and analyzed by XRPD.

HPLC Analysis for Dissolution Experiments

HPLC analyses were carried out on an Agilent 1100 series instrument equipped with a UV detector using the following materials and operating parameters:

| | |
|---|---|
| column: | Phenomenex Columbus C18, 250 mm × 3.2 mm, 5 µm |
| column temperature | 35° C. |
| detector wavelength | 210 nm |
| mobile phase | 25 mM phosphate buffer, pH 6.5:CAN:THF (57:25:18) |
| injection volume | 3 µL |
| flow rate | 0.8 mL/min |
| run time | 65 min |

The retention time of the VX-745 peak was about 6.9 minutes.

Example 1: Preparation of the Co-Crystal of VX-745 and Acesulfame Potassium (CC-1)

The co-crystal of VX-745 and acesulfame potassium, i.e., CC-1, was prepared according to the Stoichiometric Slow Evaporation protocol, using methanol as the solvent. Characterization of the resulting material demonstrated that the CC-1 was crystalline.

Example 2: Preparation of the Co-Crystal of VX-745 and Trans-Aconitic Acid (CC-2)

The co-crystal of VX-745 and trans-aconitic acid, i.e., CC-2, was prepared according to the Stoichiometric Slurry protocol, using 2:1 THF:hexane as the solvent. Characterization of the resulting material demonstrated that the CC-2 was crystalline.

Example 3: Preparation of the Co-Crystal of VX-745 and Calcium Chloride (CC-3)

The co-crystal of VX-745 and calcium chloride, i.e., CC-3, was prepared according to the Stoichiometric Slurry protocol, using 2:1 methanol:heptane as the solvent. Characterization of the resulting material demonstrated that the CC-3 was crystalline.

Example 4: Preparation of the Co-Crystal of VX-745 and Choline Chloride (CC-4)

The co-crystal of VX-745 and choline chloride (CC-4) was prepared by multiple methods. The co-crystal of VX-745 and choline chloride, i.e., CC-4a, was prepared according to the Stoichiometric Slow Evaporation protocol, using methanol as a solvent. The co-crystal of VX-745 and choline chloride, i.e., CC-4b, was prepared according to the Stoichiometric Slurry protocol, using 2:1 methanol:heptane as the solvent. Characterization of the resulting material demonstrated that both CC-4a and CC-4b were crystalline.

Example 5: Preparation of the Co-Crystal of VX-745 and Gentisic Acid (CC-5)

A solution of 100.0 mg of VX-745 (0.229 mmol) and 35.3 mg of gentisic acid (0.229 mmol) in 6 mL of acetonitrile was placed in a vial. The opening was covered with aluminium foil having 3 pinholes and the sample was left at ambient temperature overnight, during which time the solvent evaporated to give VX-745/gentisic acid cocrystal. The material was characterized and the results as follows.

The $^1$H NMR of CC-5 is consistent with the structure of CC-5 having 1:1 ratio of VX-745 to coformer. The DSC thermogram shows endothermic events at 135.9 and 150.8° C. The endothermic event observed by DSC at 135.9° C. is likely melting. The TG results show 1.95% weight loss below 150° C., corresponding to 0.48 moles of water or 0.21 moles of acetonitrile. The DVS discloses a 0.36% loss on drying to 5% relative humidity (RH), a 0.93% gain from 5 to 95% RH, and a 1.57% loss from 95 to 5% RH.

Example 6: Preparation of the Co-Crystal of VX-745 and Glutaric Acid (CC-6)

A solution of 100.0 mg of VX-745 (0.229 mmol) and 30.4 mg of glutaric acid (0.230 mmol) in 6 mL of acetonitrile was placed in a vial. The opening was covered with aluminum foil having 3 pinholes and the sample was left at ambient temperature overnight, during which time the solvent evaporated to give VX-745/glutaric acid cocrystal. The material was characterized and the results as follows.

The $^1$H NMR of CC-6 is consistent with the structure of CC-6 having 1:1 ratio of VX-745 to coformer. The DSC thermogram shows endothermic events at 94.8 and 161.7° C. The endothermic event observed by DSC at 94.8° C. is likely melting. The TG results show 0.06% weight loss up to 90° C., and a 20.06% loss from 90 to 195° C. The DVS discloses a 0.001% loss on drying to 5% relative humidity (RH), a 10.16% gain from 5 to 95% RH, and a 10.19% loss from 95 to 5% RH.

Example 7: Preparation of the Co-Crystal of VX-745 and 1-Hydroxy-2-Naphthoic Acid (CC-7)

The co-crystal of VX-745 and 1-hydroxy-2-naphthoic acid (CC-7) was prepared by multiple methods. The co-crystal of VX-745 and 1-hydroxy-2-naphthoic acid, i.e., CC-7a, was prepared according to Stoichiometric Slow Evaporation protocol, using acetonitrile as a solvent. The co-crystal of VX-745 and 1-hydroxy-2-napthoic acid, i.e., CC-7b, was prepared according to the Stoichiometric Slurry protocol, using 2:1 acetonitrile:hexane as the solvent. Characterization of the resulting material demonstrated that the CC-7 was crystalline.

Example 8: Preparation of the Co-Crystal of VX-745 and Ketoglutaric Acid (CC-8)

The co-crystal of VX-745 and ketoglutaric acid, i.e., CC-8, was prepared according to the Stoichiometric Slurry protocol, using 2:1 acetonitrile:hexane as the solvent. Characterization of the resulting material demonstrated that the CC-8 was crystalline.

Example 9: Preparation of the Co-Crystal of VX-745 and Malonic Acid (CC-9)

The co-crystal of VX-745 and malonic acid, i.e., CC-9, was prepared according to the Stoichiometric Slurry protocol, using 2:1 acetonitrile:hexane as the solvent. Characterization of the resulting material demonstrated that the CC-9 was crystalline.

Example 10: Preparation of the Co-Crystal of VX-745 and Nicotinic Acid (CC-10)

The co-crystal of VX-745 and nicotinic acid, i.e., CC-10, was prepared according to the Stoichiometric Slow Evaporation protocol, using methanol as the solvent. Characterization of the resulting material demonstrated that the CC-10 was crystalline.

Example 11: Preparation of the Co-Crystal of VX-745 and Phenol (CC-11)

The co-crystal of VX-745 and phenol (CC-11) was prepared by multiple methods. The co-crystal of VX-745 and phenol, i.e., CC-11a, was prepared according to the Stoichiometric Slow Evaporation protocol, using acetone as a solvent. The co-crystal of VX-745 and phenol, i.e., CC-11b, was prepared according to the Stoichiometric Slurry protocol, using 2:1 acetone:hexane as the solvent. Characterization of the resulting material demonstrated that the CC-11 was crystalline.

Example 12: Preparation of the Co-Crystal of VX-745 and L-Proline (CC-12)

The co-crystal of VX-745 and L-proline, i.e., CC-12, was prepared according to the Stoichiometric Slow Evaporation protocol, using methanol as the solvent. Characterization of the resulting material demonstrated that the CC-12 was crystalline.

Example 13: Preparation of the Co-Crystal of VX-745 and Salicylic Acid (CC-13)

The co-crystal of VX-745 and salicylic acid, i.e., CC-13, was prepared according to the Stoichiometric Slurry protocol, using 2:1 acetone:hexane as the solvent. Characterization of the resulting material demonstrated that the CC-13 was crystalline.

Example 14: Preparation of the Co-Crystal of VX-745 and Sorbic Acid (CC-14)

The co-crystal of VX-745 and sorbic acid, i.e., CC-14, was prepared according to the Stoichiometric Slow Evaporation protocol, using acetone as the solvent. Characterization of the resulting material demonstrated that the CC-14 was crystalline.

Example 15: Preparation of the Co-Crystal of VX-745 and Thiamine Hydrochloride (CC-15)

The co-crystal of VX-745 and thiamine hydrochloride, i.e., CC-15, was prepared according to the Stoichiometric Slow Evaporation protocol, using methanol as the solvent. Characterization of the resulting material demonstrated that the CC-15 was crystalline.

Example 16: Preparation of the Co-Crystal of VX-745 and L-Threonine (CC-16)

The co-crystal of VX-745 and L-threonine, i.e., CC-16, was prepared according to the Stoichiometric Slow Evaporation protocol, methanol as the solvent. Characterization of the resulting material demonstrated that the CC-16 was crystalline.

Example 17: Preparation of the Co-Crystal of VX-745 and Urea (CC-17)

The co-crystal of VX-745 and urea, i.e., CC-17, was prepared according to the Stoichiometric Slow Evaporation protocol, using 2:1 methanol:heptane as the solvent. Characterization of the resulting material demonstrated that the CC-17 was crystalline.

Example 18: Preparation of the Co-Crystal of VX-745 and Zinc Chloride (CC-18)

A mixture of 100.0 mg of VX-745 (0:229 mmol) and 31.2 mg of zinc chloride (0.229 mmol) was placed in a PEEK grinding cup with 20 μL of acetone and a steel ball. The sample was placed on a Retsch mill and milled at 100% power for 20 minutes to give VX-745/zinc chloride co-crystal. The material was characterized and the results as follows.

The $^1$H NMR of CC-18 is consistent with the structure of CC-18 having 1:1 ratio of VX-745 to coformer. The DSC analysis shows endothermic events at 84.46, 155.72, and 188.83° C. The endothermic event observed by DSC at 188.83° C. is likely melting. The TG results show 1.11% weight loss up to 50° C., corresponding to 0.62 moles of water or 0.19 moles of acetonitrile, and a 2.50% loss from 50 to 125° C. The DVS discloses a 0.27% loss on drying to 5% relative humidity (RH), a 11.30% gain from 5 to 95% RH, and a 11.32% loss from 95 to 5% RH.

Example 19: Solubility of VX-745

Solubilities of VX-745 in several solvents were estimated. The experiments were carried out by adding test solvents in aliquots to weighed portions of solid. Whether dissolution had occurred was judged by visual inspection after addition of each solvent aliquot. The results are shown in Table 2. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot.

TABLE 2

Solubilities of VX-745 in various solvents

| Solvent | Sample Weight (mg) | Solvent Amount (mL) | Solubility (mg/mL) |
|---|---|---|---|
| acetone | 2.9 | 0.4 | 7 |
| acetonitrile | 2.6 | 0.3 | 9 |
| ethyl acetate | 2.5 | 3 | <1 |
| ethanol | 2.7 | 1.8 | 2 |
| isopropyl alcohol | 3.2 | 2.5 | 1 |
| methanol | 3.1 | 0.3 | 10 |
| tetrahydrofuran (THF) | 2.2 | 0.5 | 4 |
| water | 2.6 | 3 | <1 |

Example 20: Dissolution Results of VX-745

Dissolution studies were carried out for VX-745 at ambient temperature using water, as described by the HPLC Analysis protocol described above. Results are presented in Table 3, below. Upon the completion of each experiment, the remaining solid was recovered and analyzed by XRPD.

TABLE 3

Solubilities of VX-745

| Time | Solubility (μg/mL) |
|---|---|
| 2 mins | 11.32 |
| 5 mins | 15.67 |
| 10 mins | 14.94 |
| 15 mins | 17.80 |
| 25 mins | 15.52 |
| 40 mins | 10.67 |
| 1 hr | 6.59 |
| 2 hrs | 5.67 |
| 3 hrs | 6.32 |
| 4 hrs | 11.32 |

Example 21: Dissolution Results of the Co-Crystal of VX-745 and Gentisic Acid (CC-5)

Dissolution studies were carried out for the CC-5 at ambient temperature using water, as described by the HPLC Analysis protocol described above. Results are presented in Table 4, below. Upon the completion of each experiment, the remaining solid was recovered and analyzed by XRPD.

TABLE 4

Solubilities of CC-5

| Time | Solubility μg/mL |
|---|---|
| 2 mins | 47.09 |
| 5 mins | 86.61 |
| 10 mins | 107.83 |
| 15 mins | 117.98 |
| 25 mins | 102.96 |
| 40 mins | 92.44 |
| 1 hr | 79.30 |
| 2 hrs | 69.93 |
| 3 hrs | 58.93 |
| 4 hrs | 57.38 |

Example 22: Dissolution Results of the Co-Crystal of VX-745 and Glutaric Acid (CC-6)

Dissolution studies were carried out for the CC-6 at ambient temperature using water, as described by the HPLC Analysis protocol described above. Results are presented in Table 5, below. Upon the completion of each experiment, the remaining solid was recovered and analyzed by XRPD.

TABLE 5

| | Solubilities of CC-6 |
|---|---|
| Time | Solubility µg/mL |
| 2 mins | 23.78 |
| 5 mins | 39.17 |
| 10 mins | 51.39 |
| 15 mins | 67.49 |
| 25 mins | 68.93 |
| 40 mins | 65.28 |
| 1 hr | 59.85 |
| 2 hrs | 54.11 |
| 3 hrs | 50.75 |
| 4 hrs | 57.07 |

Example 23: Dissolution Results of the Co-Crystal of VX-745 and Phenol (CC-11)

Dissolution studies were carried out for the CC-11 at ambient temperature using water, as described by the HPLC Analysis protocol described above. Results are presented in Table 6, below. Upon the completion of each experiment, the remaining solid was recovered and analyzed by XRPD.

TABLE 6

| | Solubilities of CC-11 |
|---|---|
| Time | Solubility µg/mL |
| 2 mins | 10.19 |
| 5 mins | 57.50 |
| 10 mins | 43.26 |
| 15 mins | 36.28 |
| 25 mins | 35.33 |
| 40 mins | 21.33 |
| 1 hr | 15.09 |
| 2 hrs | 17.11 |
| 3 hrs | 12.30 |
| 4 hrs | 13.98 |

Example 24: Additional Examples of Co-Crystals of VX-745

Summary

VX-745 (its structure as shown below) is poorly water soluble and does not contain readily ionizable functional groups that allow salt formation.

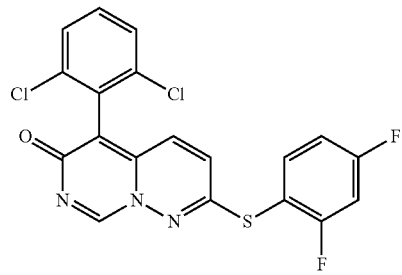

A cocrystal screen identified eighteen potential cocrystals. Three cocrystals were made at larger scales and characterized. Those are the gentisic acid, glutaric acid, and zinc chloride cocrystals. Dissolution testing of VX-745 cocrystals were carried out to estimate the level of supersaturation that can be obtained and the time supersaturation can be maintained. For example, dissolution experiments were carried out using VX-745 and the VX-745 gentisic acid, glutaric acid, and zinc chloride cocrystals. The first dissolution medium tested was fasted state simulated intestinal fluid (FaSSIF) at ambient temperature. The VX-745 gentisic acid and glutaric acid cocrystals remained unchanged after 24 hours. The X-ray powder diffraction (XRPD) pattern of the remaining solids from the VX-745 zinc chloride cocrystal was unique. The second dissolution medium tested was fed state simulated intestinal fluid (FeSSIF) at ambient temperature. The VX-745 gentisic acid and glutaric acid cocrystals remained unchanged after 24 hours. The XRPD pattern of the remaining solids from the VX-745 zinc chloride cocrystal was unique.

The dissolutions results are summarized in Table 7 below.

TABLE 7

| | Characteristics of VX-745 and co-crystals thereof | | | | | |
|---|---|---|---|---|---|---|
| | medium: FaSSIF | | | medium: FeSSIF | | |
| cocrystal | peak solubility (µg/mL) | ending solubility (µg/mL) | XRPD pattern of solids | peak solubility (µg/mL) | ending solubility (µg/mL) | XRPD pattern of solids |
| free API | 17.78 | 9.07 | unchanged | 21.35 | 14.01 | unchanged |
| gentisic acid | 91.52 | 20.16 | unchanged | 34.40 | 5.55 | unchanged |
| glutaric acid | 3.75 | 1.59 | unchanged | 1.87 | 2.38 | unchanged |
| zinc chloride | 34.49 | 22.57 | unique | 88.50 | 34.18 | unique |

Results and Discussion

Characterization of Starting Material

A sample of VX-745 was characterized by x-ray powder diffraction (XRPD). The results are summarized in Table 8.

TABLE 8

Analyses of Samples Received

| | |
|---|---|
| Lot No. | 13L145 |
| Triclinic No. | TCL1670 |
| XRPD Filename | RX5240 |
| XRPD Page No. | 16 |
| XRPD Result | crystalline, API A |

Figure 10:
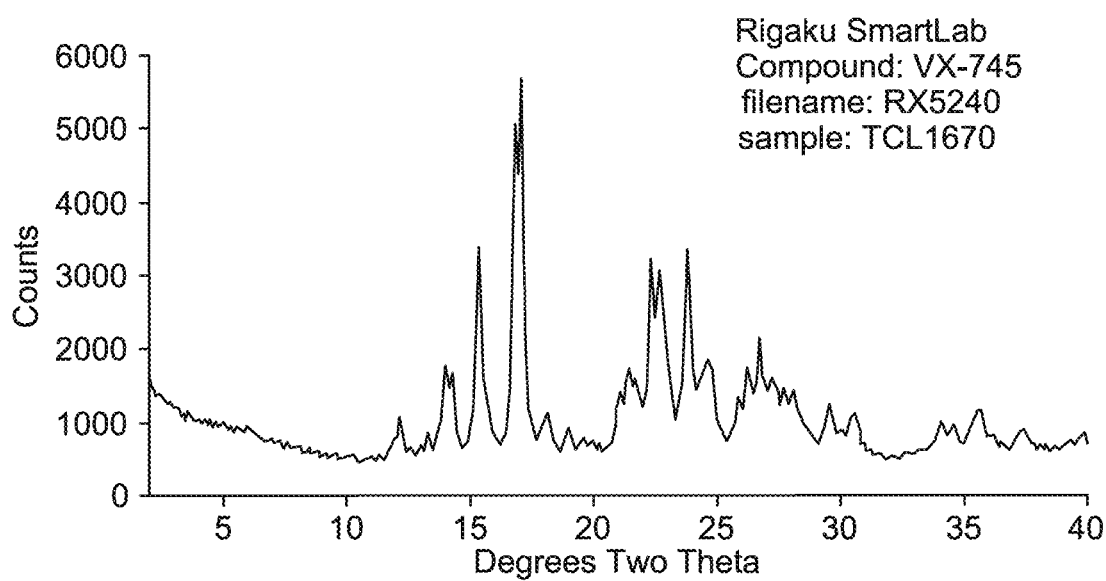
FIG. 10 shows the XRPD result of free VX-745.
Figure 11:
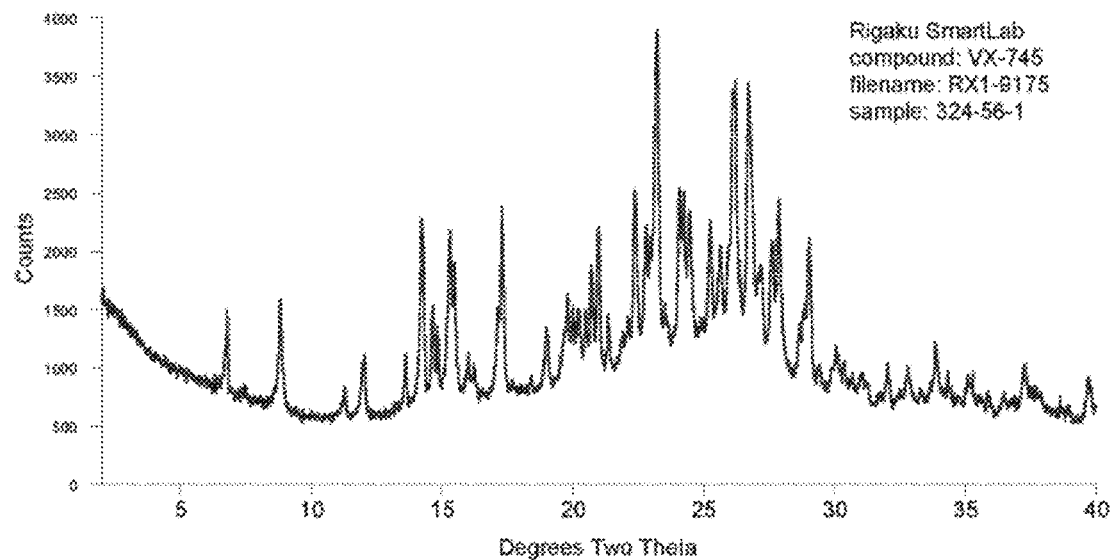
FIGS. 11-14 show XRPD results of cocrystals comprising VX-745 and gentisic acid.
Figure 12:
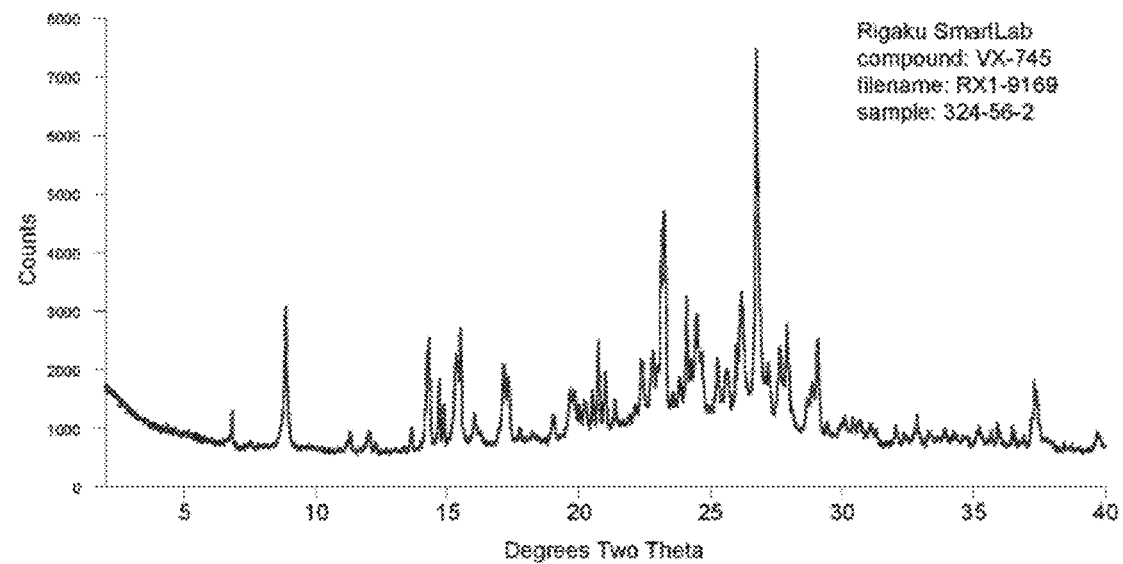
Figure 13:
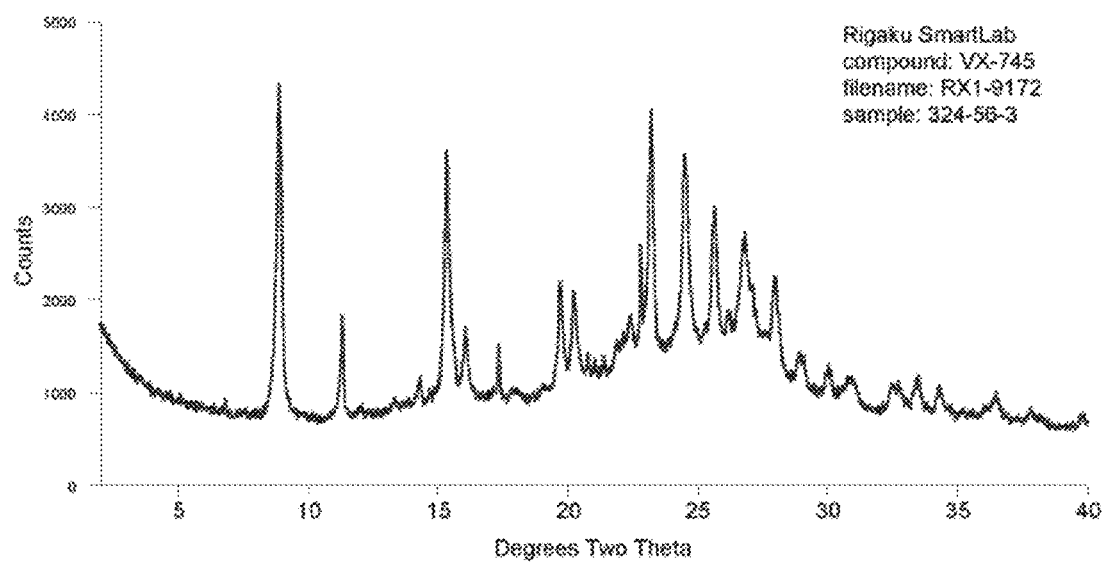
Figure 14:
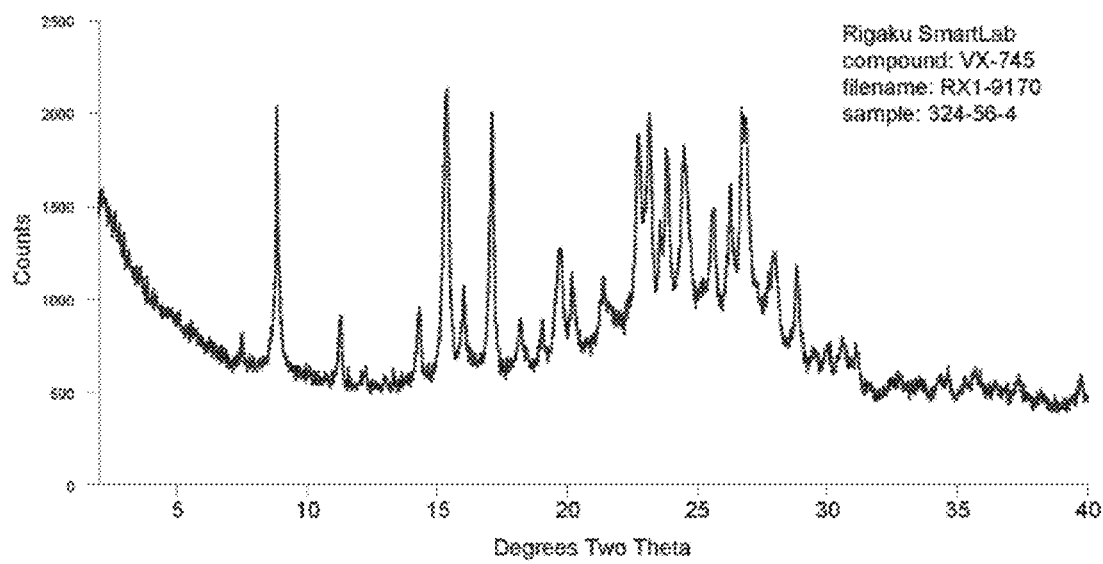
Figure 15:
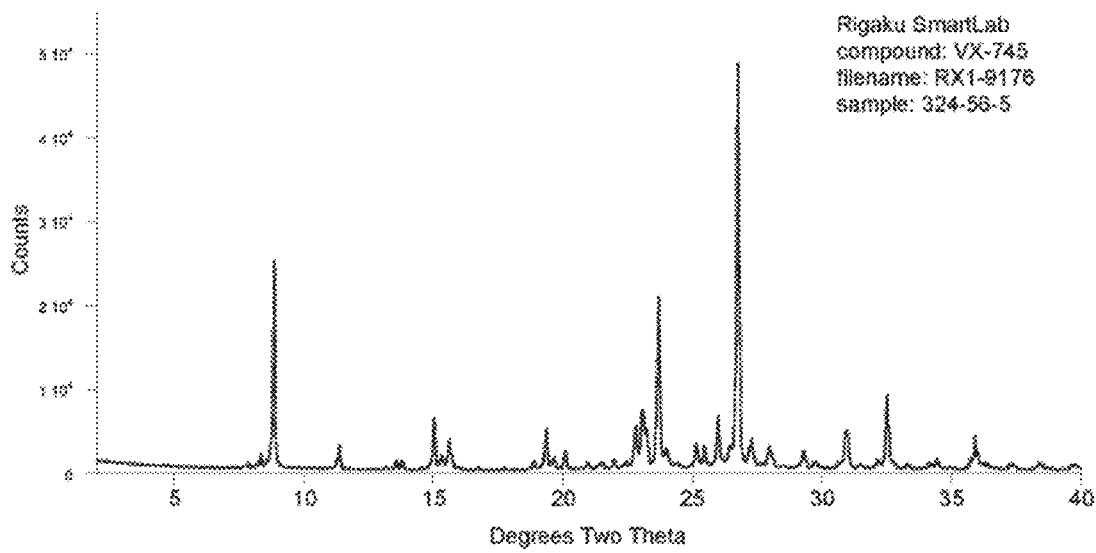
FIGS. 15-18 show XRPD results of cocrystals comprising VX-745 and glutaric acid.
Figure 16:
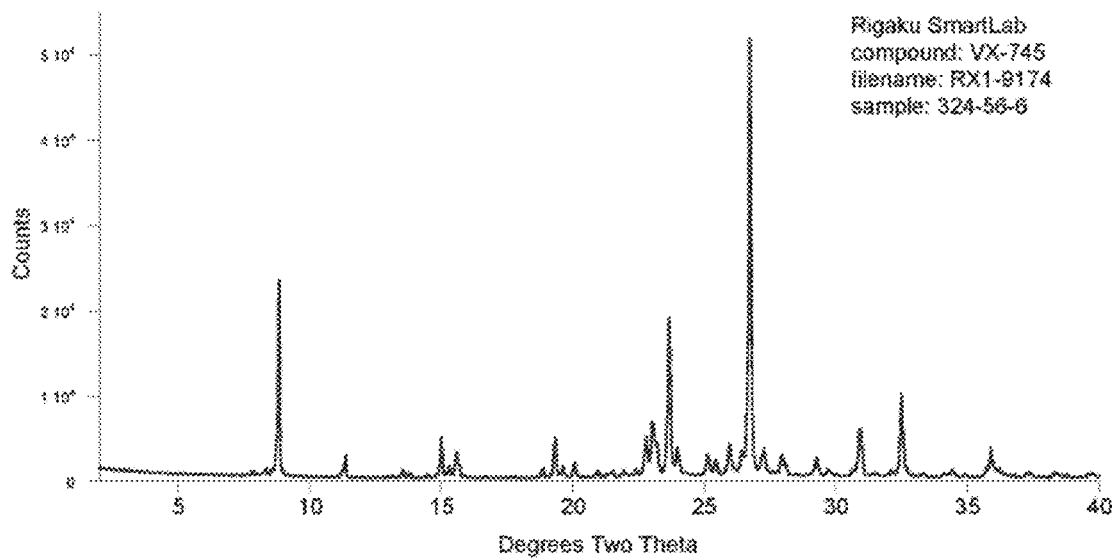
Figure 17:
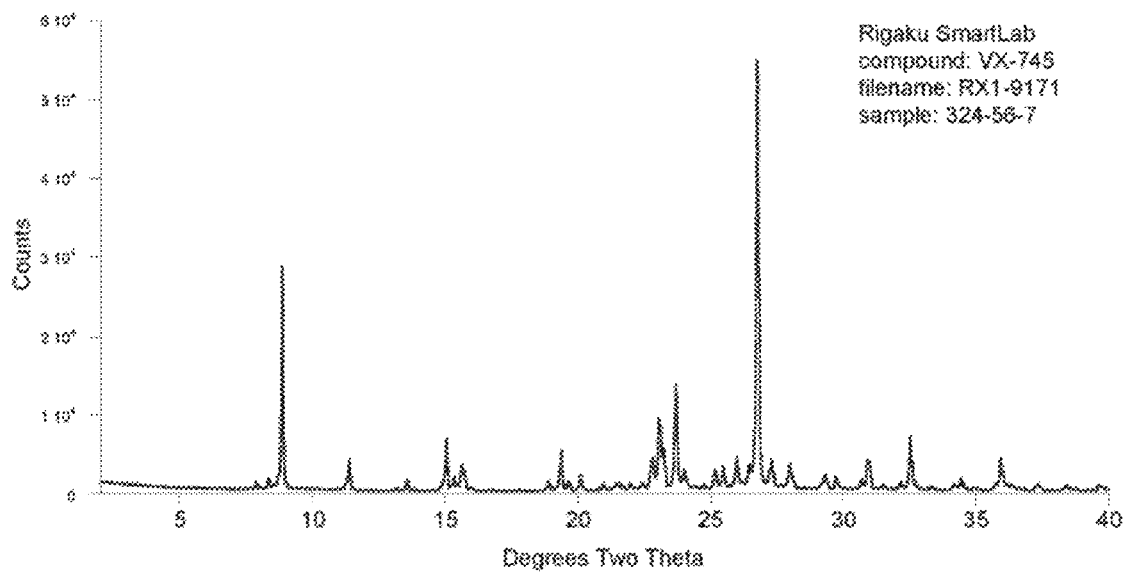
Figure 18:
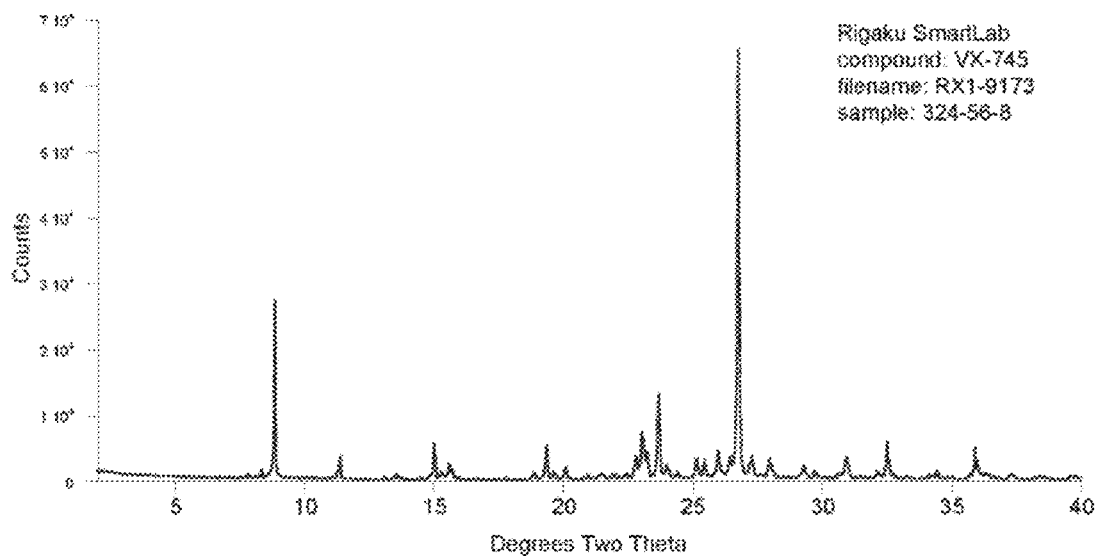
Figure 19:
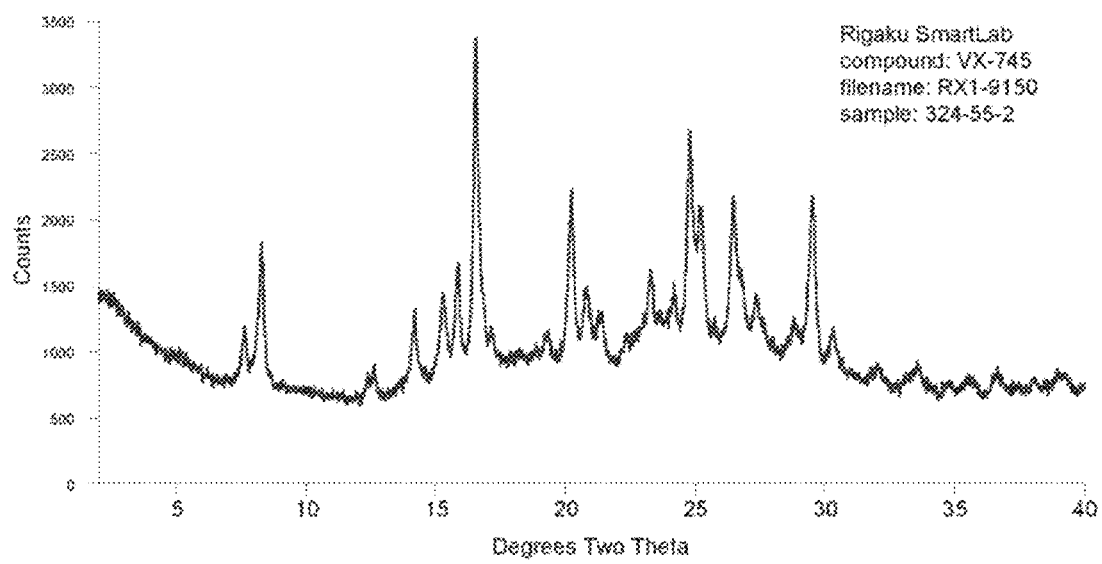
FIGS. 19-22 show XRPD results of cocrystals comprising VX-745 and zinc chloride.
Figure 20:
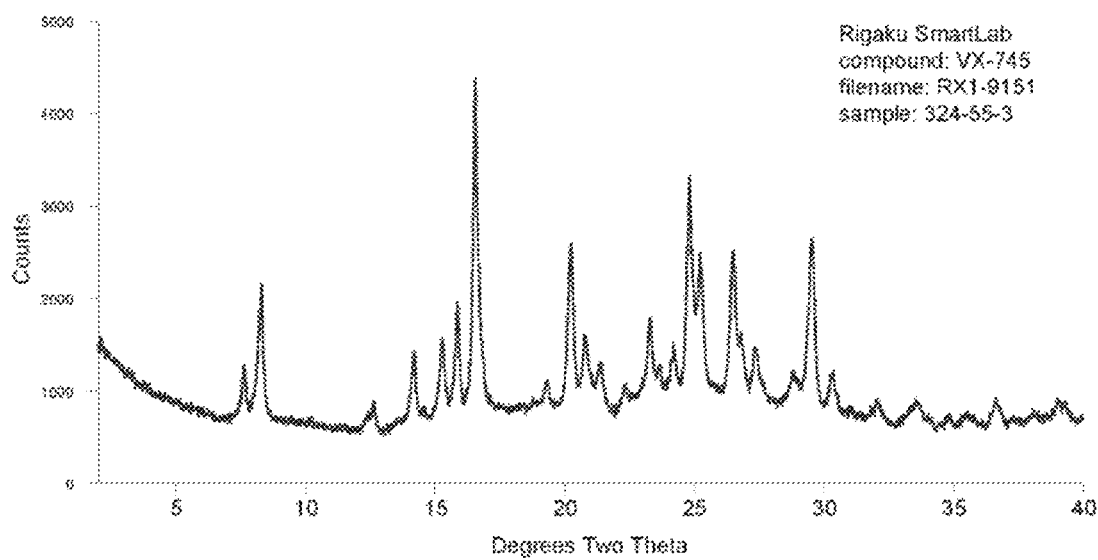
Figure 21:
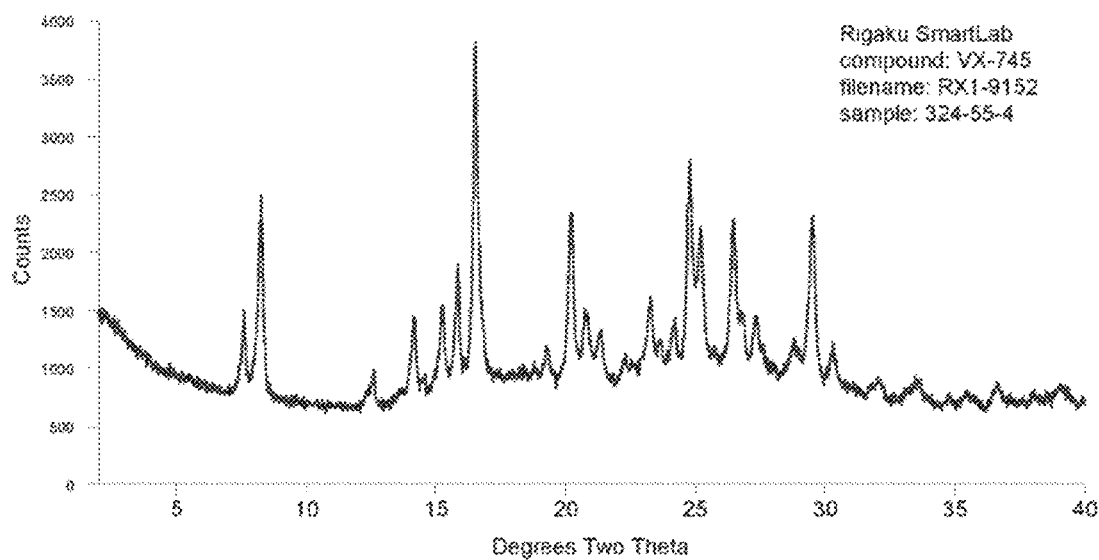
Figure 22:
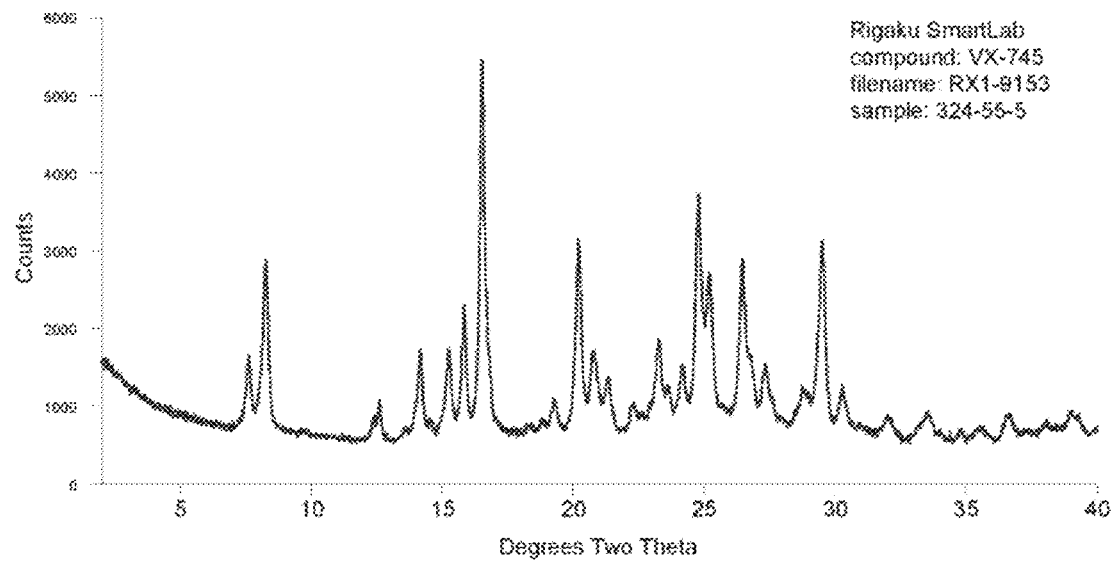

The XRPD result is shown in FIG. 10.

Preparation of Cocrystals

Three cocrystals were prepared in large enough quantities to be used in dissolution studies (Table 9).

TABLE 9

Samples Generated and Analyzed

| Guest (API: guest) | Method | Solvent | Sample No. | XRPD Filename | XRPD Page No. | XRPD Pattern [a] |
|---|---|---|---|---|---|---|
| gentisic acid (1:1) | stoichiometric slow evaporation | acetonitrile | 324-56-1 | RX1-9175 | 16 | gentisic acid cocrystal A |
| | | | 324-56-2 | RX1-9169 | 17 | gentisic acid cocrystal A |
| | | | 324-56-3 | RX1-9172 | 17 | API F + gentisic acid + peaks |
| | | | 324-56-4 | RX1-9170 | 18 | API F + gentisic acid + peaks |
| glutaric acid (1:1) | stoichiometric slow evaporation | acetonitrile | 324-56-5 | RX1-9176 | 18 | glutaric acid cocrystal A |
| | | | 324-56-6 | RX1-9174 | 19 | glutaric acid cocrystal A |
| | | | 324-56-7 | RX1-9171 | 19 | glutaric acid cocrystal A |
| | | | 324-56-8 | RX1-9173 | 20 | glutaric acid cocrystal A |
| zinc chloride (1:1) | stoichiometric milling | acetone | 324-55-2 | RX1-9150 | 20 | zinc chloride cocrystal A |
| | | | 324-55-3 | RX1-9151 | 21 | zinc chloride cocrystal A |
| | | | 324-55-4 | RX1-9152 | 21 | zinc chloride cocrystal A |
| | | | 324-55-5 | RX1-9153 | 22 | zinc chloride cocrystal A |

FIGS. 11-14 show XRPD results of cocrystals comprising VX-745 and gentisic acid. FIGS. 15-18 show XRPD results of cocrystals comprising VX-745 and glutaric acid. FIGS. 19-22 show XRPD results of cocrystals comprising VX-745 and zinc chloride.

Dissolution Studies in FaSSIF at Ambient Temperature

Dissolution studies were carried out for VX-745 and each cocrystal of VX-745 FaSSIF at ambient temperature. Upon the completion of each experiment, the remaining solid was recovered and analyzed by XRPD. The results are shown in Tables 10-13 and FIGS. 1-4.

TABLE 10

Dissolution Results for free VX-745 (sample TCL 1670)

| Time | Sample No. | HPLC Filename | Injection # | Concentration (µg/mL) |
|---|---|---|---|---|
| 2 mins | 324-66-1a | LC2-3739 | 24, 49 | 10.64 |
| 5 mins | 324-66-1b | | 25, 50 | 17.78 |
| 15 mins | 324-66-1d | | 27, 52 | 4.36 |

TABLE 10-continued

Dissolution Results for free VX-745 (sample TCL 1670)

| Time | Sample No. | HPLC Filename | Injection # | Concentration (µg/mL) |
|---|---|---|---|---|
| 25 mins | 324-66-1e | | 28, 53 | 5.38 |
| 40 mins | 324-66-1f | | 29, 54 | 5.48 |
| 1 hr | 324-66-1g | | 30, 55 | 9.83 |
| 2 hrs | 324-66-1h | | 31, 56 | 5.14 |
| 3 hrs | 324-66-1i | | 32, 57 | 5.81 |
| 4 hrs | 324-66-1j | | 33, 58 | 5.12 |
| 24 hrs | 324-66-1k | | 34, 59 | 9.07 |

XRPD of remaining solids: file RX1-9204, result: VX-745 polymorph A, page 22

Figure 23:
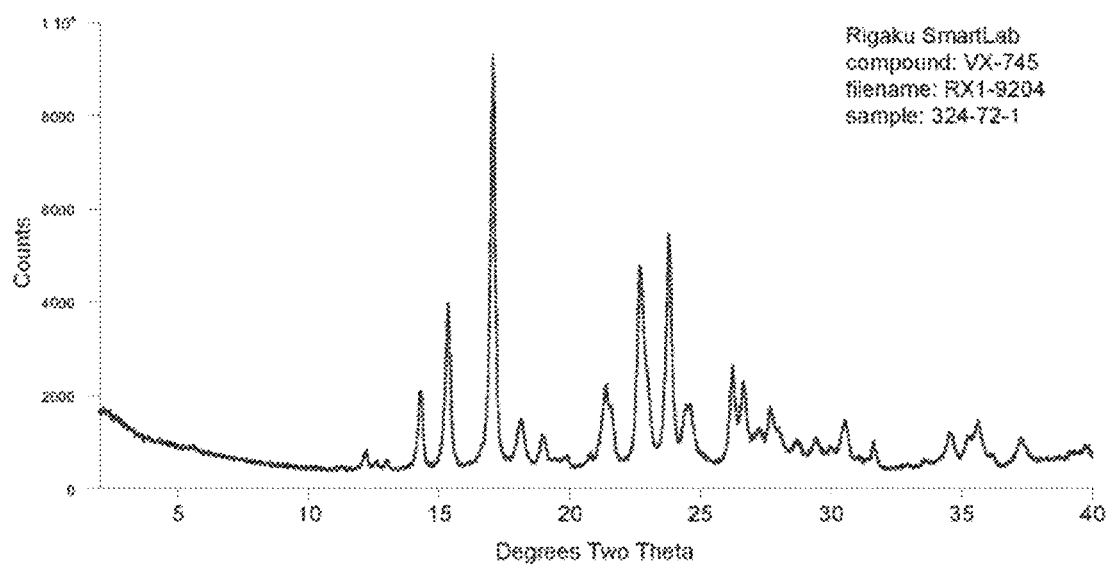
FIG. 23 shows XRPD result of free VX-745.

FIG. 23 shows XRPD result of free VX-745.

TABLE 11

Dissolution Results for VX-745 Gentisic Acid Cocrystal (sample 324-56-1)

| Time | Sample No. | HPLC File Name | Injection # | Concentration (µg/mL) |
|---|---|---|---|---|
| 2 mins | 324-69-1a | | 15, 67 | 46.85 |
| 5 mins | 324-69-1b | | 16, 68 | 65.49 |
| 10 mins | 324-69-1c | | 17, 69 | 75.42 |
| 15 mins | 324-69-1d | | 18, 70 | 74.21 |
| 25 mins | 324-69-1e | | 19, 71 | 79.78 |
| 40 mins | 324-69-1f | | 20, 72 | 61.18 |
| 1 hr | 324-69-1g | | 21, 73 | 88.59 |
| 2 hrs | 324-69-1h | | 22, 74 | 91.52 |
| 4 hrs | 324-69-1i | | 23, 75 | 85.14 |
| 6 hrs | 324-69-1j | | 24, 76 | 79.81 |
| 24 hrs | 324-69-1k | | 25, 77 | 20.16 |

XRPD of remaining solids: file RX1-9288, result: gentisic acid cocrystal + 31.7 pk (from residual NaCl), page 23

Figure 24:
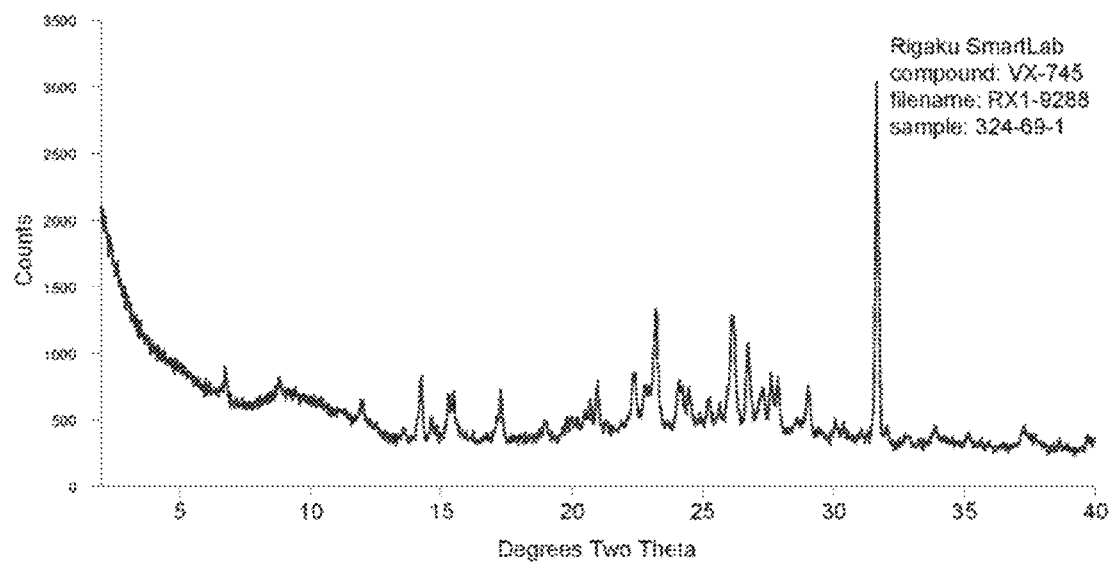
FIG. 24 shows XRPD result of a co-crystal comprising VX-745 and gentisic acid.

FIG. 24 shows XRPD result of a co-crystal comprising VX-745 and gentisic acid.

TABLE 12

Dissolution Results for VX-745 Glutaric Acid Cocrystal (sample 324-56-5)

| Time | Sample No. | HPLC File Name | Injection # | Concentration (µg/mL) |
|---|---|---|---|---|
| 2 mins | 324-82-1a | | 26, 78 | 1.59 |
| 5 mins | 324-82-1b | | 27, 79 | 1.88 |
| 10 mins | 324-82-1c | | 28, 80 | 2.10 |
| 15 mins | 324-82-1d | | 29, 81 | 2.36 |
| 25 mins | 324-82-1e | | 30, 82 | 2.50 |
| 40 mins | 324-82-1f | | 31, 83 | 3.06 |
| 1 hr | 324-82-1g | | 32, 84 | 3.75 |
| 2 hrs | 324-82-1h | | | |
| 4 hrs | 324-82-1i | | | |
| 6 hrs | 324-82-1j | | | |
| 24 hrs | 324-82-1k | | | |

XRPD of remaining solids: file RX1-9292, result: glutaric acid cocrystal + 31.7 pk (from residual NaCl), page 23

Figure 25:
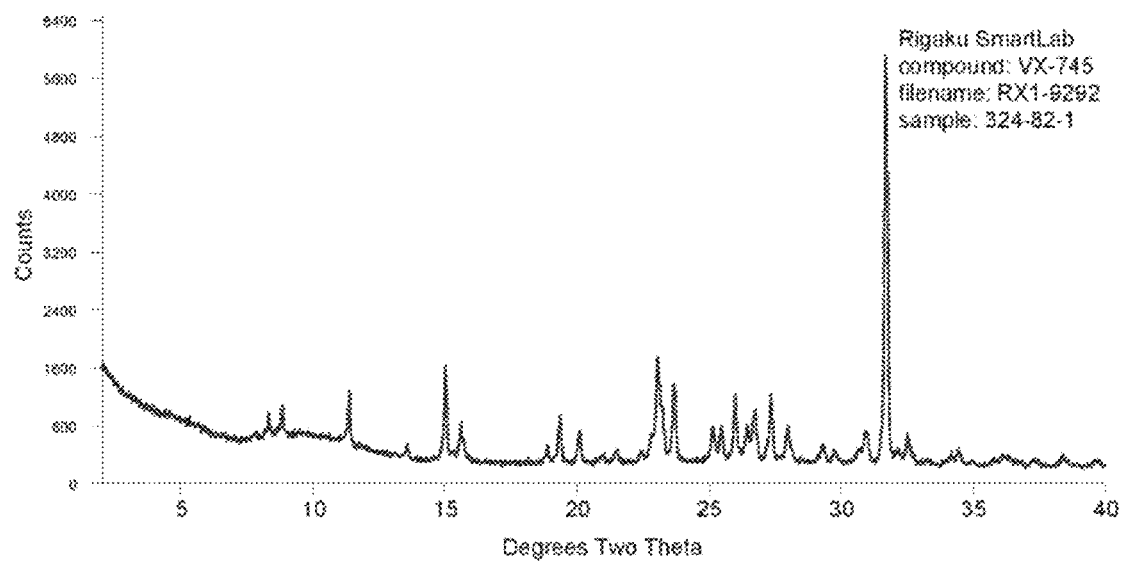
FIG. 25 shows XRPD result of a co-crystal comprising VX-745 and glutaric acid.

FIG. 25 shows XRPD result of a co-crystal comprising VX-745 and glutaric acid.

TABLE 13

Dissolution Results for VX-745 Zinc Chloride Cocrystal (sample 324-55-2)

| Time | Sample No. | HPLC File Name | Injection # | Concentration (µg/mL) |
|---|---|---|---|---|
| 2 mins | 324-67-1a | LC2-3740 | 24, 38 | 33.40 |
| 5 mins | 324-67-1b | | 25, 39 | 34.49 |
| 10 mins | 324-67-1c | | 26, 40 | 33.84 |
| 15 mins | 324-67-1d | | 27, 41 | 29.32 |
| 25 mins | 324-67-1e | | 28, 42 | 28.16 |
| 40 mins | 324-67-1f | | 29, 43 | 25.87 |
| 1 hr | 324-67-1g | | 30, 44 | 24.26 |
| 2 hrs | 324-67-1h | | 31, 45 | 23.68 |
| 3 hrs | 324-67-1i | | 32, 46 | 23.63 |
| 4 hrs | 324-67-1j | | 33, 47 | 23.56 |
| 24 hrs | 324-67-1k | | 34, 48 | 22.57 |

XRPD of remaining solids: file RX1-9206, result: unique pattern, page 24

Figure 26:
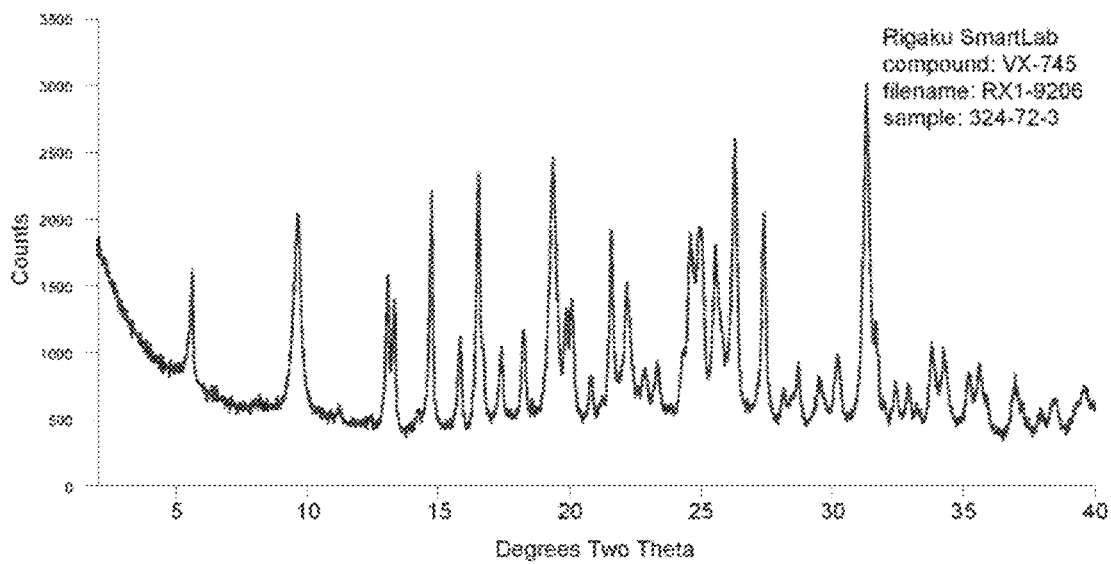
FIG. 26 shows XRPD result of a co-crystal comprising VX-745 and zinc chloride.

FIG. 26 shows XRPD result of a co-crystal comprising VX-745 and zinc chloride.

Dissolution Studies in FeSSIF at Ambient Temperature

Dissolution studies were carried out for VX-745 and each cocrystal of VX-745 FeSSIF at ambient temperature. Upon the completion of each experiment, the remaining solid was recovered and analyzed by XRPD. The results are shown in Tables 14-17 and FIGS. 5-8.

TABLE 14

Dissolution Results for VX-745 (sample TCL 1670)

| Time | Sample No. | HPLC File Name | Injection # | Concentration (µg/mL) |
|---|---|---|---|---|
| 2 mins | 288-2-1a | LC2-3739 | 35, 60 | 9.62 |
| 5 mins | 288-2-1b | | 36, 61 | 12.26 |
| 10 mins | 288-2-1c | | 38, 62 | 11.36 |
| 15 mins | 288-2-1d | | 39, 63 | 13.58 |
| 25 mins | 288-2-1e | | 40, 64 | 13.93 |
| 40 mins | 288-2-1f | | 41, 65 | 13.13 |
| 1 hr | 288-2-1g | | 42, 66 | 11.89 |
| 2 hrs | 288-2-1h | | 43, 67 | 18.64 |
| 3 hrs | 288-2-1i | | 44, 68 | 21.35 |

TABLE 14-continued

Dissolution Results for VX-745 (sample TCL 1670)

| Time | Sample No. | HPLC File Name | Injection # | Concentration (µg/mL) |
|---|---|---|---|---|
| 4 hrs | 288-2-1j | | 45, 69 | 15.36 |
| 24 hrs | 288-2-1k | | 46, 70 | 14.01 |

XRPD of remaining solids: file RX1-9205, result: VX-745 polymorph A, page 24

Figure 27:
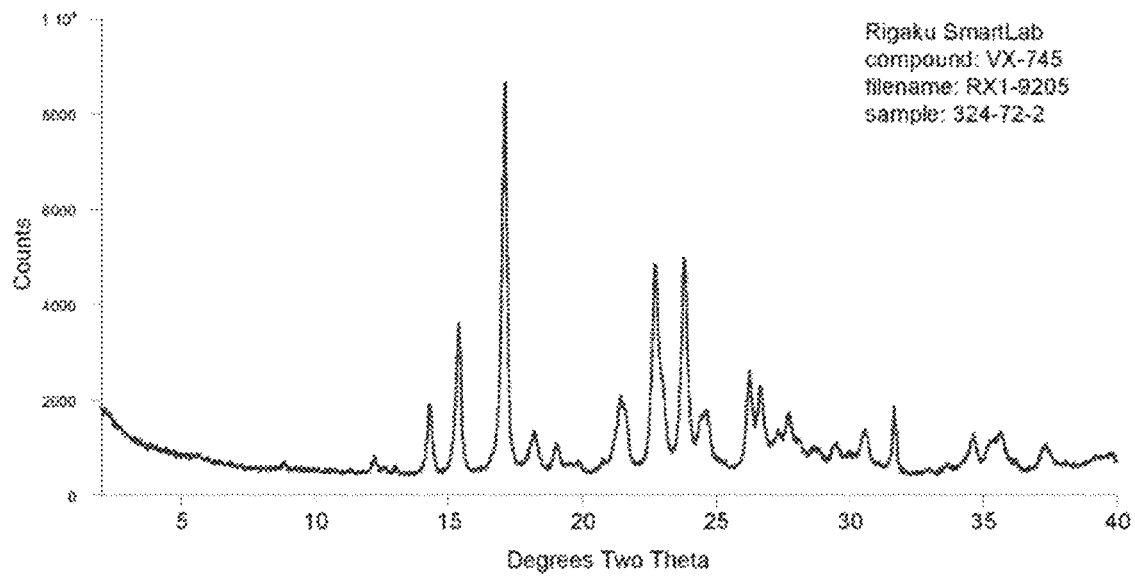
FIG. 27 shows XRPD result of free VX-745

FIG. 27 shows XRPD result of free VX-745

TABLE 15

Dissolution Results for VX-745 Gentisic Acid Cocrystal (sample 324-56-2)

| Time | Sample No. | HPLC File Name | Injection # | Concentration (µg/mL) |
|---|---|---|---|---|
| 2 mins | 324-69-2a | LC2-3741 | 33, 85 | 6.98 |
| 5 mins | 324-69-2b | | 34, 86 | 10.85 |
| 10 mins | 324-69-2c | | 35, 87 | 15.99 |
| 15 mins | 324-69-2d | | 36, 88 | 22.61 |
| 25 mins | 324-69-2e | | 37, 89 | 34.40 |
| 40 mins | 324-69-2f | | 38, 90 | 32.11 |
| 1 hr | 324-69-2g | | 39, 91 | 28.27 |
| 2 hrs | 324-69-2h | | 40, 92 | 13.65 |
| 4 hrs | 324-69-2i | | 41, 93 | 9.48 |
| 5 hrs | 324-69-2j | | 42, 94 | 6.38 |
| 24 hrs | 324-69-2k | | 43, 95 | 5.55 |

XRRD of remaining solids: file RX1-9289, result: gentisic acid cocrystal + 31.7 pk (from residual NaCl), page 25

Figure 28:
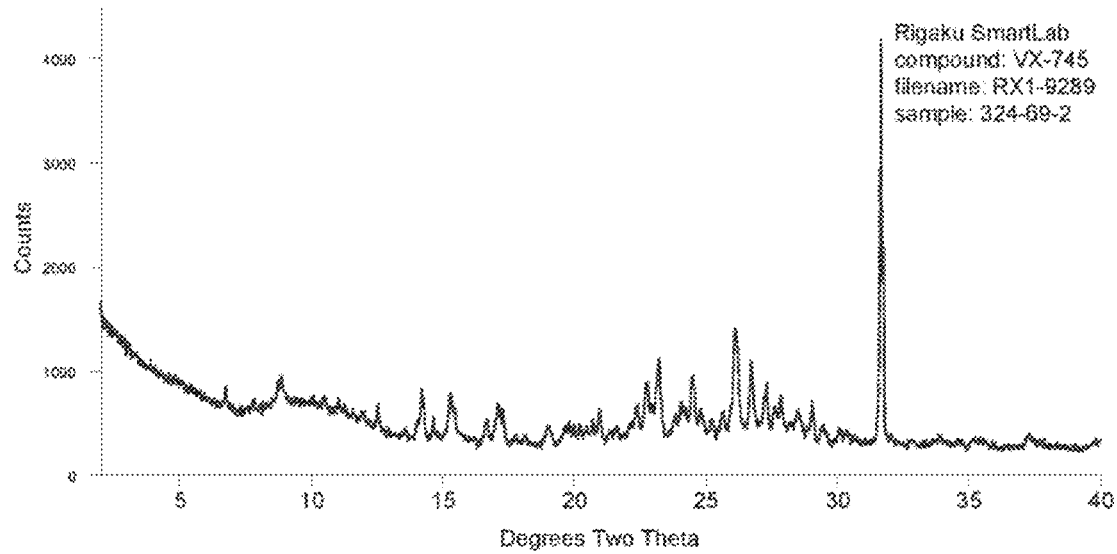
FIG. 28 shows XRPD result of a co-crystal comprising VX-745 and gentisic acid.

FIG. 28 shows XRPD result of a co-crystal comprising VX-745 and gentisic acid.

TABLE 16

Dissolution Results for VX-745 Glutaric Acid Cocrystal (sample 324-56-6)

| Time | Sample No. | HRLC File Name | Injection # | Concentration (µg/mL) |
|---|---|---|---|---|
| 2 mins | 324-82-2a | | 44, 96 | 1.31 |
| 3 mins | 324-82-2b | | 45, 97 | 1.28 |
| 10 mins | 324-82-2c | | 46, 98 | 1.87 |
| 15 mins | 324-82-2d | | 47, 99 | 1.74 |
| 25 mins | 324-82-2e | | 48, 100 | 1.71 |
| 40 mins | 324-82-2f | | 49, 101 | 1.87 |
| 1 hr | 324-82-2g | | 50, 102 | 2.38 |
| 2 hrs | 324-82-2h | | | |
| 4 hrs | 324-82-2i | | | |
| 6 hrs | 324-82-2j | | | |
| 24 hrs | 324-82-2k | | | |

XRPD of remaining solids: file RX1-9293, result: glutaric acid cocrystal + 31.7 pk (from residual NaCl), page 25

Figure 29:
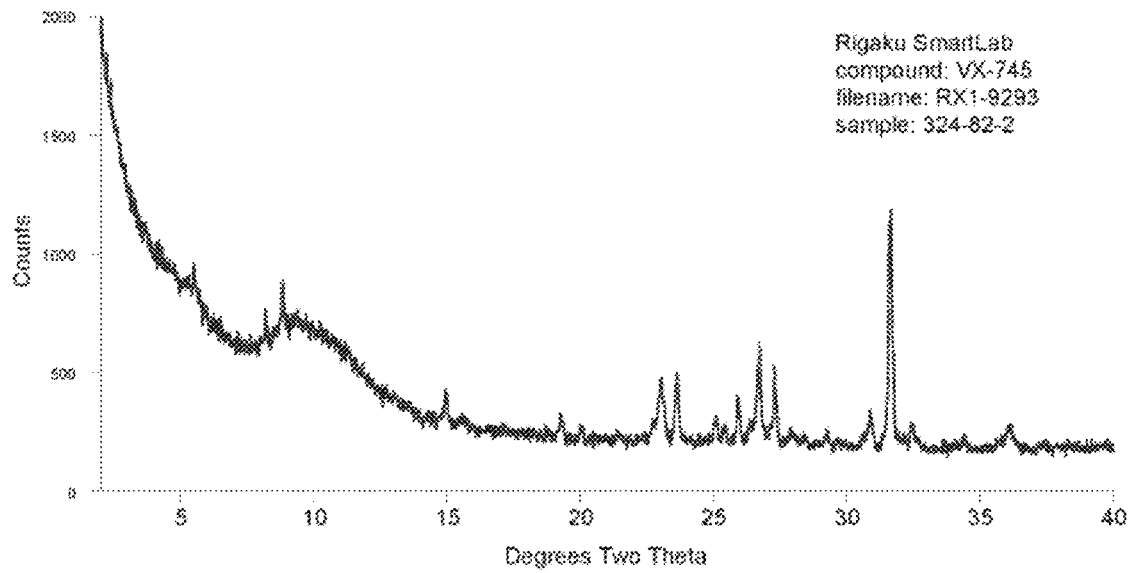
FIG. 29 shows XRPD result of a co-crystal comprising VX-745 and glutaric acid.

FIG. 29 shows XRPD result of a co-crystal comprising VX-745 and glutaric acid.

TABLE 17

Dissolution Results for VX-745 Zinc Chloride Cocrystal (sample 324-55-3)

| Time | Sample No. | HPLC File Name | Injection # | Concentration (µg/ml) |
|---|---|---|---|---|
| 2 mins | 324-67-2a | LC2-3741 | 51, 103 | 88.50 |
| 5 mins | 324-67-2b | | 52, 104 | 68.53 |
| 10 mins | 324-67-2c | | 53, 105 | 56.84 |
| 15 mins | 324-67-2d | | 54, 106 | 59.40 |
| 25 mins | 324-67-2e | | 55, 107 | 47.55 |
| 40 mins | 324-67-2f | | 56, 108 | 50.99 |
| 1 hr | 324-67-2g | | 57, 109 | 47.83 |

TABLE 17-continued

Dissolution Results for VX-745 Zinc
Chloride Cocrystal (sample 324-55-3)

| Time | Sample No. | HPLC File Name | Injection # | Concentration (µg/ml) |
|---|---|---|---|---|
| 2 hrs | 324-67-2h | | 56, 110 | 50.17 |
| 3 hrs | 324-67-2i | | 59, 111 | 47.34 |
| 4 hrs | 324-67-2j | | 60, 112 | 49.24 |
| 24 hrs | 324-67-2k | | 61, 113 | 34.18 |

XRPD of remaining solids: file RX1-9207, result: unique pattern, page 26

Figure 30:
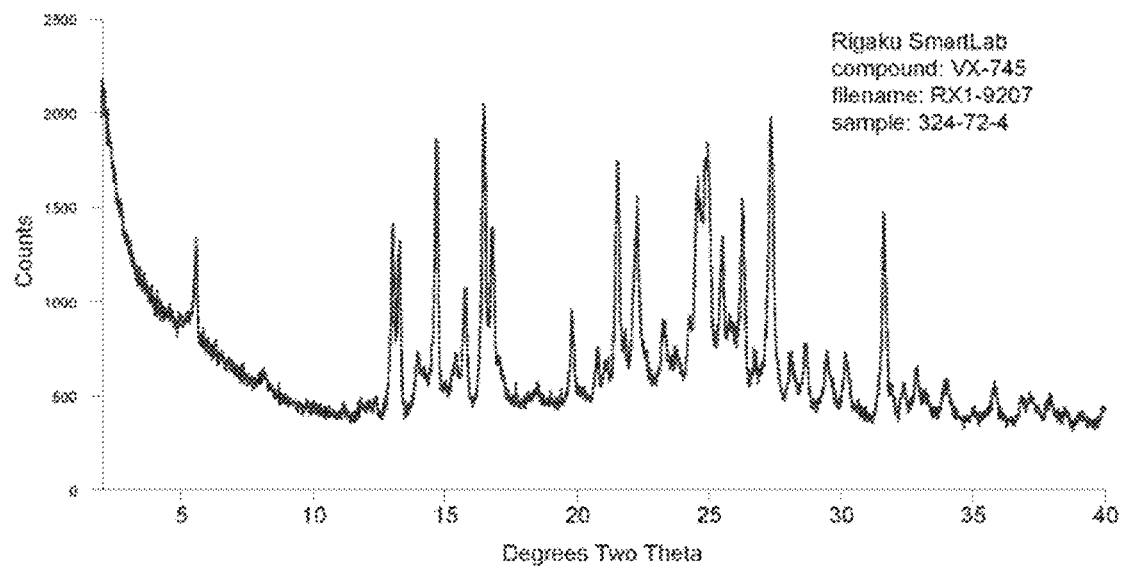
FIG. 30 shows XRPD result of a co-crystal comprising VX-745 and zinc chloride.
Figure 31:
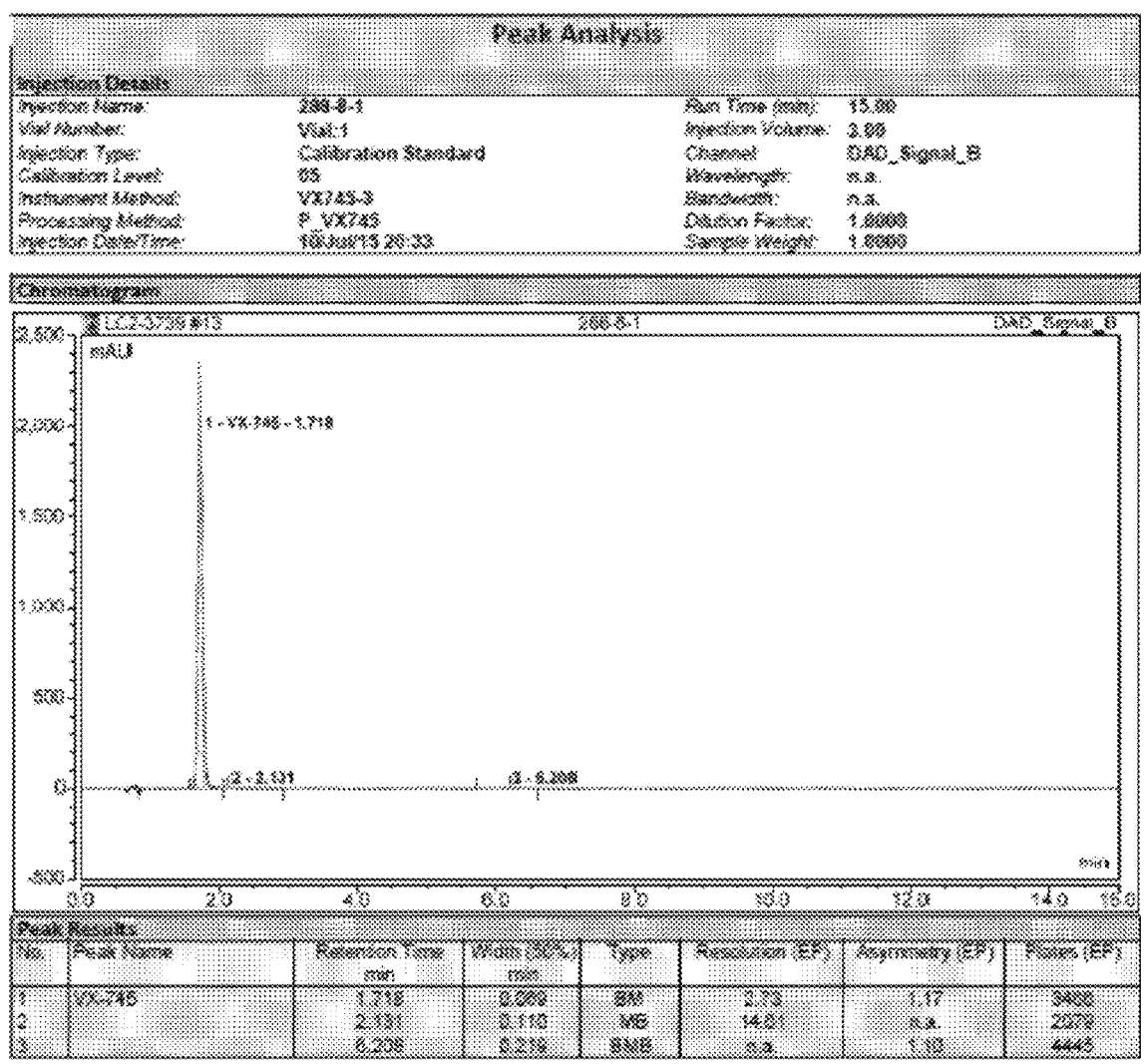
FIGS. 31-35 show HPLC results corresponding to VX-745 at different concentrations.
Figure 32:
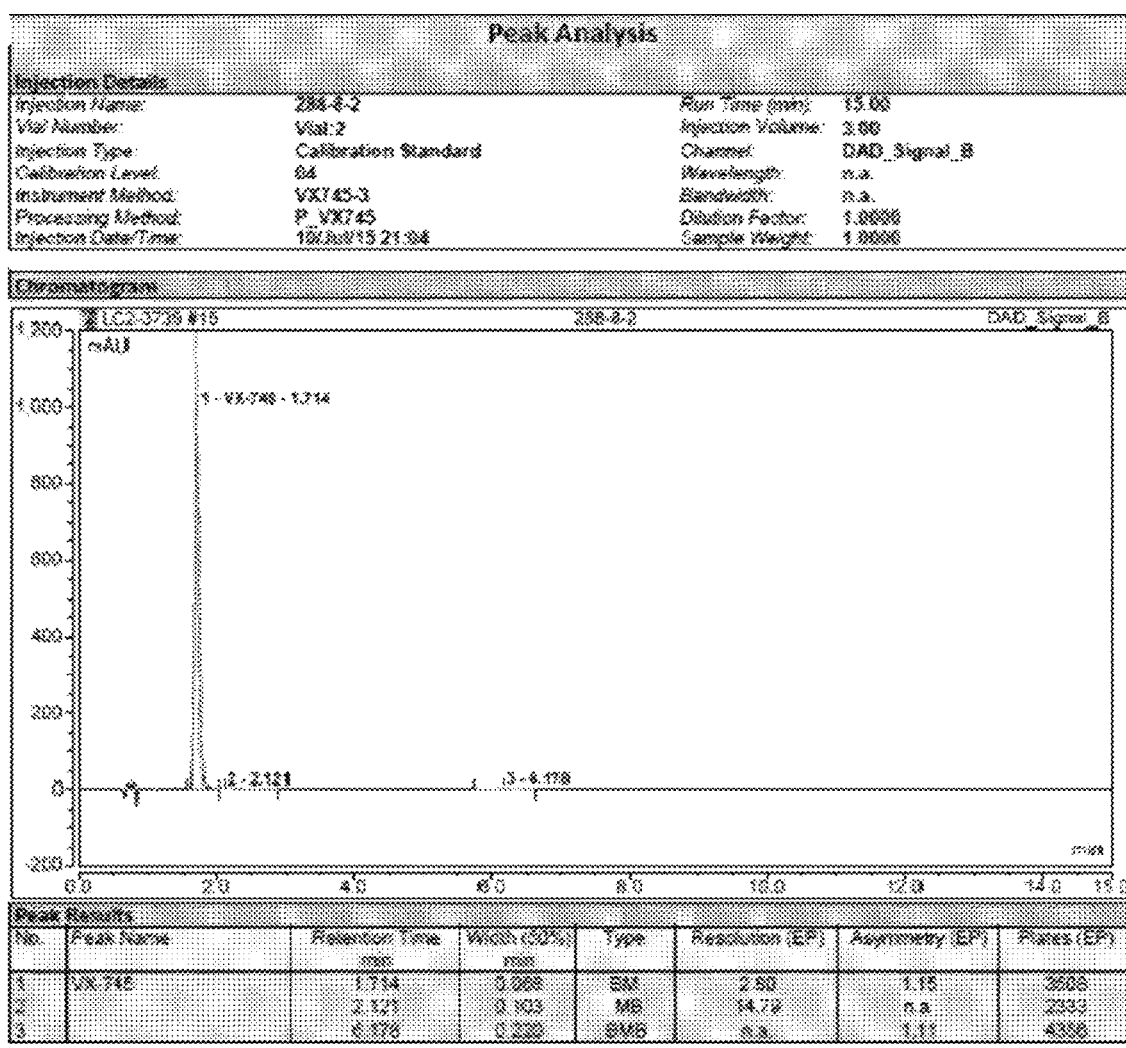
Figure 33:
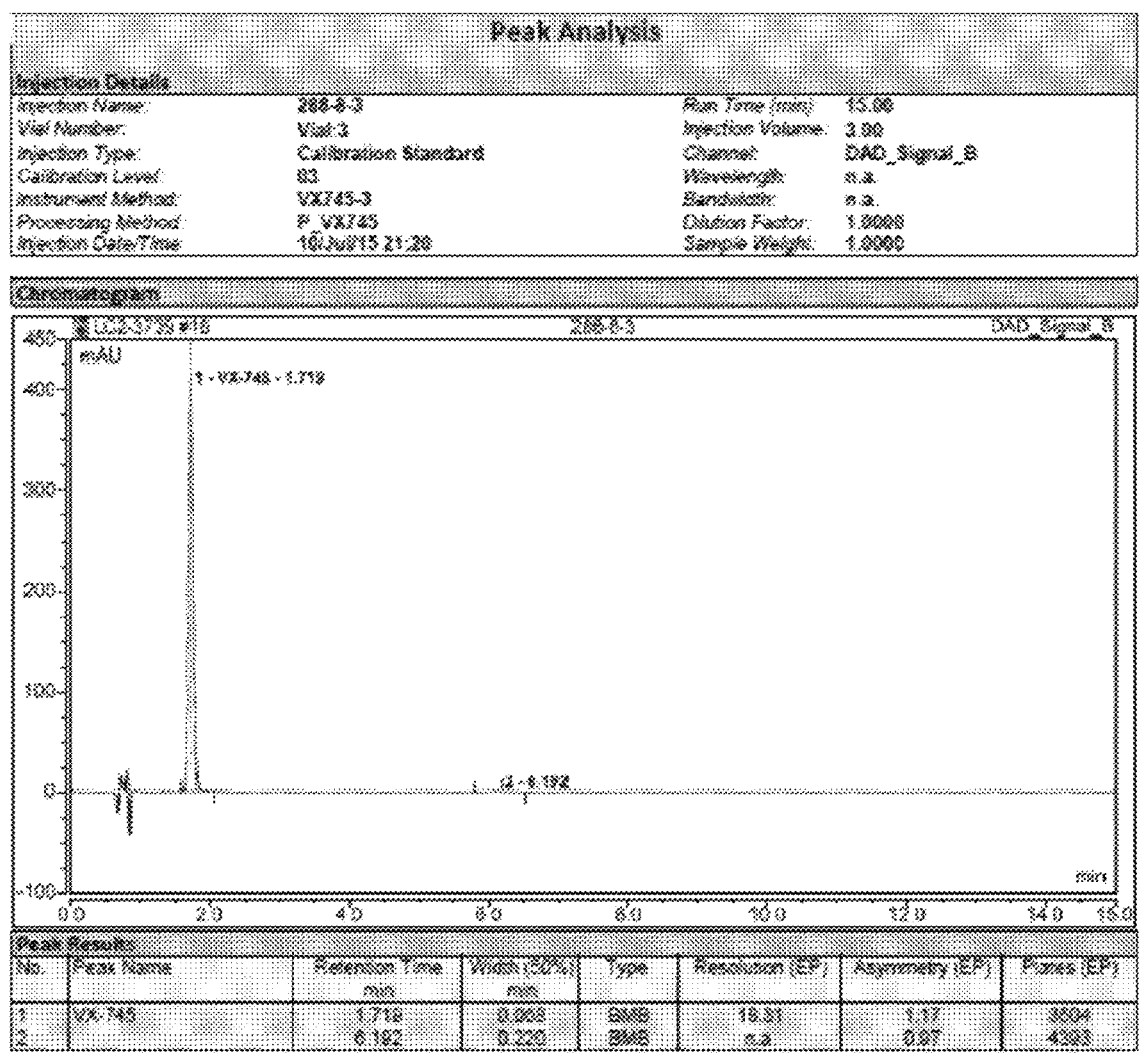
Figure 34:
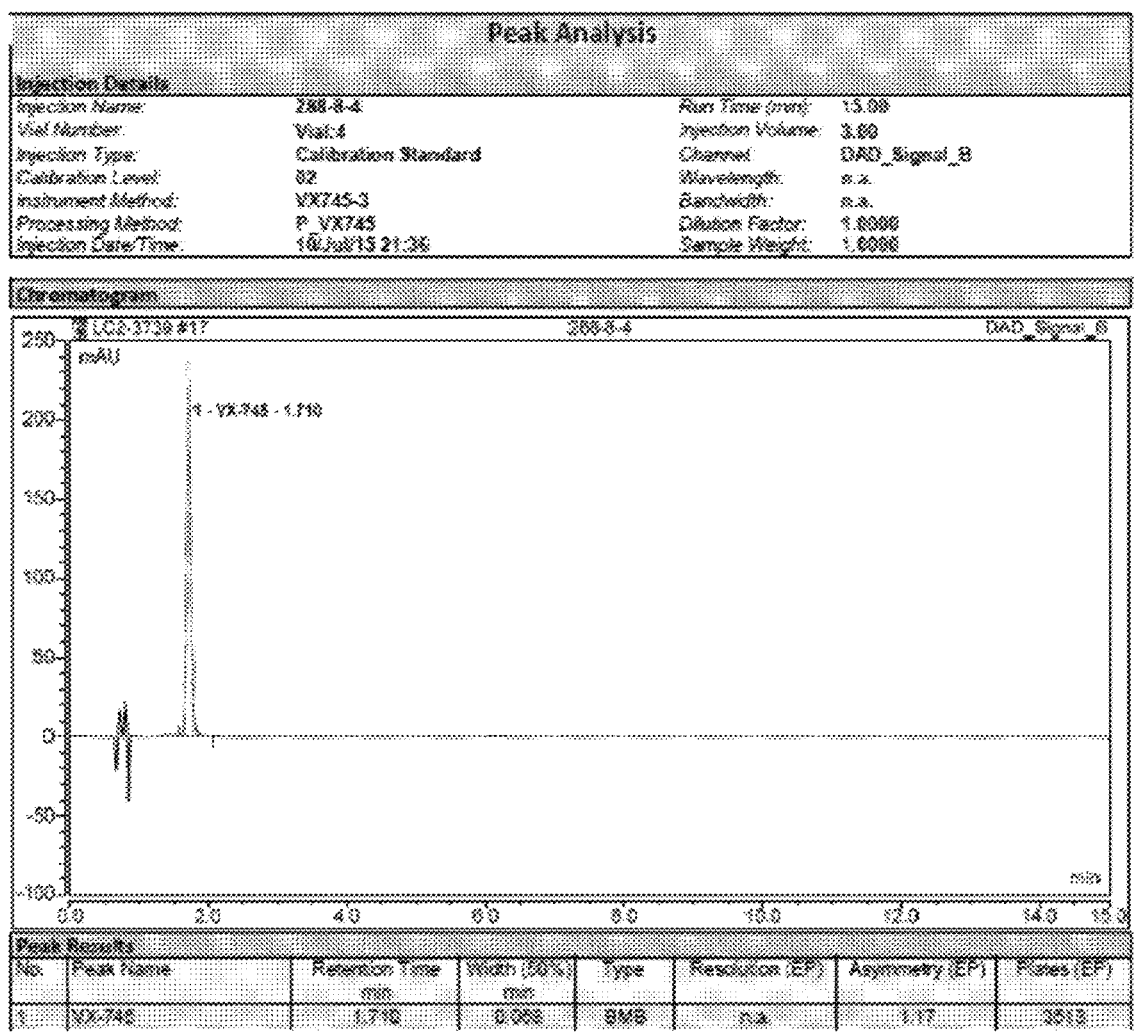
Figure 35:
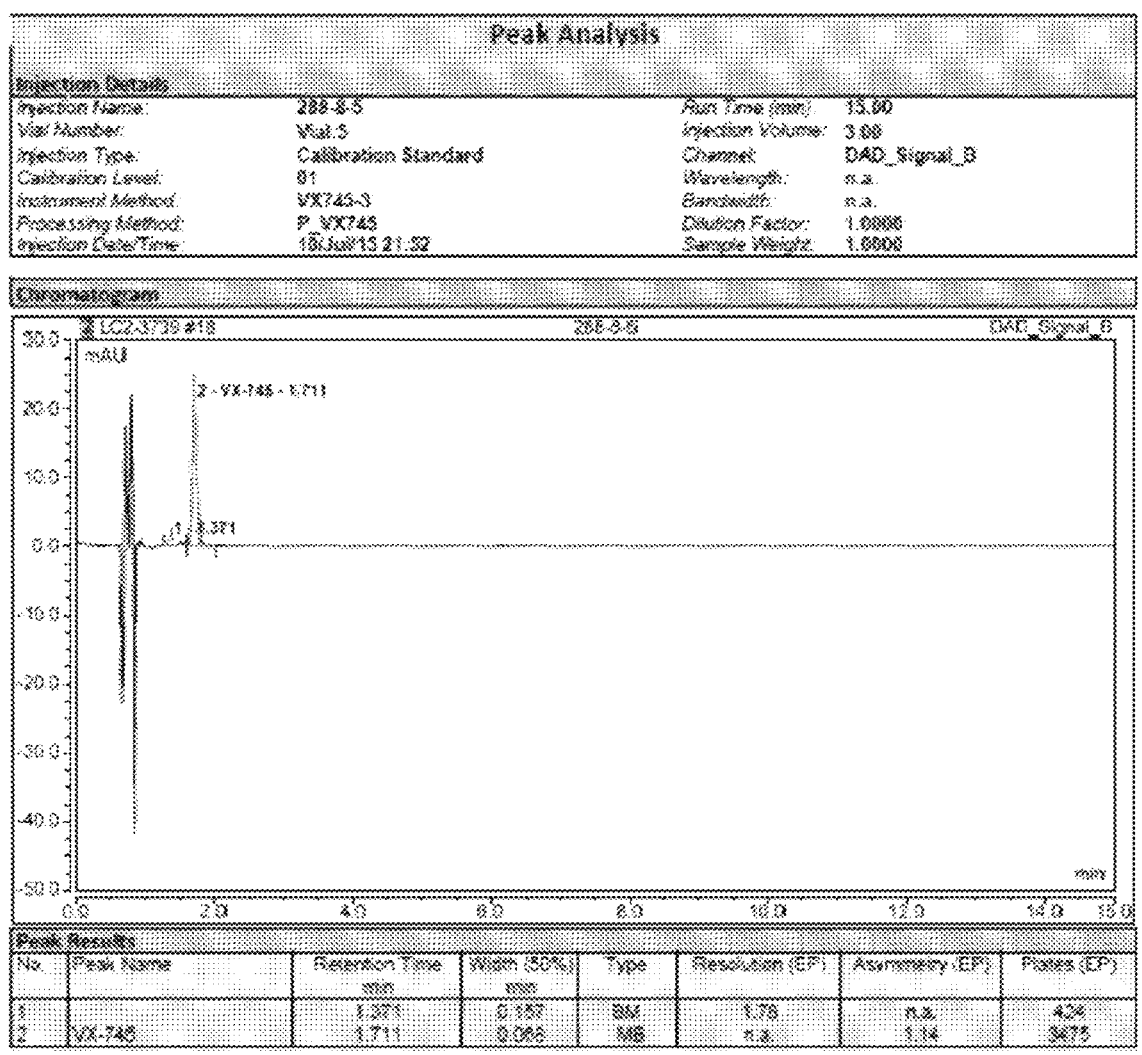

FIG. 30 shows XRPD result of a co-crystal comprising VX-745 and zinc chloride.

Exemplary Characterization Methods

X-Ray Powder Diffraction (XRPD). The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths. Powder samples were prepared in a low background Si holder using light manual pressure to keep the sample surfaces flat and level with the reference surface of the sample holder. The single-crystal, Si, low-background holder has a small circular recess (5 mm diameter and about 1 mm depth) that holds between 5 and 10 mg of powdered material. Each sample was analyzed from 2 to 40° 2θ using a continuous scan of 6° 2θ per minute with an effective step size of 0.02° 2θ.

Stoichiometric Slow Evaporation Experiments. Stoichiometric slow evaporation experiments were carried out in glass vials. Each of the vials was charged with about 25 mg of VX-745 and an approximately equimolar amount of coformer. The contents were dissolved in a given solvent and placed in glass vials. The vials were covered with aluminium foil having three pinholes and allowed to evaporate at ambient temperature. The resulting solids were analyzed by XRPD.

Stoichiometric Wet Milling Experiments. For each experiment, A PEEK grinding cup was charged with about 25 mg of VX-745, an approximately equimolar amount of conformer, about 10 µL of either acetone or water, and one steel grinding ball. The cup was sealed and shaken on a Retsch mill for 20 min. The solid was removed and analyzed by XRPD.

Figure 9:
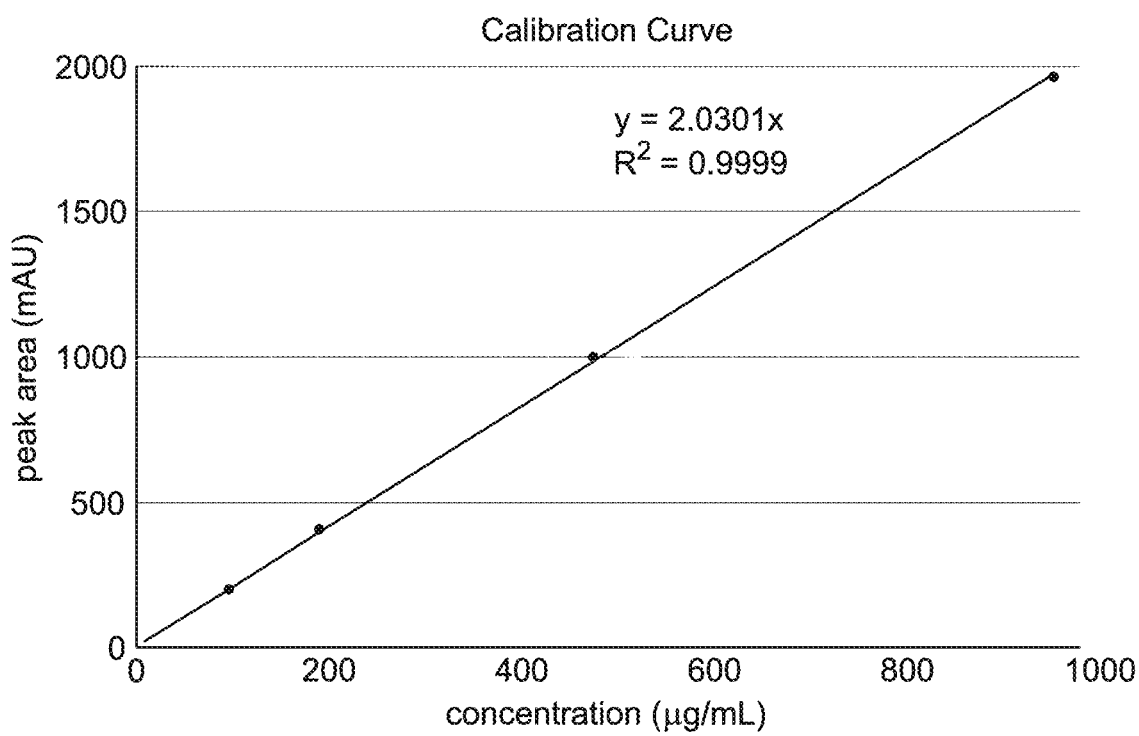
FIG. 9 shows a calibration curve of free VX-745.

High-Performance Liquid Chromatography (HPLC) Analyses. A calibration curve was constructed using the solutions shown in Table 18. The calibration curve is plotted in FIG. 9. FIGS. 31-35 show HPLC results corresponding to VX-745 at different concentrations.

TABLE 18

Samples Used in the Calibration Curve

| Sample No. | Concentration (µg/mL) | HPLC File Name | Injection # | HPLC page No. |
|---|---|---|---|---|
| 288-8-1 | 970.0 | LC2-3739 | 13 | 27 |
| 288-8-2 | 485.0 | | 15 | 28 |
| 288-8-3 | 194.0 | | 16 | 29 |
| 288-8-4 | 97.0 | | 17 | 30 |
| 288-8-5 | 9.7 | | 18 | 31 |

Example 25: Additional Examples of Co-Crystals of VX-745

Summary

Approximately 160 experiments were carried out using 79 different coformers. Several samples were found to exhibit XRPD patterns suggestive of new phase formation. The coformers used in the experiments are listed below.
Coformers used in experiments where new solid phases were observed are shown in Table 19 below.

TABLE 19

Exemplary coformers used to form co-crystals of VX-745 according to some embodiments described herein.

| | | |
|---|---|---|
| acesulfame potassium | gallic acid | L-pyroglutamic acid |
| trans-aconitic acid | gentisic acid | saccharin |
| adenine | glutaric acid | salicyclic acid |
| adipic acid | L-histidine | L-serine |
| 4-aminobenzoic acid | 1-hydroxy-2-naphthoic acid | sorbic acid |
| L-ascorbic acid | ketoglutaric acid | sorbitol |
| asparagine | lithium chloride | sucrose |
| benzoic acid | malonic acid | thiamine hydrochloride |
| betaine HCl | nicotinic acid | L-threonine |
| calcium chloride | oxalic acid | urea |
| choline chloride | phenol | zinc chloride |
| cyclamic acid | L-proline | — |

Results and Discussion

Characterization

A sample of VX-745 was characterized by x-ray powder diffraction (XRPD), differential scanning calorimetry (DSC), and thermogravimetry (TG). The results are summarized in Table 20.

TABLE 20

Analyses of Samples Received

| | |
|---|---|
| Lot No. | 13L145 |
| Triclinic No. | TCL1277 |
| XRPD Filename | RX3418 |
| XRPD Page No. | 29 |
| XRPD Result | crystalline |
| DSC Filename | DSC2.492 |
| DSC Page No. | 115 |
| DSC Result | endo 265.6, broad exo 267.3° C. |
| TG Filename | TG2.390 |
| TG Page No. | 115 |
| TG Result | 1.967% loss up to 265° C. |
| NMR Filename | NMR1S2 |
| NMR Page No. | 120 |
| NMR Results | consistent with structure |

Figure 55:
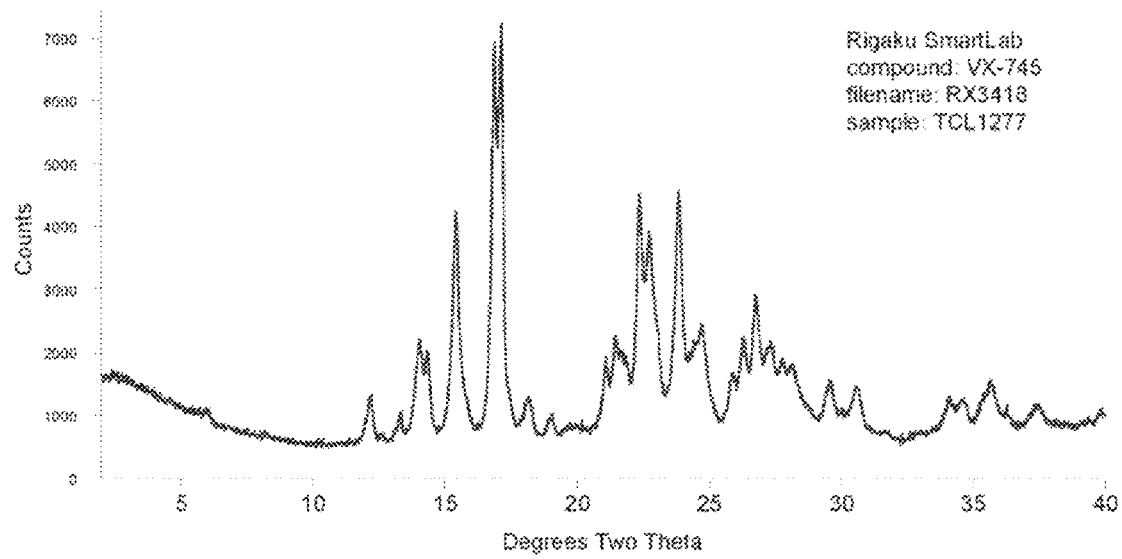
FIG. 55 shows XRPD result of free VX-745.
Figure 226:
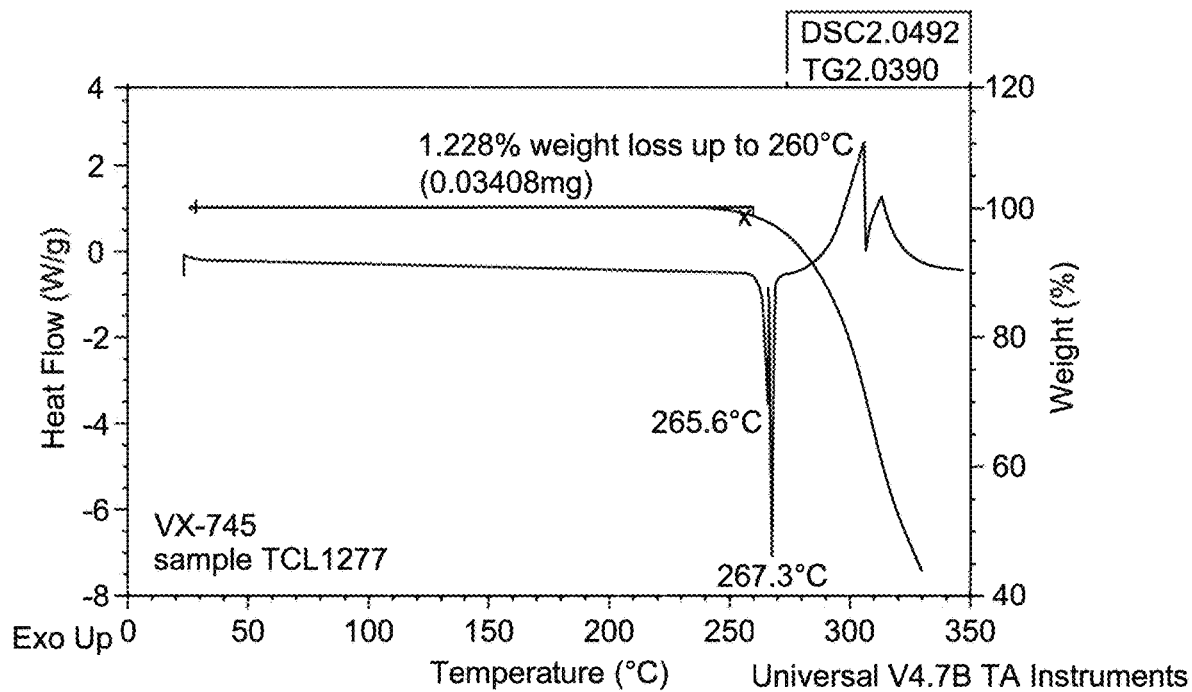
FIG. 226 shows thermogravimetric analysis of free VX-745.
Figure 235A:
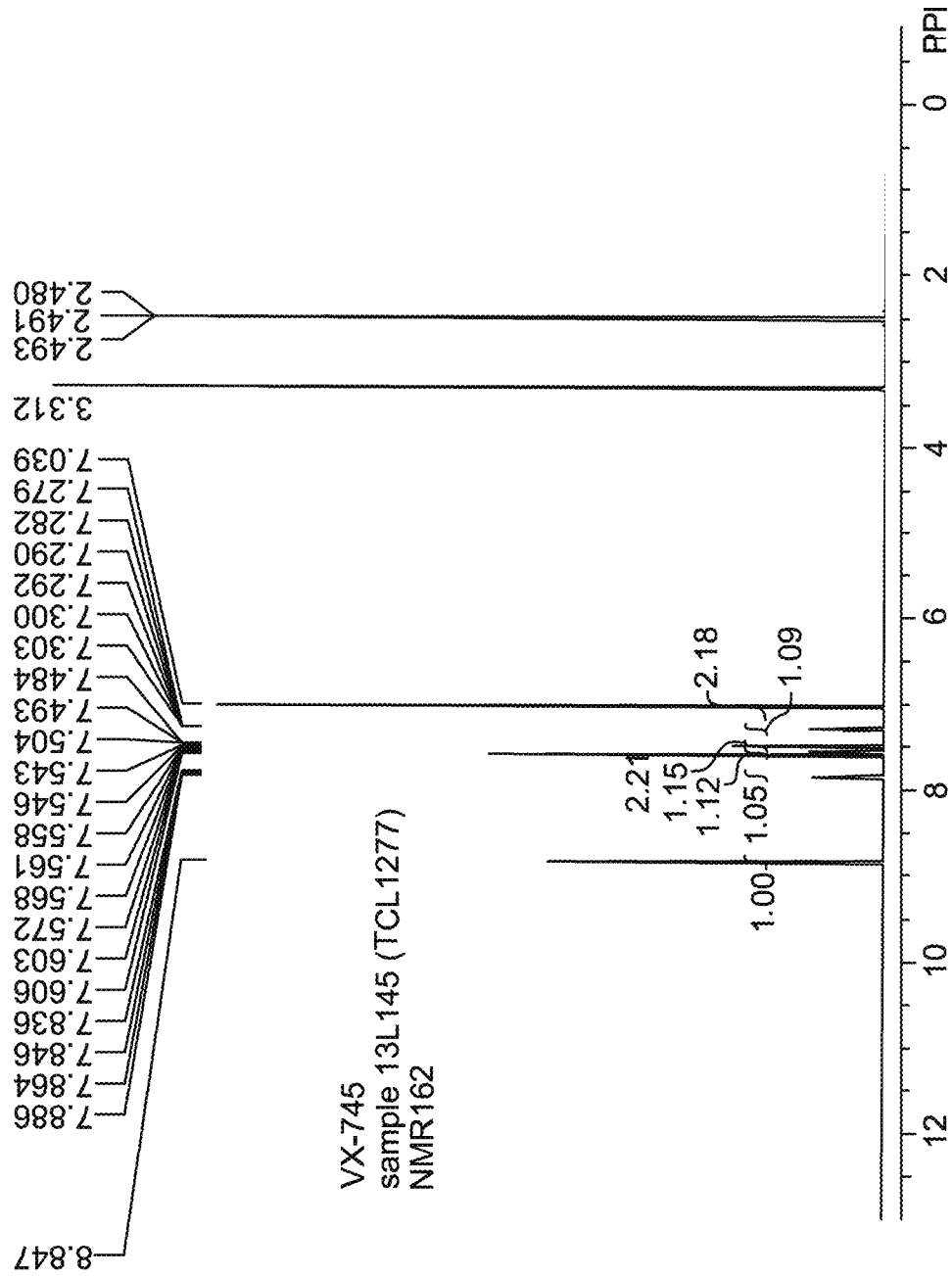
FIG. 235A shows Nuclear Magnetic Resonance (NMR) Spectroscopic data for free VX-745 and FIG. 235B shows zoom-in NMR spectroscopic data.
Figure 235B:
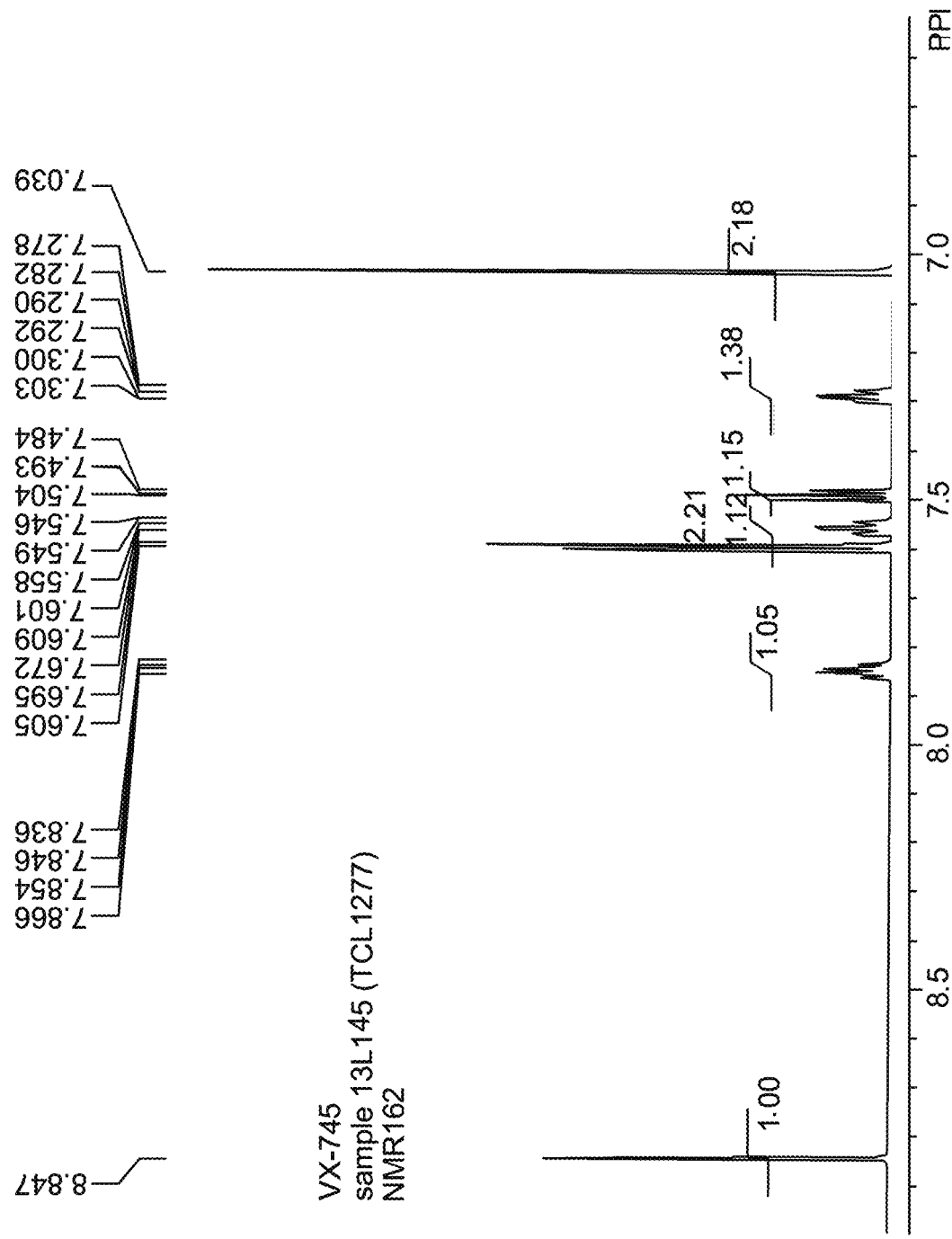

FIG. 55 shows XRPD result of free VX-745.
FIG. 226 shows thermogravimetric analysis of free VX-745.
FIG. 235A shows Nuclear Magnetic Resonance (NMR) Spectroscopic data for free VX-745 and FIG. 235B shows zoom-in NMR spectroscopic data.

Solubility Estimations

Solubilities of VX-745 in several solvents were estimated. The experiments were carried out by adding test solvents in aliquots to weighed portions of solid. Whether dissolution had occurred was judged by visual inspection after addition of each solvent aliquot. The results are shown in Table 21. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot.

TABLE 21

Estimated Solubilities of VX-745

| Solvent | Sample Weight (mg) | Solvent Amount (mL) | Solubility (mg/mL) | Notebook Reference |
|---|---|---|---|---|
| acetone | 2.9 | 0.4 | 7 | 178-1 |
| acetonitrile | 2.6 | 0.3 | 9 | 178-1 |
| ethyl acetate | 2.5 | 3 | <1 | 178-1 |
| ethanol | 2.7 | 1.8 | 2 | 178-1 |
| isopropyl alcohol | 3.2 | 2.5 | 1 | 178-1 |
| methanol | 3.1 | 0.3 | 10 | 178-1 |
| tetrahydrofufan | 2.2 | 0.5 | 4 | 178-1 |
| water | 2.6 | 3 | <1 | 178-1 |

Coformer Selection

A set of coformers was selected. Those are listed in Table 22.

TABLE 22

Coformers Used

| | | |
|---|---|---|
| acesulfame potassium | gallic acid | phenol |
| acetylsalicylic acid | gentisic acid | L-phenylalanine |
| trans-aconite acid | glucosamine HCl | L-proline |
| adenine | D-glucose | propyl gallate |
| adipic acid | glutaric acid | L-pyroglutamic acid |
| alanine | glycine | riboflavin |
| 4-aminobenzoic acid | glycolic acid | saccharin |
| ammonium chloride | hippuric acid | salicylic acid |
| L-arginine | L-histidine | sebacic acid |
| L-ascorbic acid | 4-hydroxybenzoic acid | L-serine |
| asparagine | 1-hydroxy-2-naphthoic acid | sodium chloride |
| benzoic acid | ketoglutaric acid | sorbic acid |
| betaine HCl | lactose | sorbitol |
| caffeine | L-leucine | succinic acid |
| calcium chloride | lithium chloride | sucralose |
| (+)-camphoric acid | L-lysine | sucrose |
| choline chloride | maleic acid | L-tartaric acid |
| cinnamic acid | L-malic acid | thiamine hydrochloride |
| citric acid | malonic acid | L-threonine |
| creatinine | maitol | tromathamine HCl |
| cyclamic acid | D,L-mandalic acid | urea |
| cysteine | D-mannitol | L-valine |
| dehydroepiandrosterone | megiumine | vanillic acid |
| ethyl maitol | methyl paraben | vanillin |
| ethyl paraben | nicotinamide | zinc chloride |
| D-fructose | nicotinic acid | — |
| fumaric acid | oxalic acid | — |

Cocrystal Screening

The cocrystal screen was carried out using three experimental methodologies, as described below.

Figure 56:
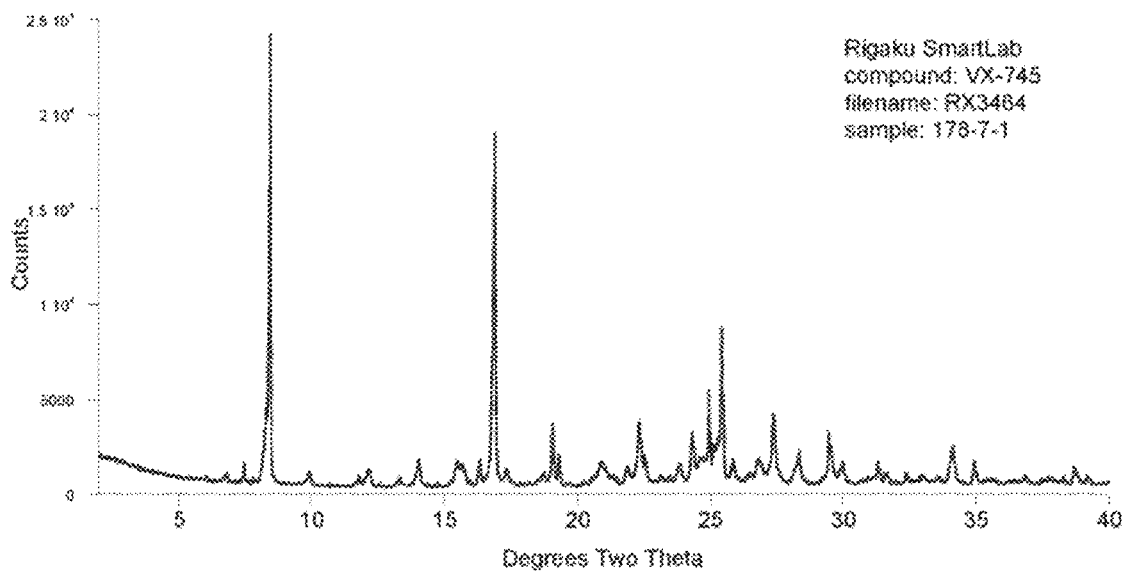
FIGS. 56-140 show XRPD results of various co-crystals of VX-745 produced by slow evaporation. The co-crystal in each figure is identified by XRPD filename, which corresponds to "XRPD File" in FIGS. 239A-239B.
Figure 57:
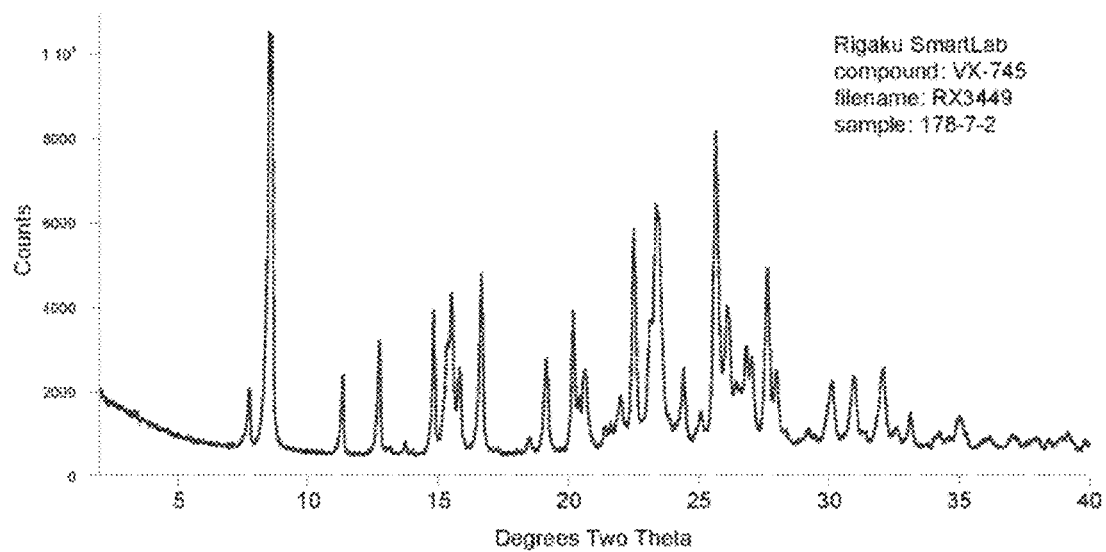
Figure 58:
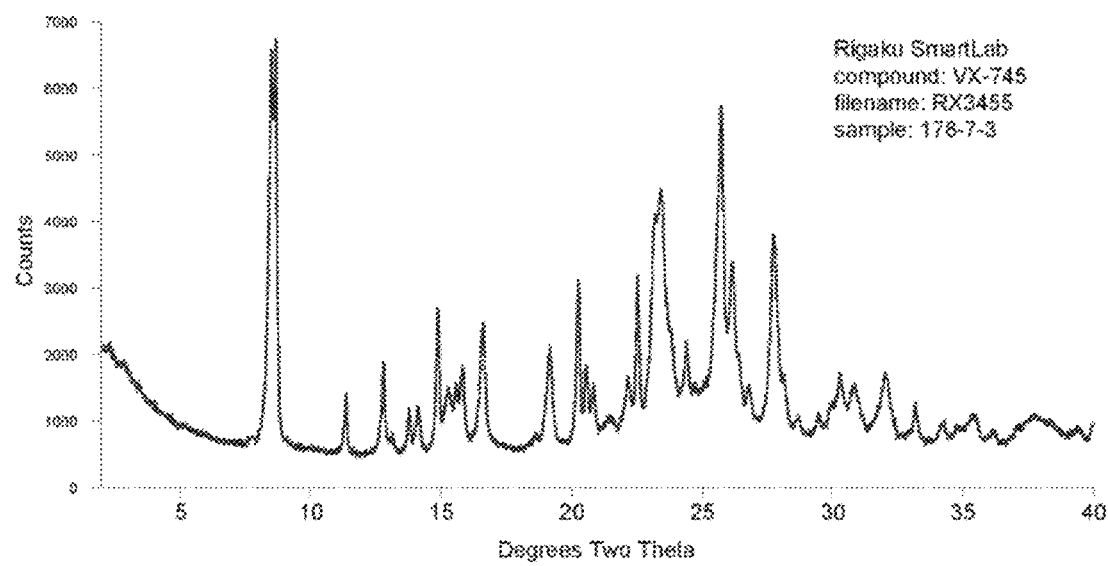
Figure 59:
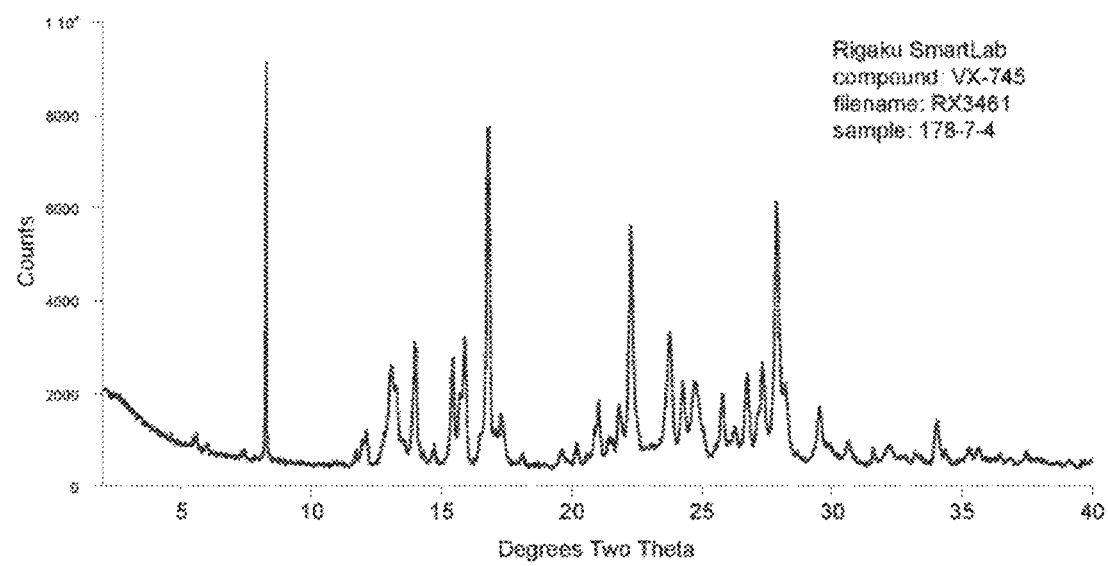
Figure 60:
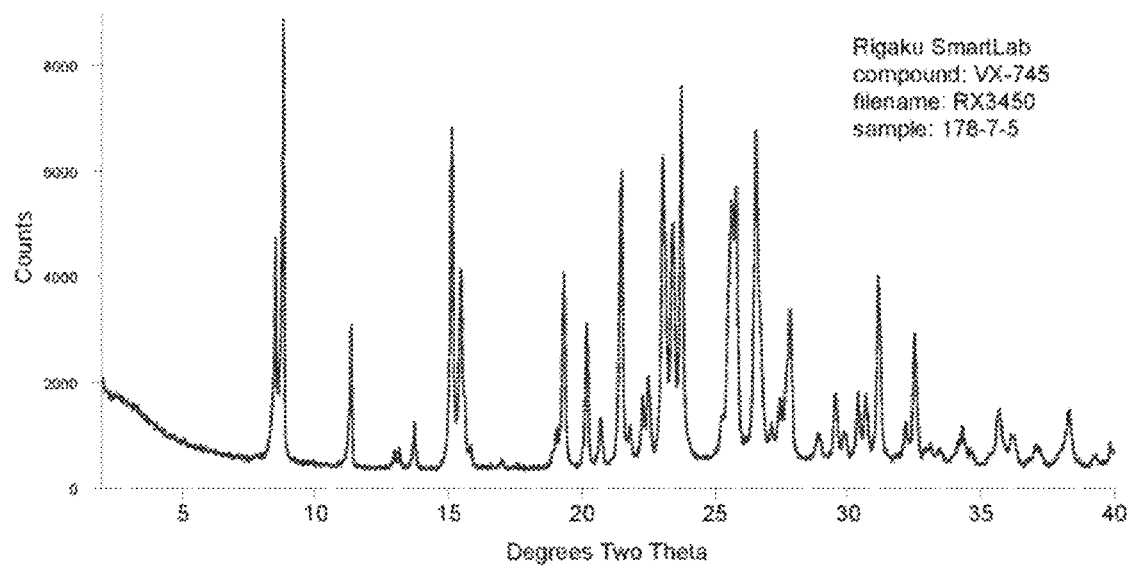
Figure 61:
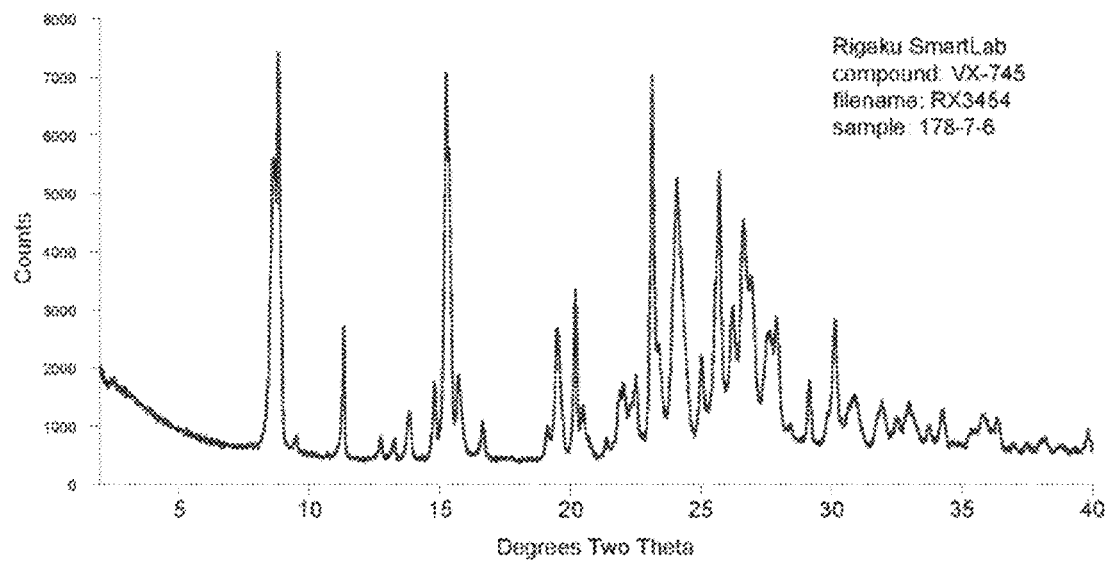
Figure 62:
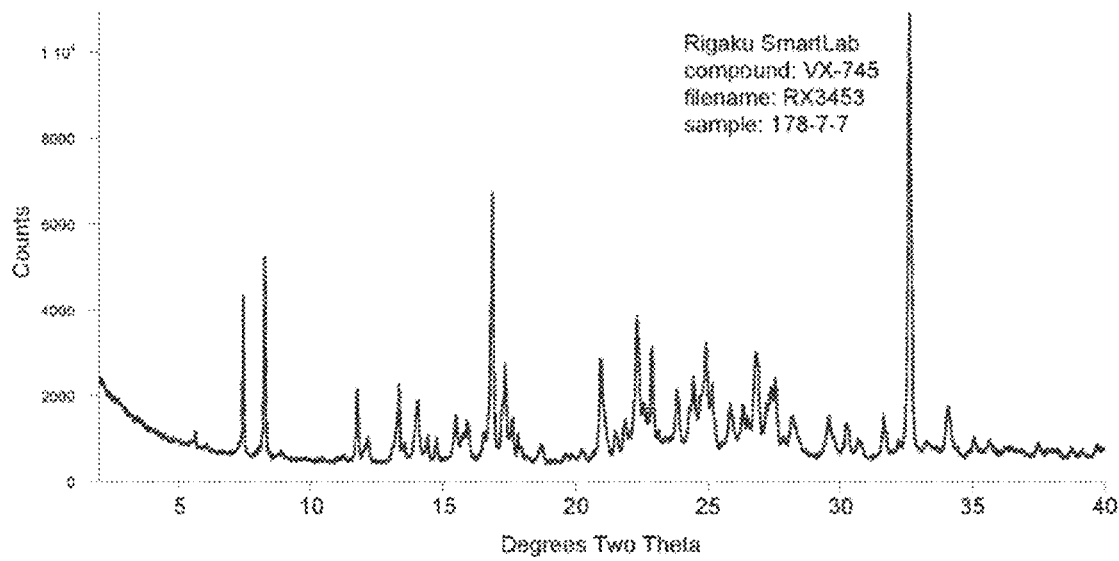
Figure 63:
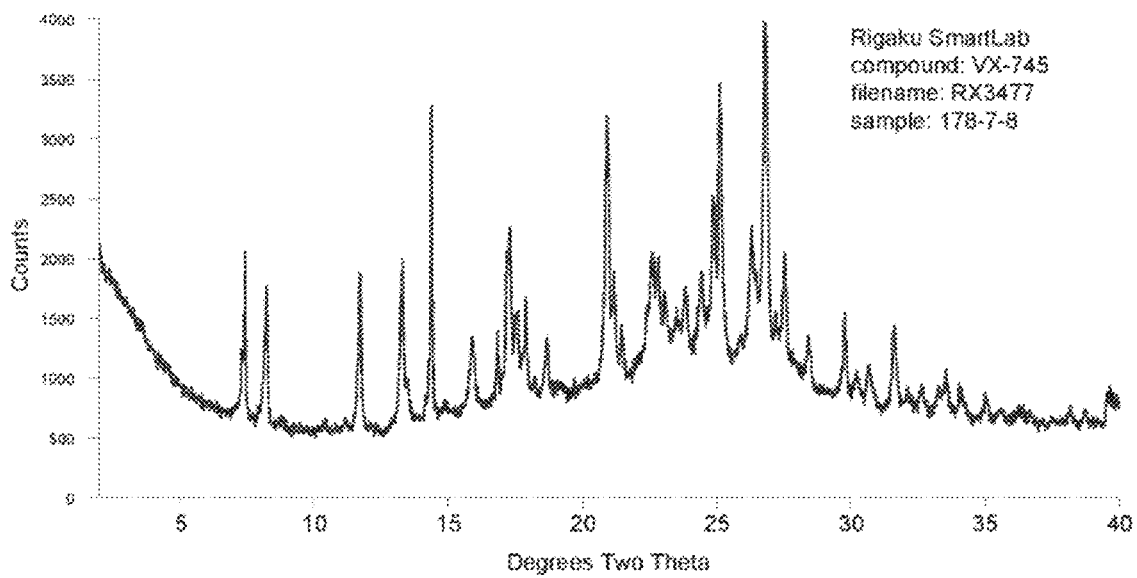
Figure 64:
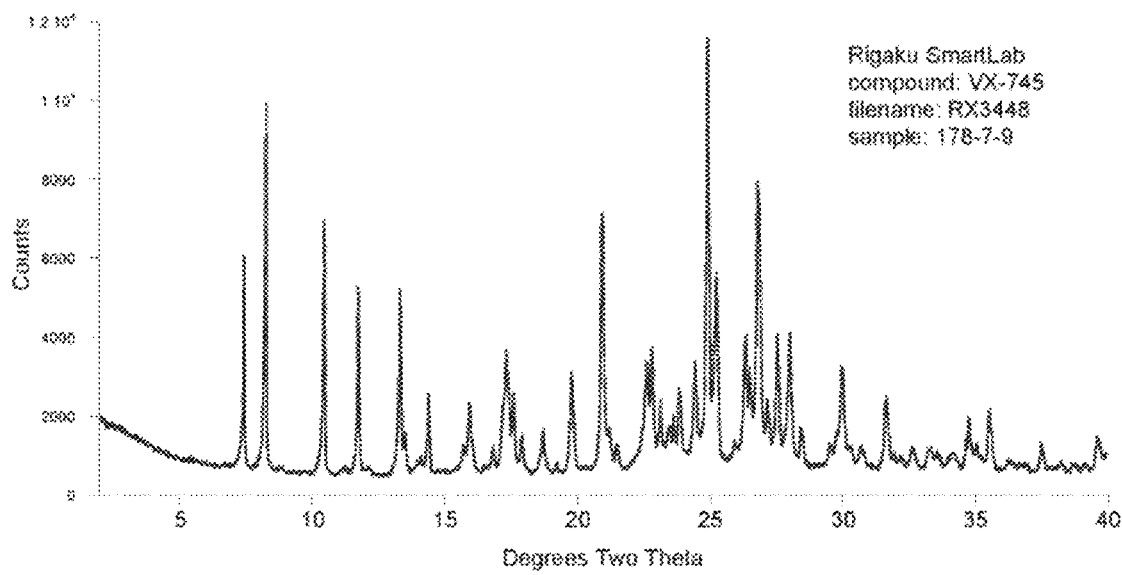
Figure 65:
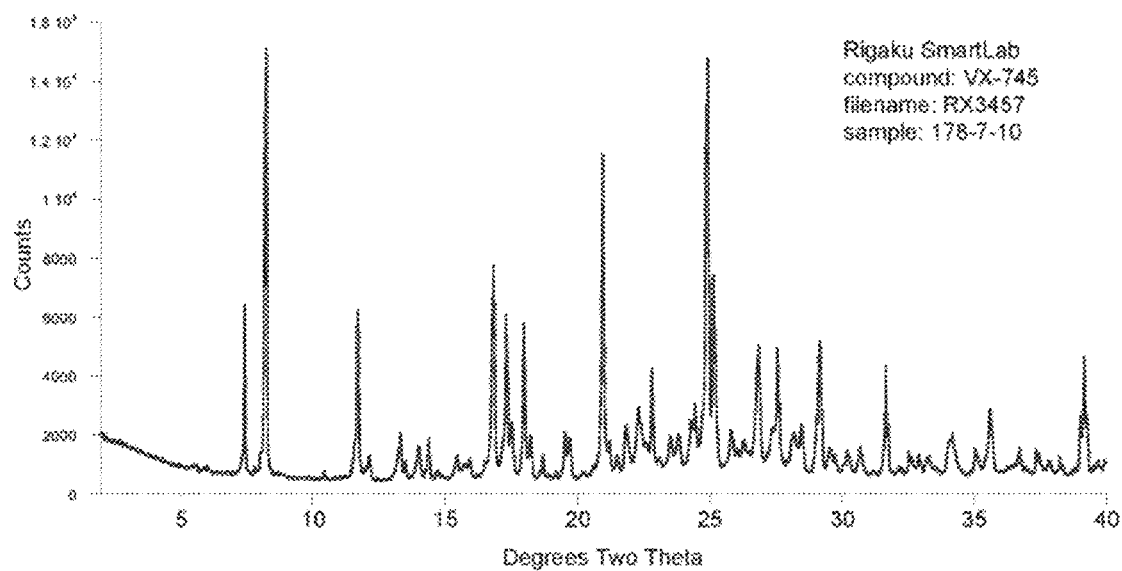
Figure 66:
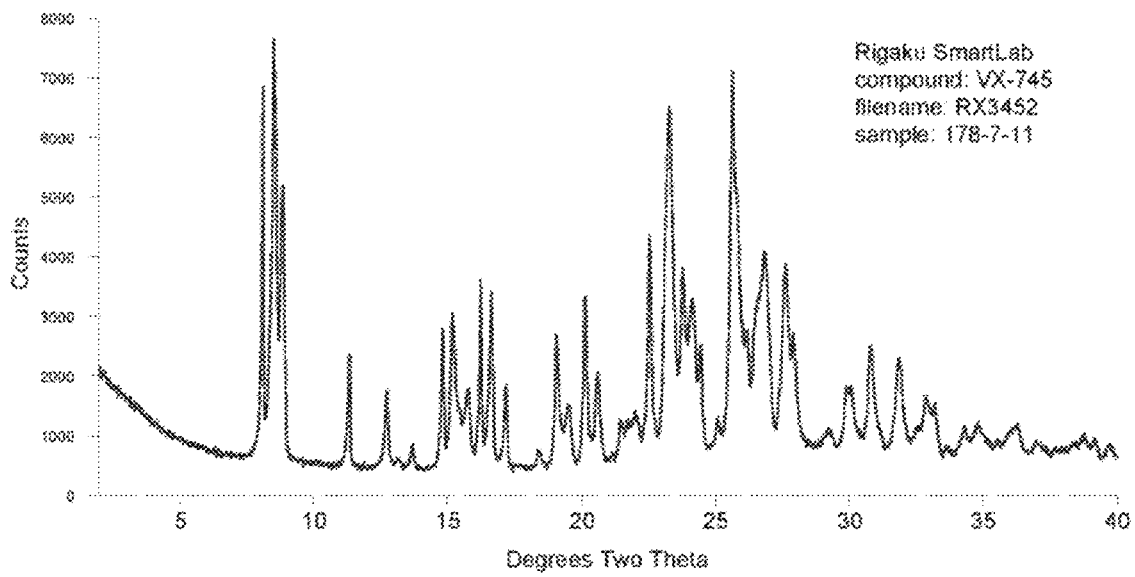
Figure 67:
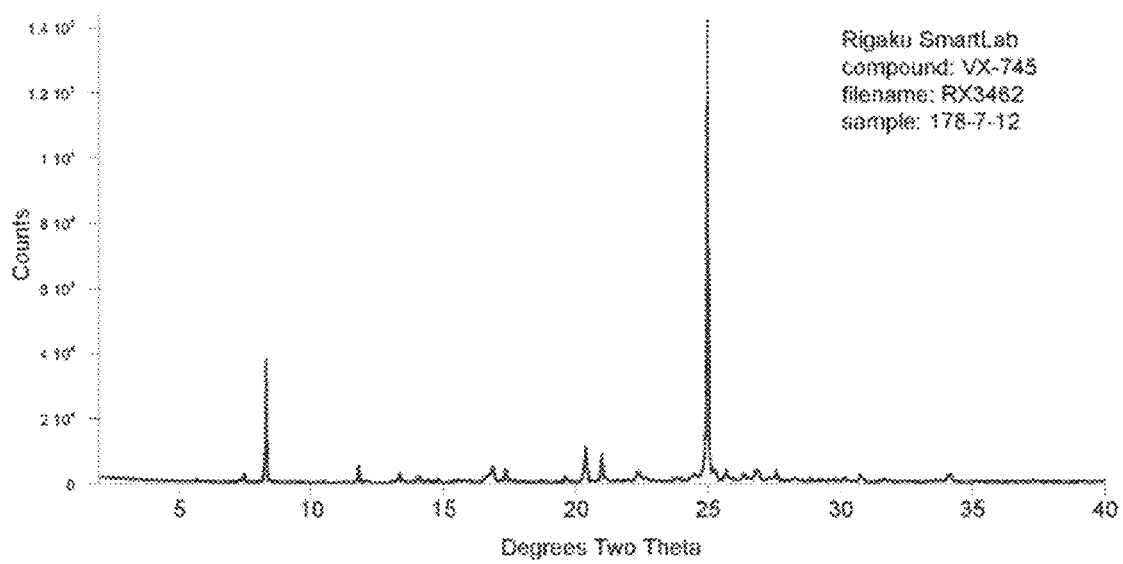
Figure 68:
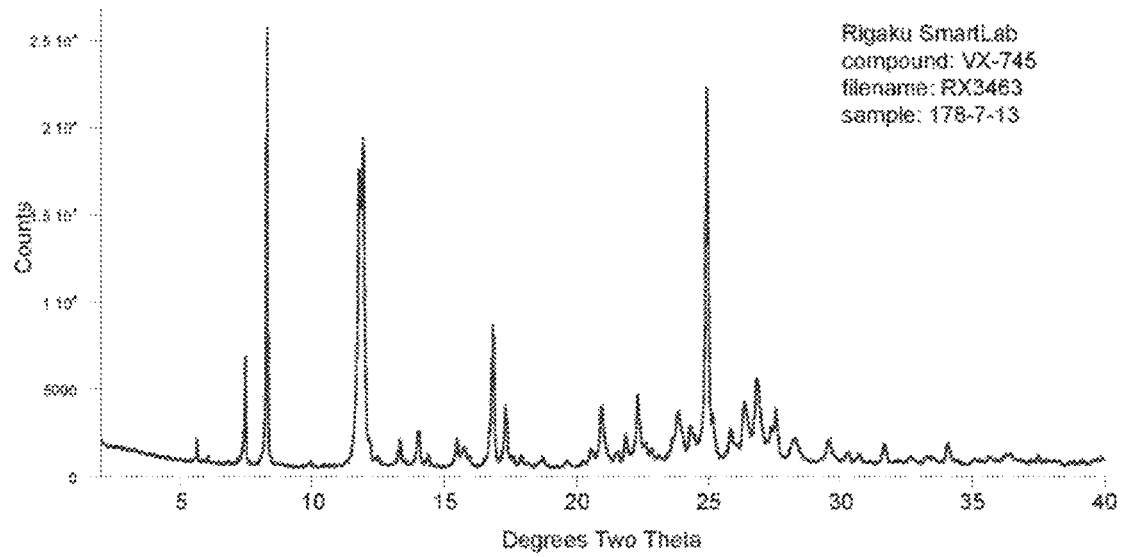
Figure 69:
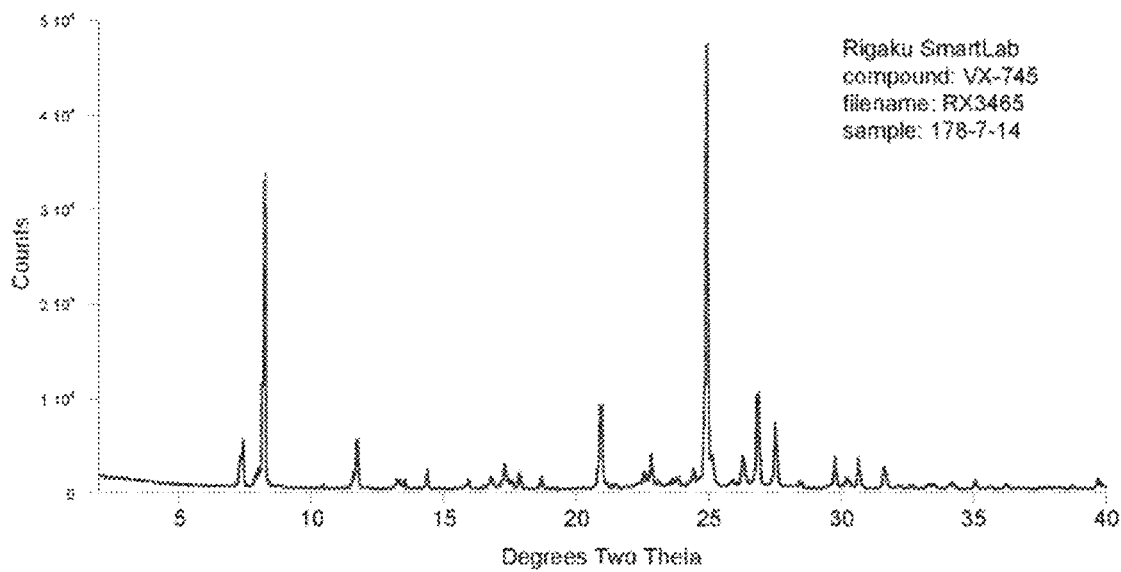
Figure 70:
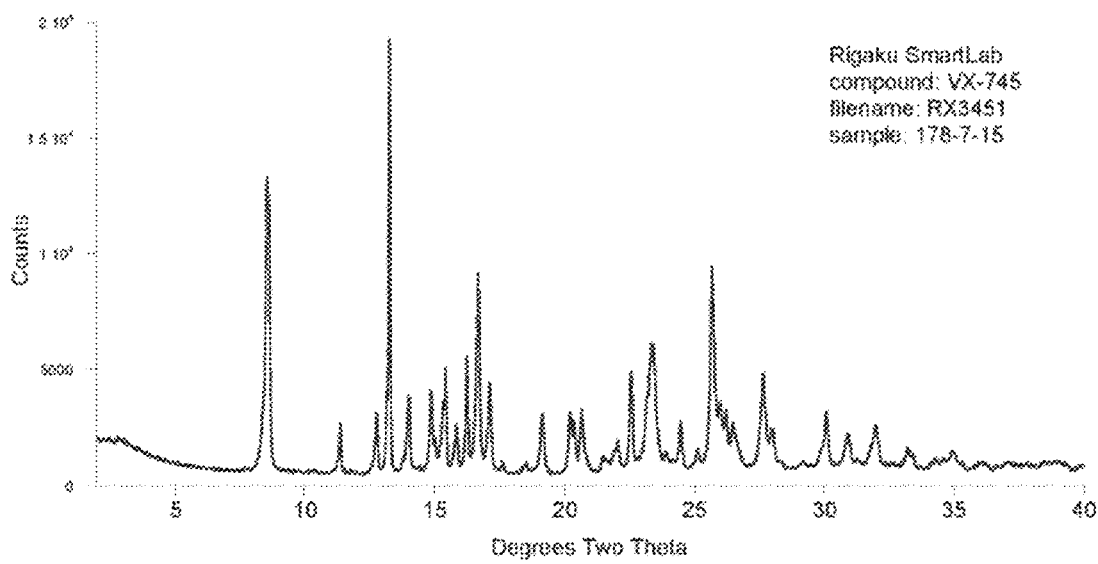
Figure 71:
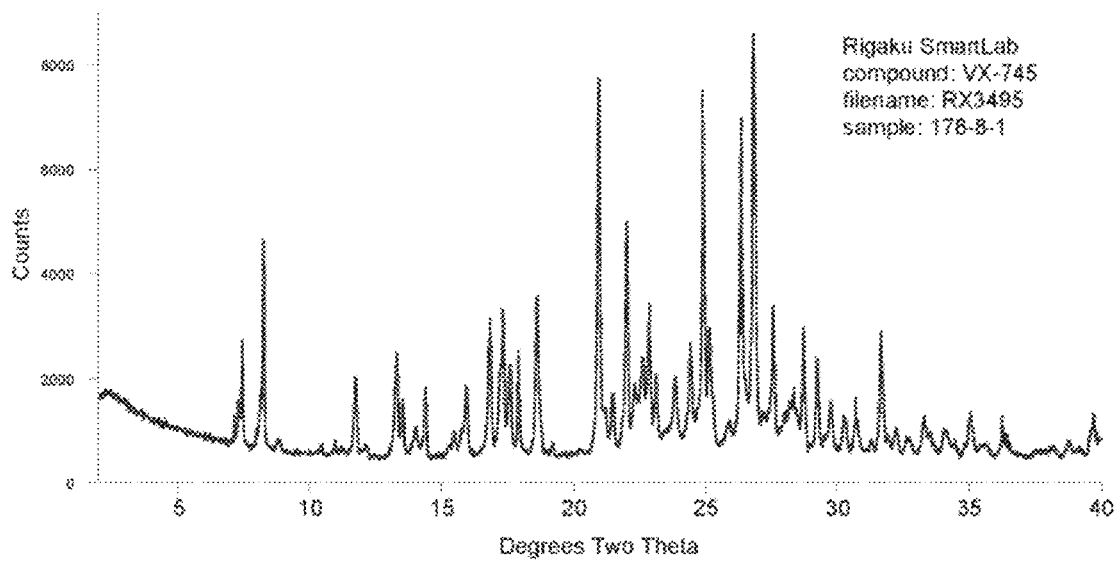
Figure 72:
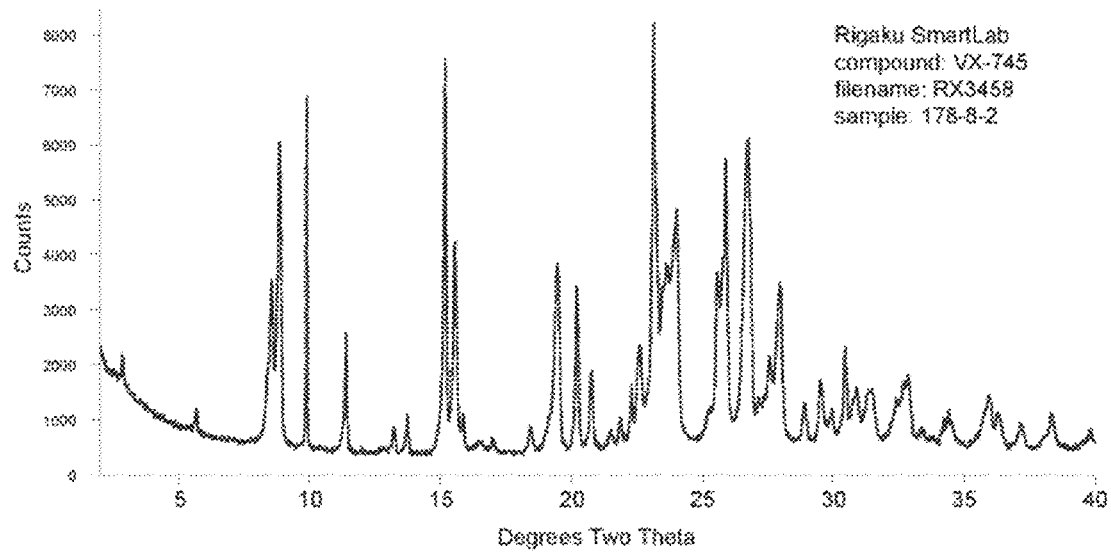
Figure 73:
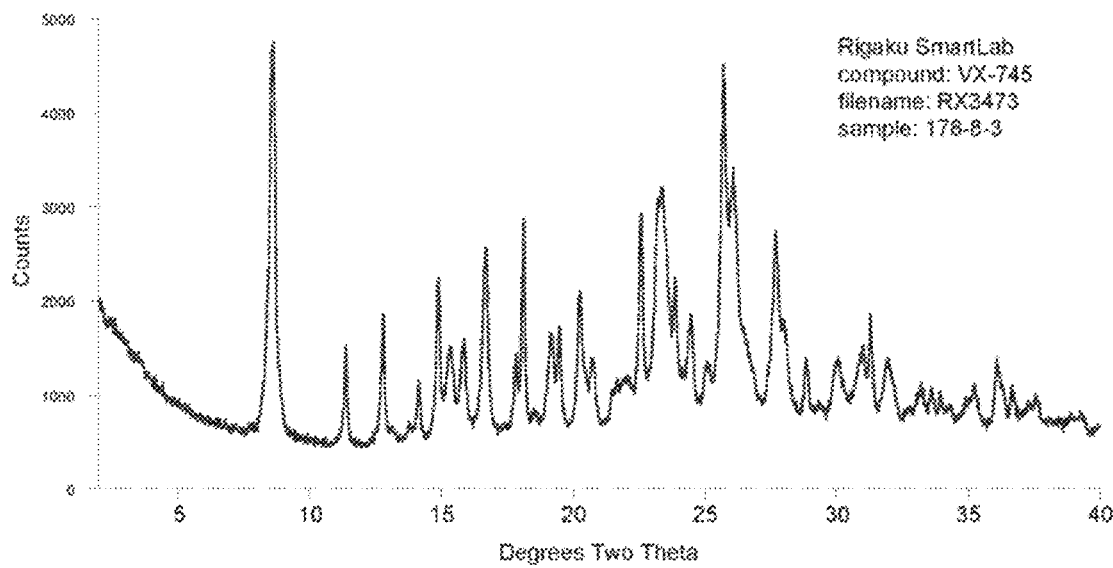
Figure 74:
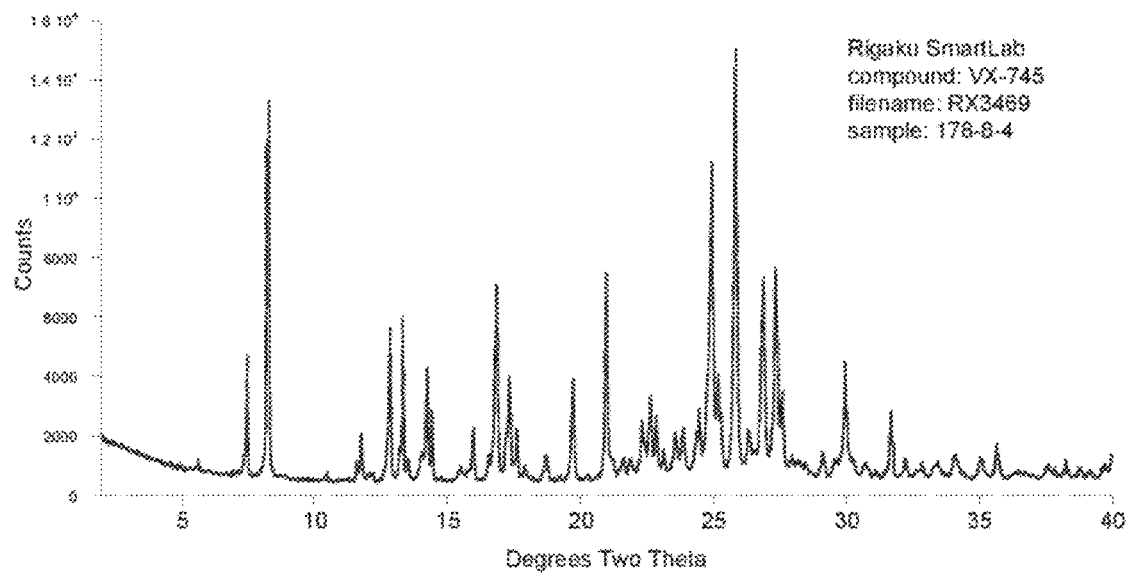
Figure 75:
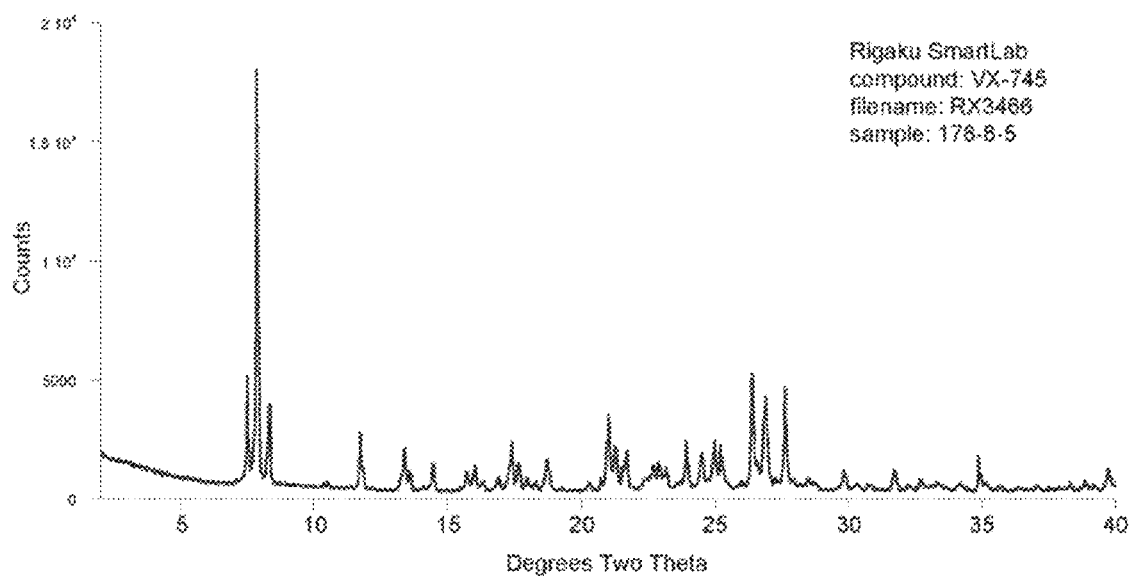
Figure 76:
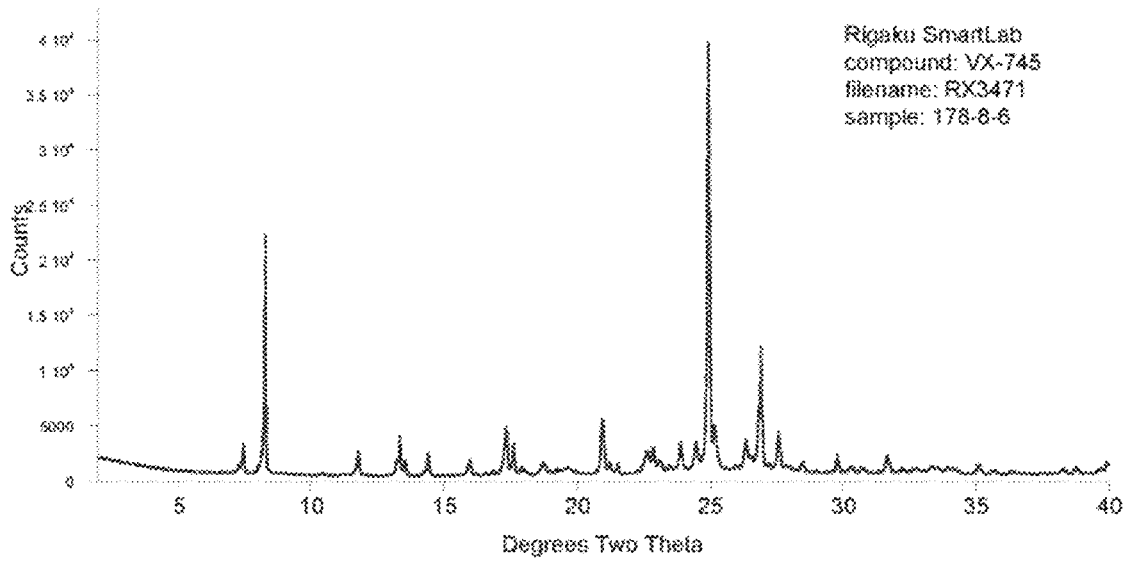
Figure 77:
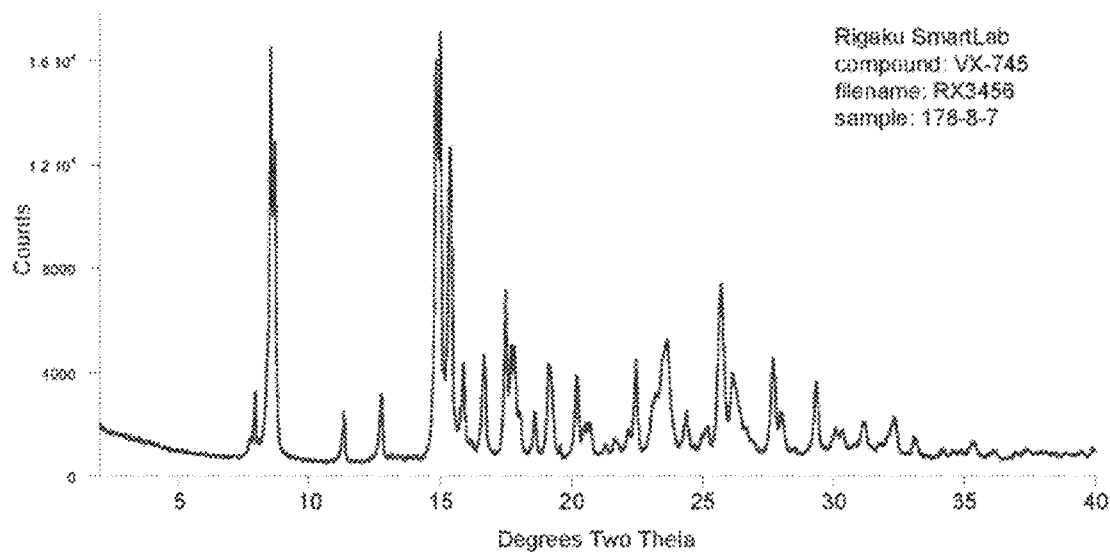
Figure 78:
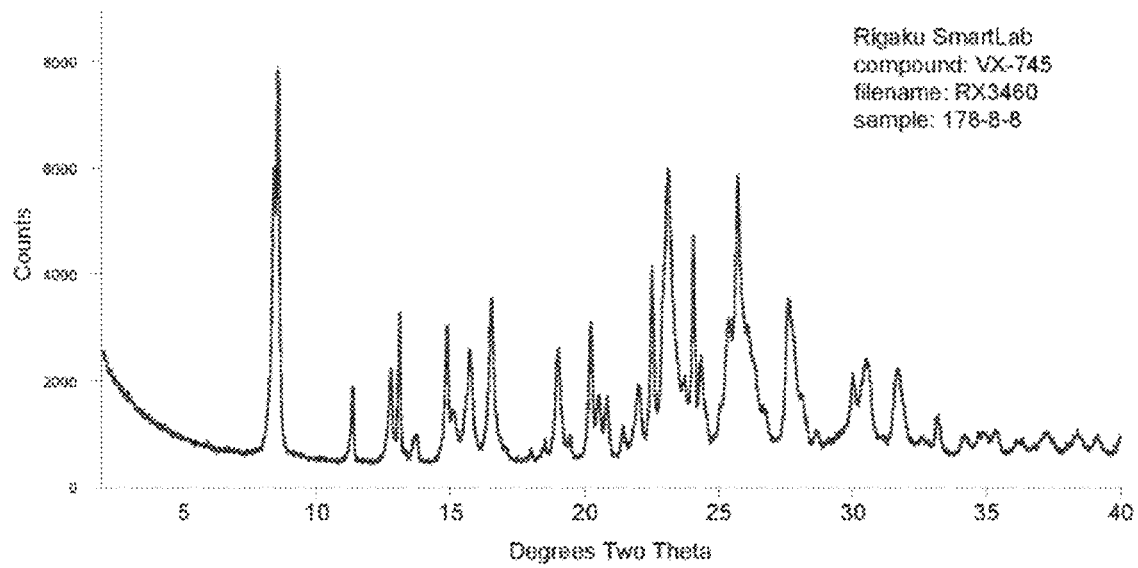
Figure 79:
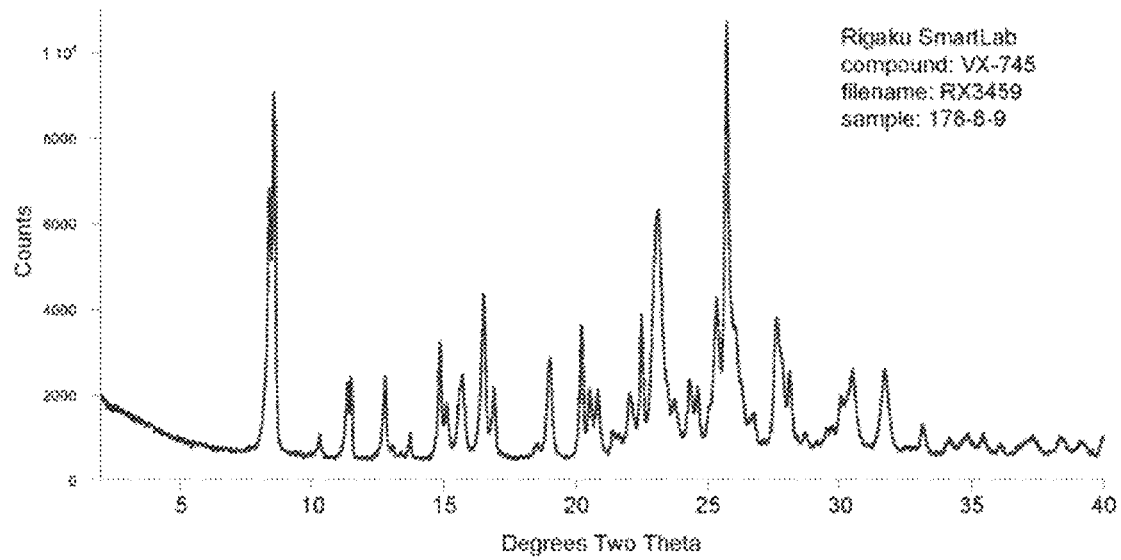
Figure 80:
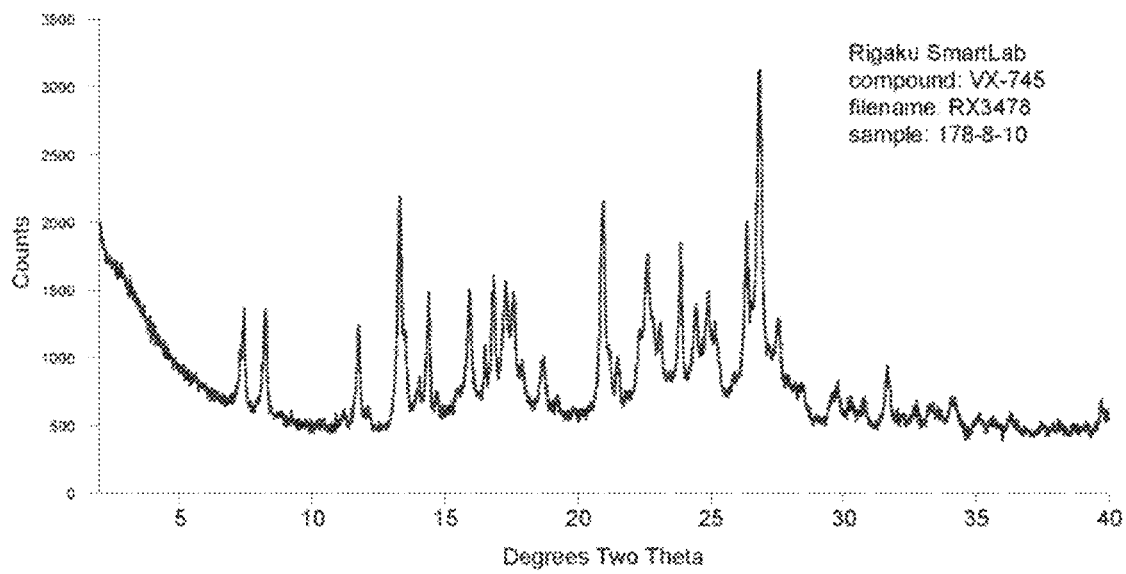
Figure 81:
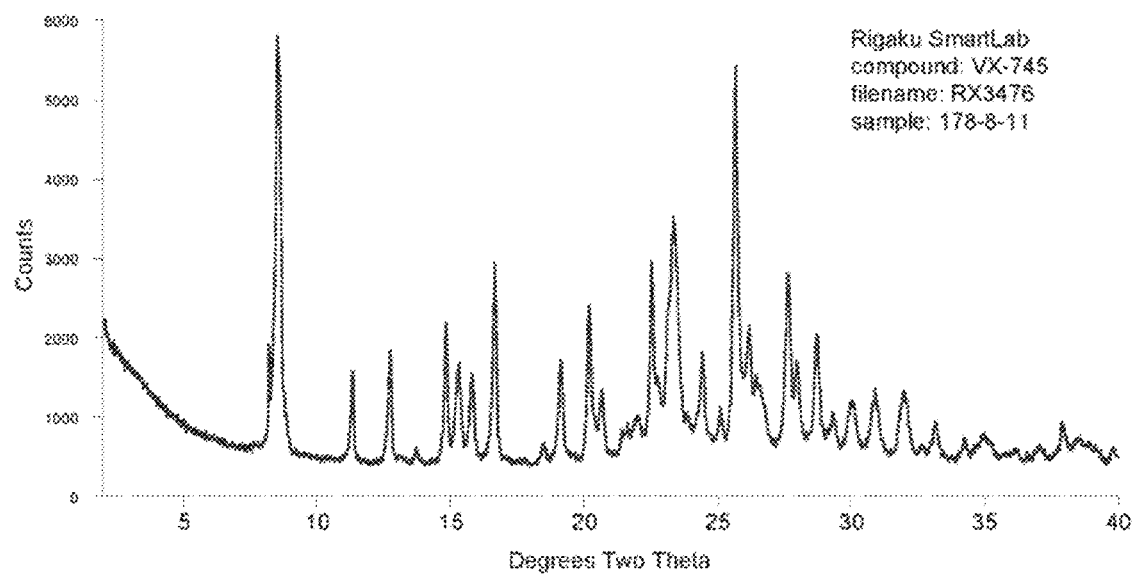
Figure 82:
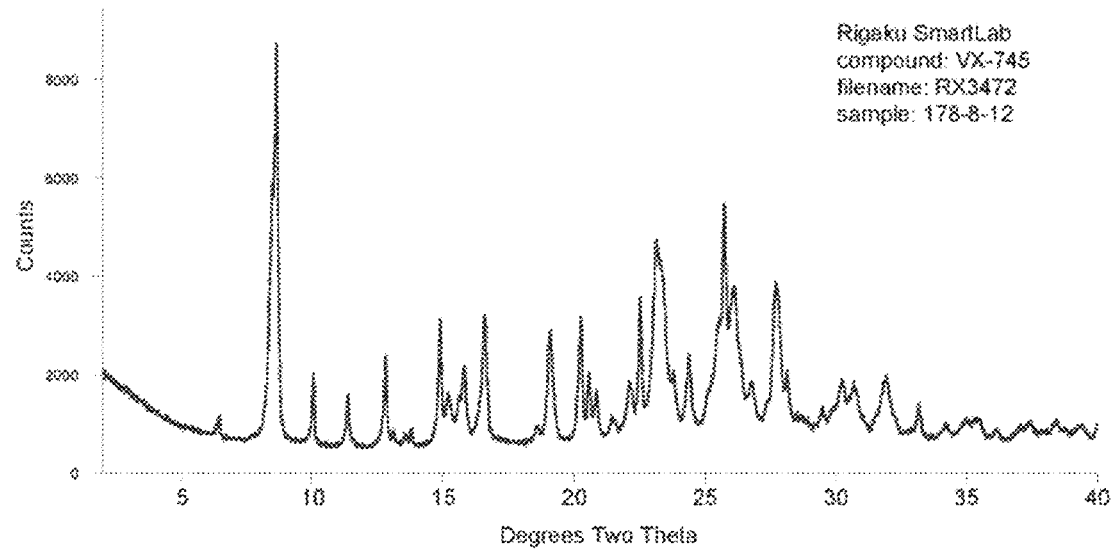
Figure 83:
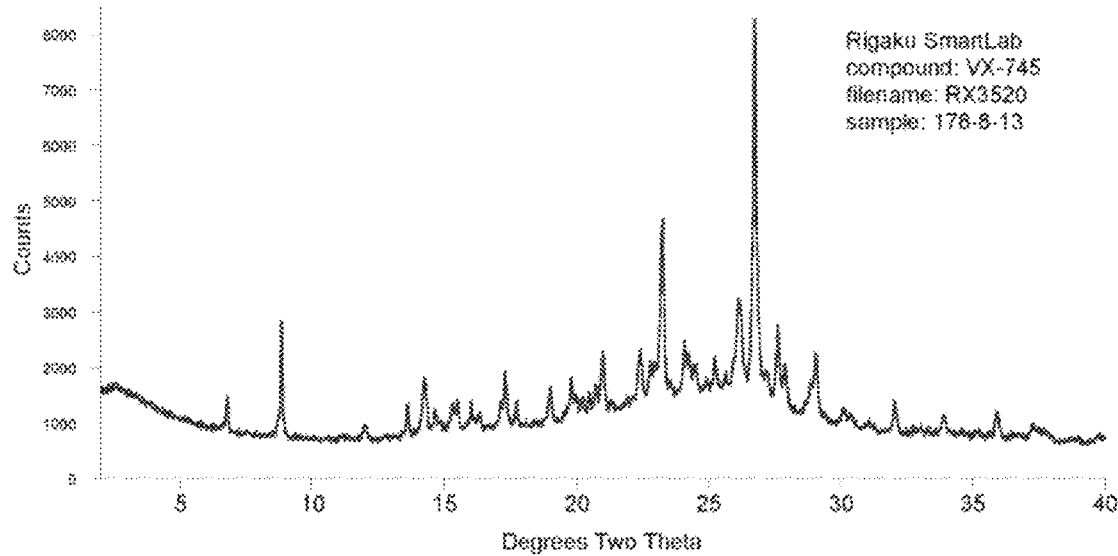
Figure 84:
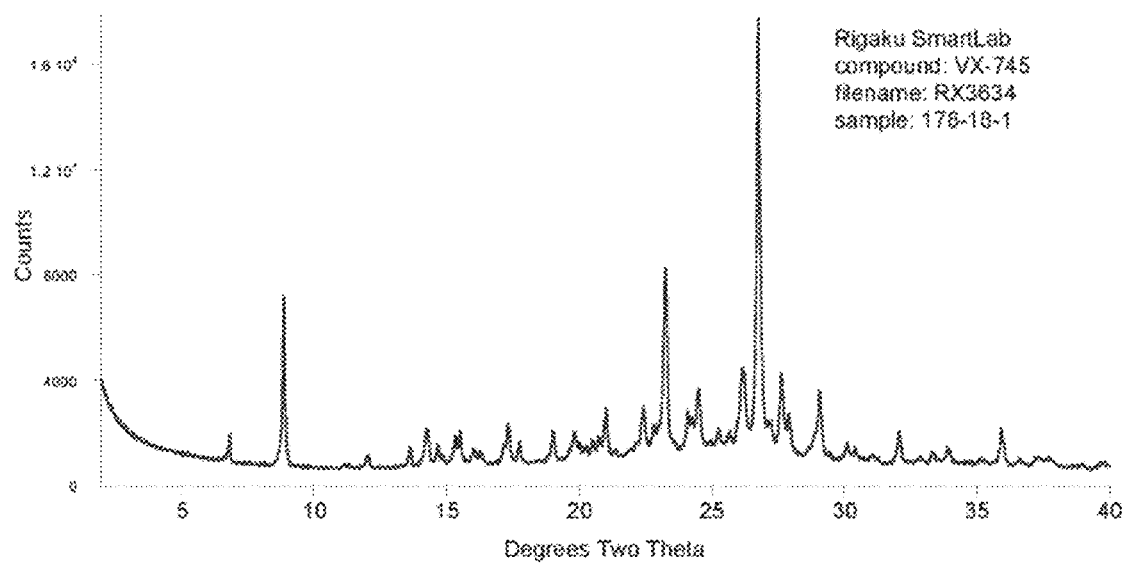
Figure 85:
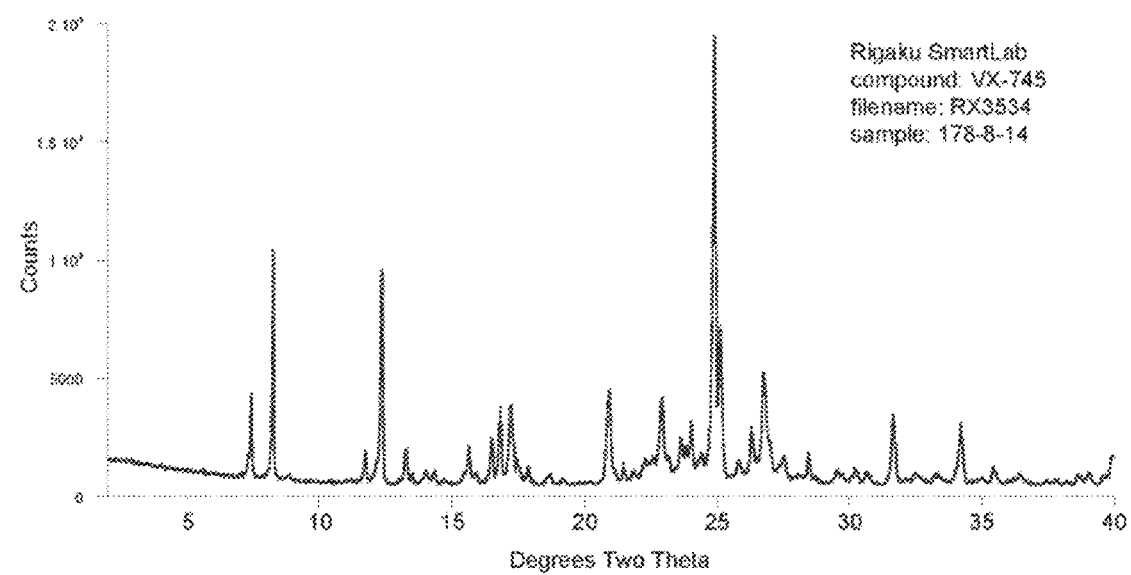
Figure 86:
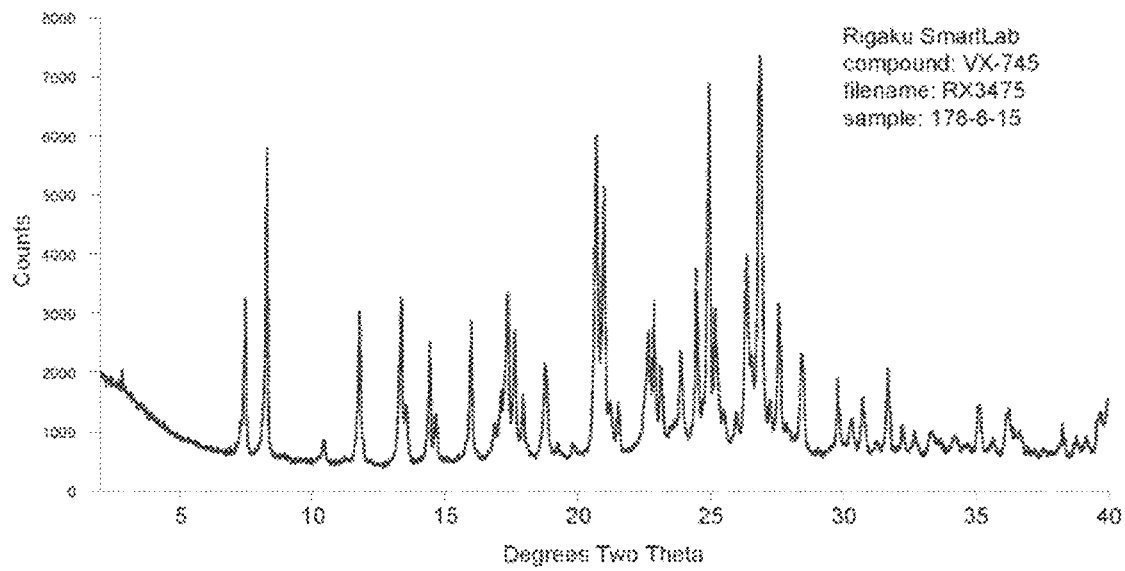
Figure 87:
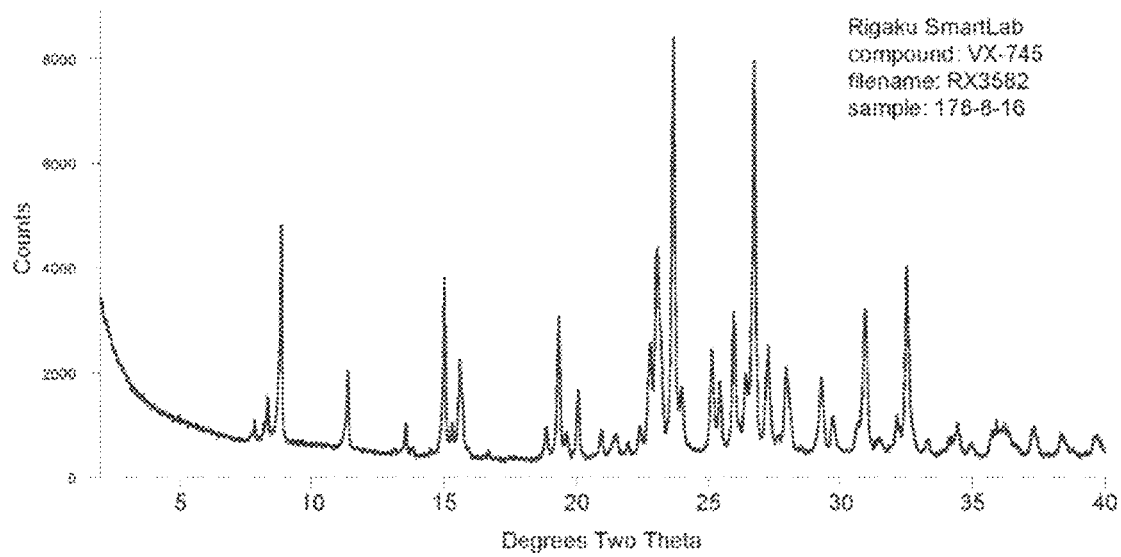
Figure 88:
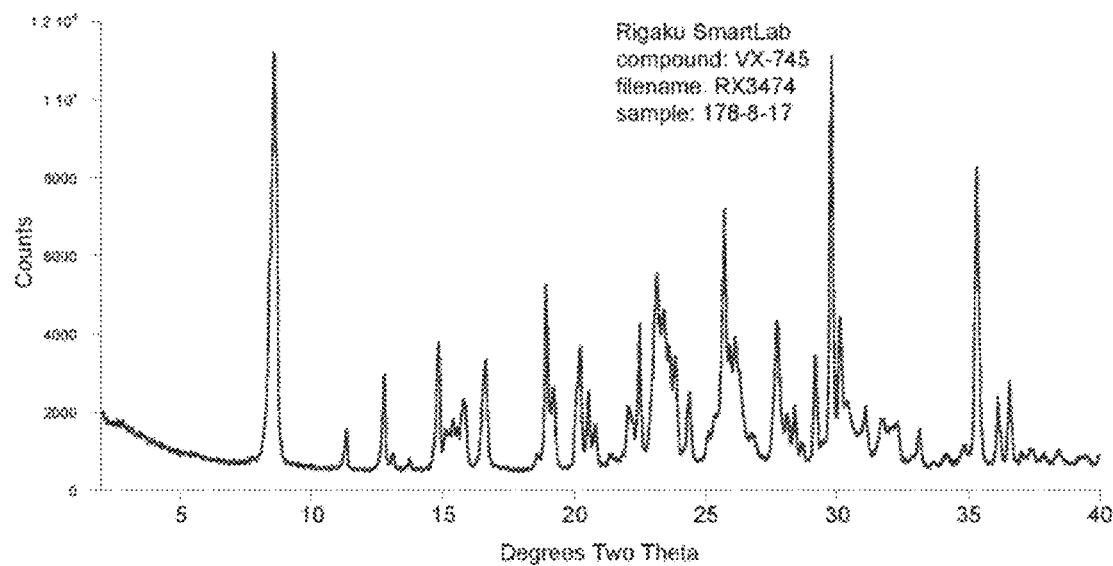
Figure 89:
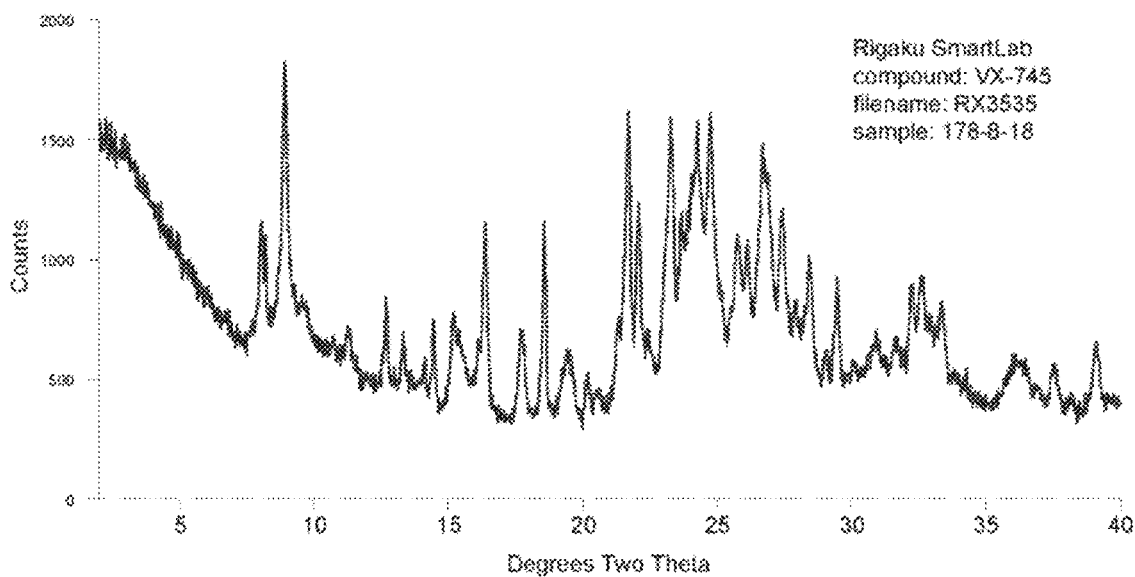
Figure 90:
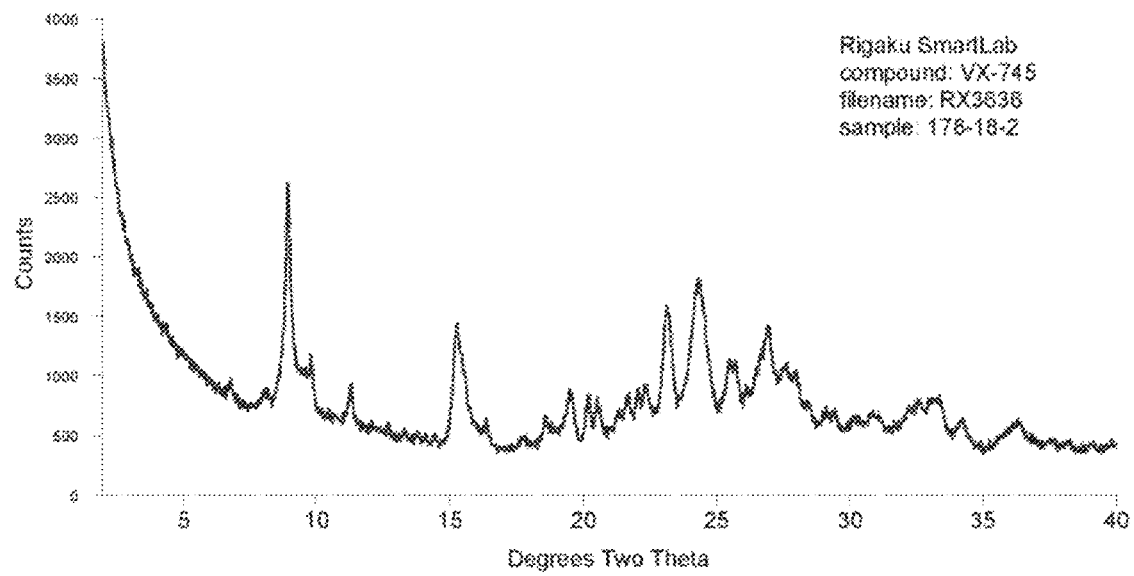
Figure 91:
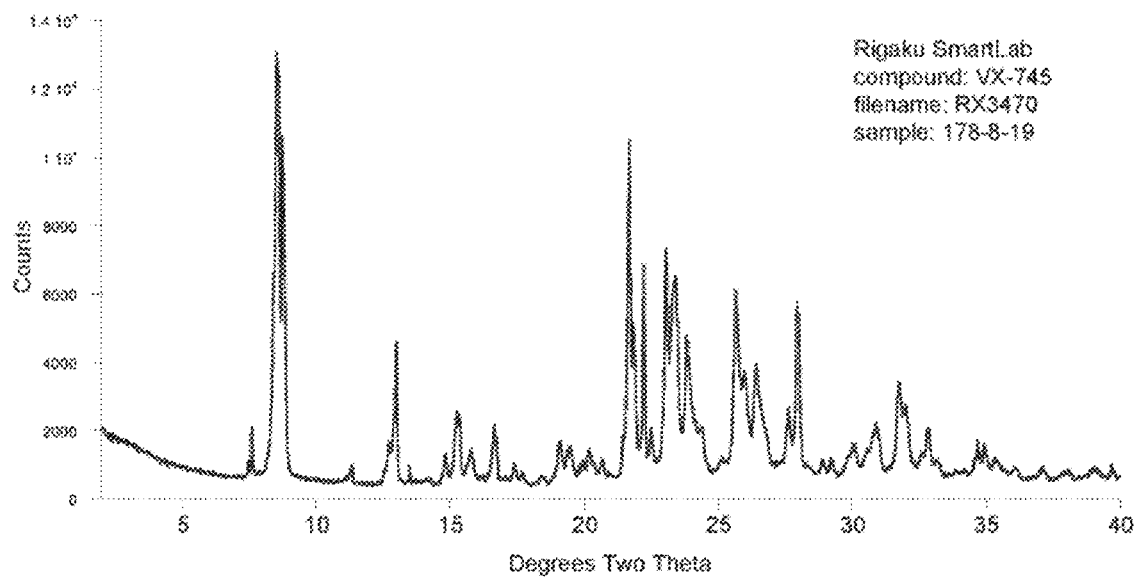
Figure 92:
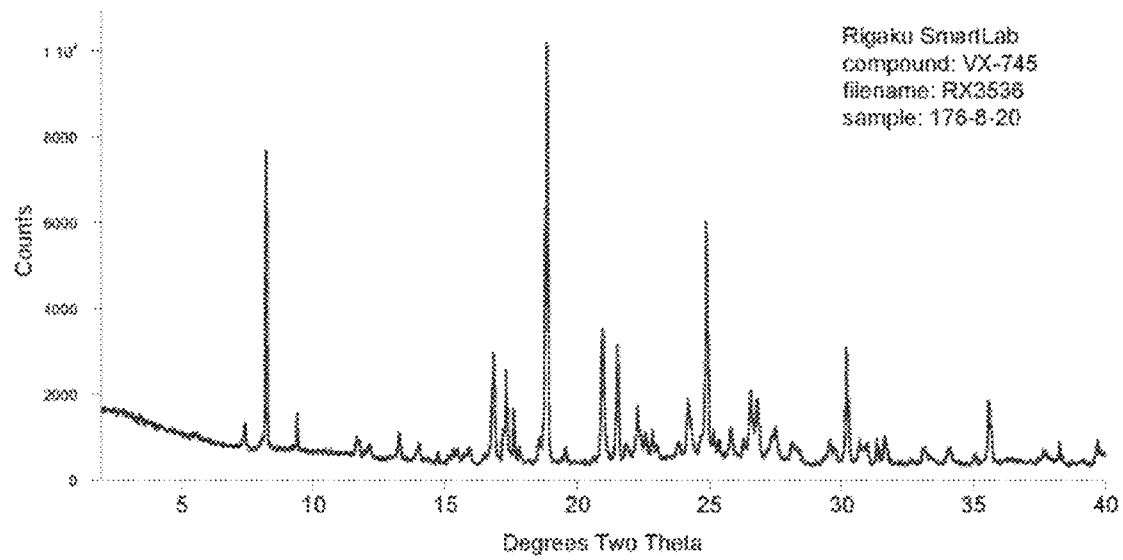
Figure 93:
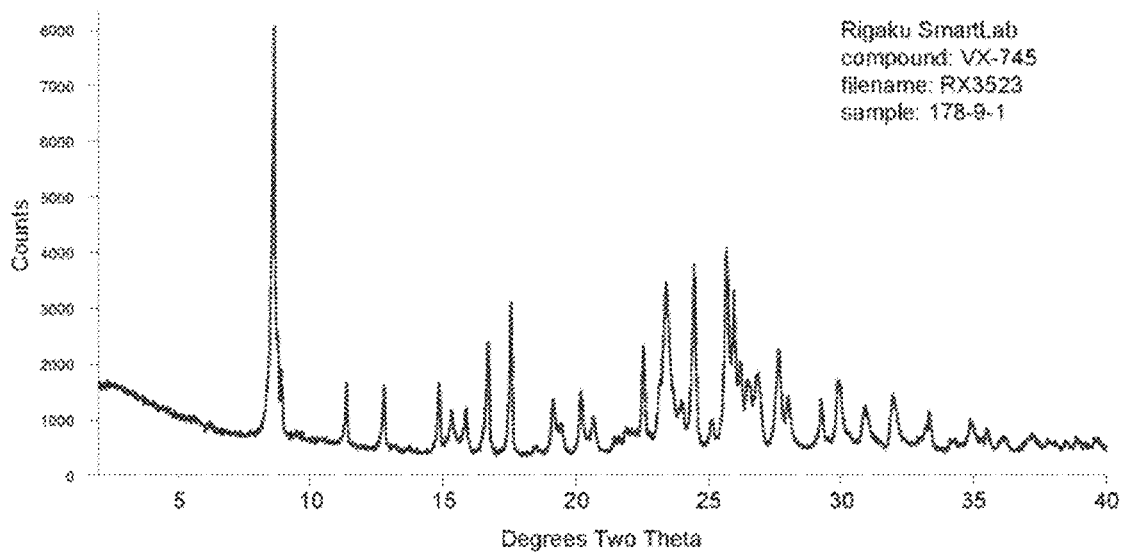
Figure 94:
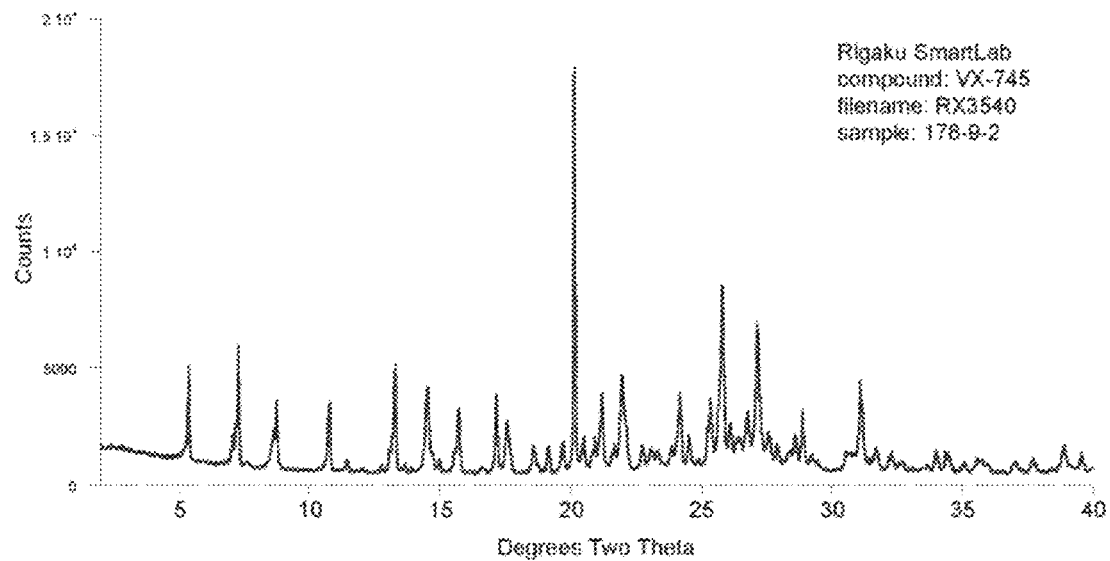
Figure 95:
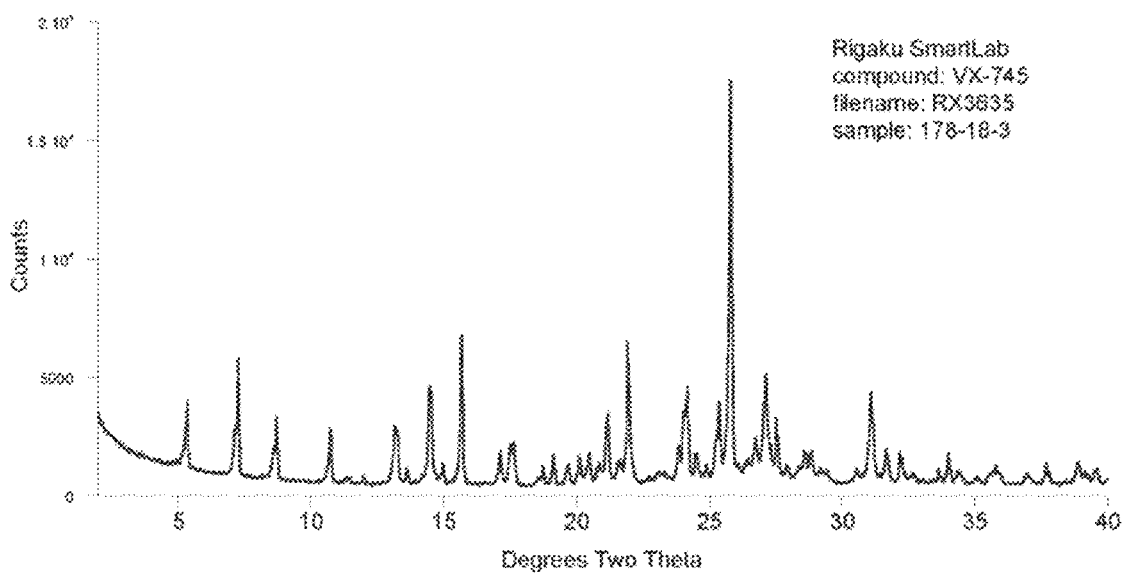
Figure 96:
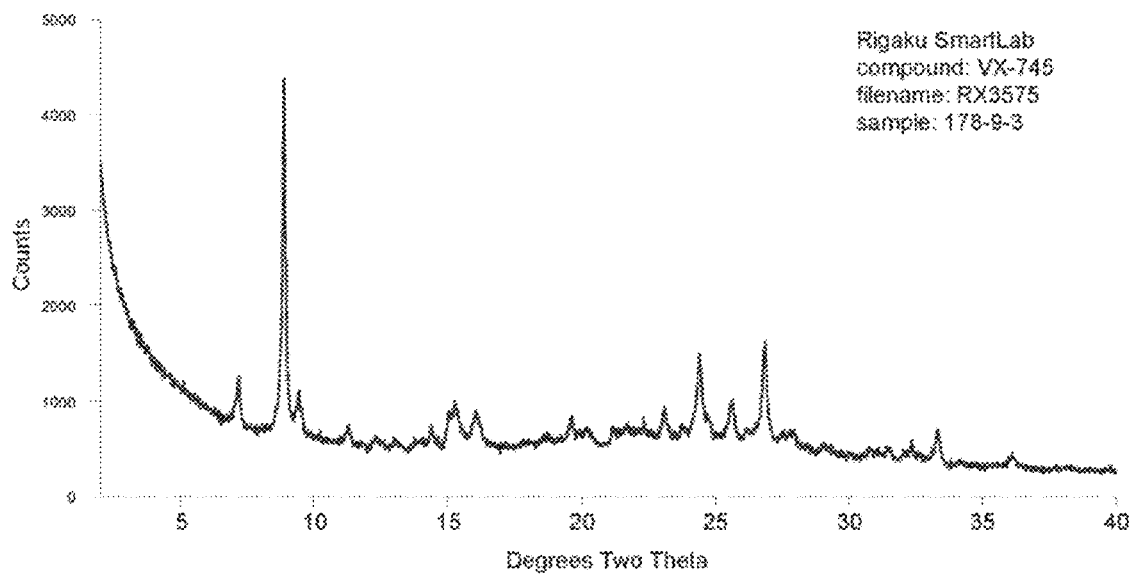
Figure 97:
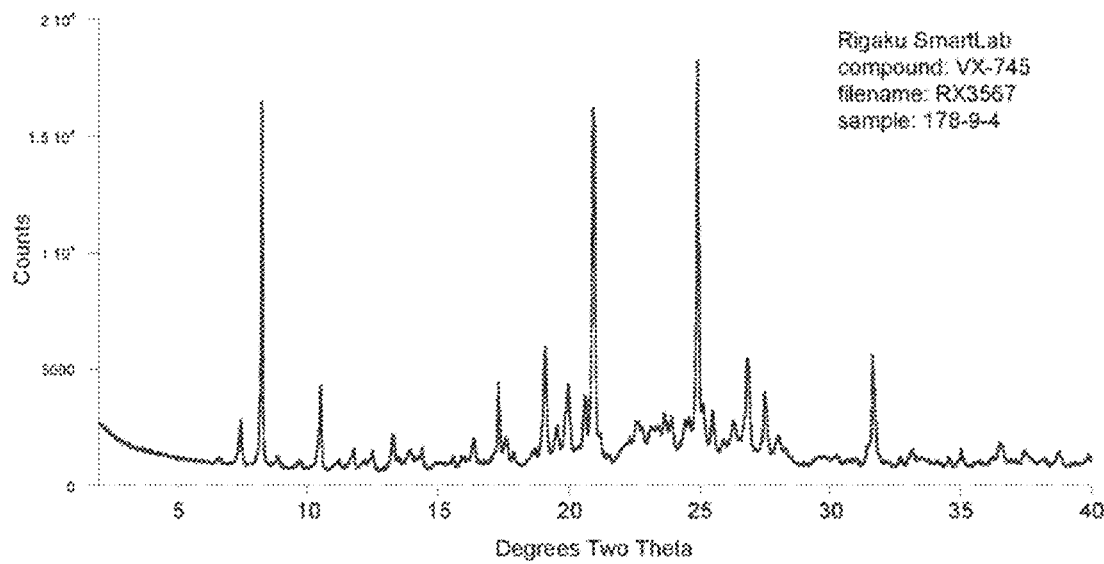
Figure 98:
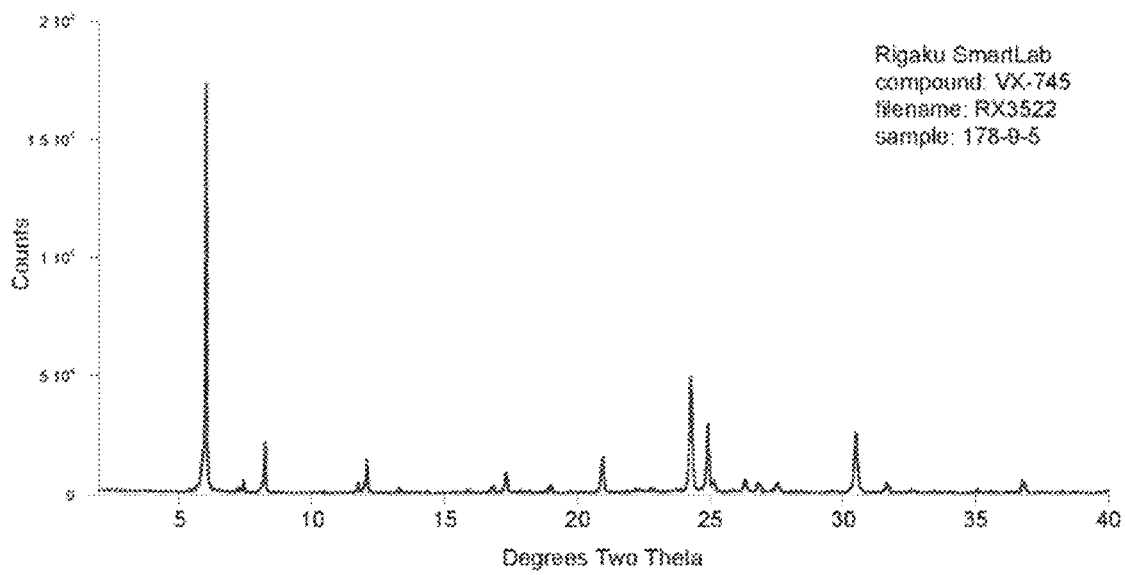
Figure 99:
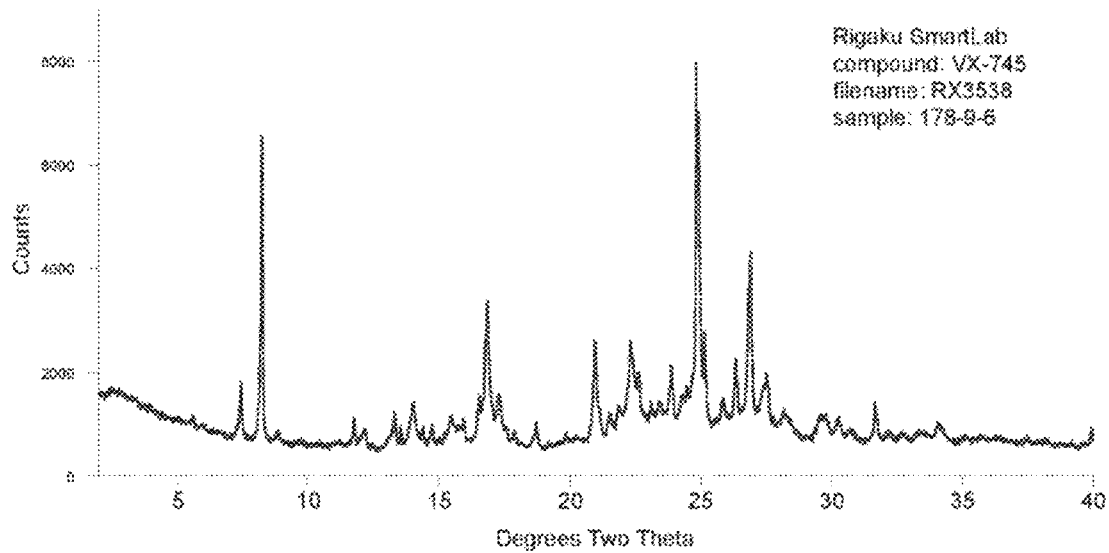
Figure 100:
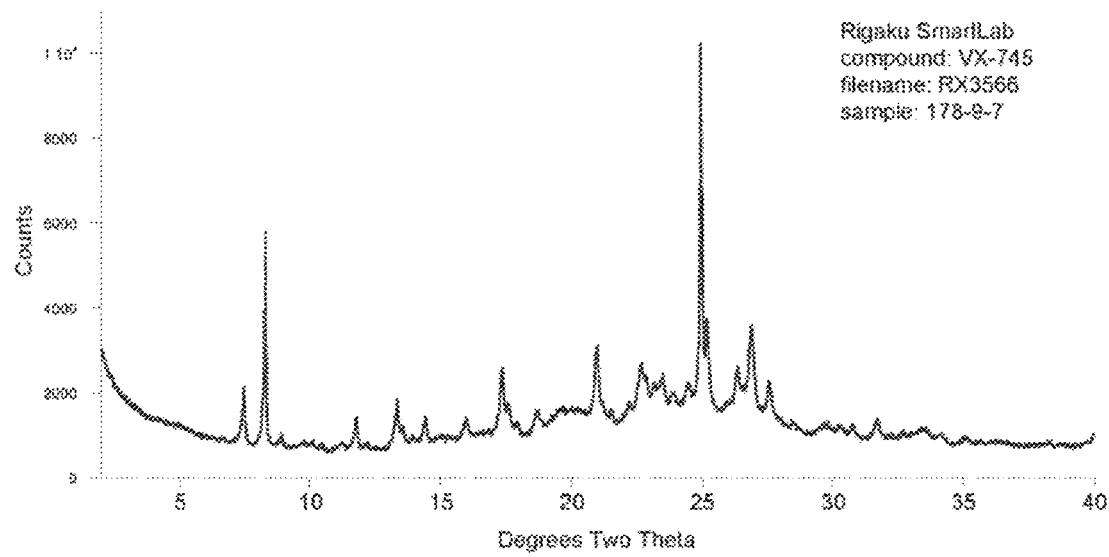
Figure 101:
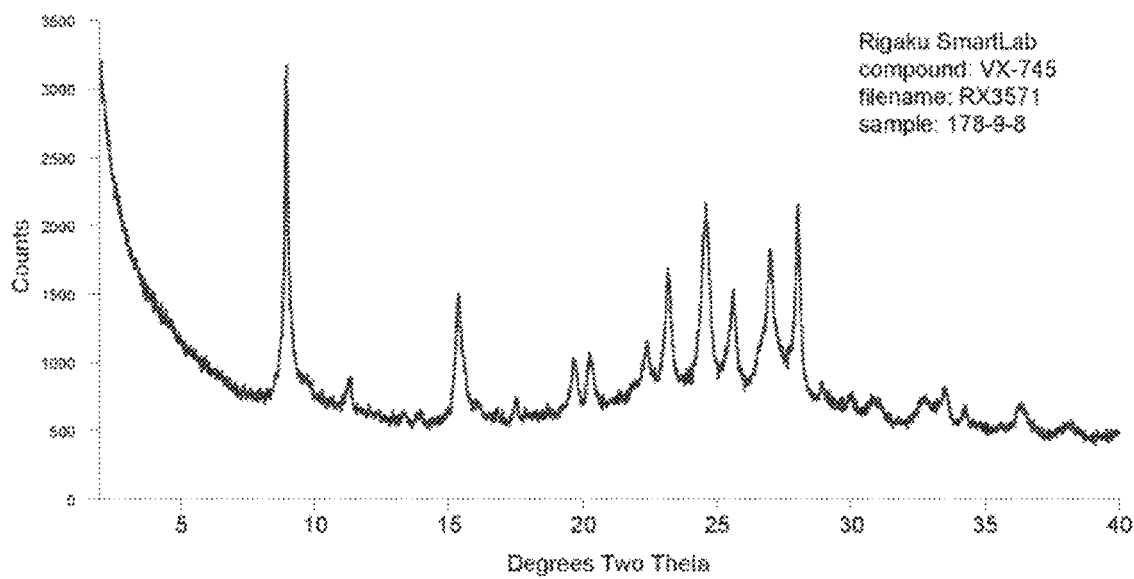
Figure 102:
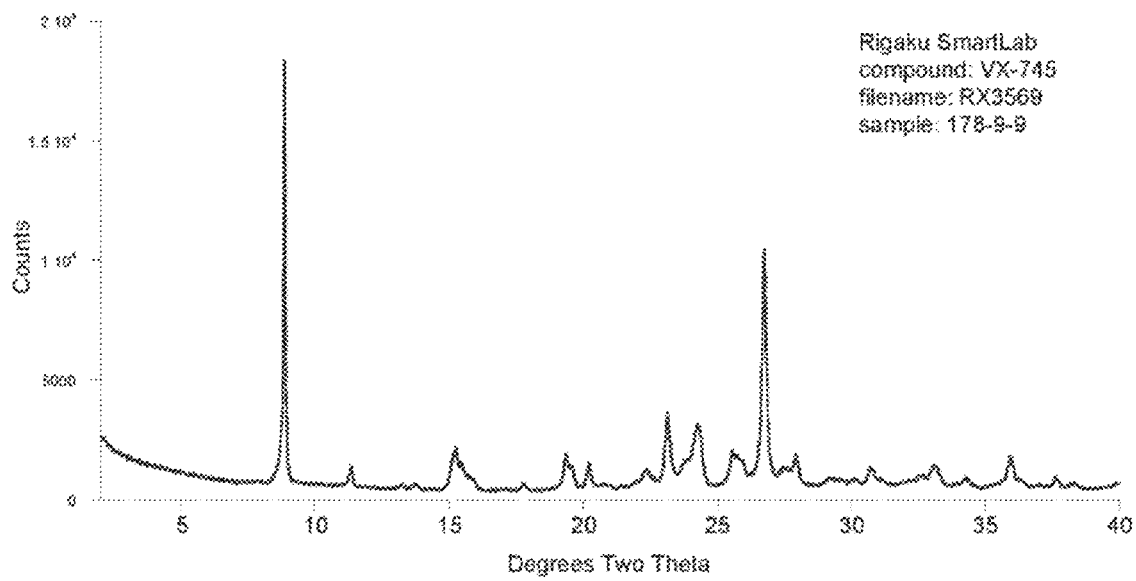
Figure 103:
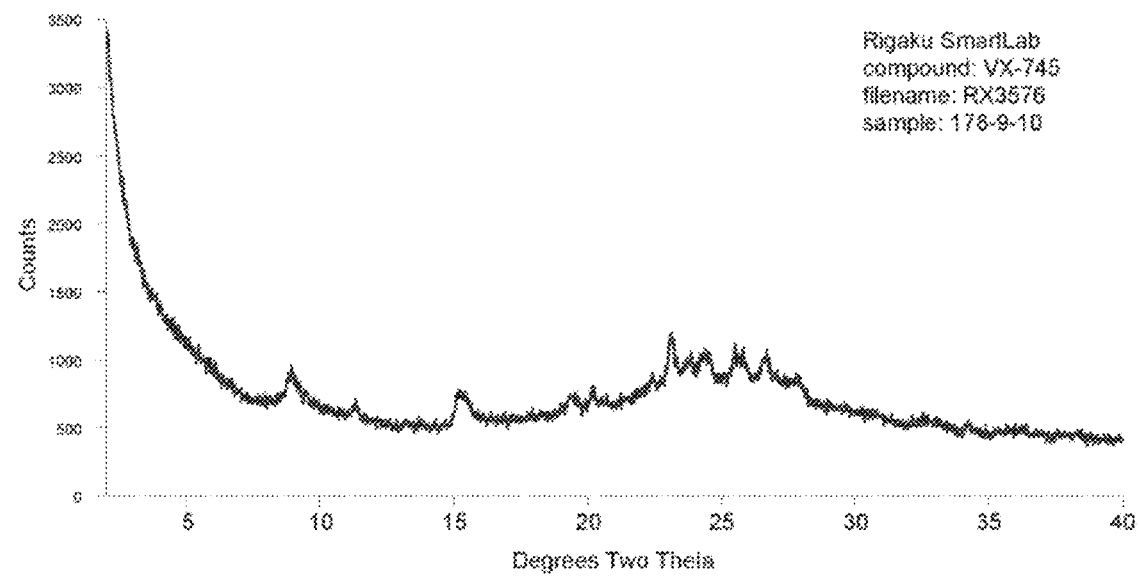
Figure 104:
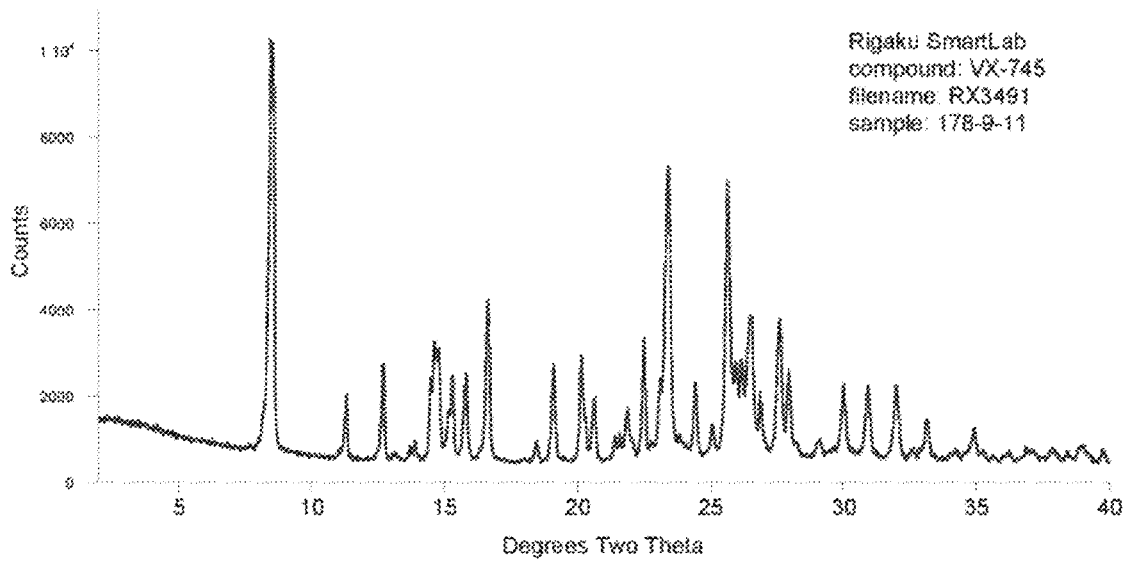
Figure 105:
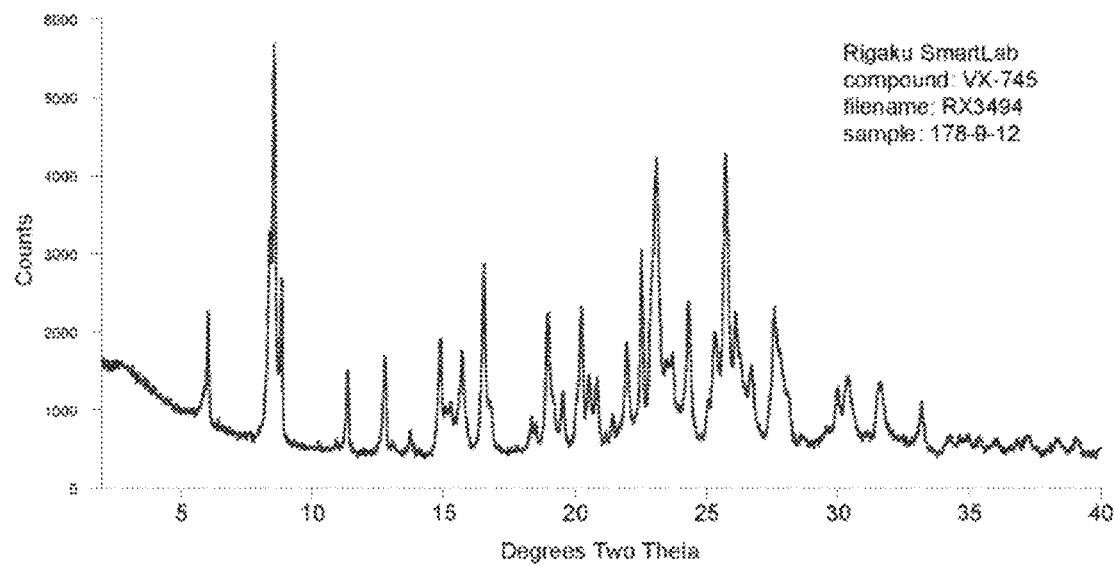
Figure 106:
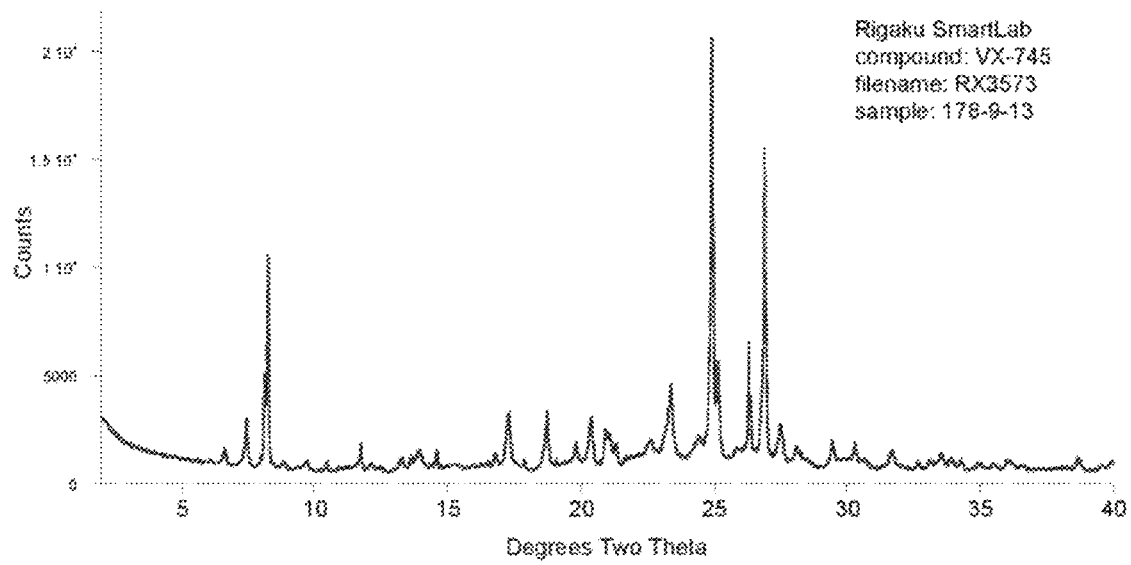
Figure 107:
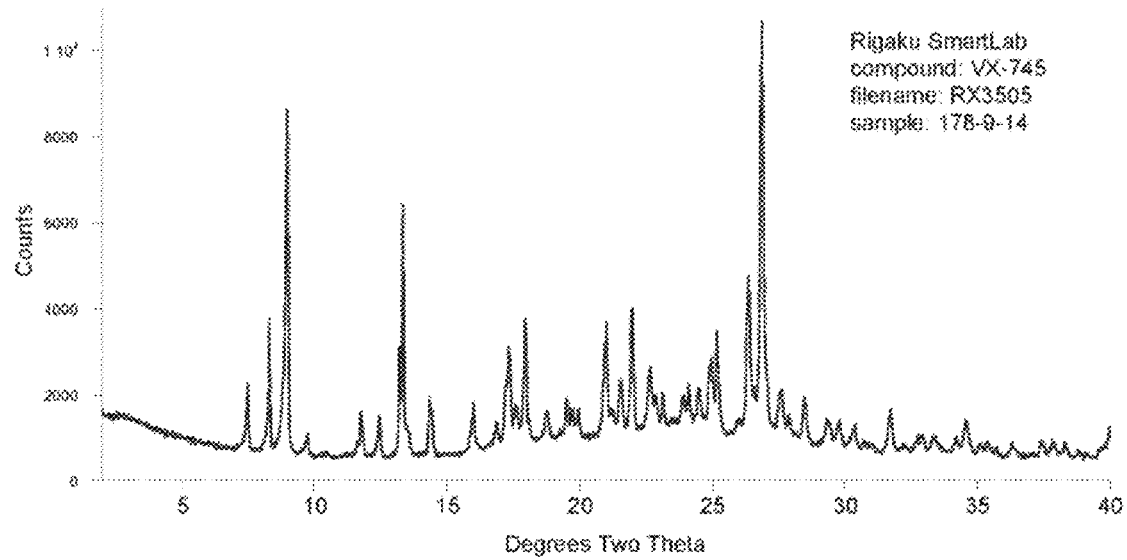
Figure 108:
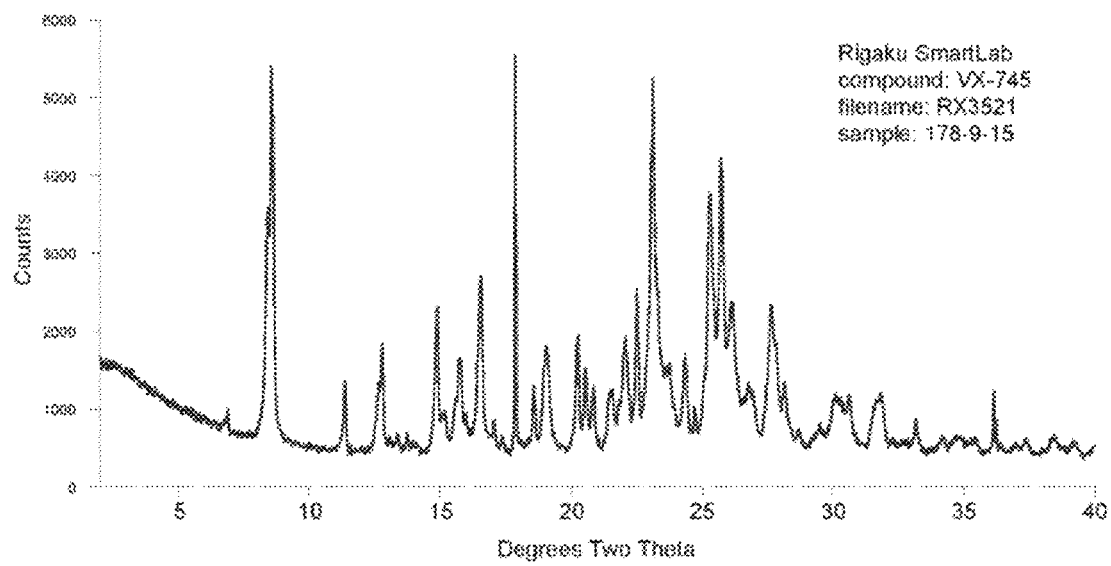
Figure 109:
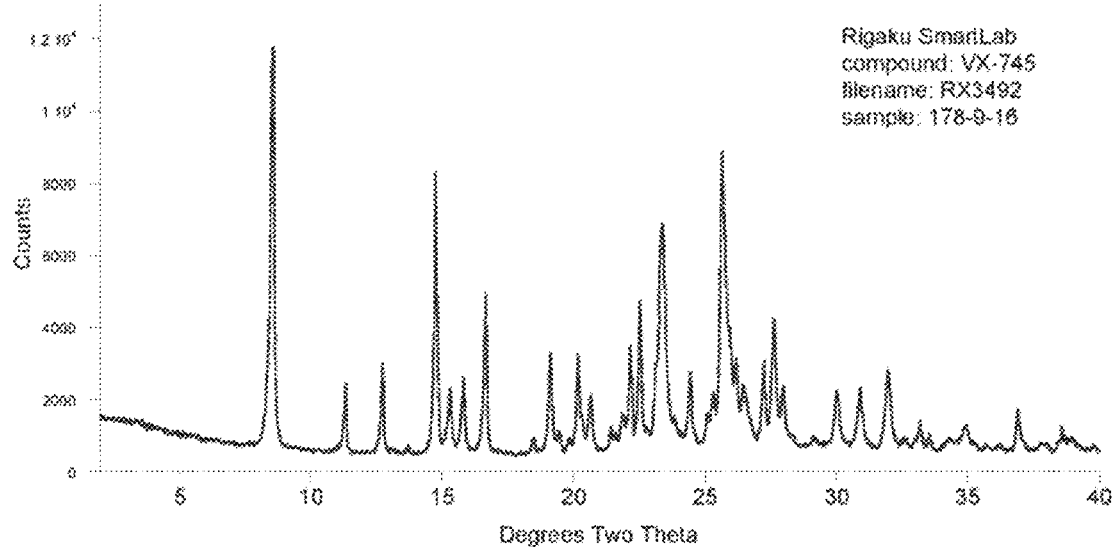
Figure 110:
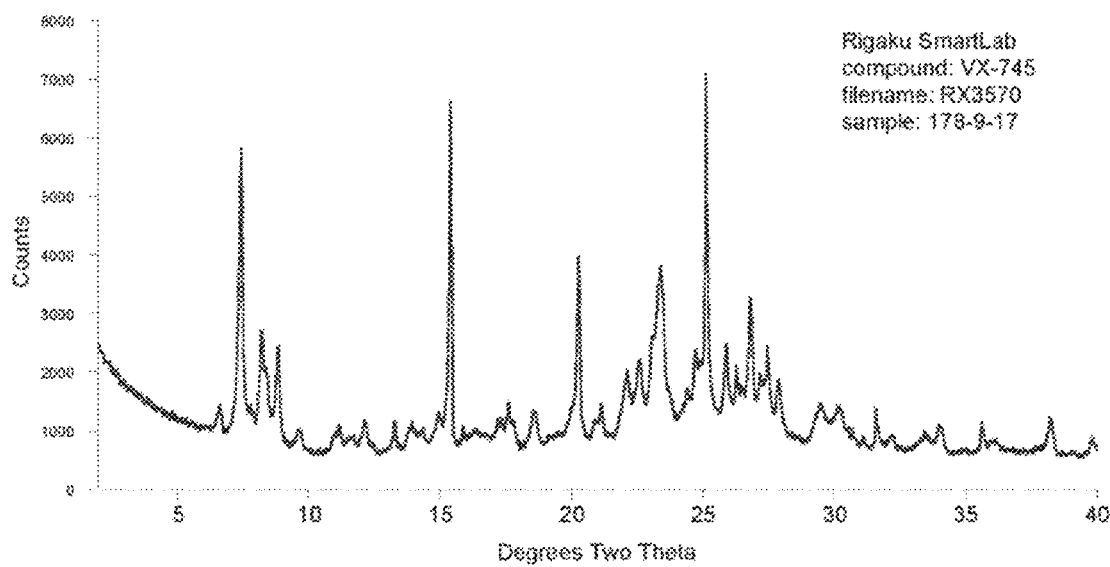
Figure 111:
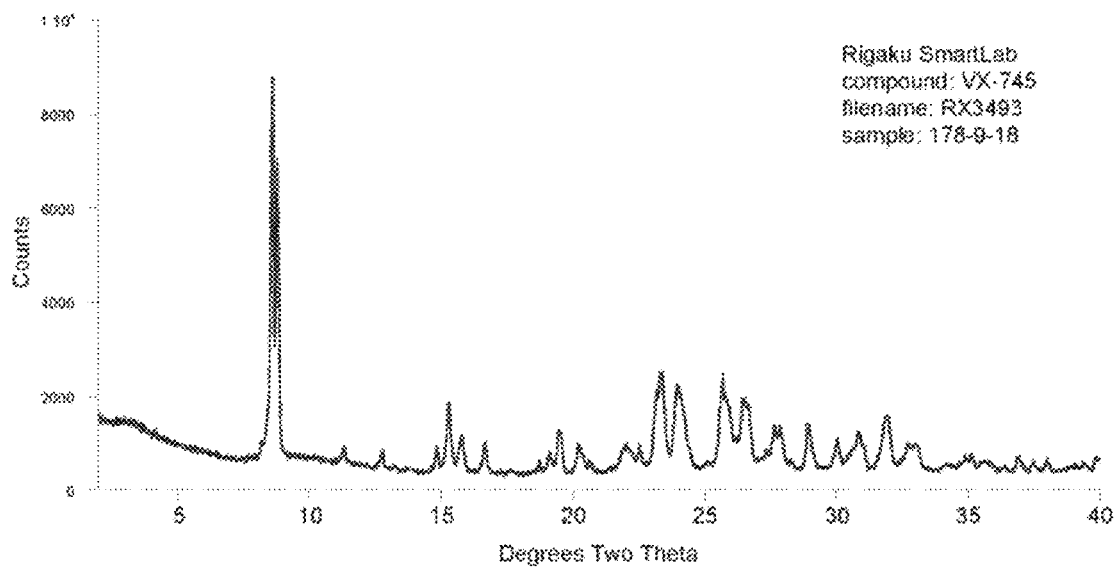
Figure 112:
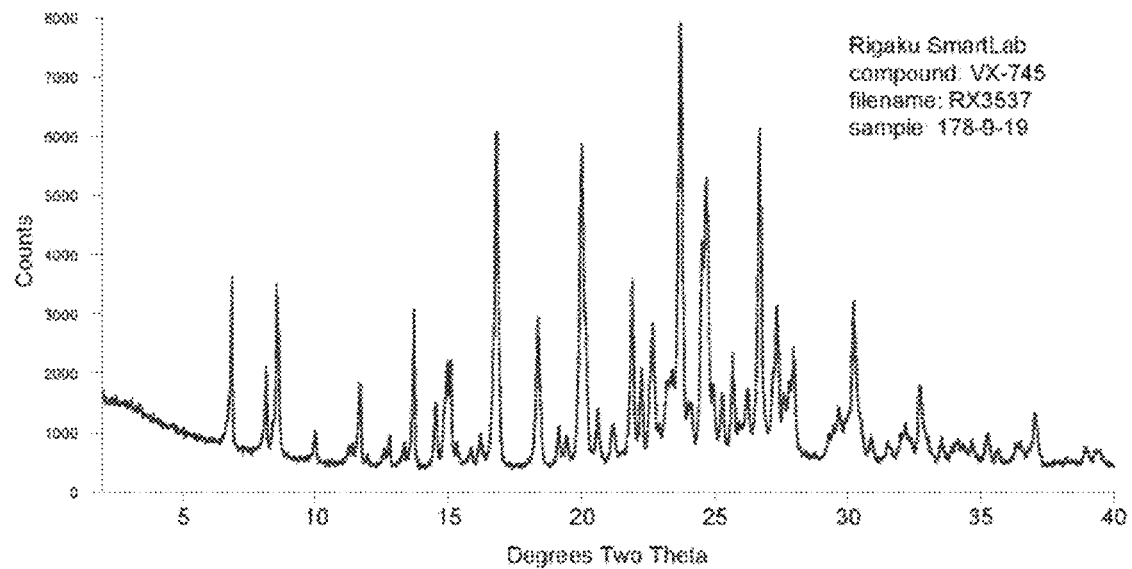
Figure 113:
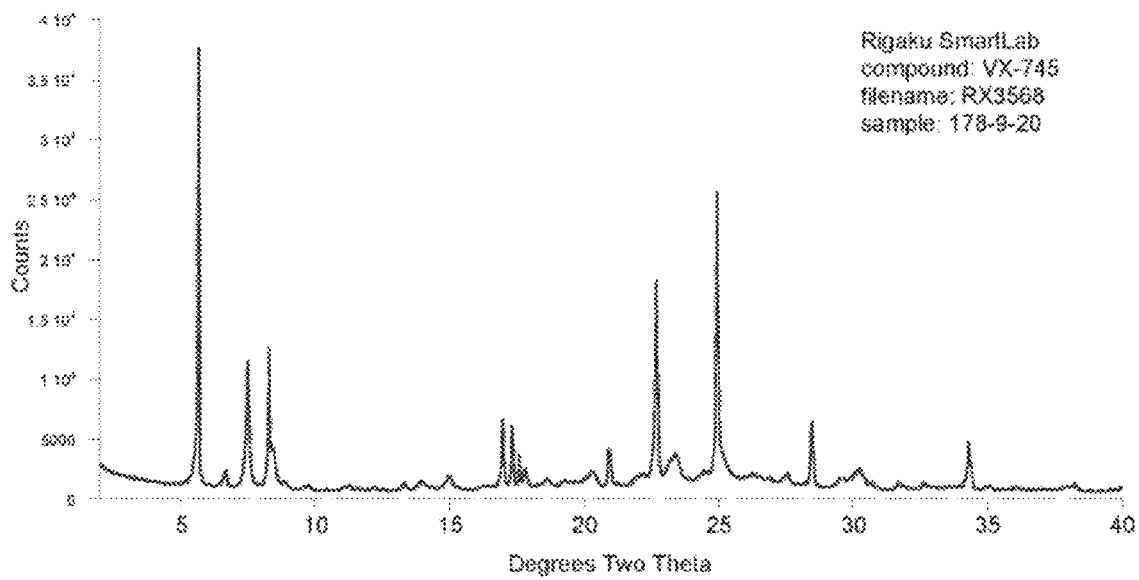
Figure 114:
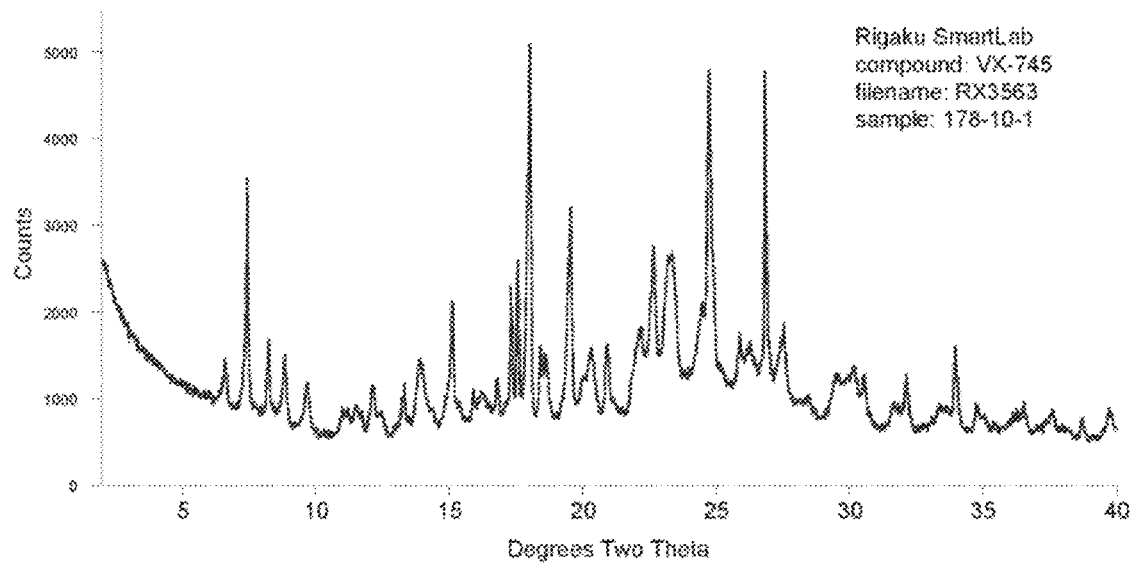
Figure 115:
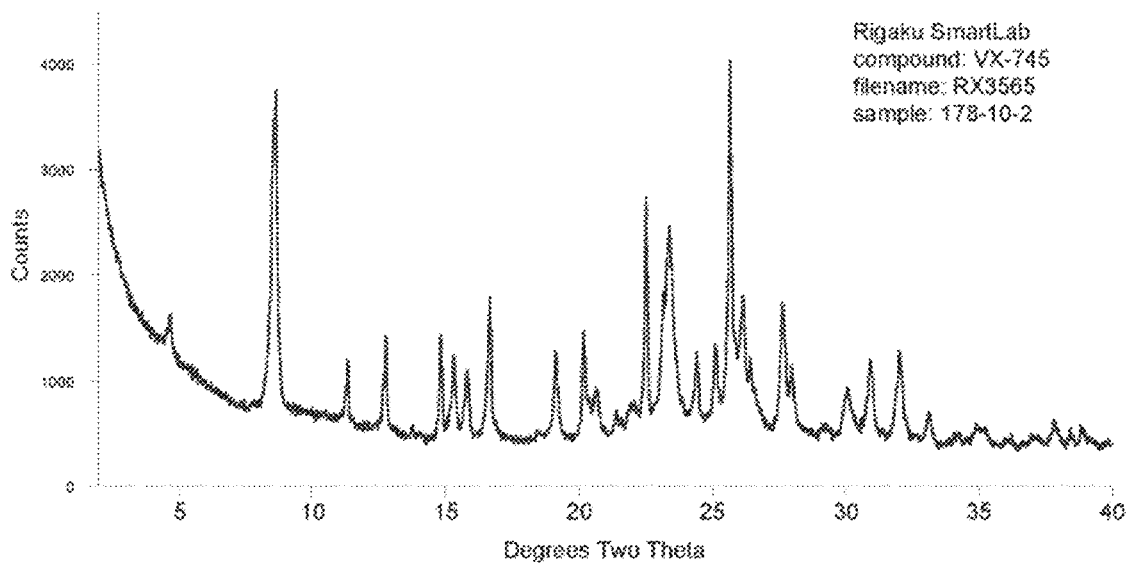
Figure 116:
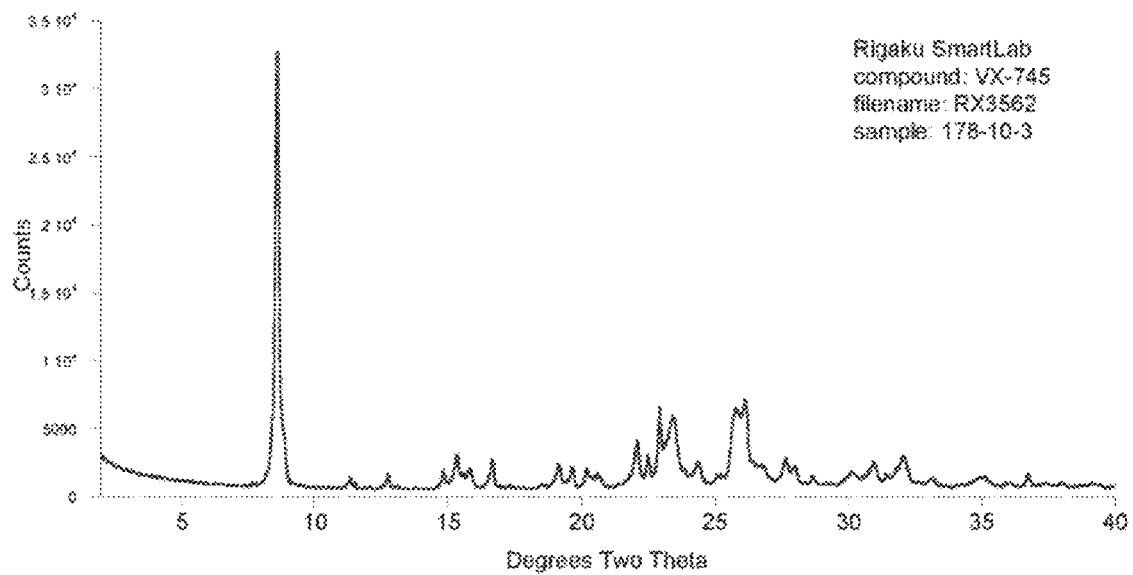
Figure 117:
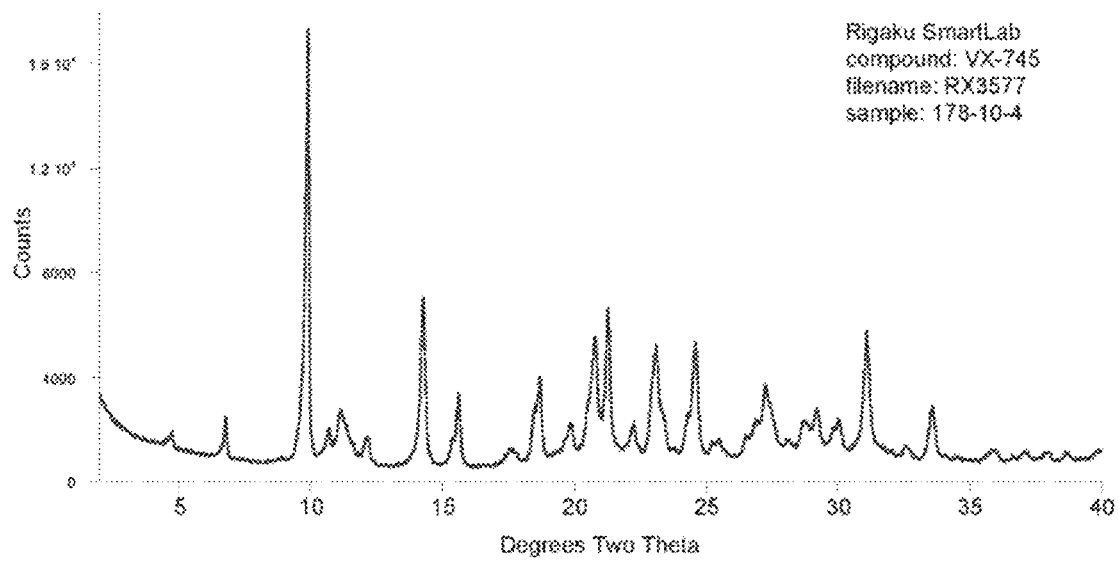
Figure 118:
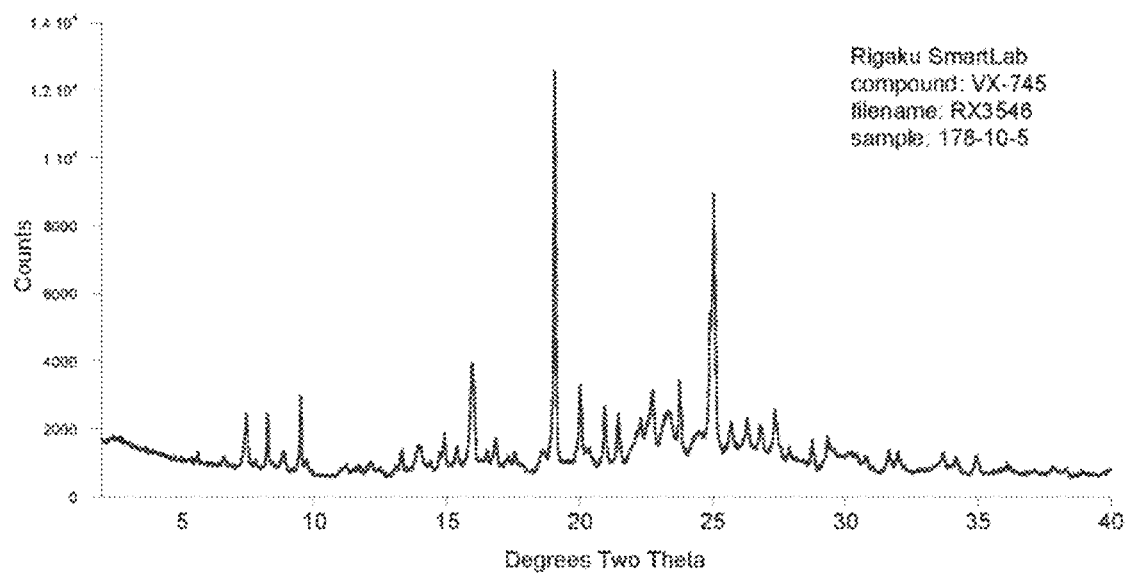
Figure 119:
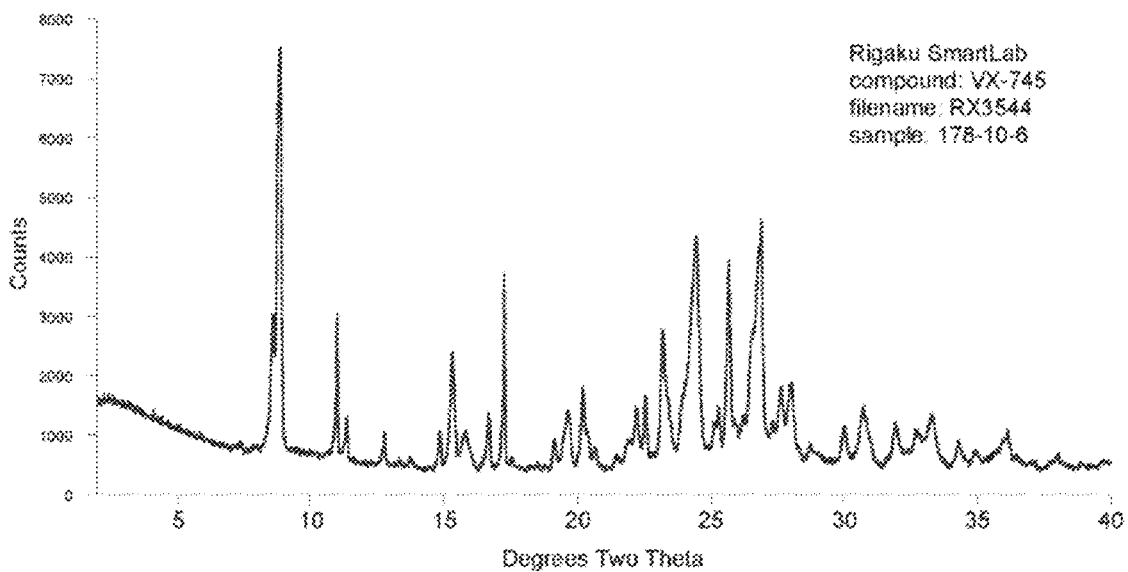
Figure 120:
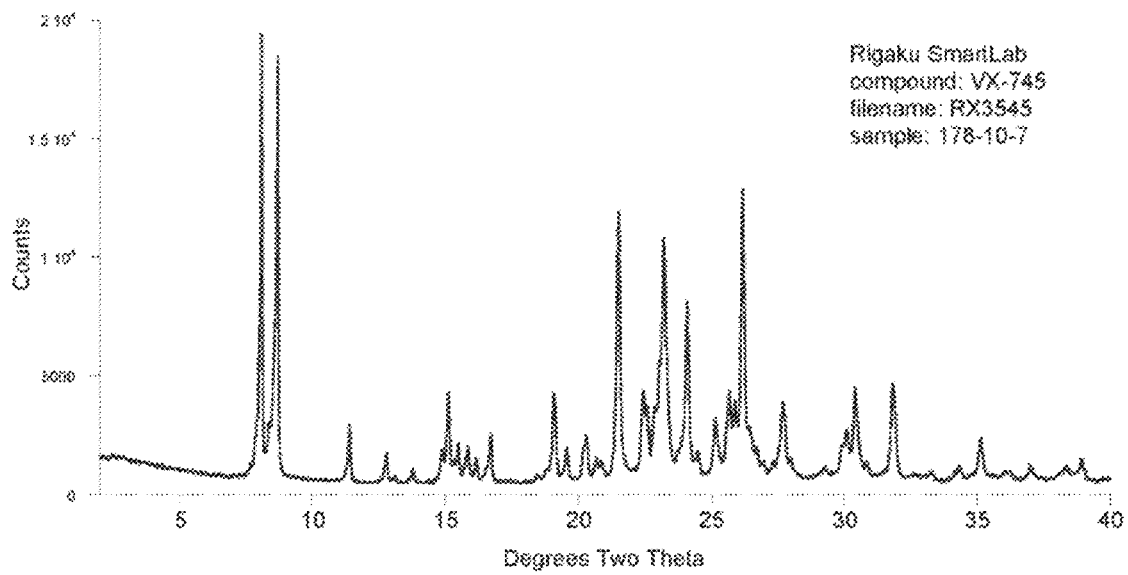
Figure 121:
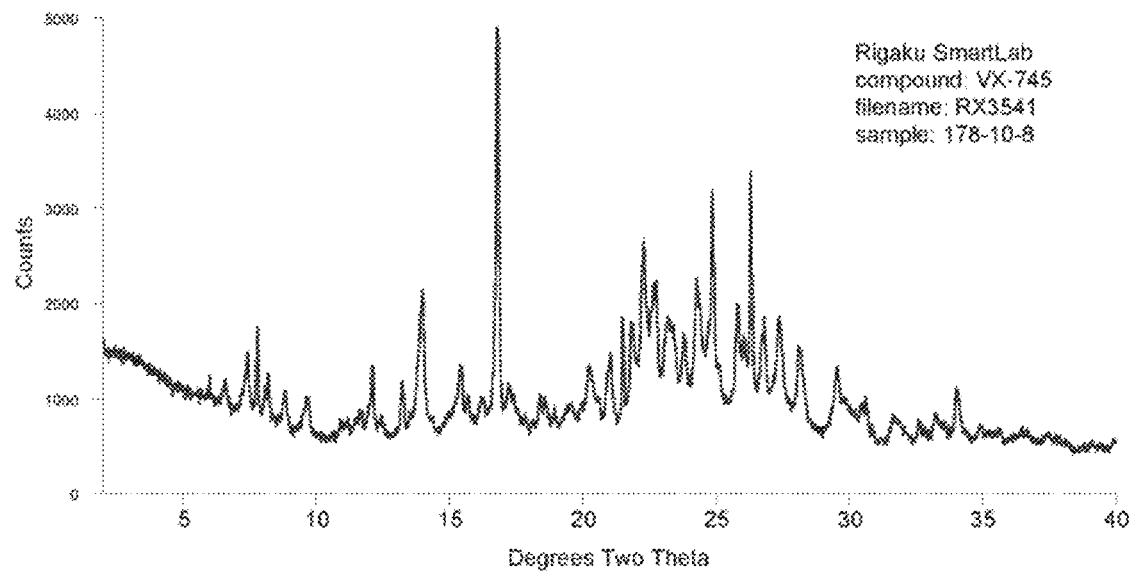
Figure 122:
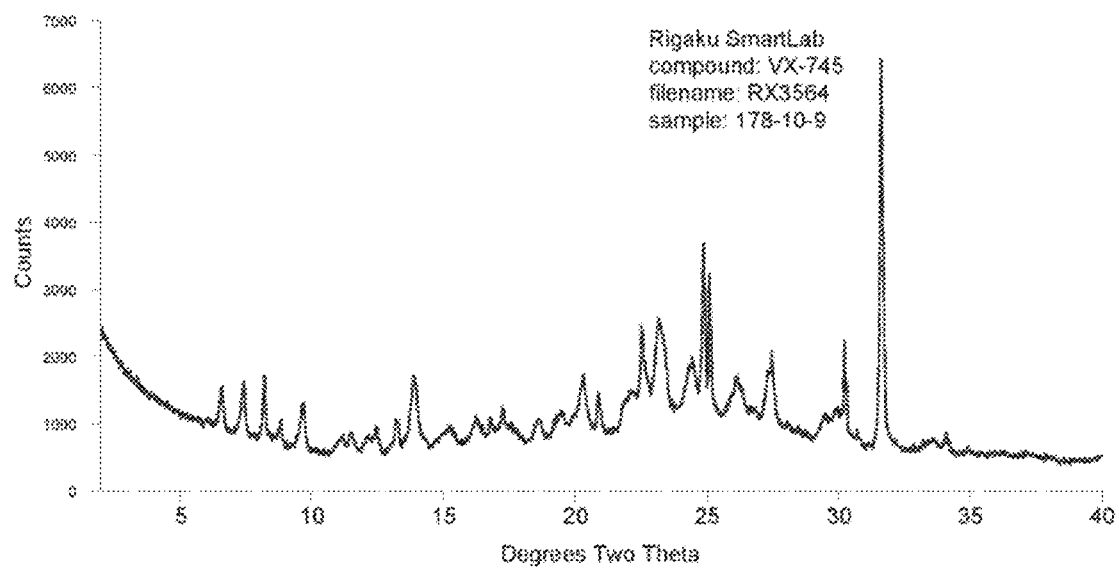
Figure 123:
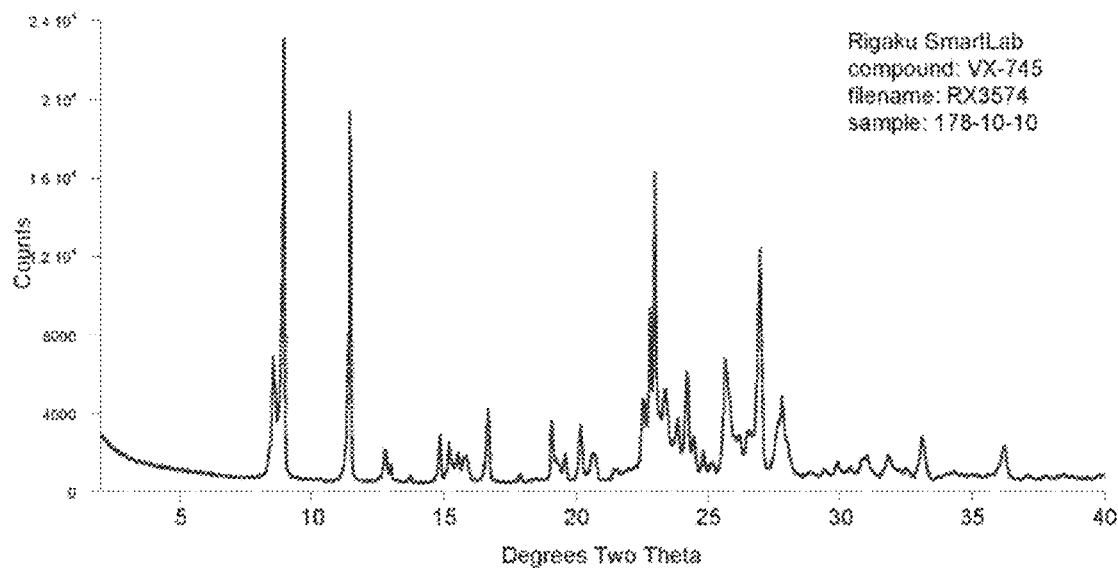
Figure 124:
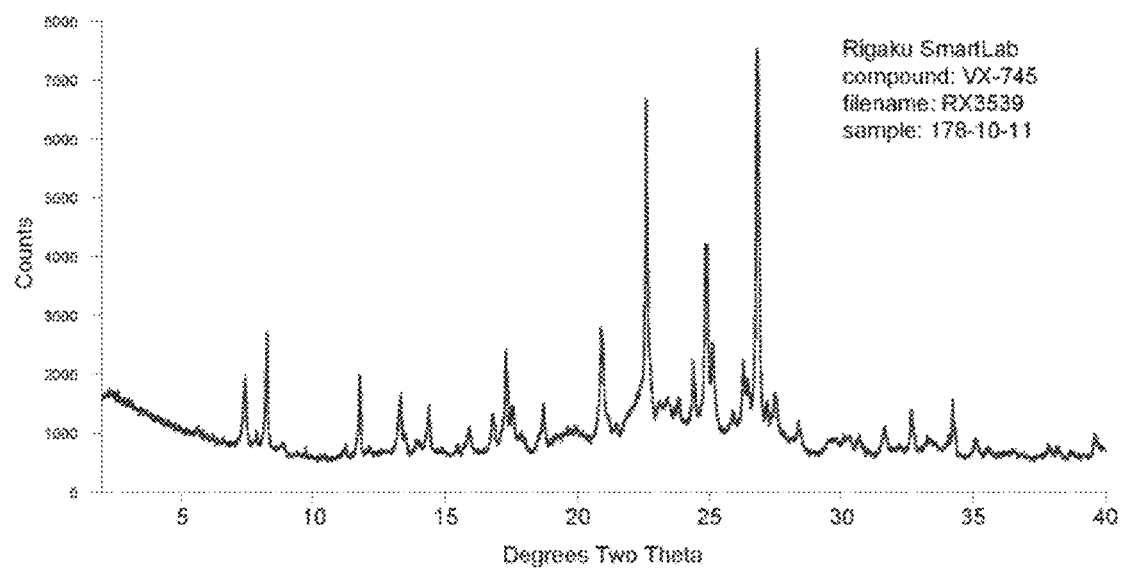
Figure 125:
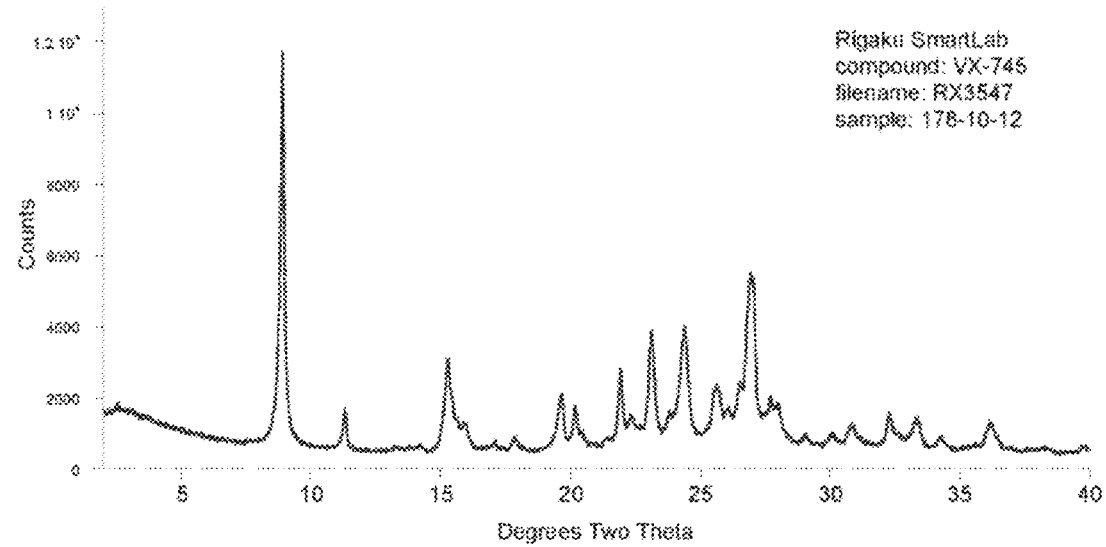
Figure 126:
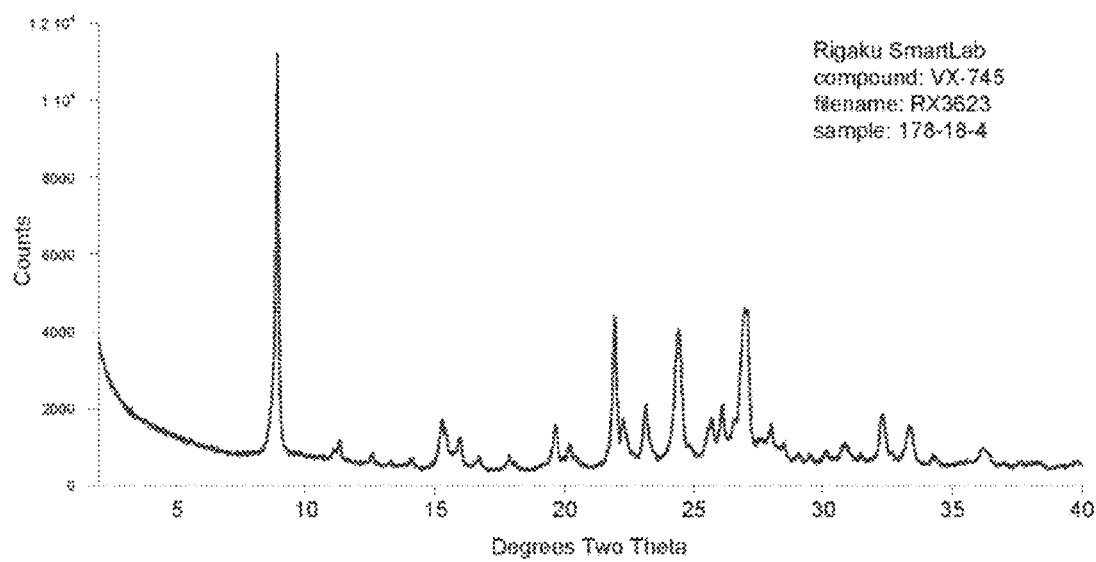
Figure 127:
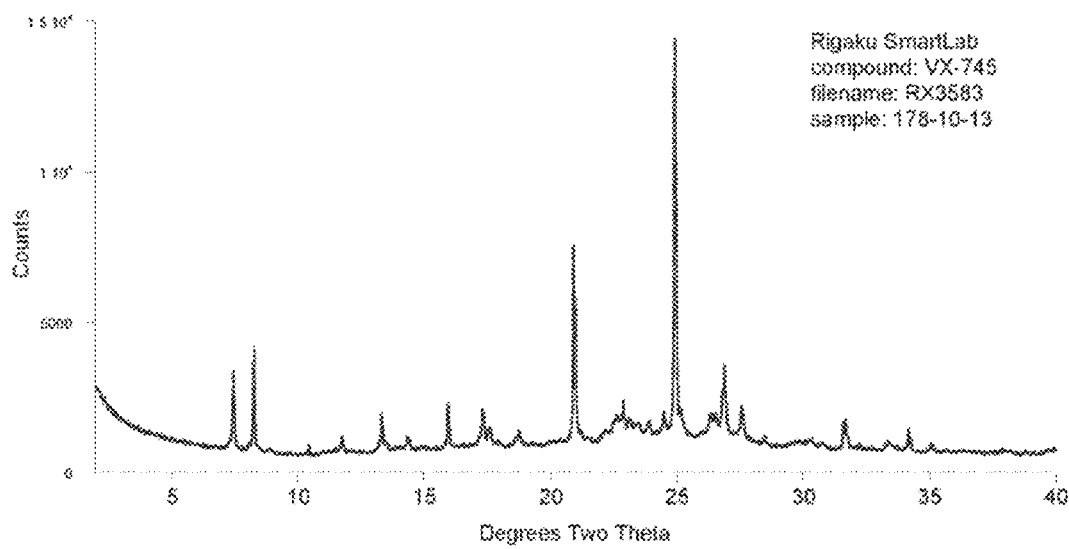
Figure 128:
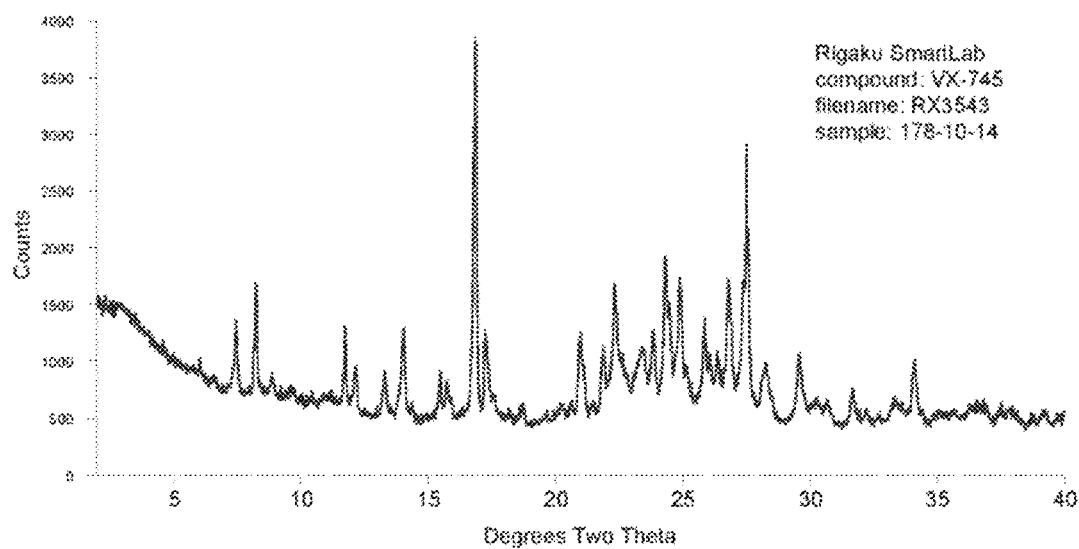
Figure 129:
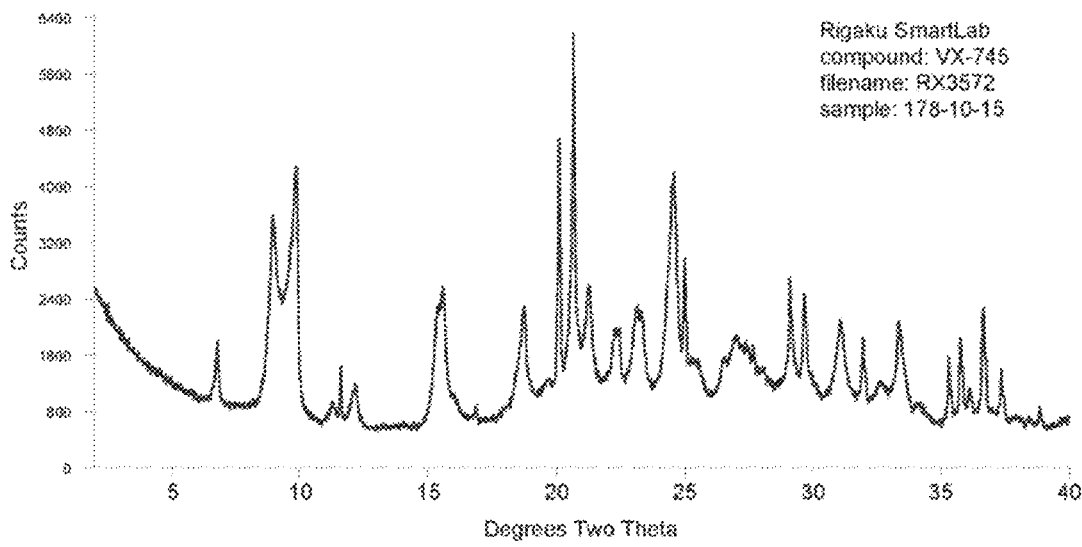
Figure 130:
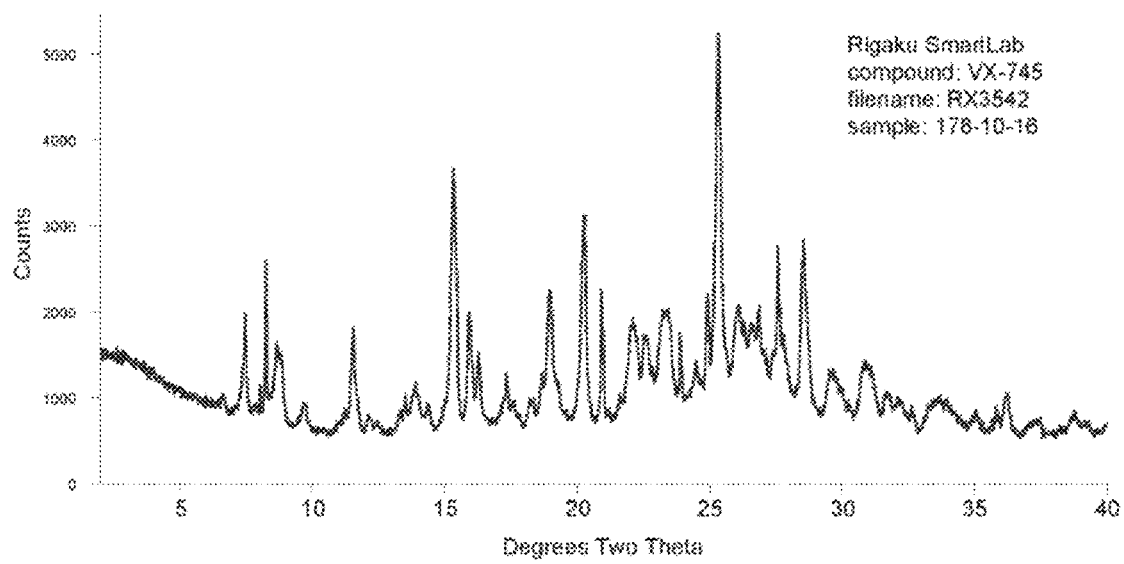
Figure 131:
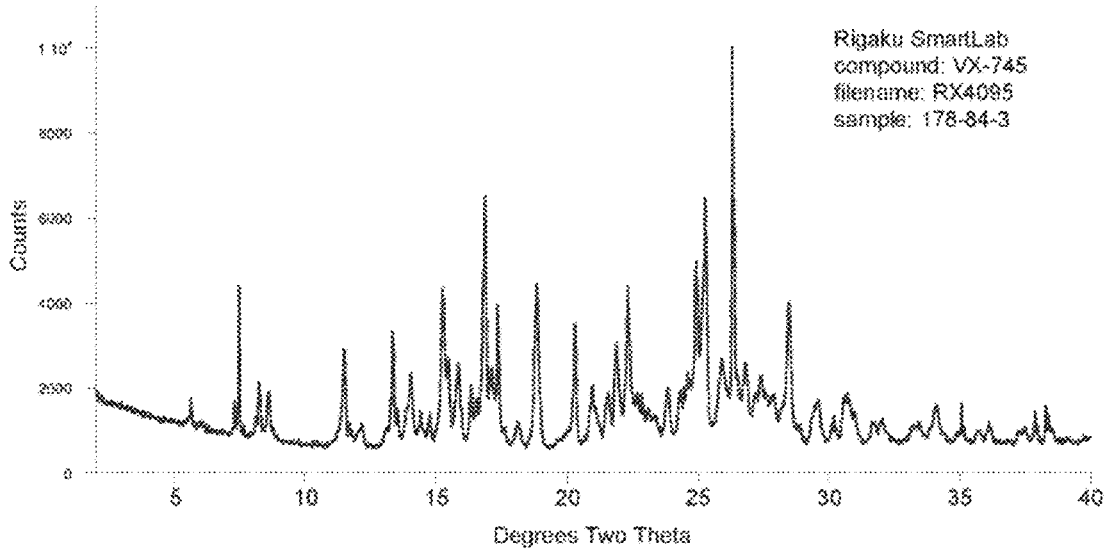
Figure 132:
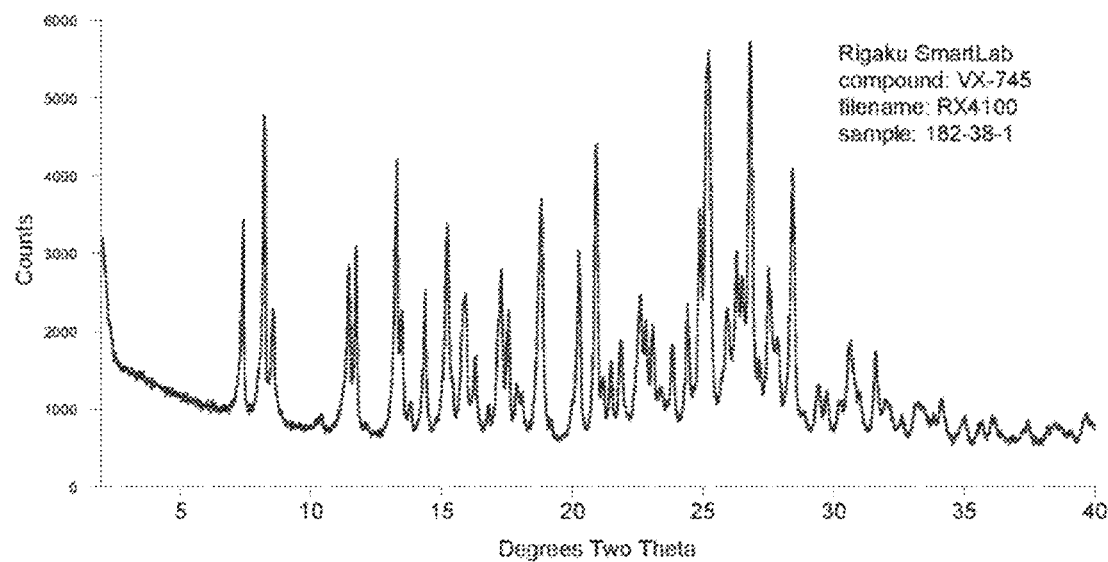
Figure 133:
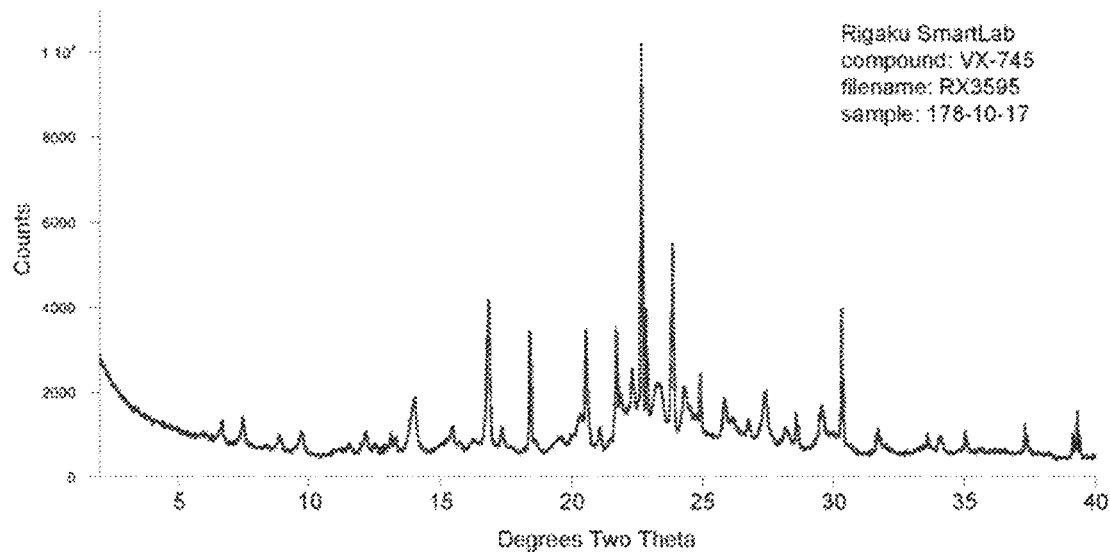
Figure 134:
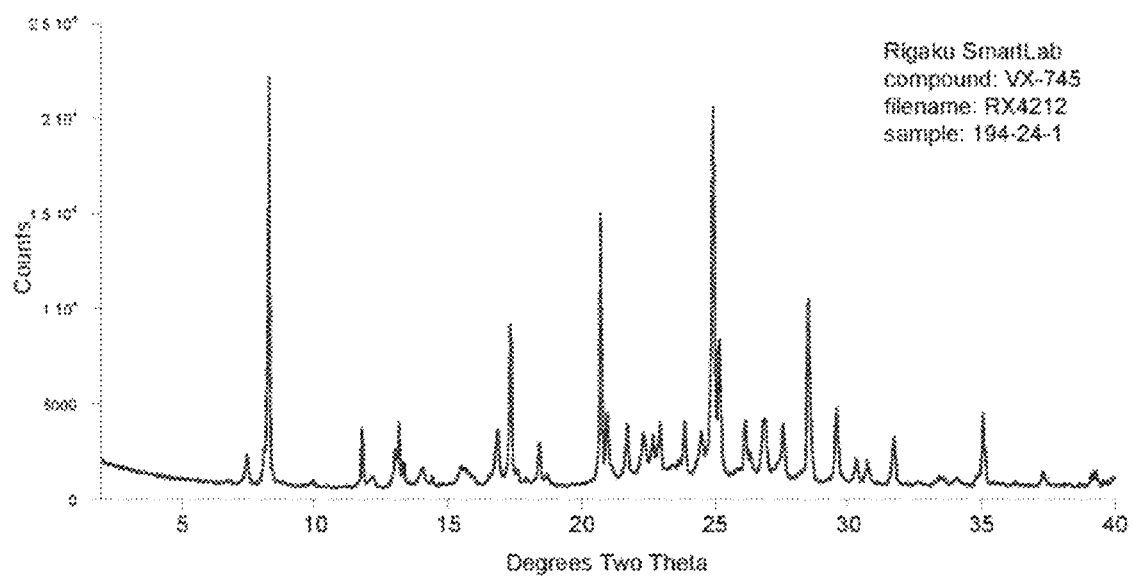
Figure 135:
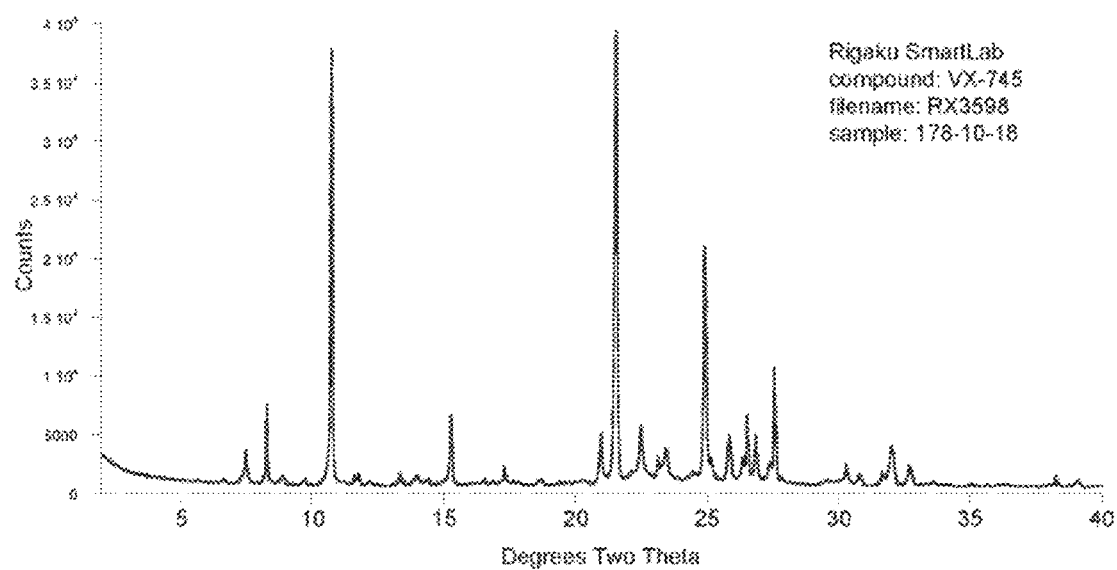
Figure 136:
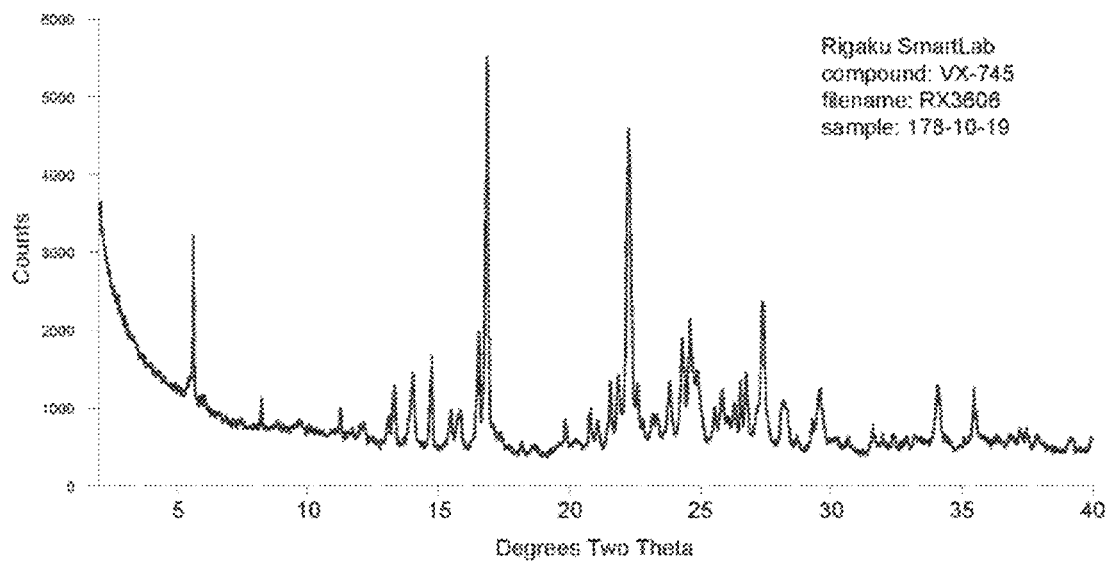
Figure 137:
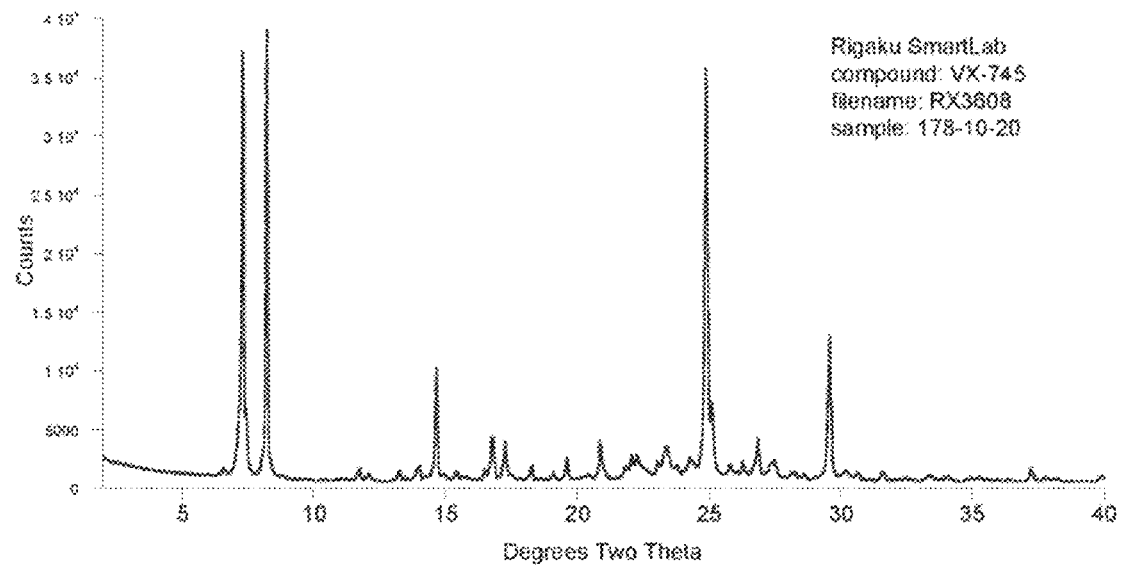
Figure 138:
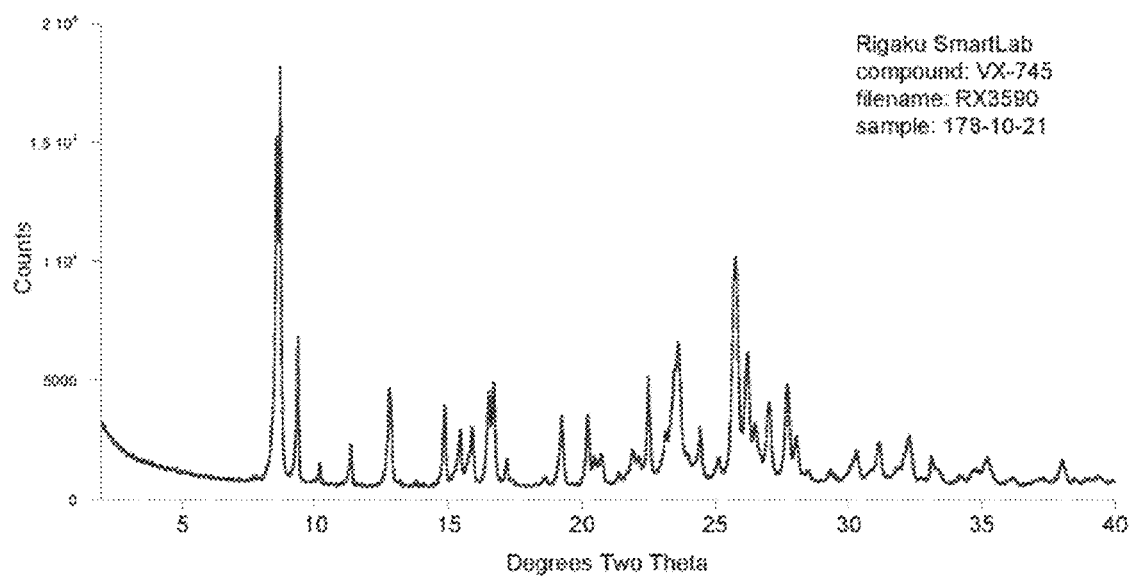
Figure 139:
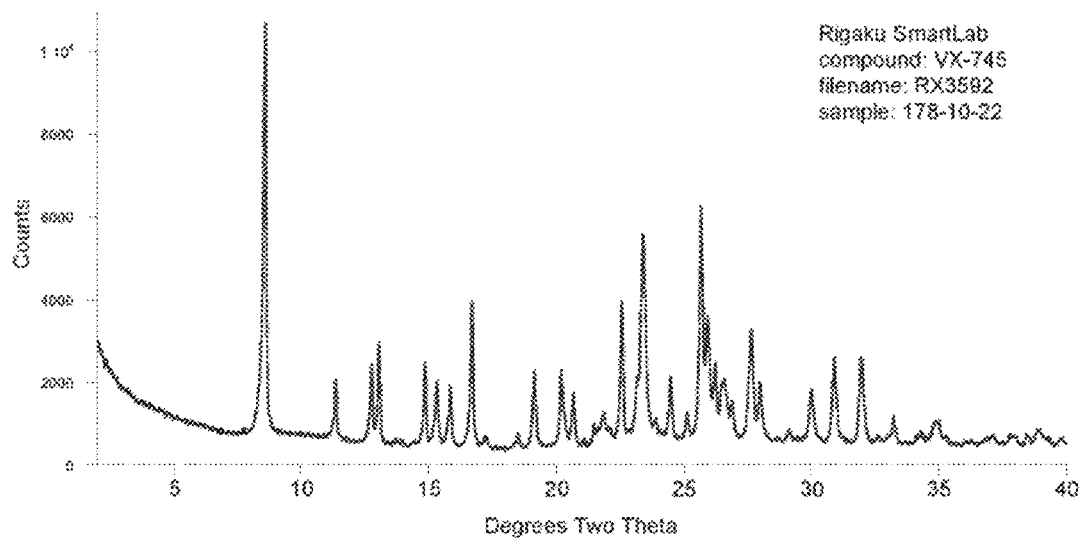
Figure 140:
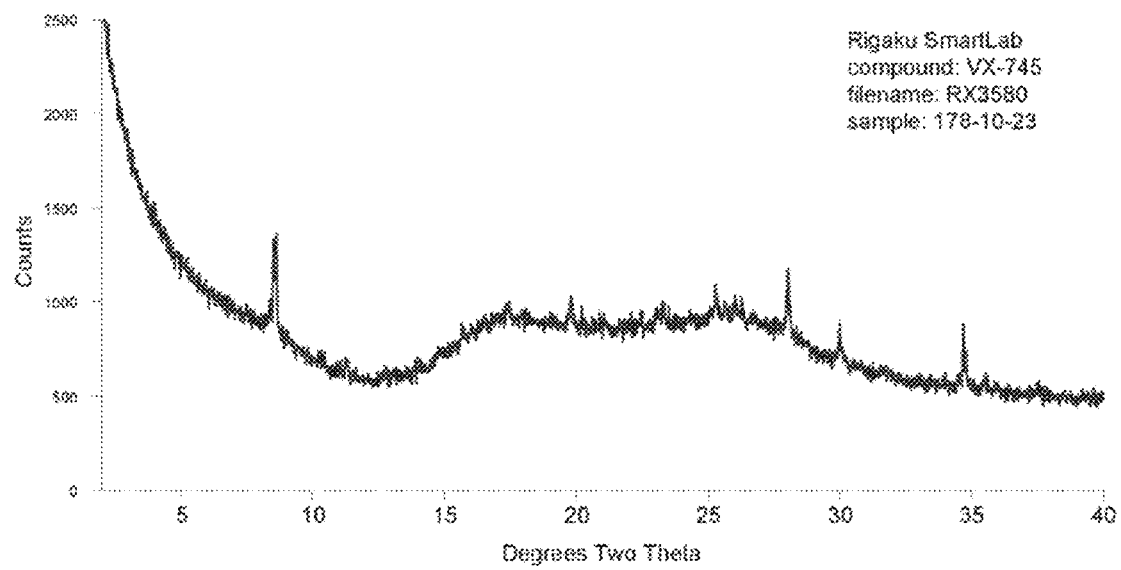

Stoichiometric Slow Evaporation Experiments. Stoichiometric slow evaporation experiments were carried out in glass vials. Each of the vials was charged with about 15 mg of VX-745 and an approximately equimolar amount of coformer. The contents were dissolved in a given solvent and placed in glass vials. The vials were covered with aluminum foil having three pinholes and allowed to evaporate at ambient. The resulting solids were analyzed by XRPD, which results are shown in FIGS. 56-140. The results are shown in FIGS. 239A-239B.

Figure 141:
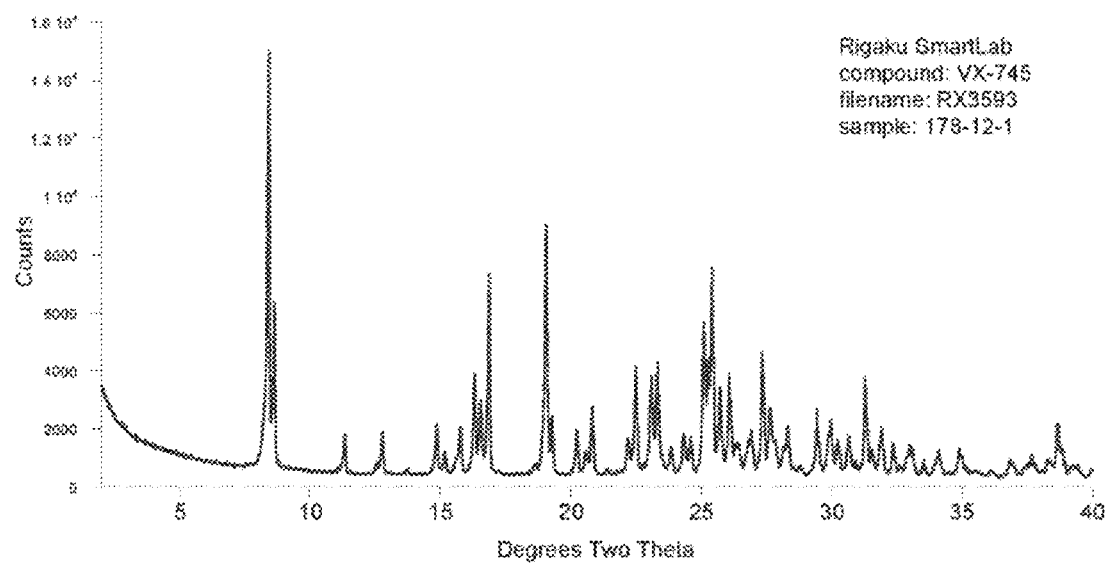
FIGS. 141-215 show XRPD results of various co-crystals of VX-745 produced by slurring. The co-crystal in each figure is identified by XRPD filename, which corresponds to "XRPD File" in FIGS. 240A-240B.
Figure 142:
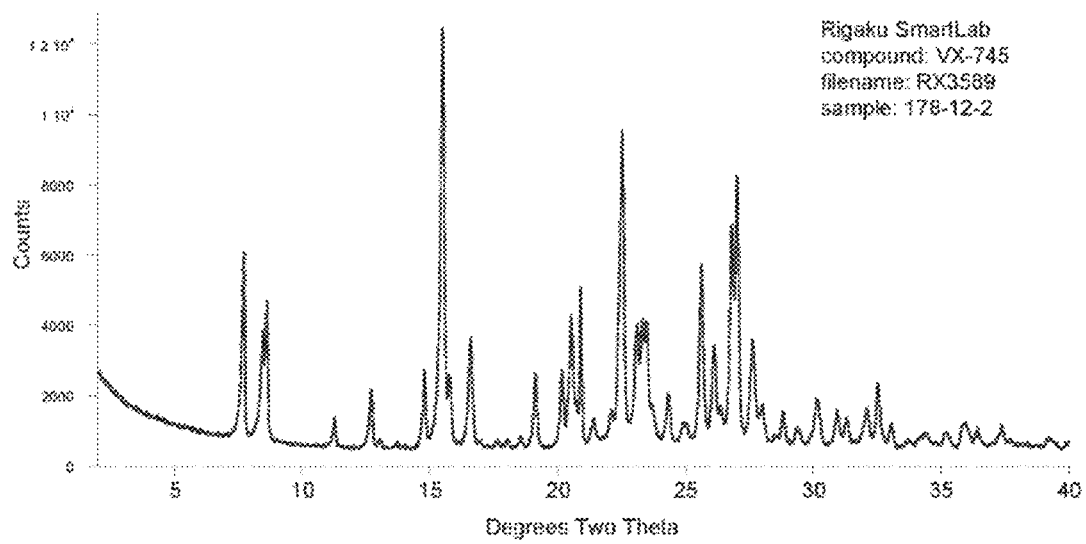
Figure 143:
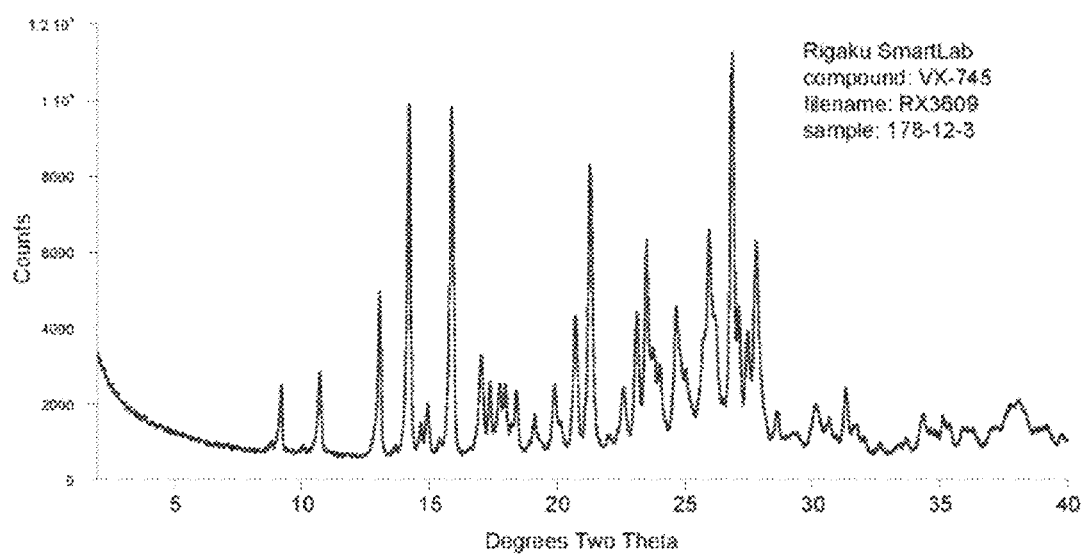
Figure 144:
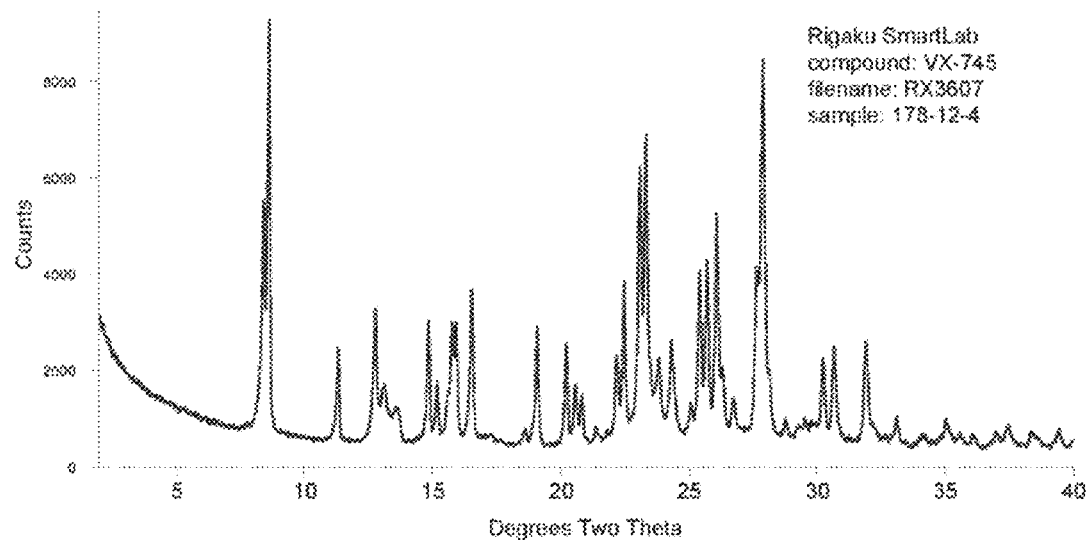
Figure 145:
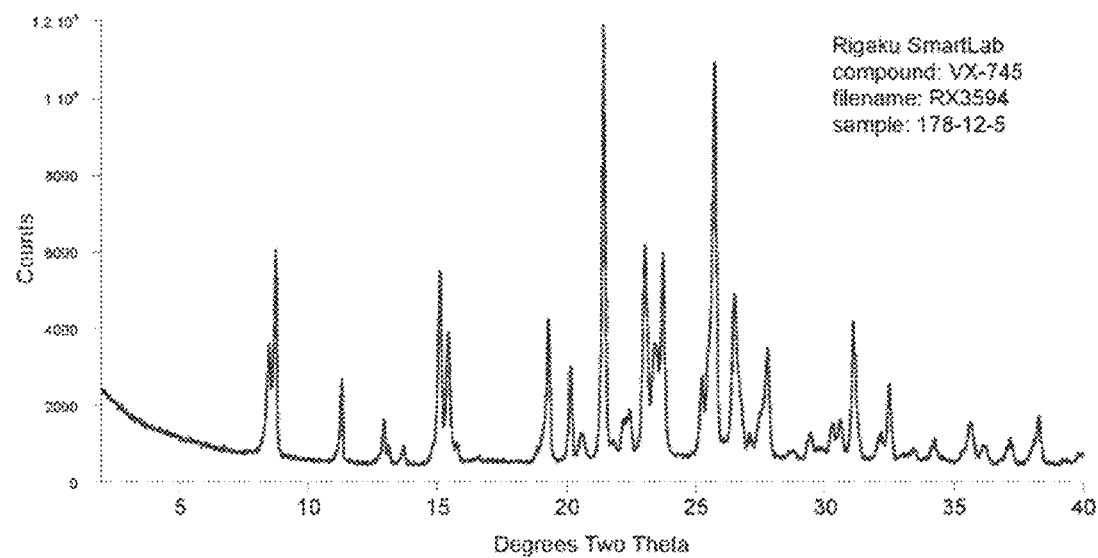
Figure 146:
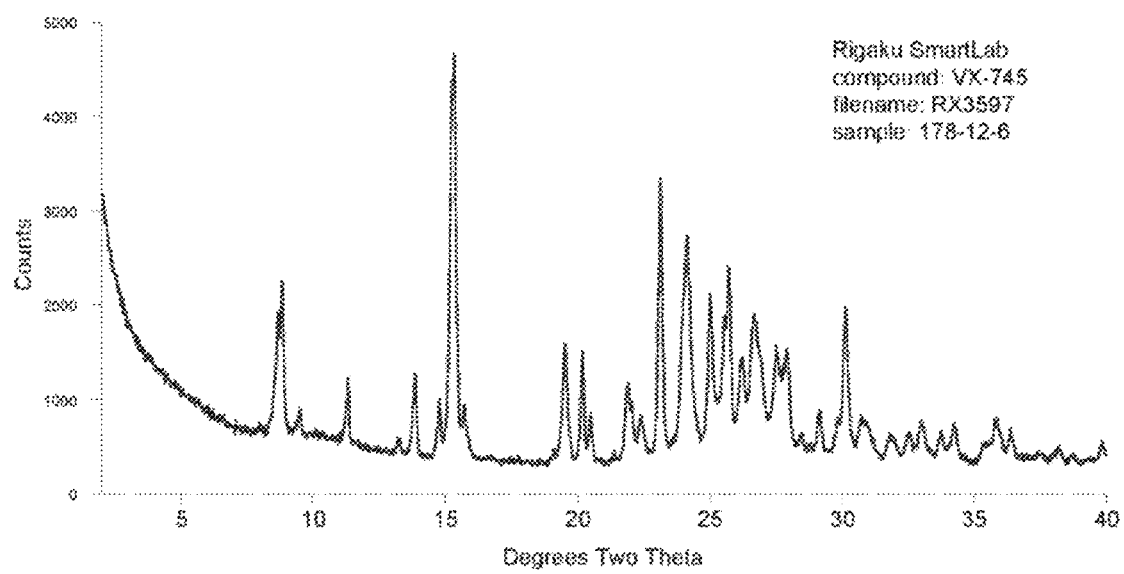
Figure 147:
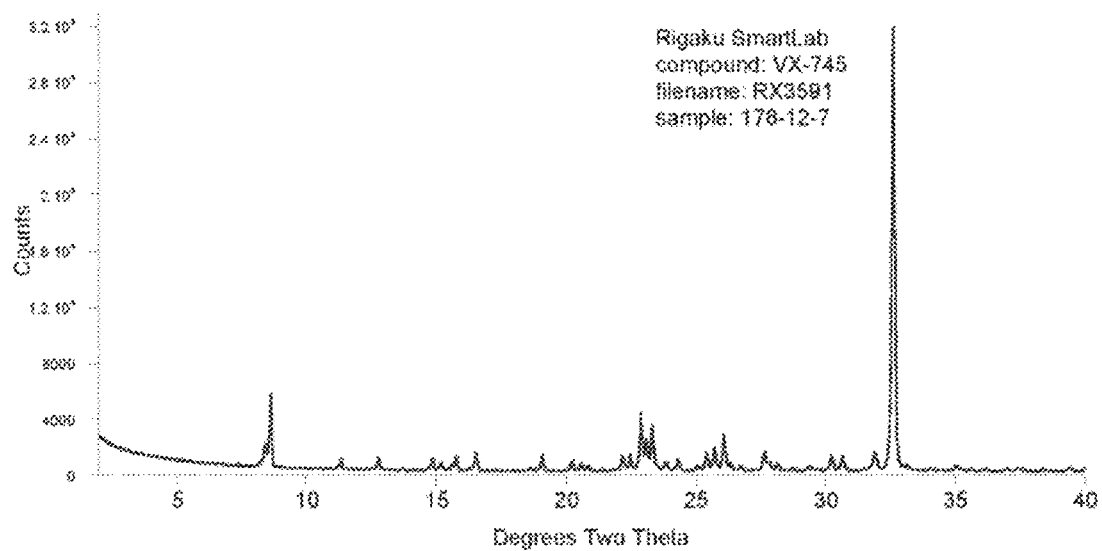
Figure 148:
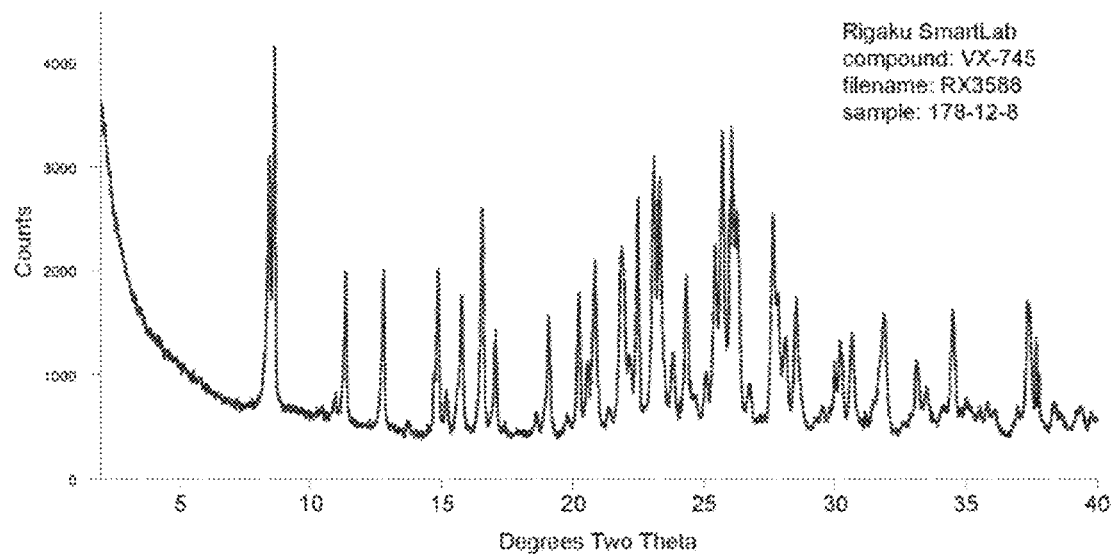
Figure 149:
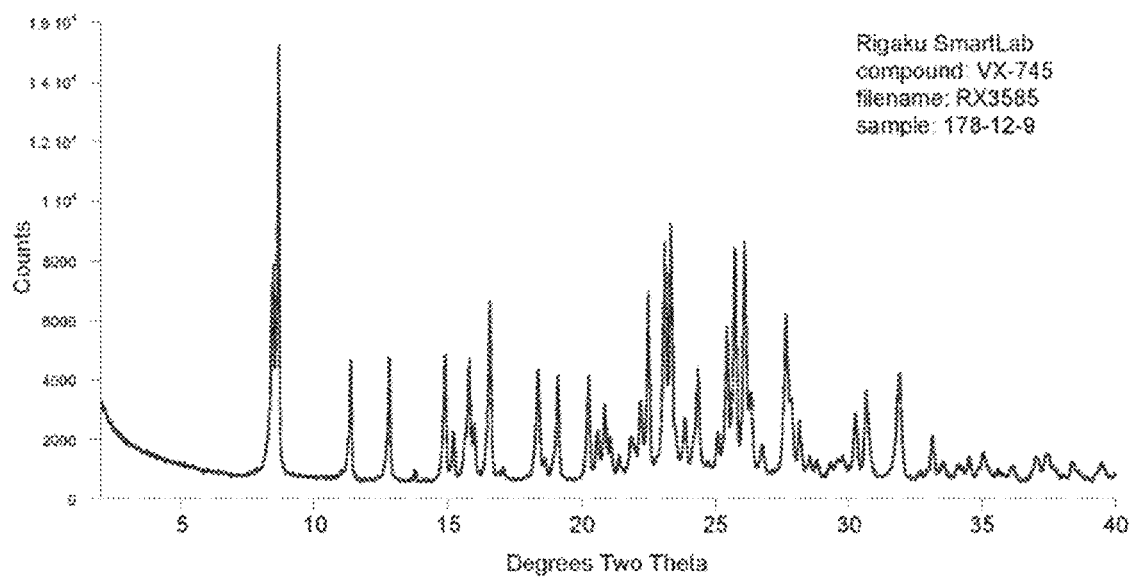
Figure 150:
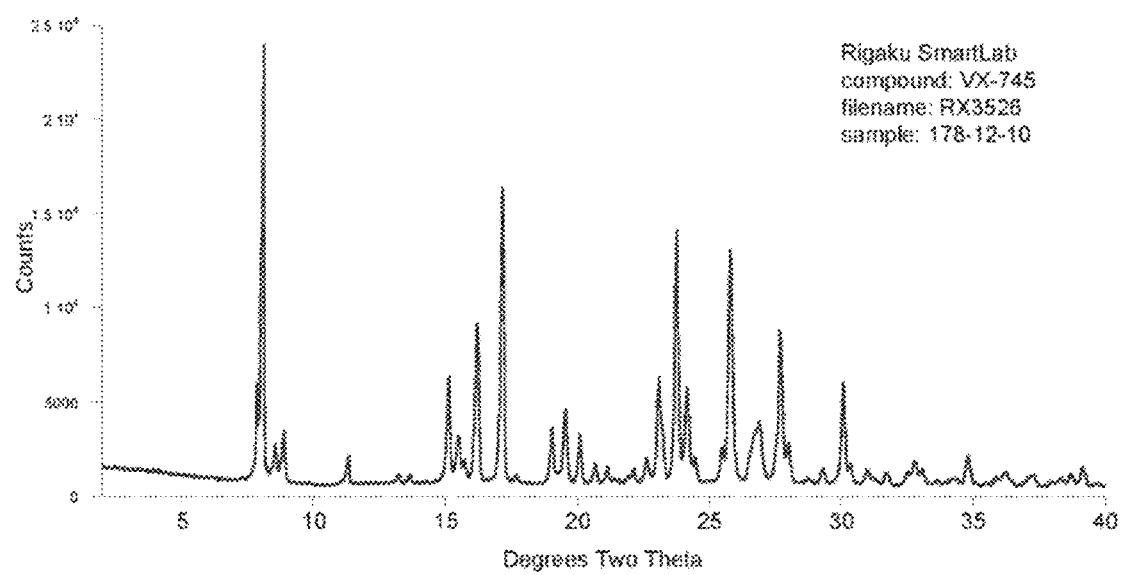
Figure 151:
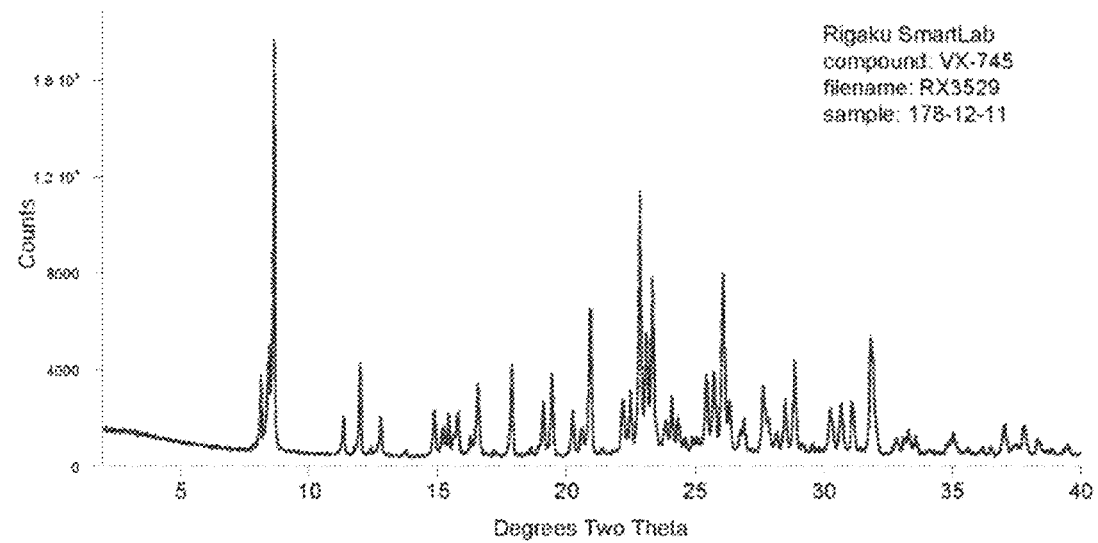
Figure 152:
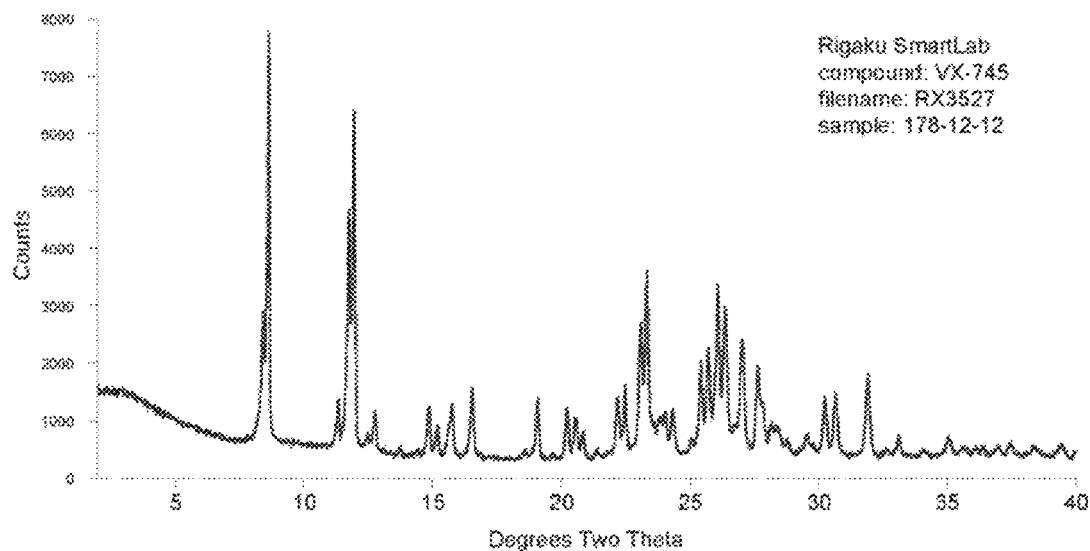
Figure 153:
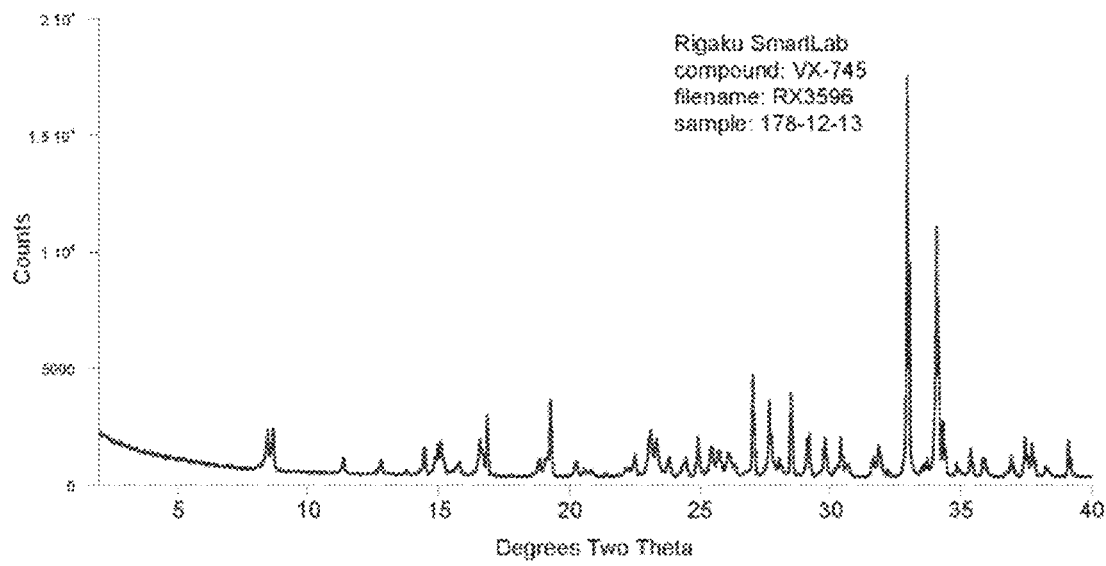
Figure 154:
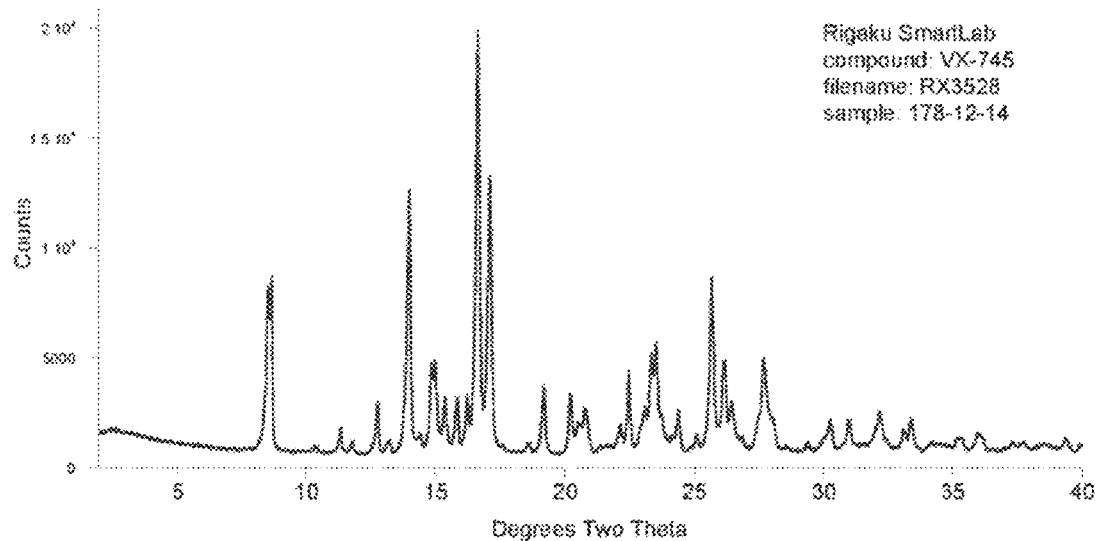
Figure 155:
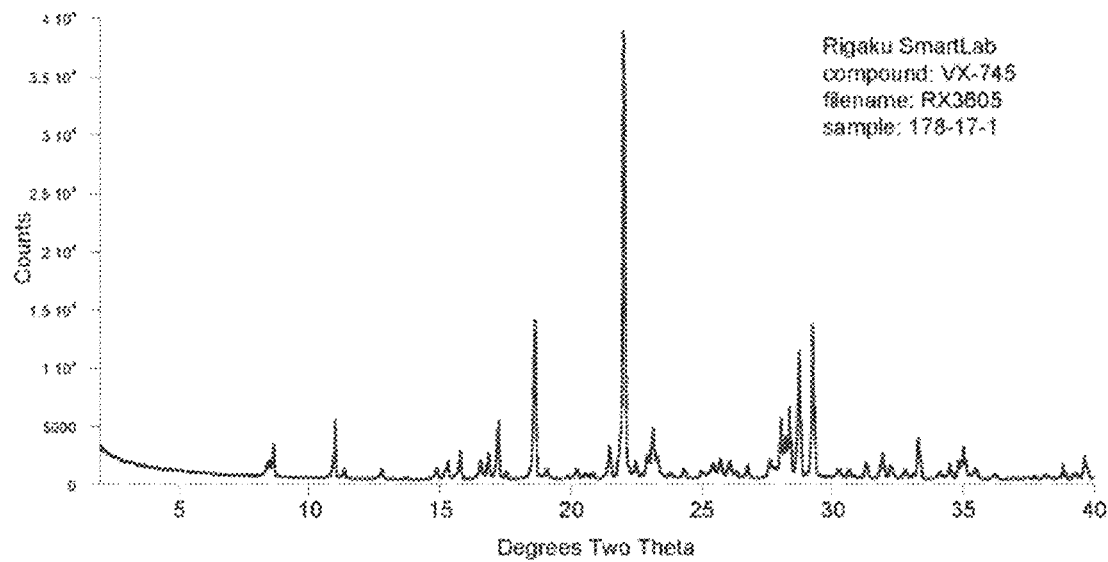
Figures 156, 157:
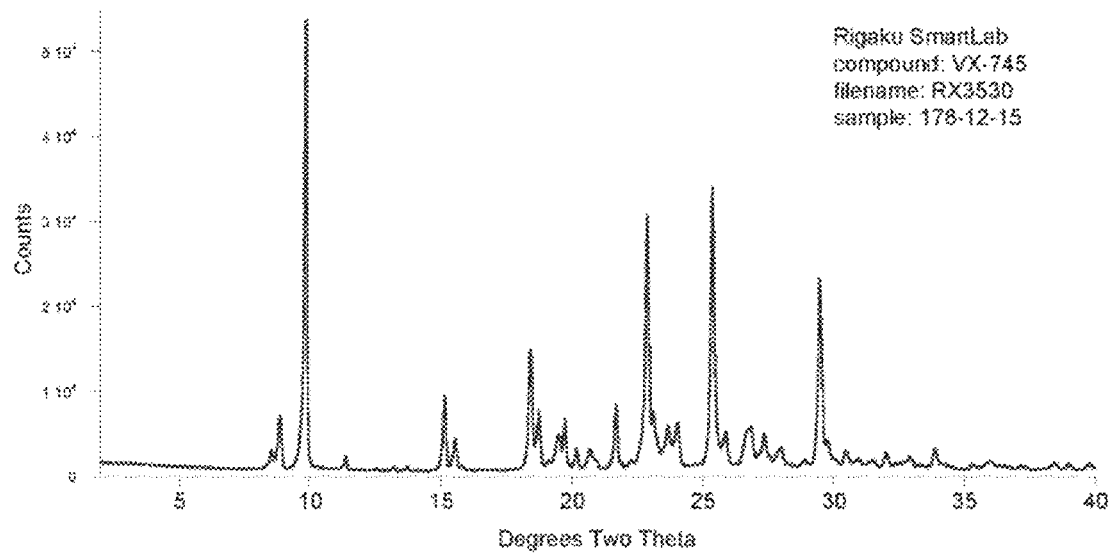
Figure 158:
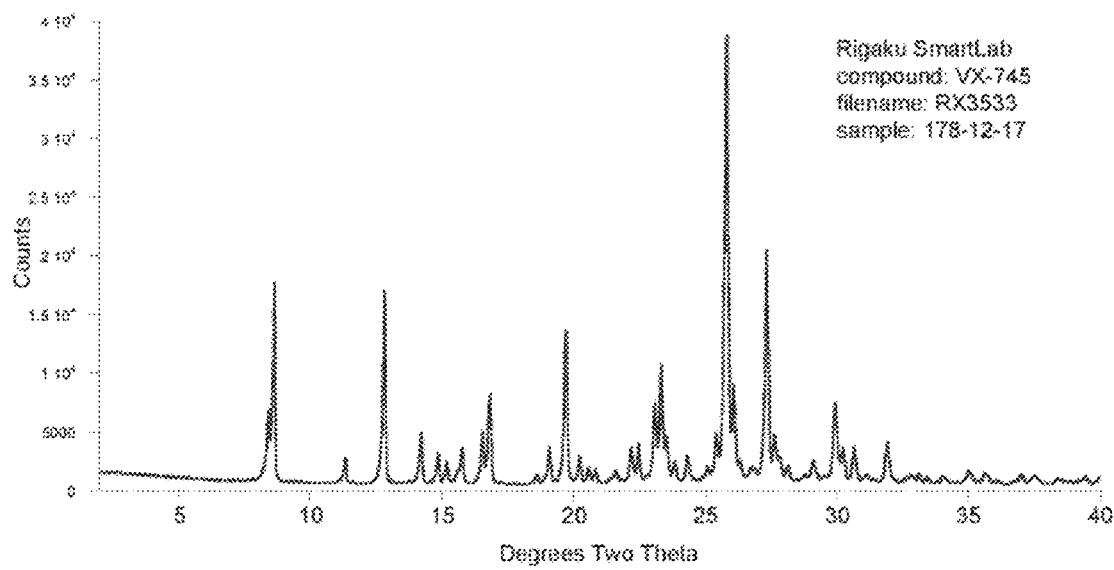
Figure 159:
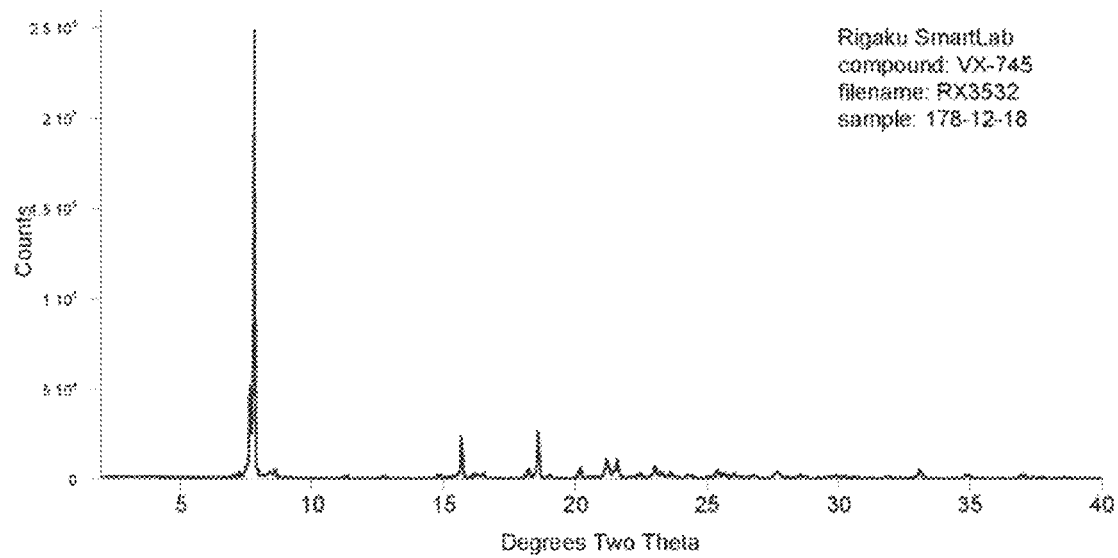
Figure 160:
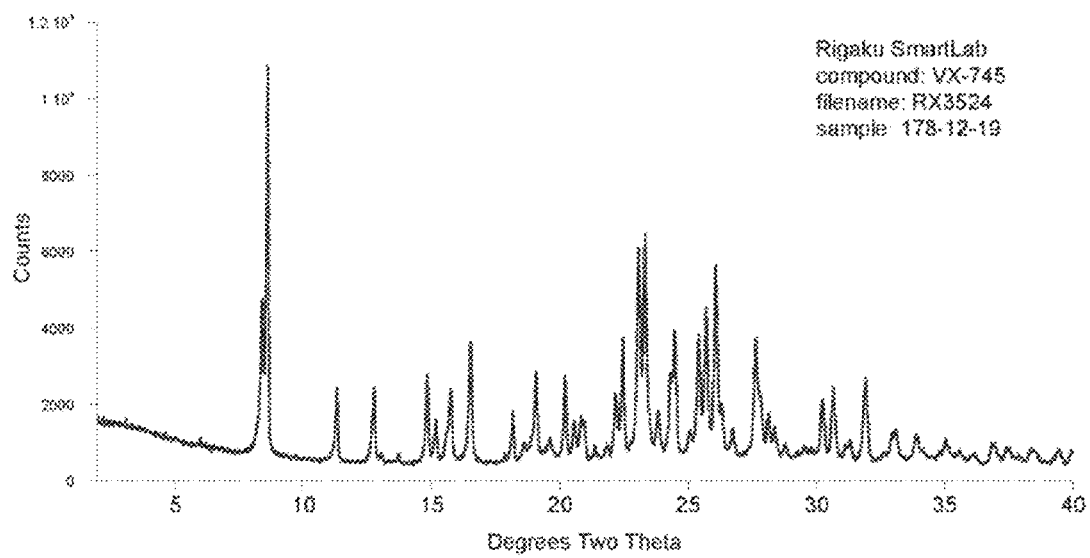
Figure 161:
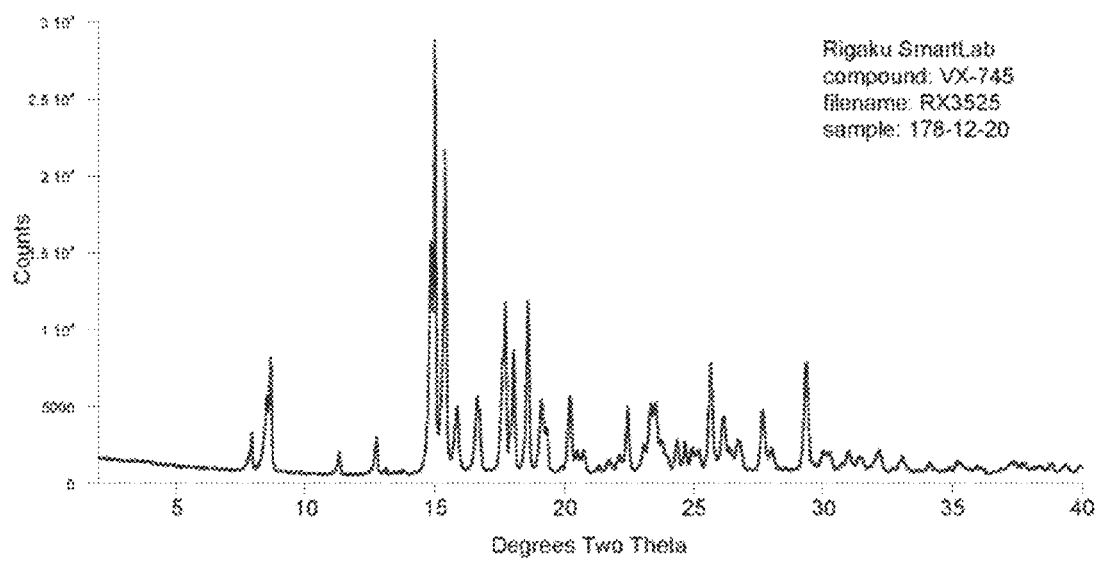
Figure 162:
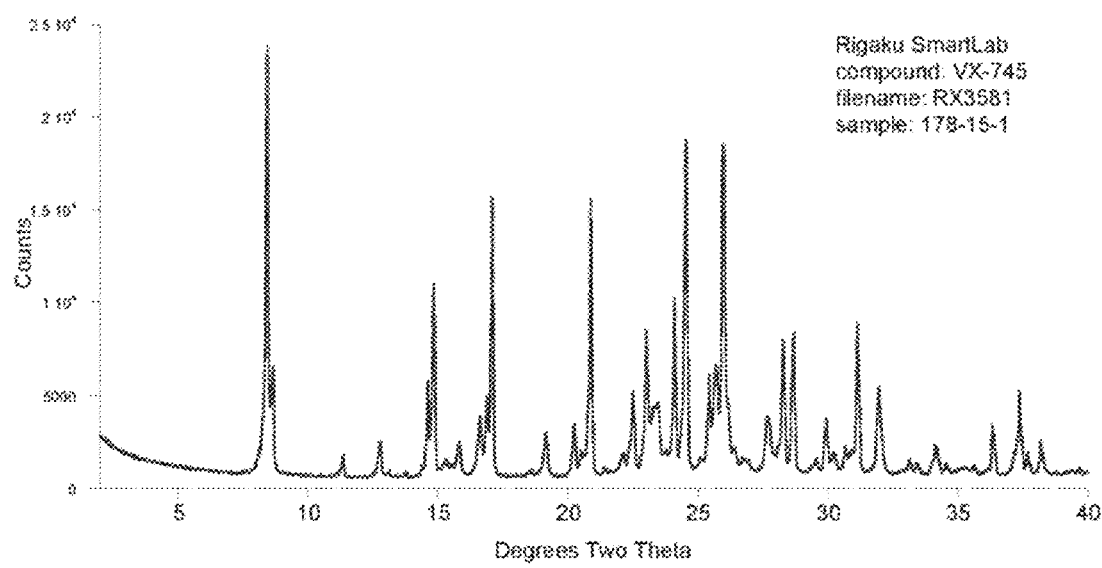
Figure 163:
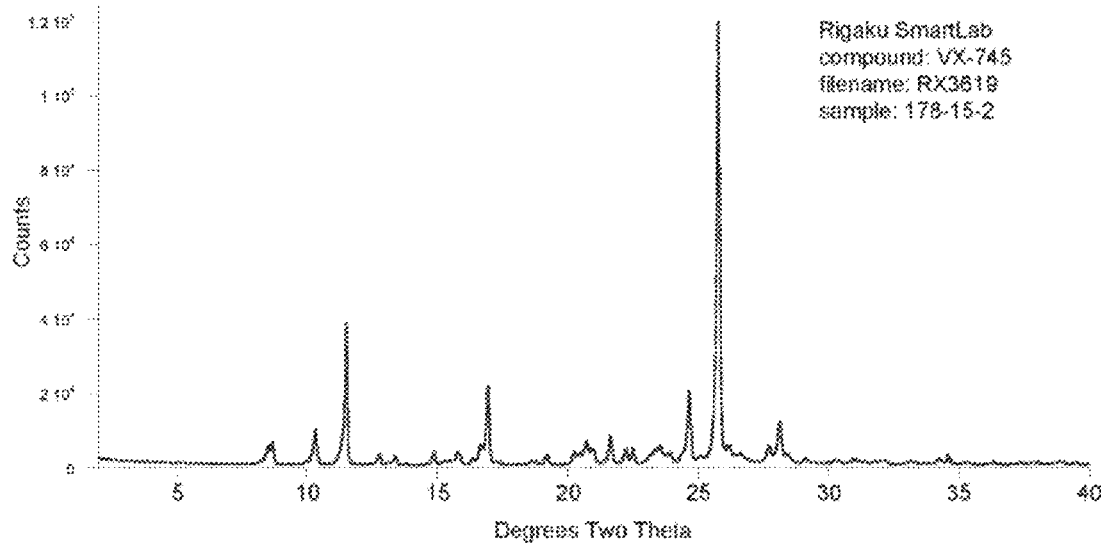
Figure 164:
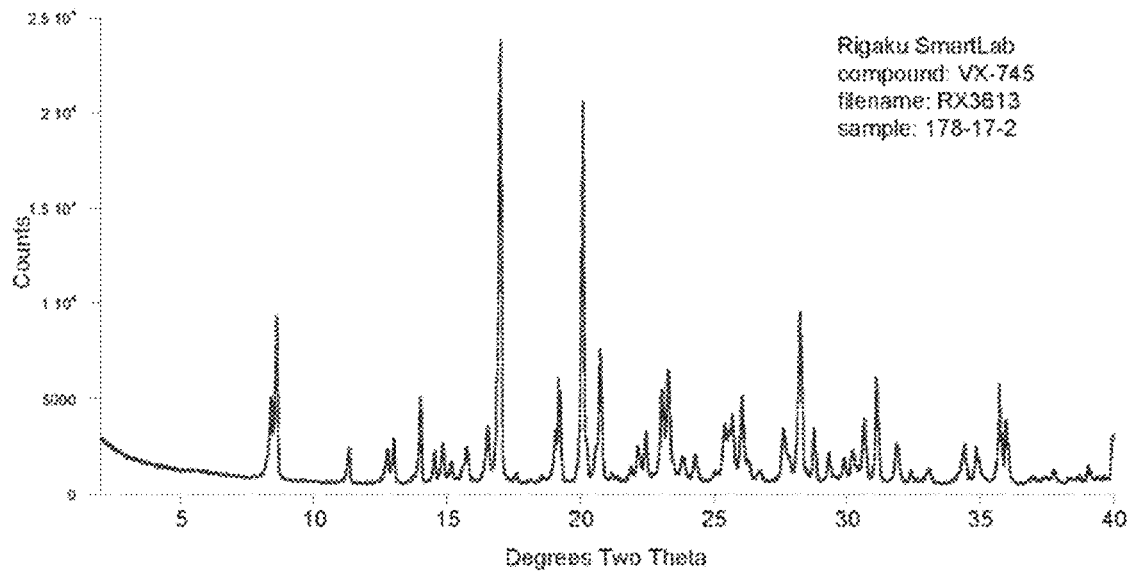
Figure 165:
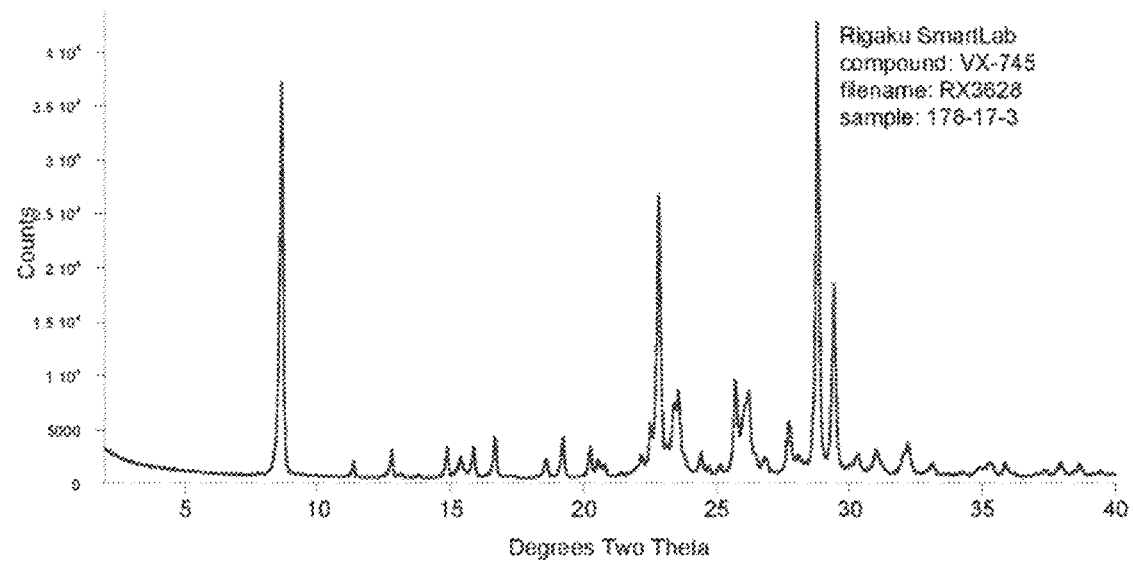
Figure 166:
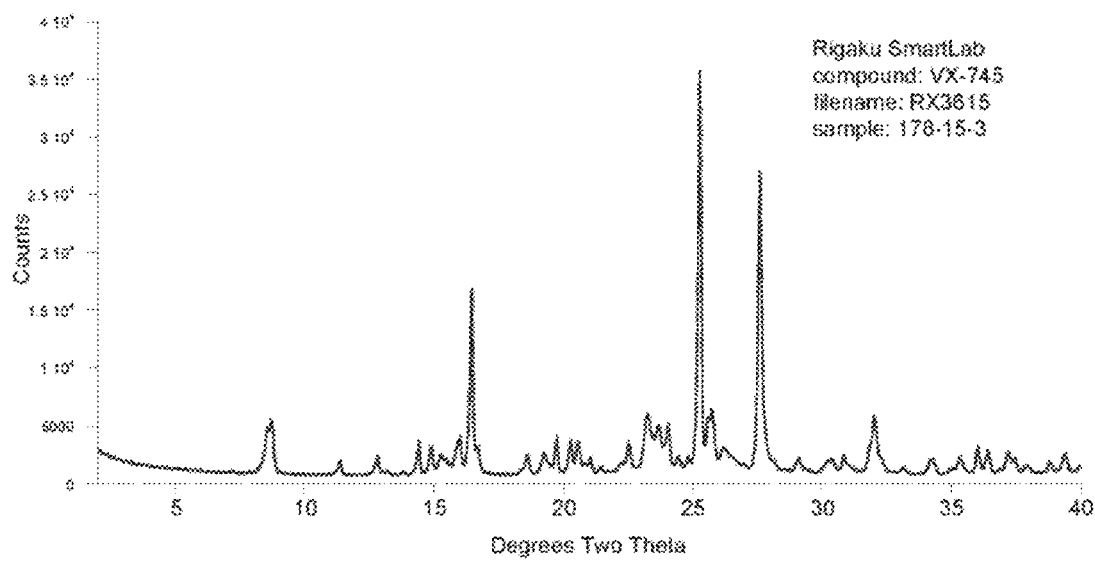
Figure 167:
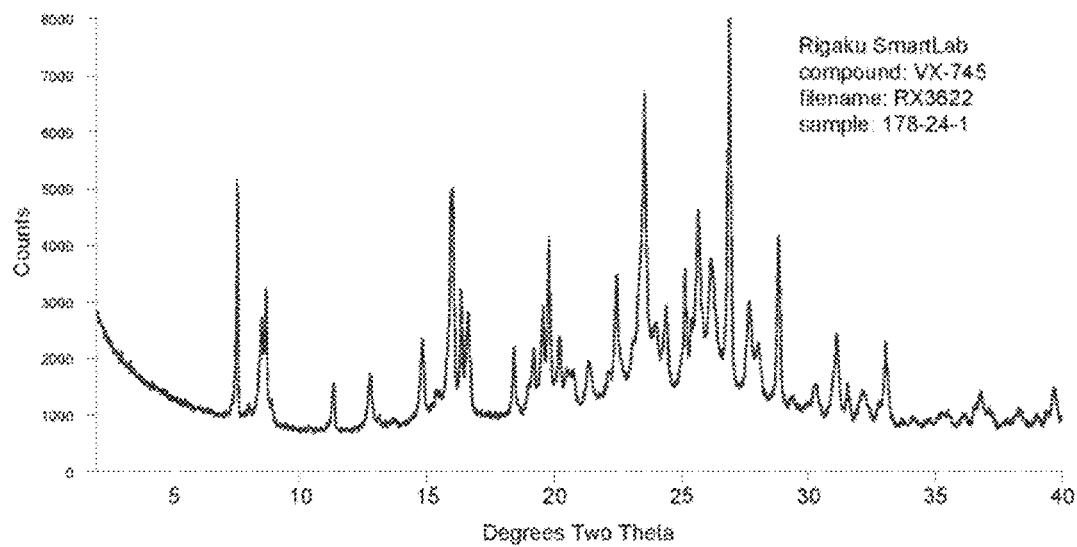
Figure 168:
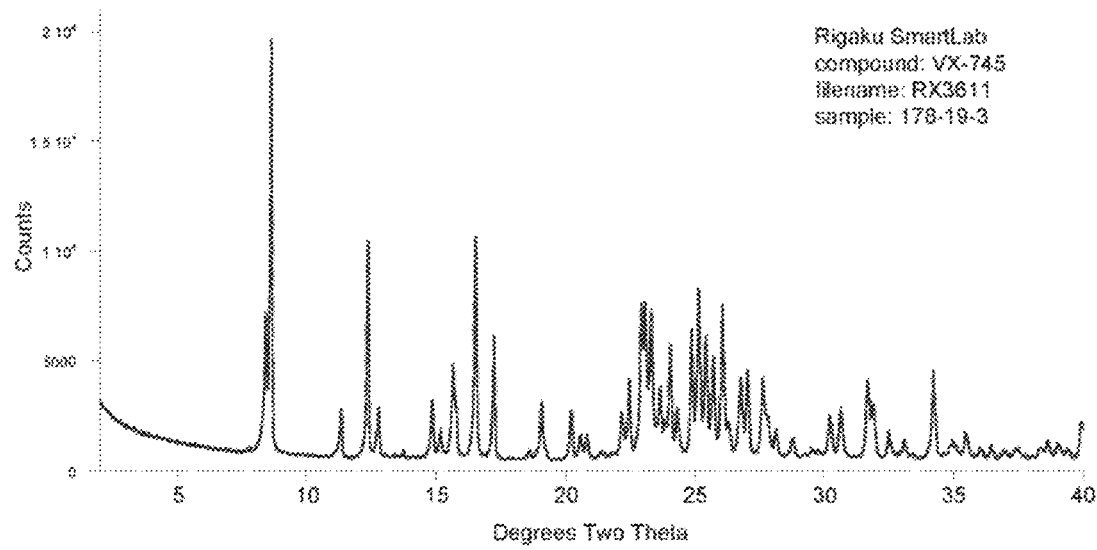
Figure 169:
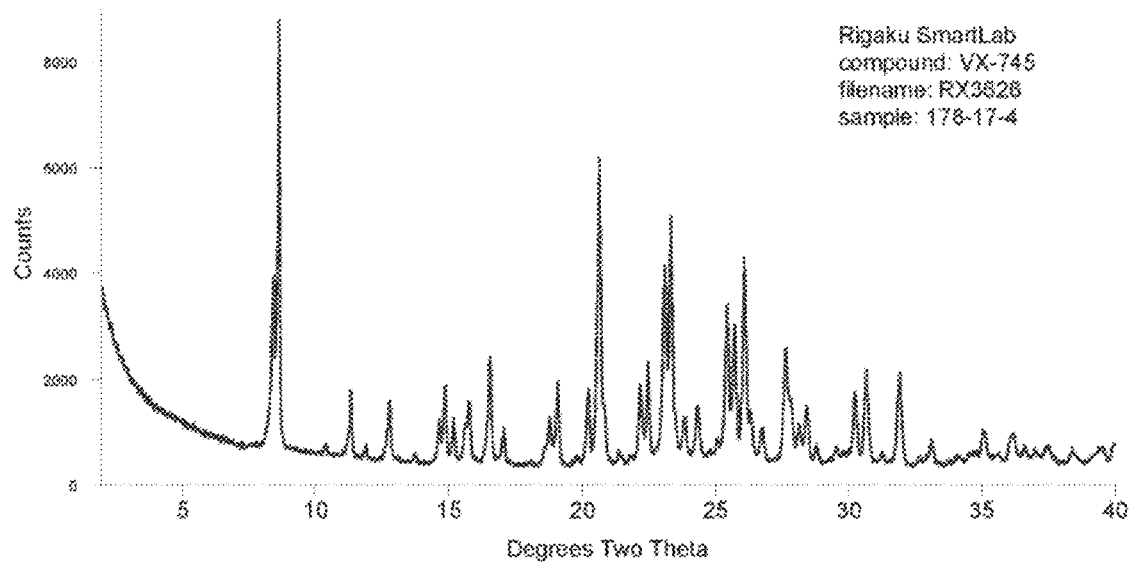
Figure 170:
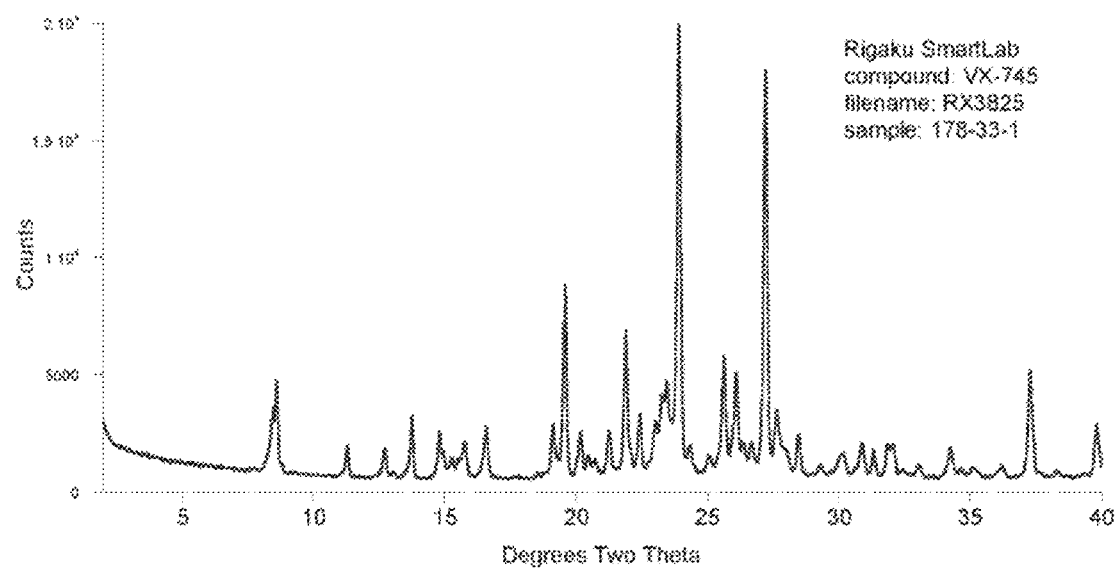
Figure 171:
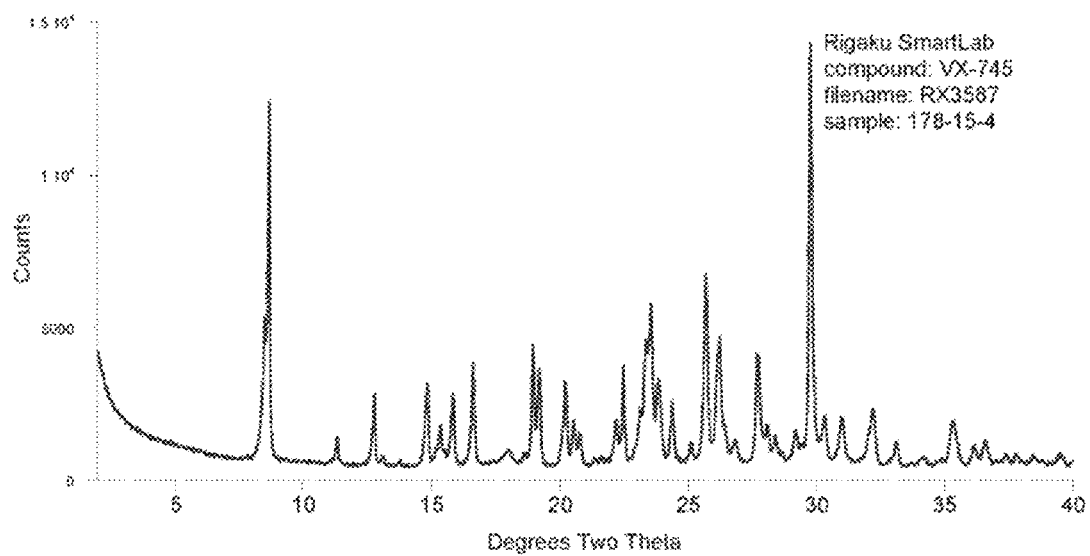
Figure 172:
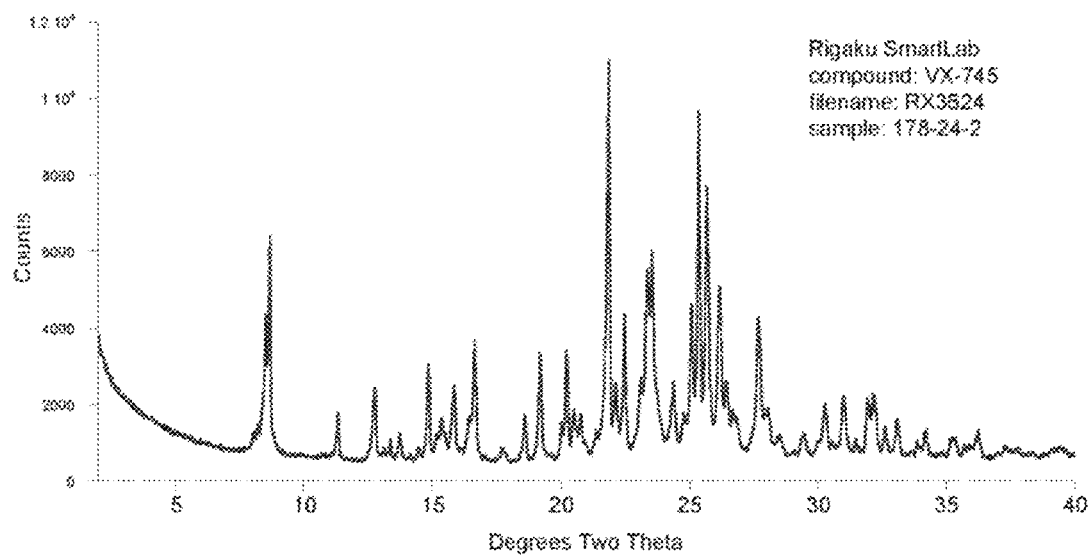
Figure 173:
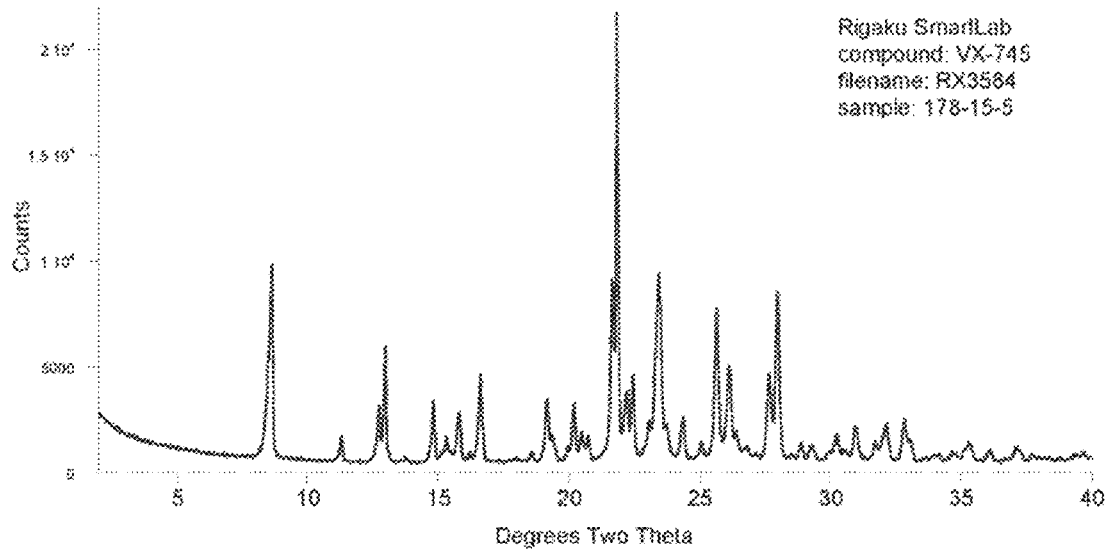
Figure 174:
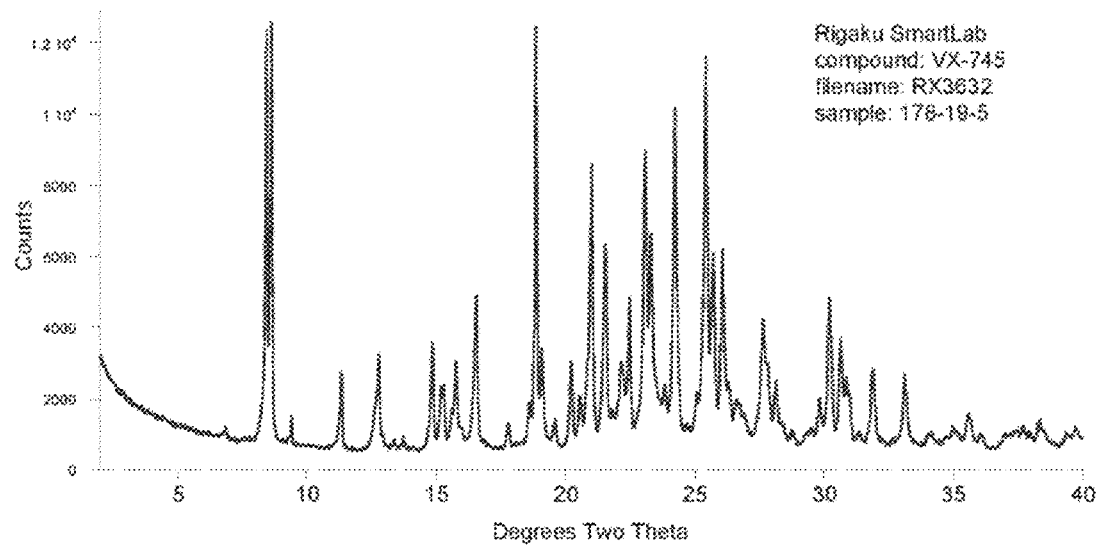
Figure 175:
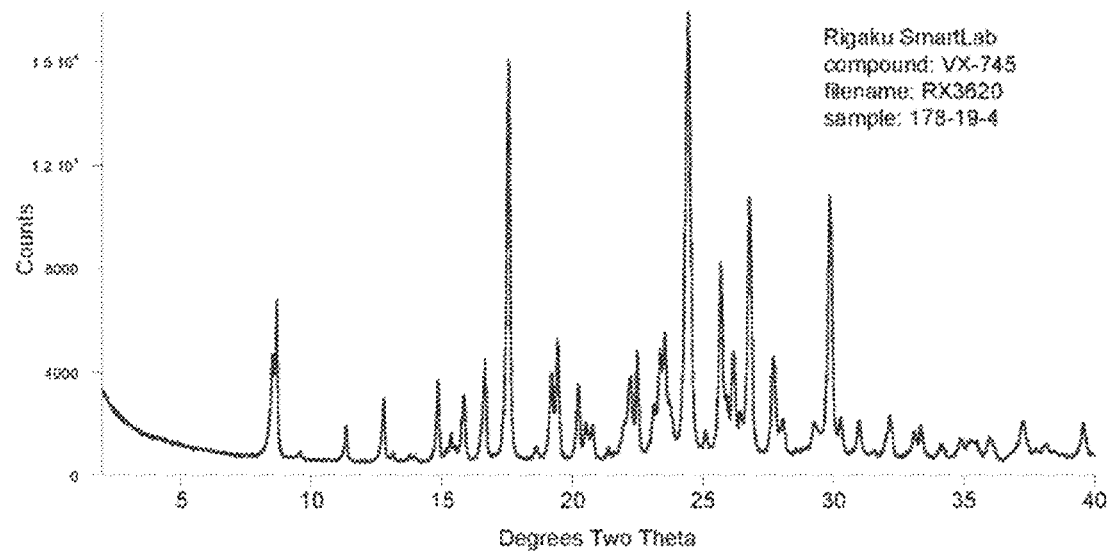
Figure 176:
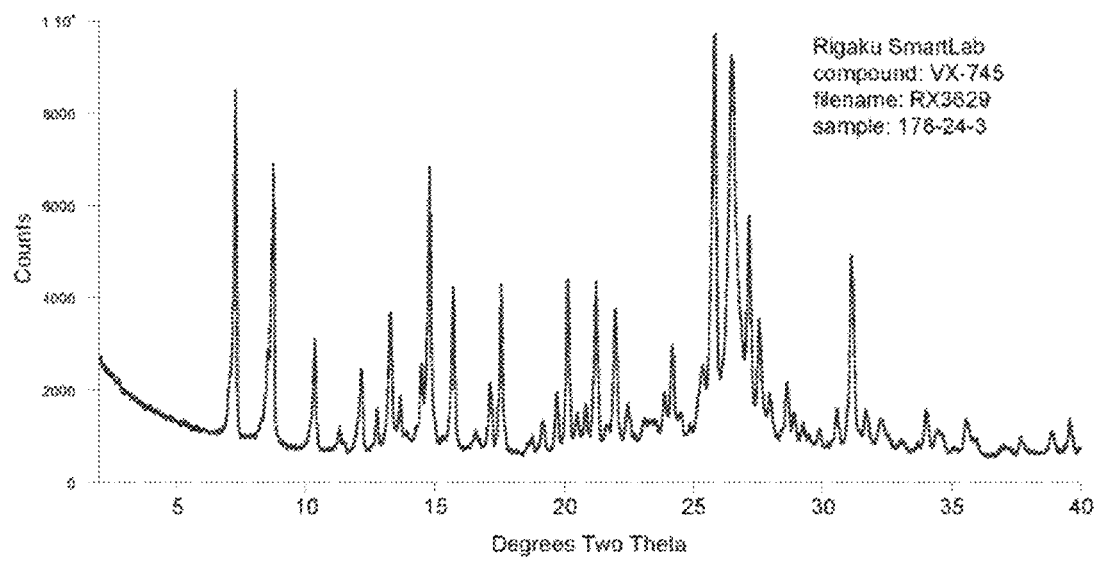
Figure 177:
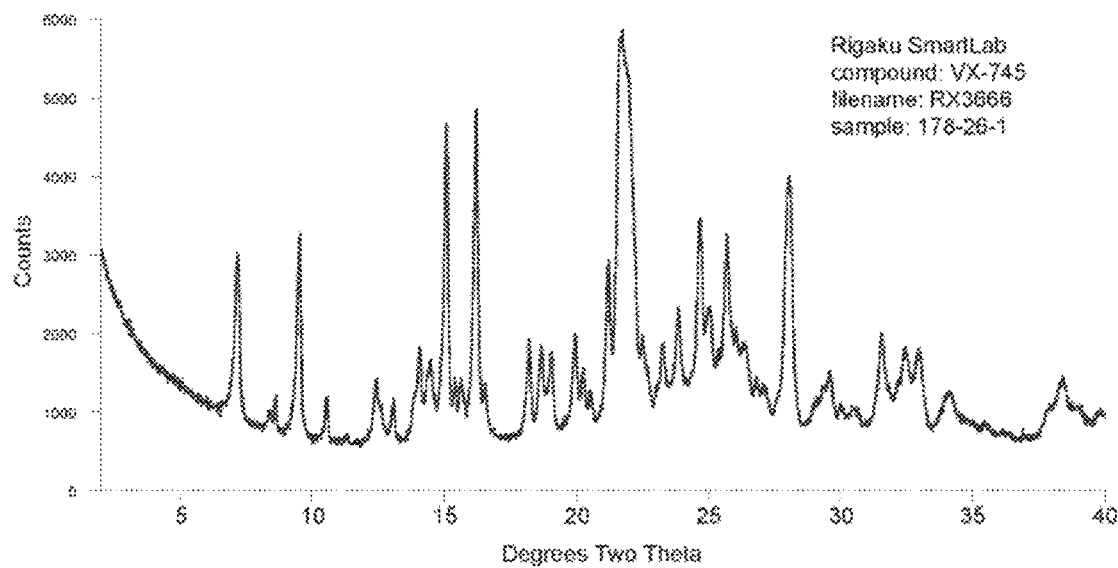
Figure 178:
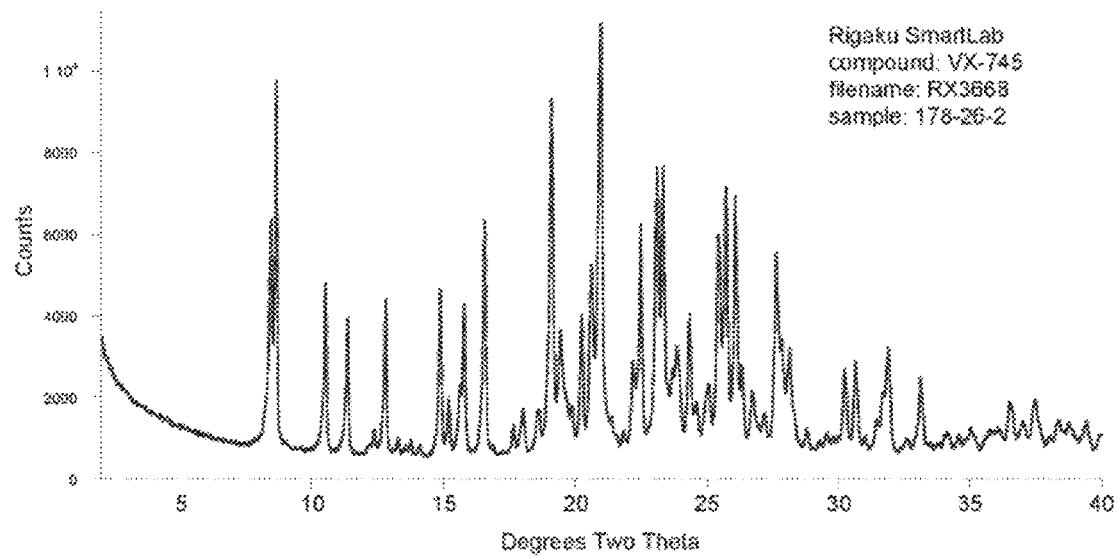
Figure 179:
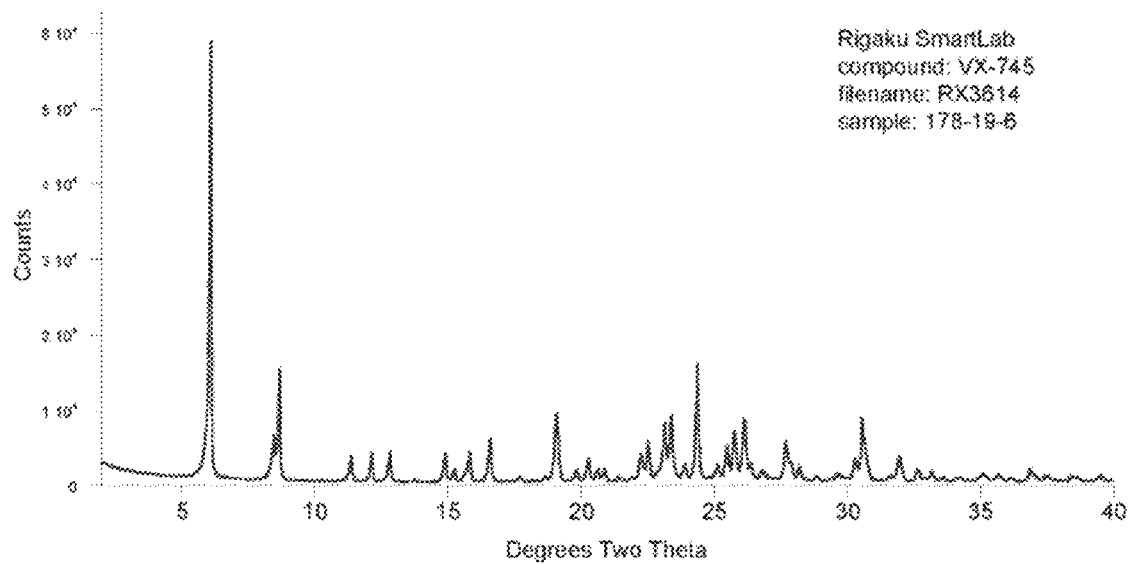
Figure 180:
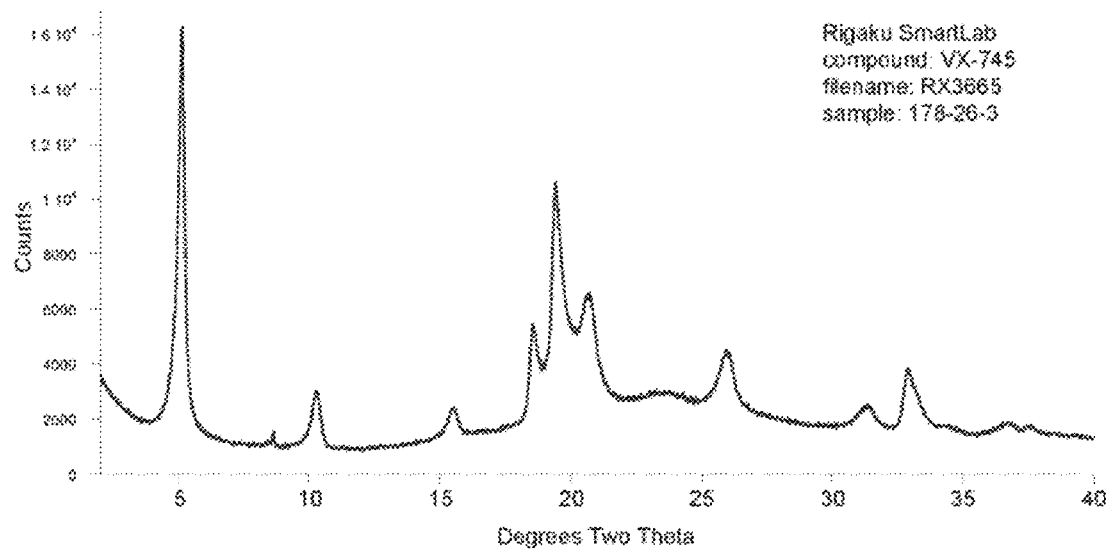
Figure 181:
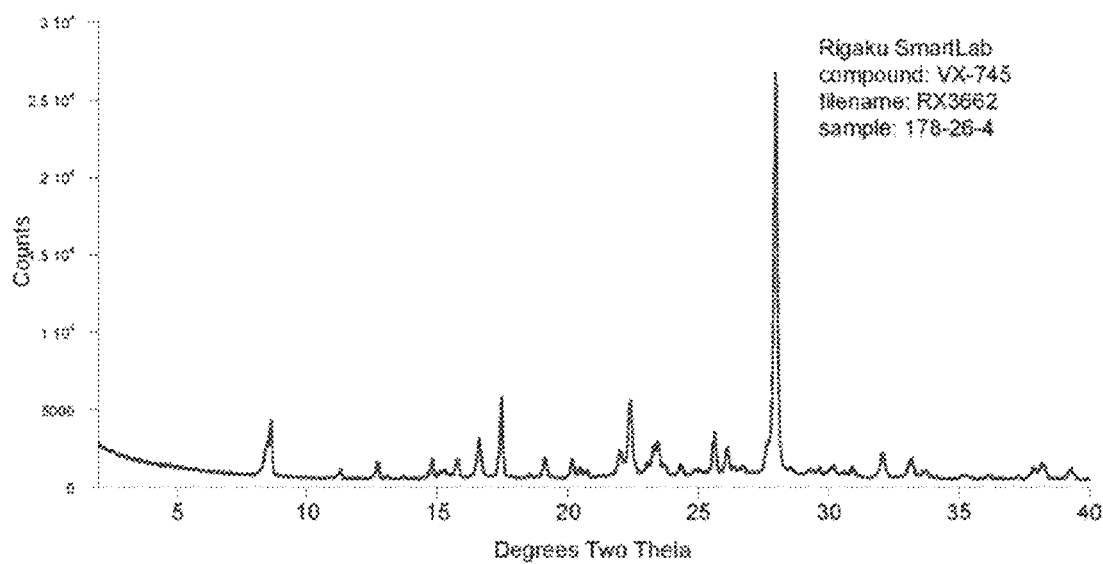
Figure 182:
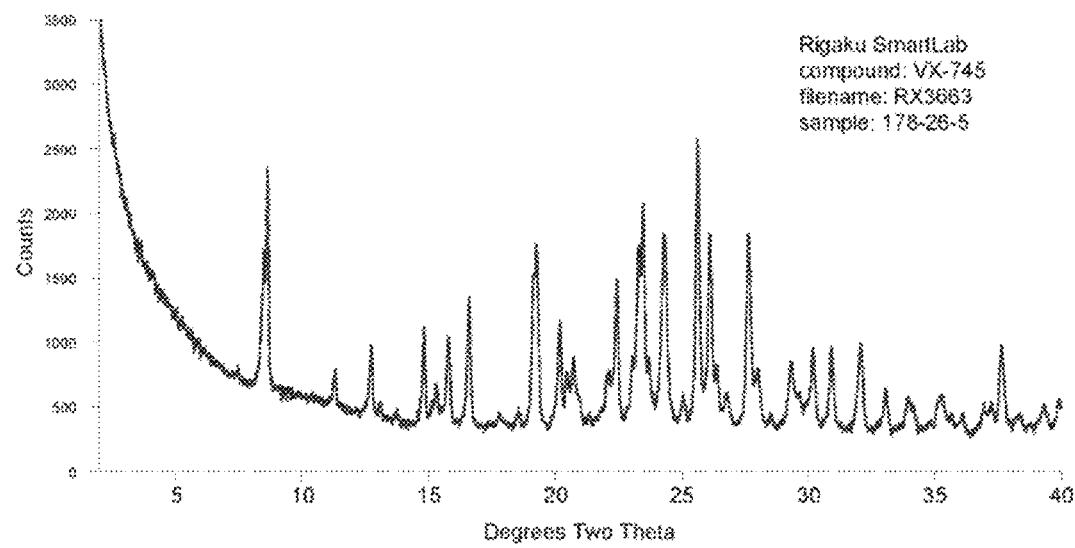
Figure 183:
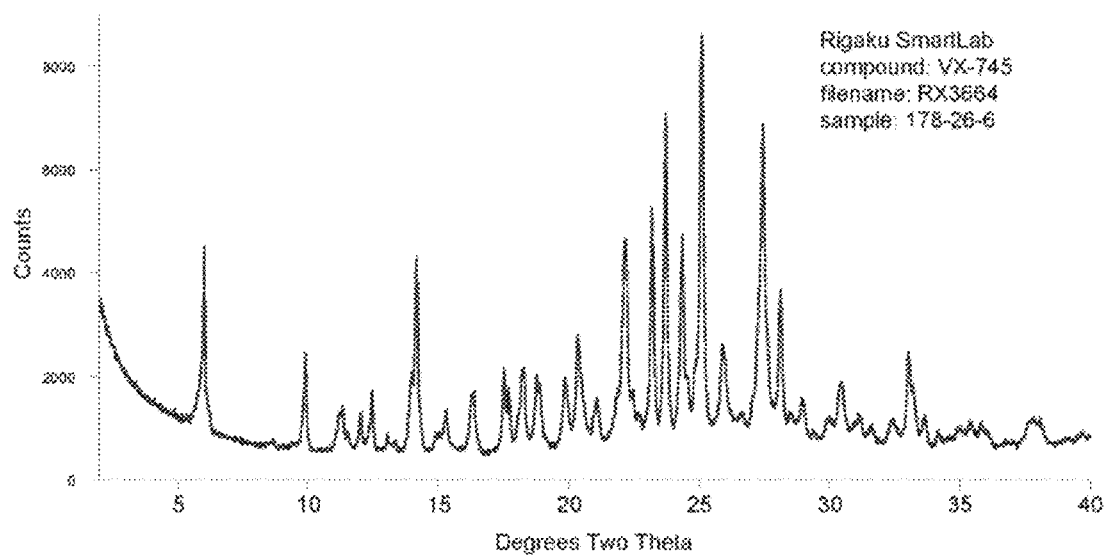
Figure 184:
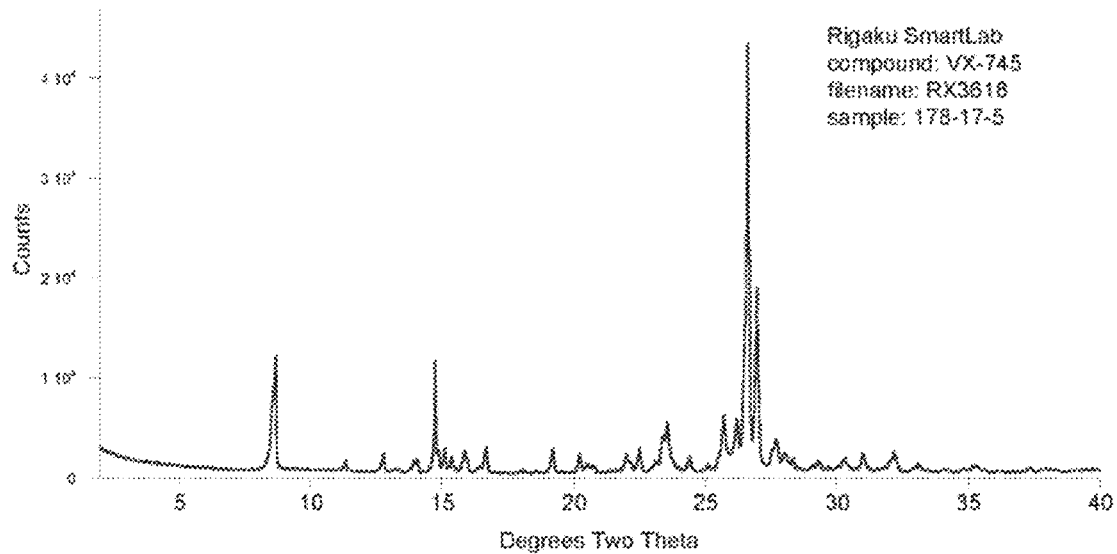
Figure 185:
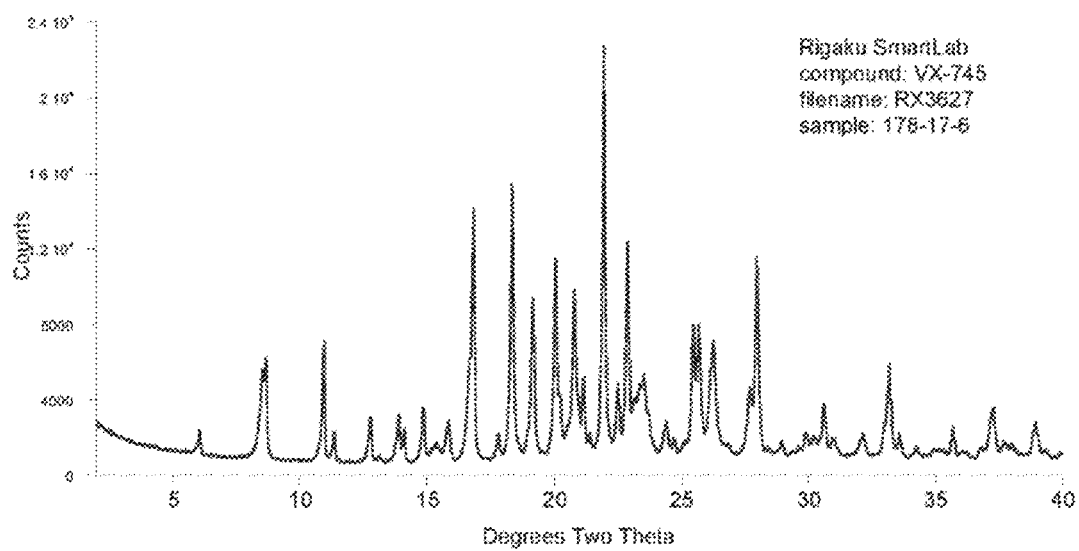
Figure 186:
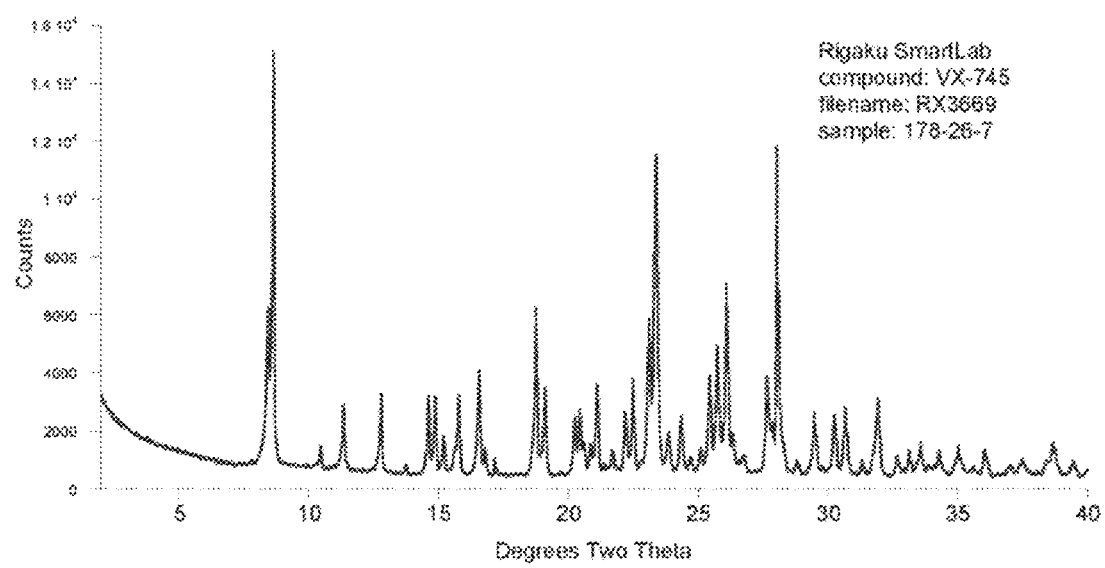
Figure 187:
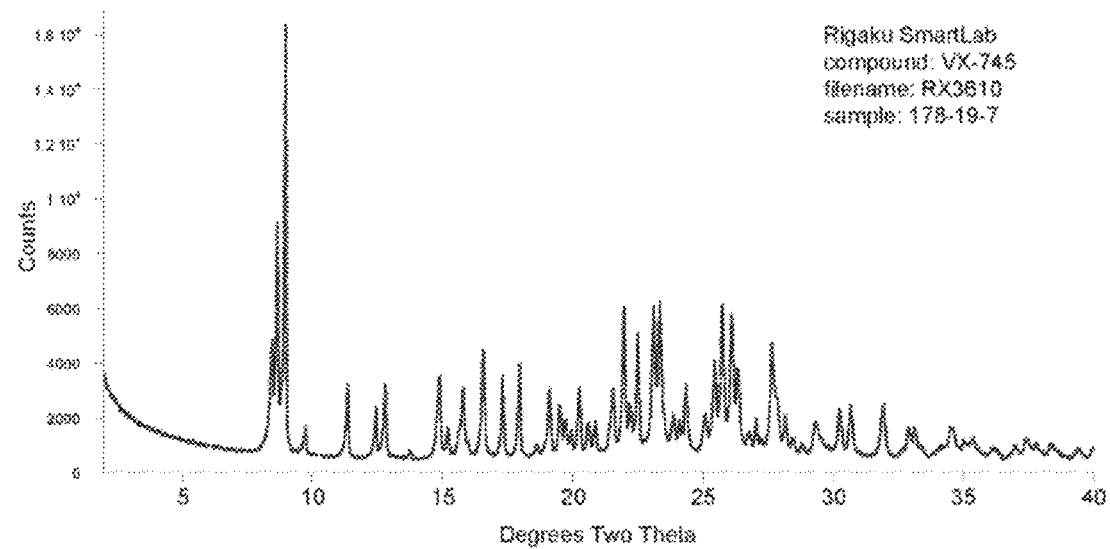
Figure 188:
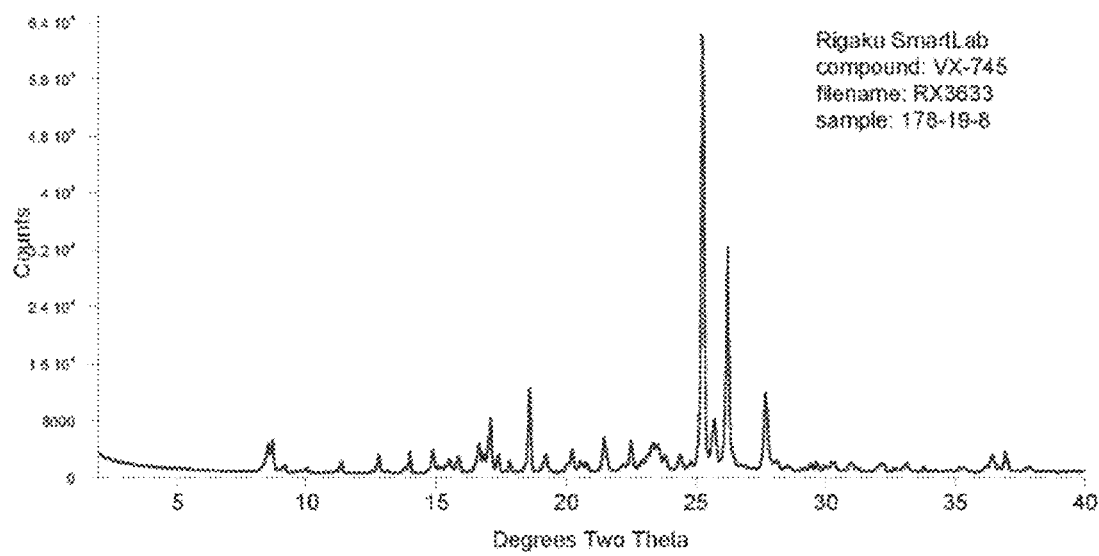
Figure 189:
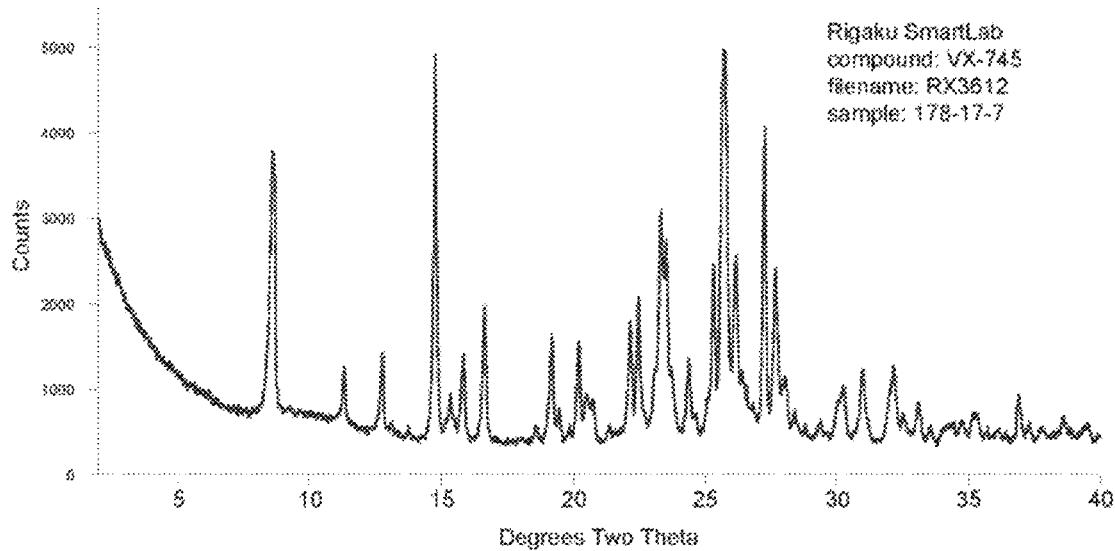
Figure 190:
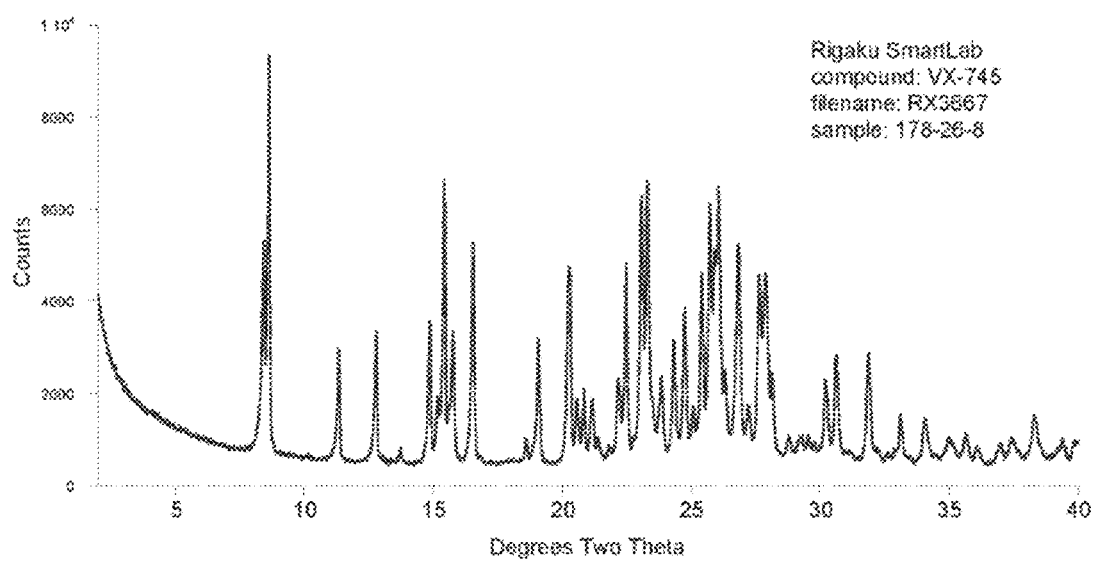
Figure 191:
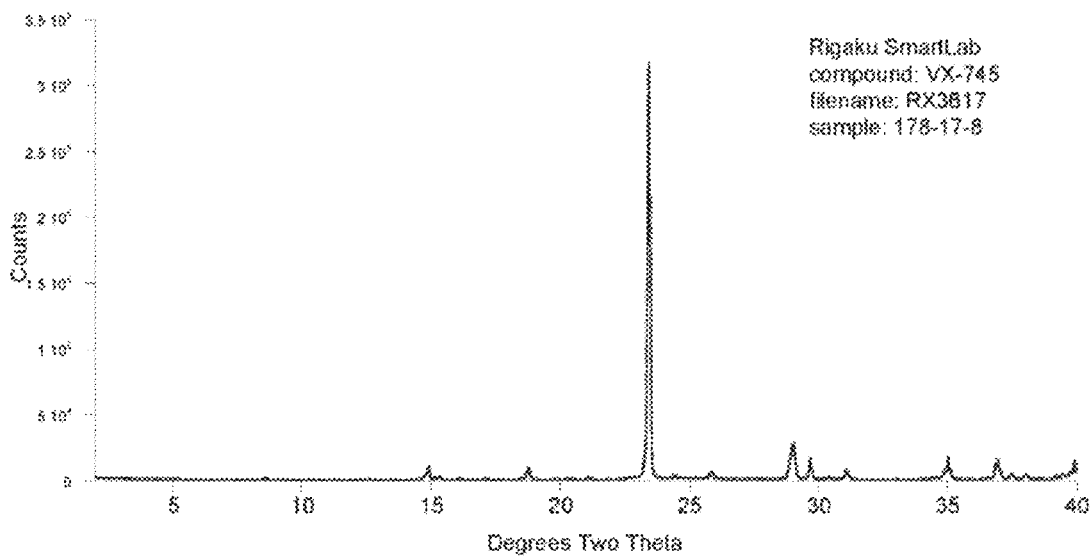
Figure 192:
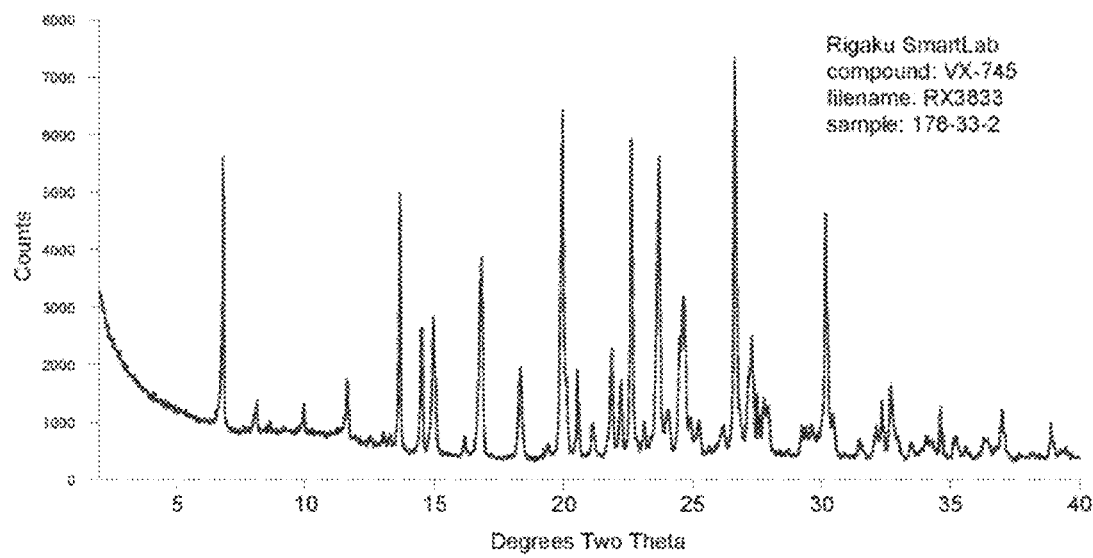
Figure 193:
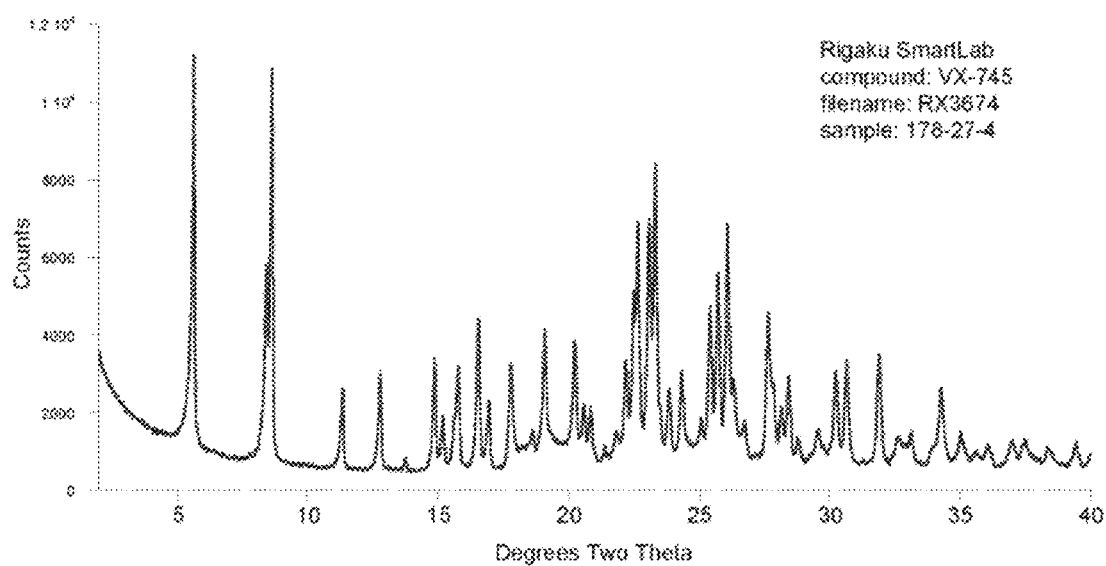
Figure 194:
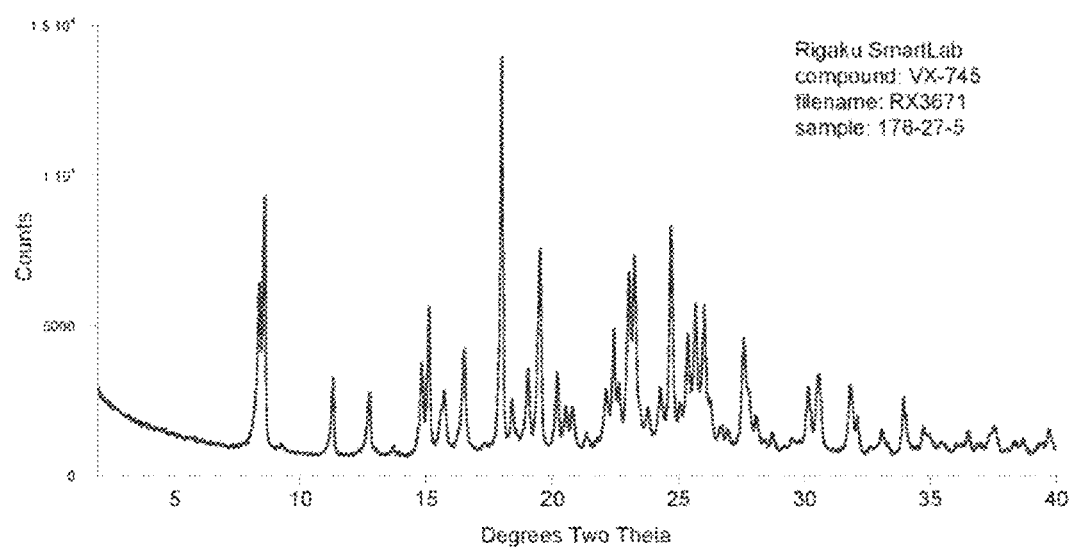
Figure 195:
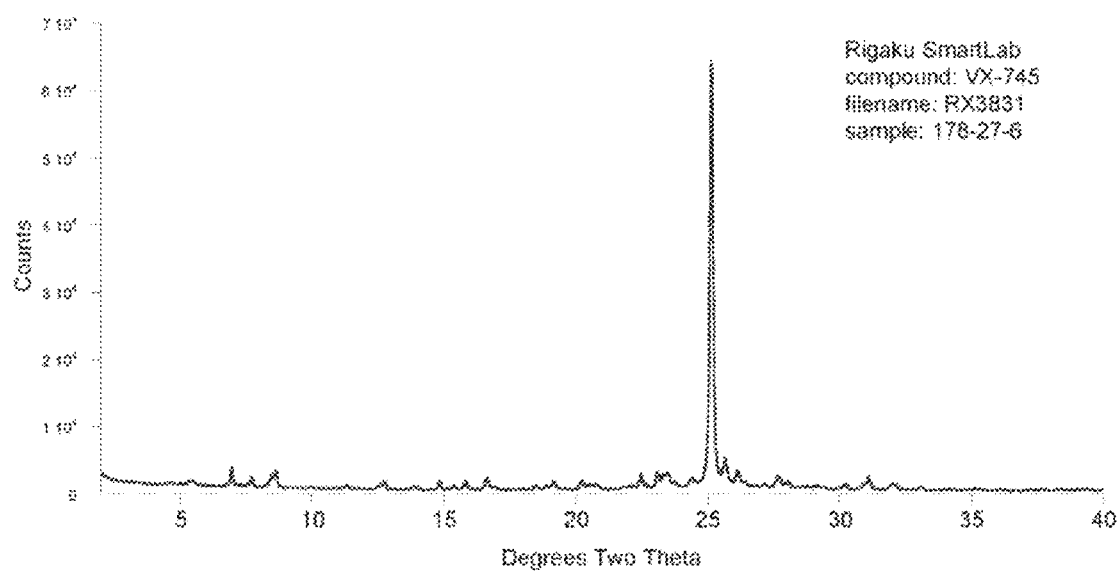
Figure 196:
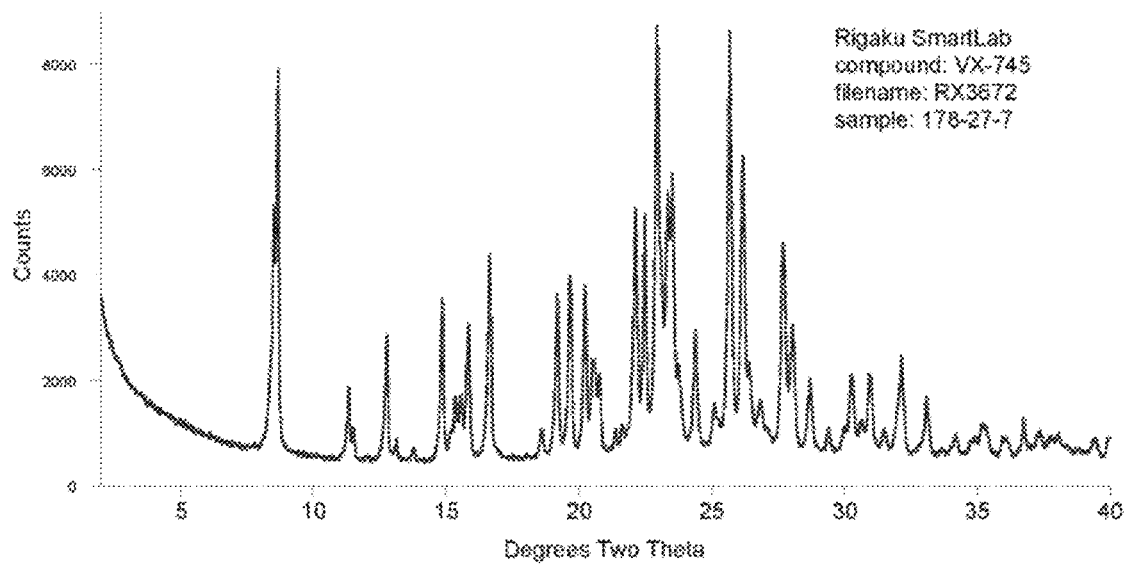
Figure 197:
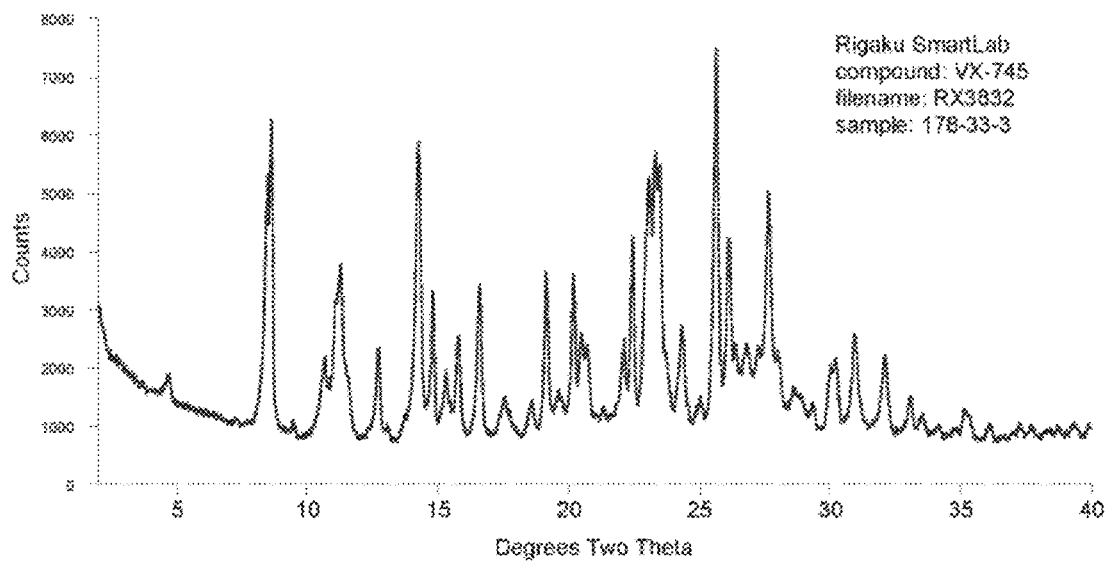
Figure 198:
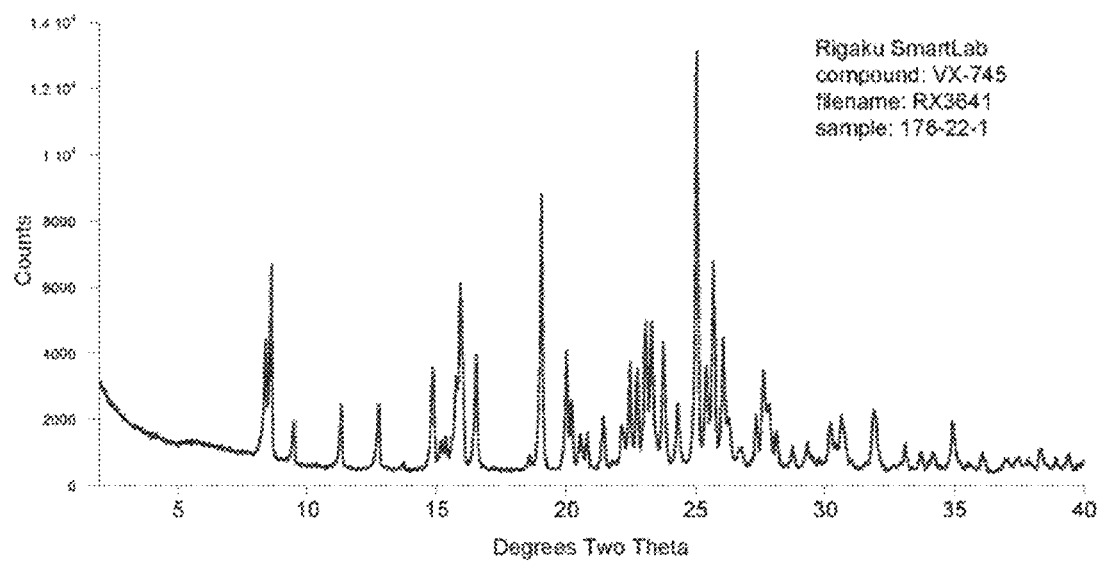
Figure 199:
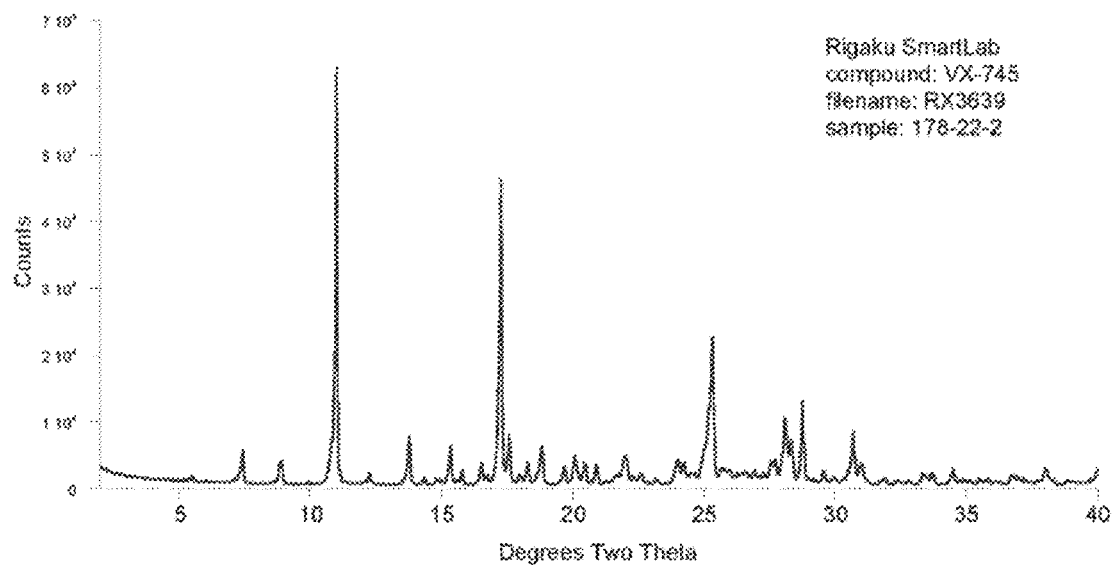
Figure 200:
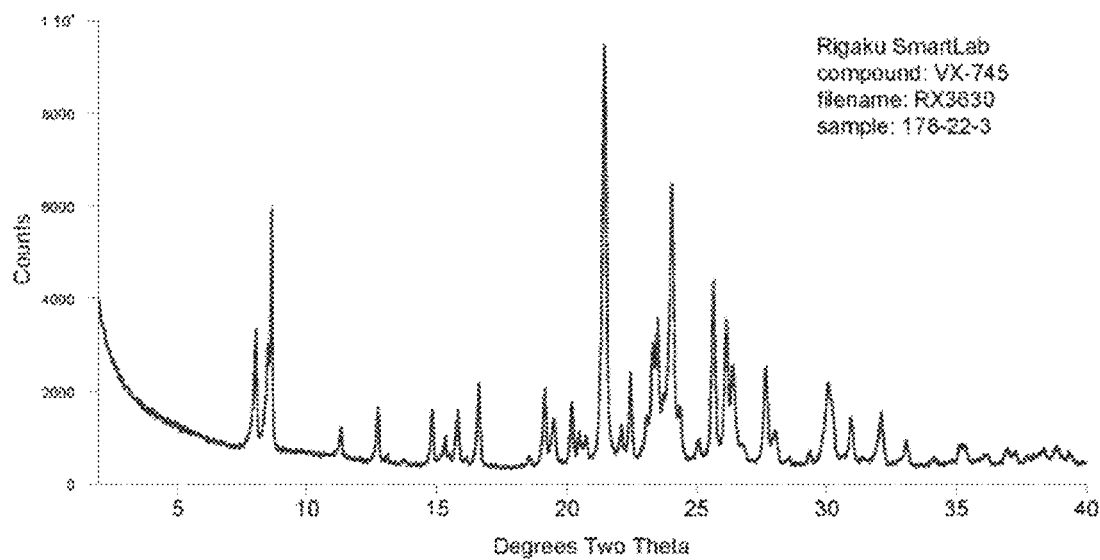
Figure 201:
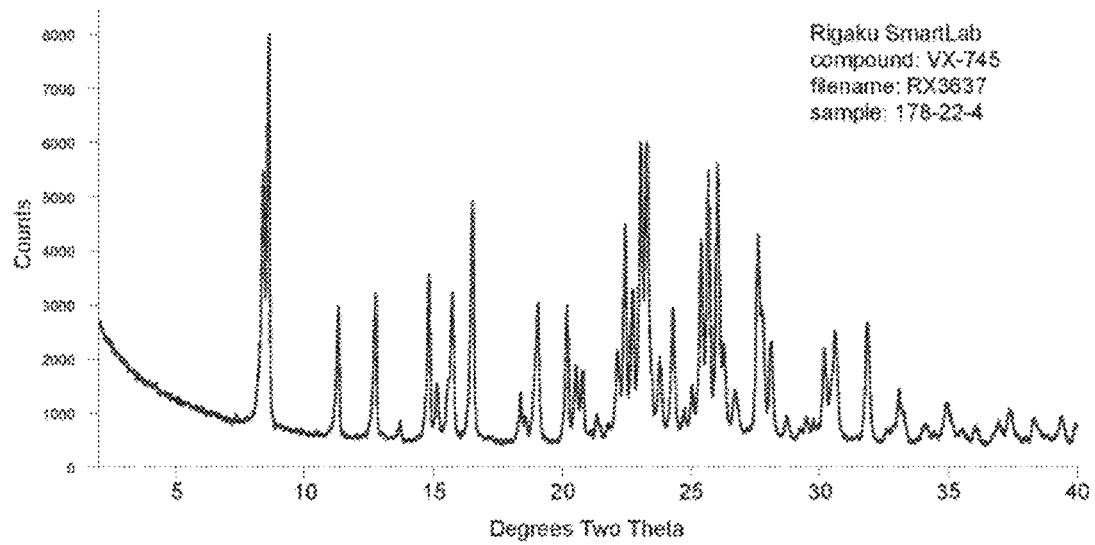
Figure 202:
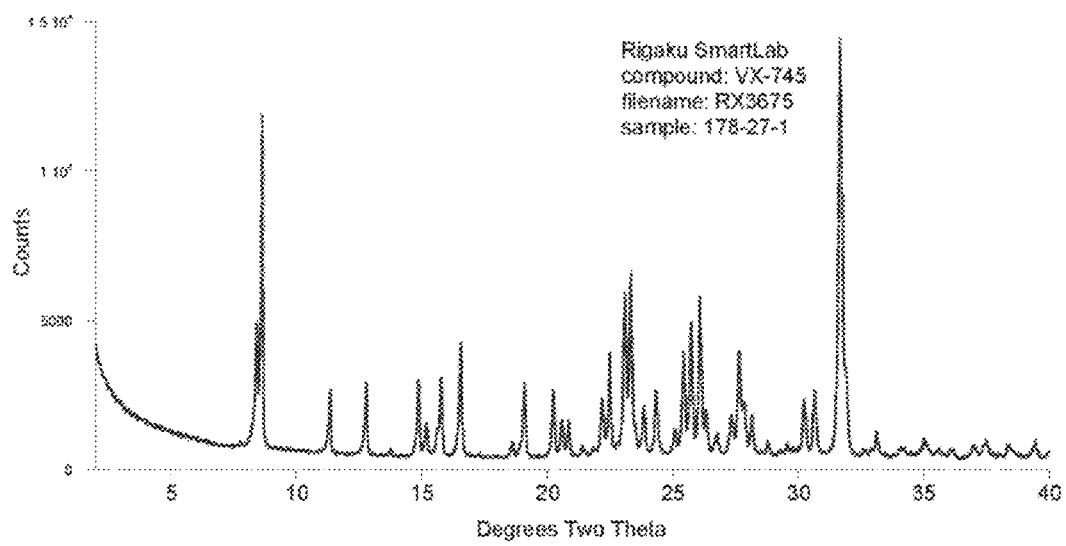
Figure 203:
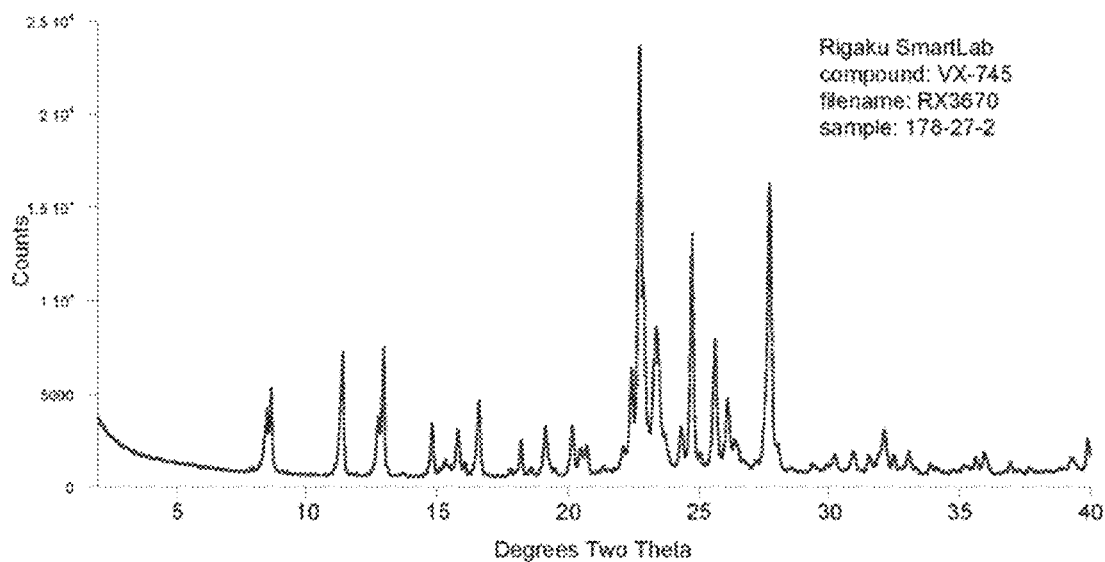
Figure 204:
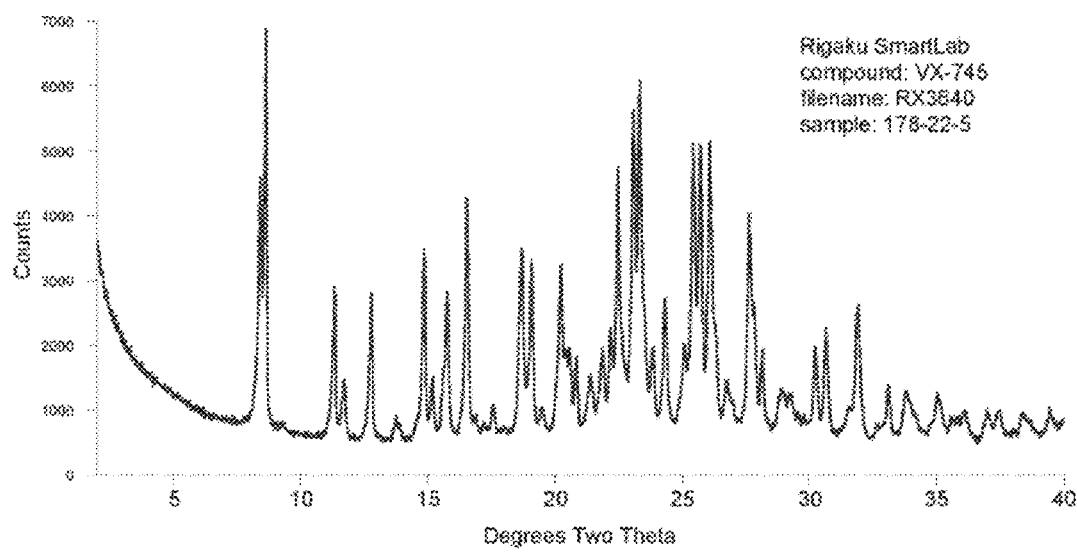
Figure 205:
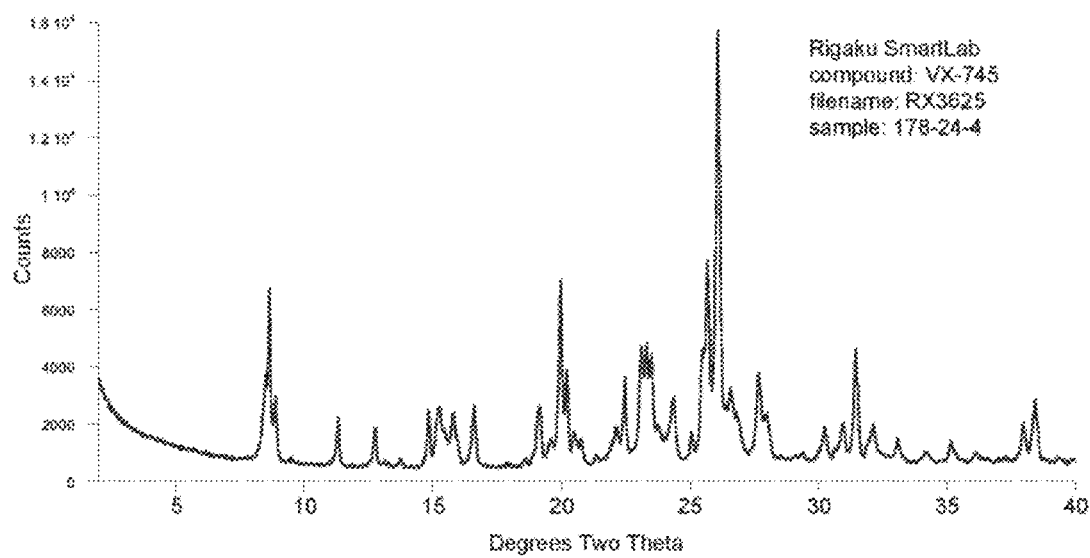
Figure 206:
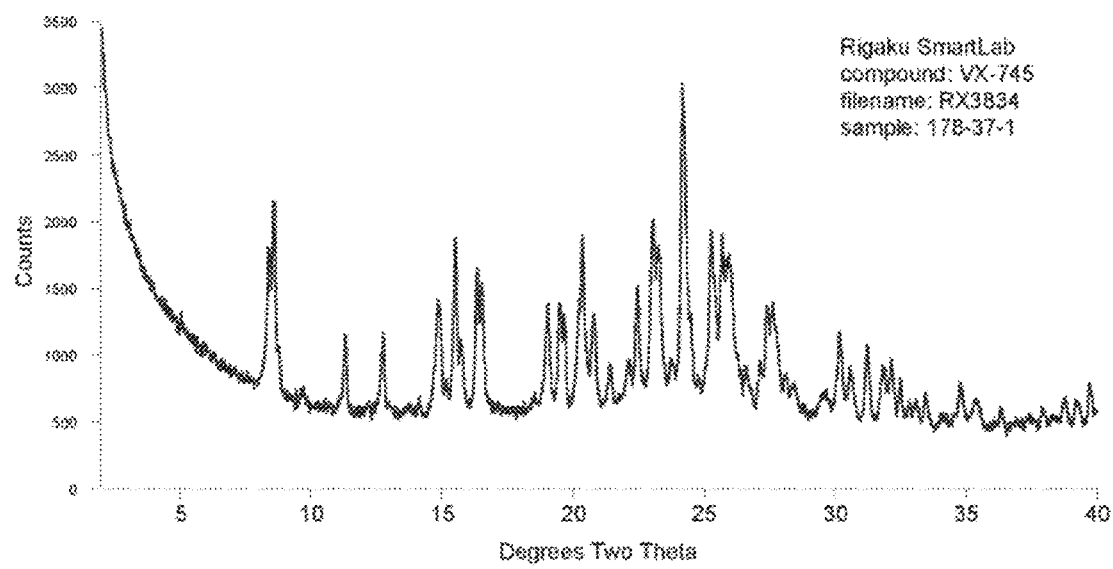
Figure 207:
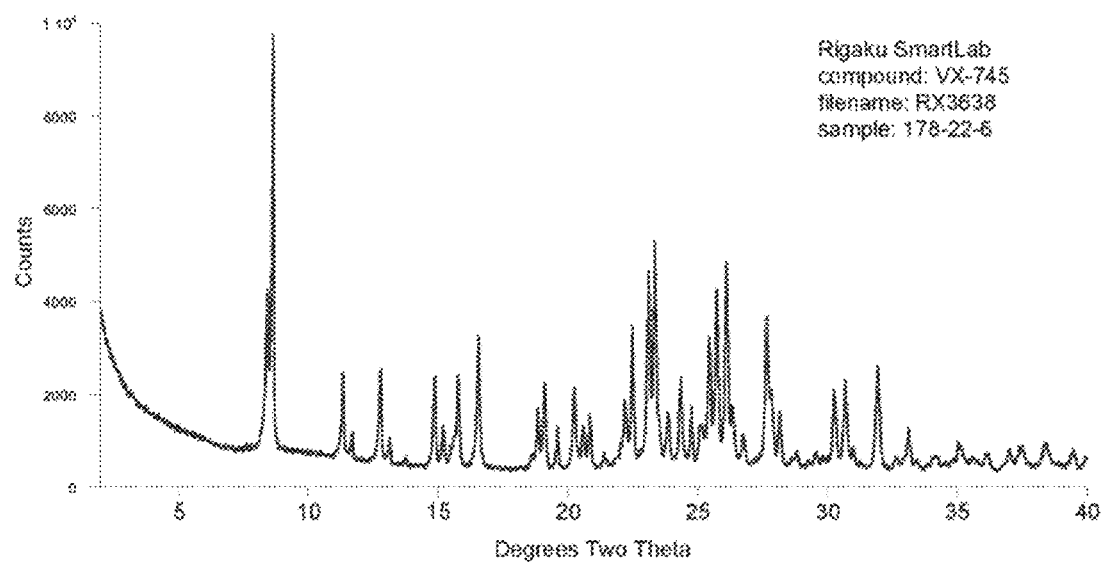
Figure 208:
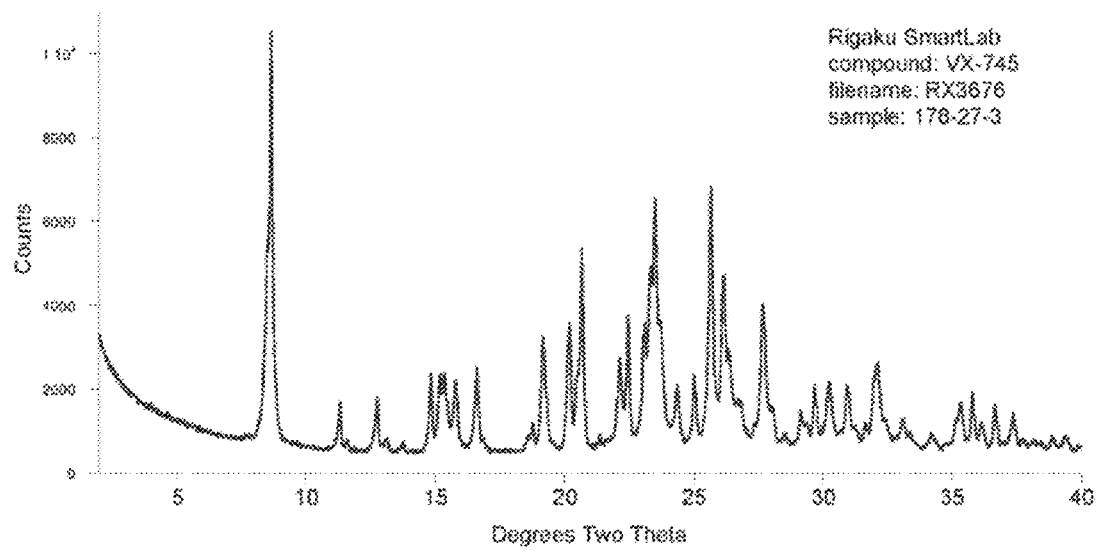
Figure 209:
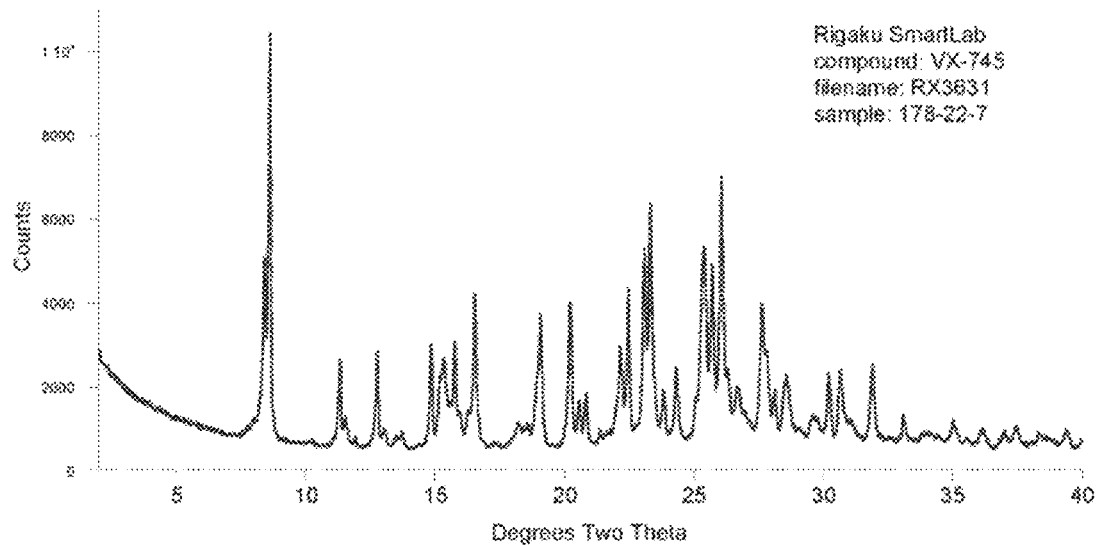
Figure 210:
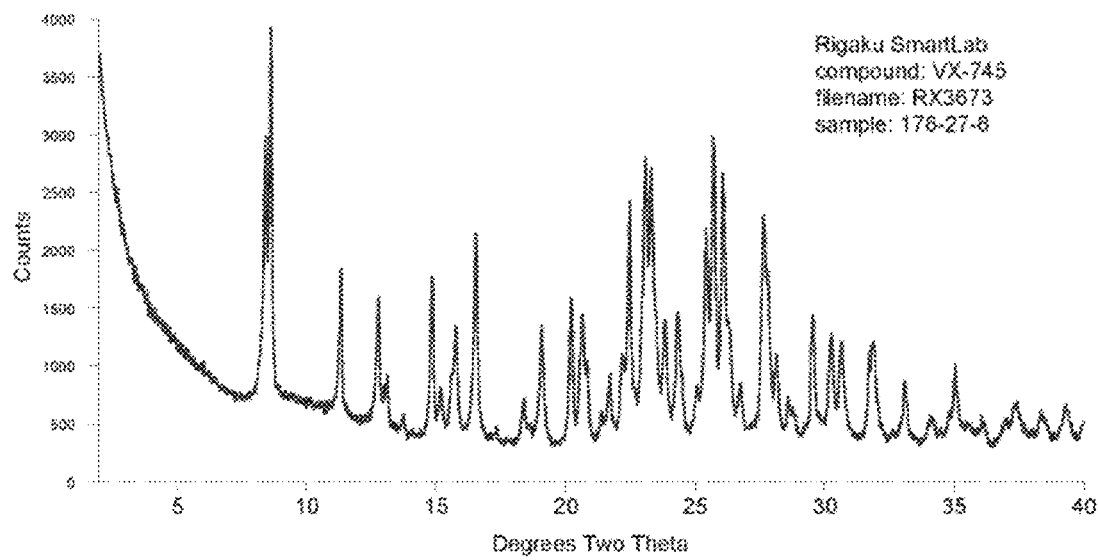
Figure 211:
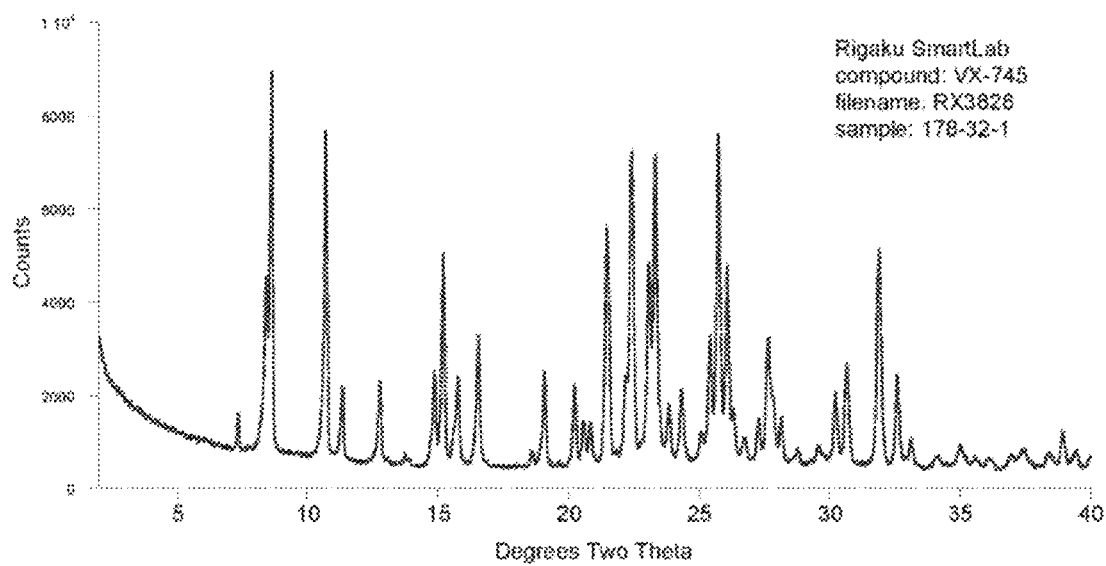
Figure 212:
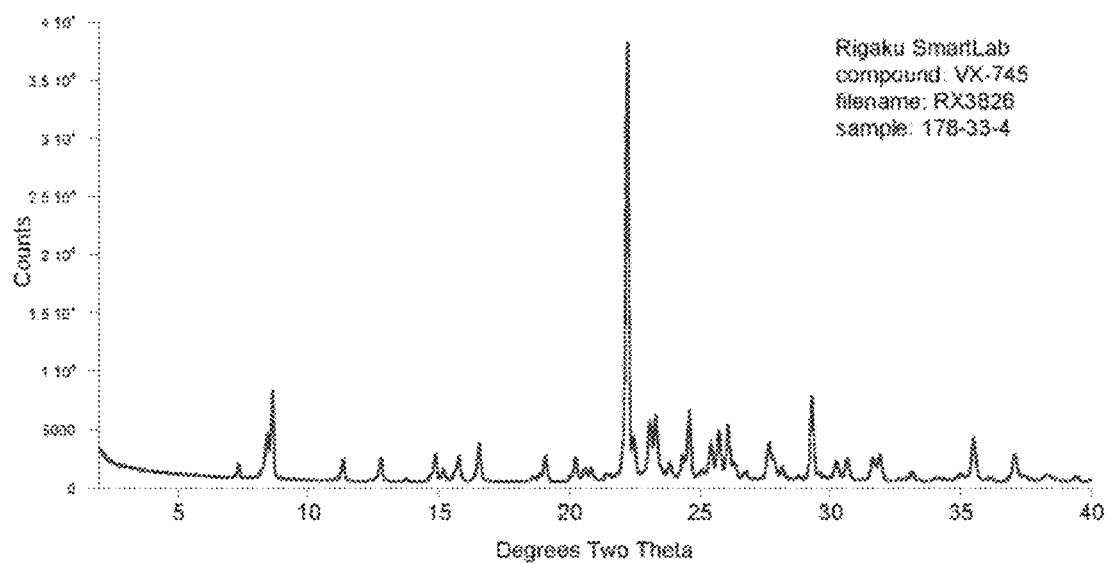
Figure 213:
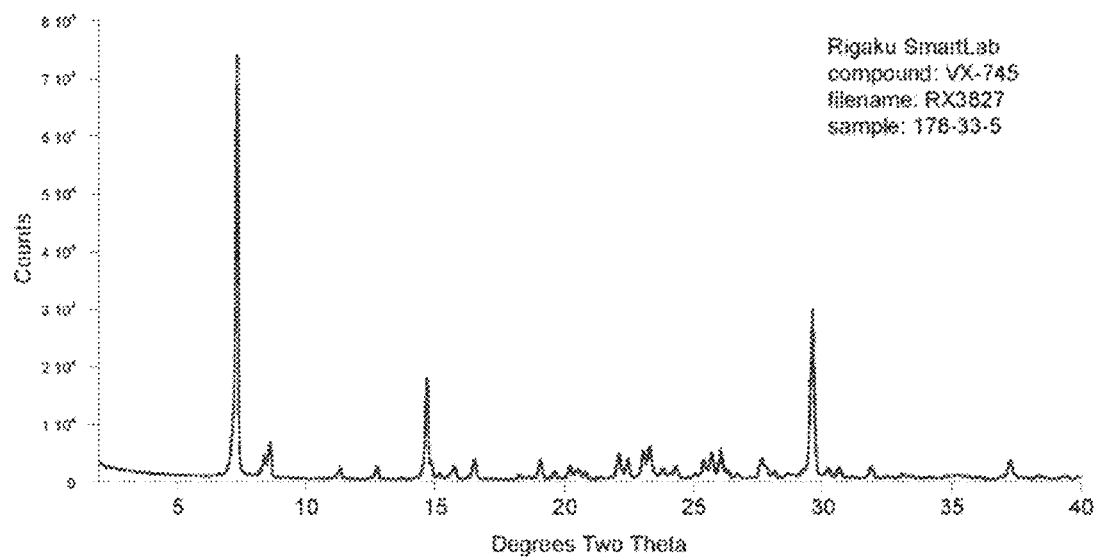
Figure 214:
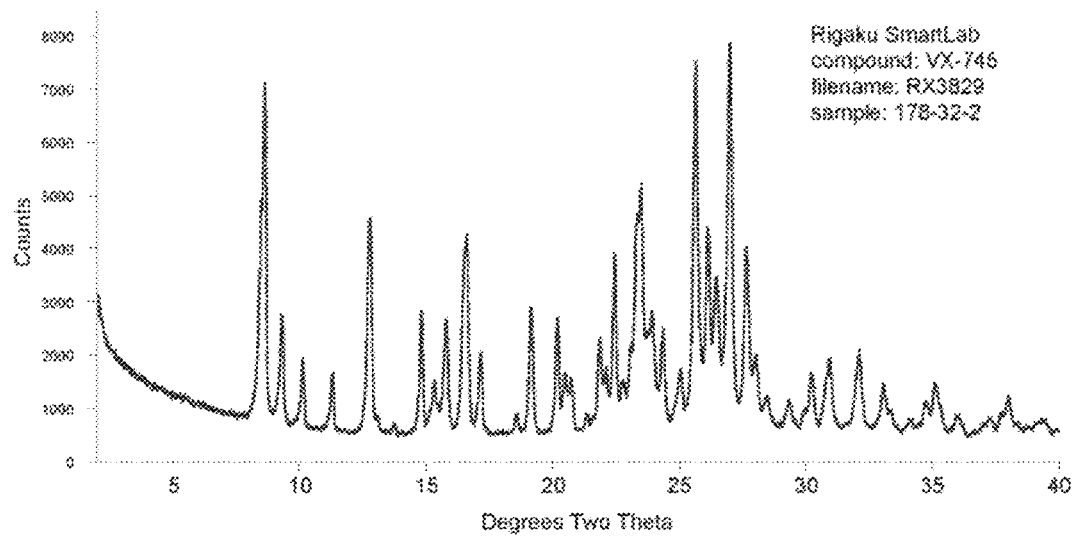
Figure 215:
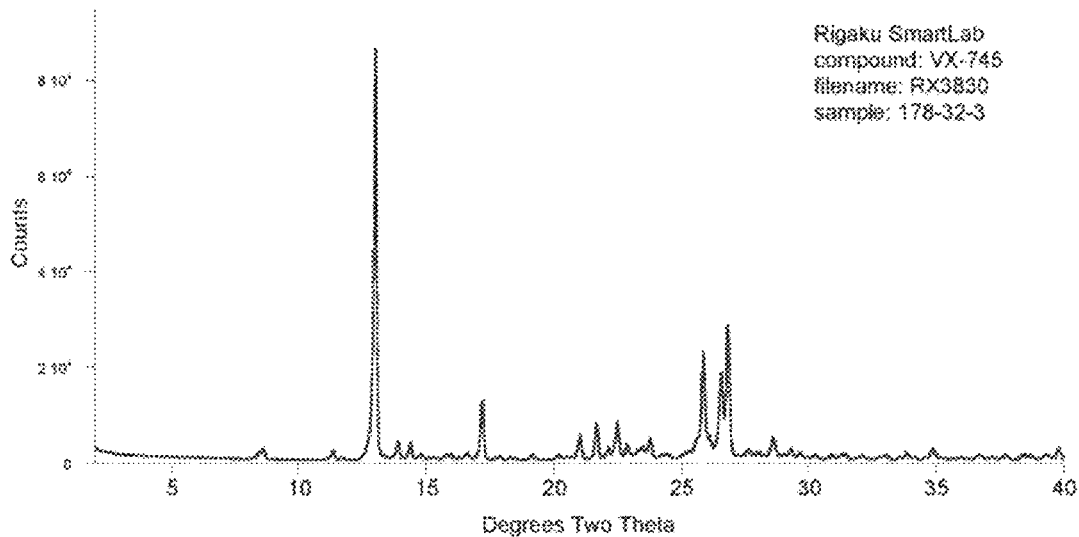

Stoichiometric Slurry Experiments. Stoichiometric slurry experiments were carried out in glass vials. Each of the vials was charged with about 15 mg of VX-745, an approximately equimolar amount of conformer, and approximately 500 µL of a saturated solution of both the VX-745 and the same coformer in the solvent used for that experiment. A magnetic stir bar was placed in each vial and the rack of vials was placed on a stir plate at room temperature for 2 days. The solids were isolated by centrifugation and analyzed by XRPD, which results are shown in FIGS. 141-215. The results are shown in FIGS. 240A-240B.

Figure 216:
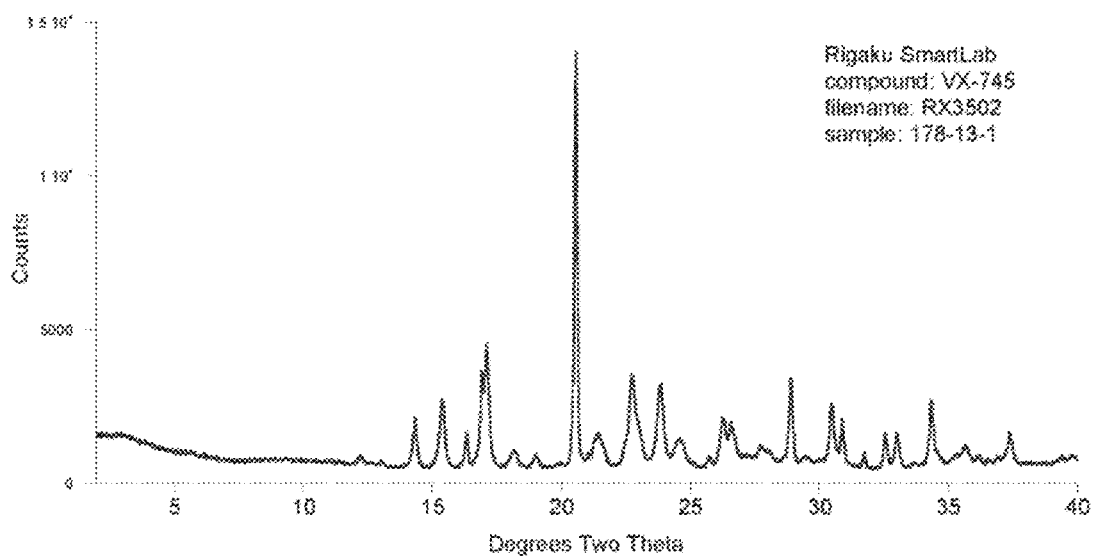
FIGS. 216-218 show XRPD results of various co-crystals of VX-745 produced by milling. The co-crystal in each figure is identified by XRPD filename, which corresponds to "XRPD File" in FIG. 241.
Figure 217:
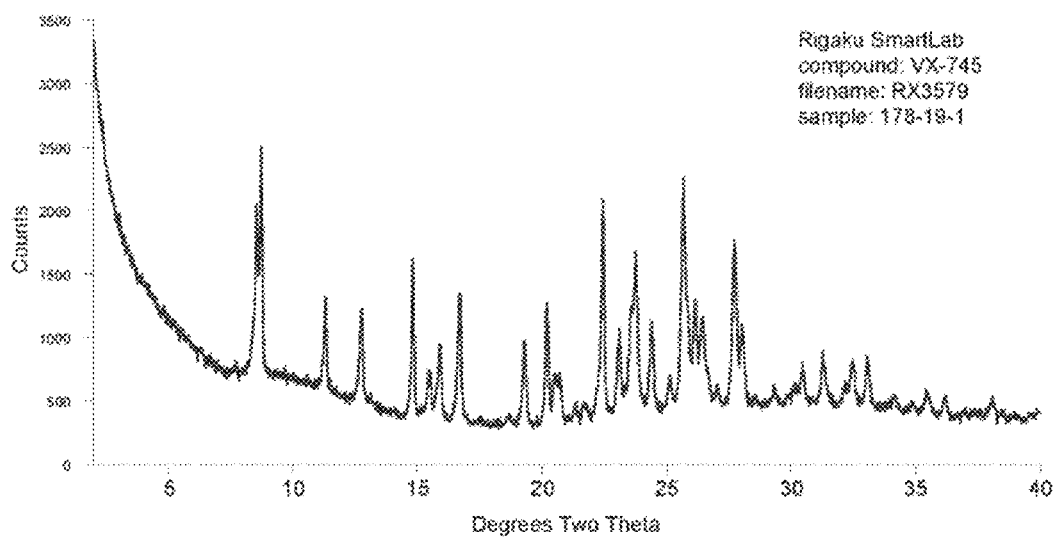
Figure 218:
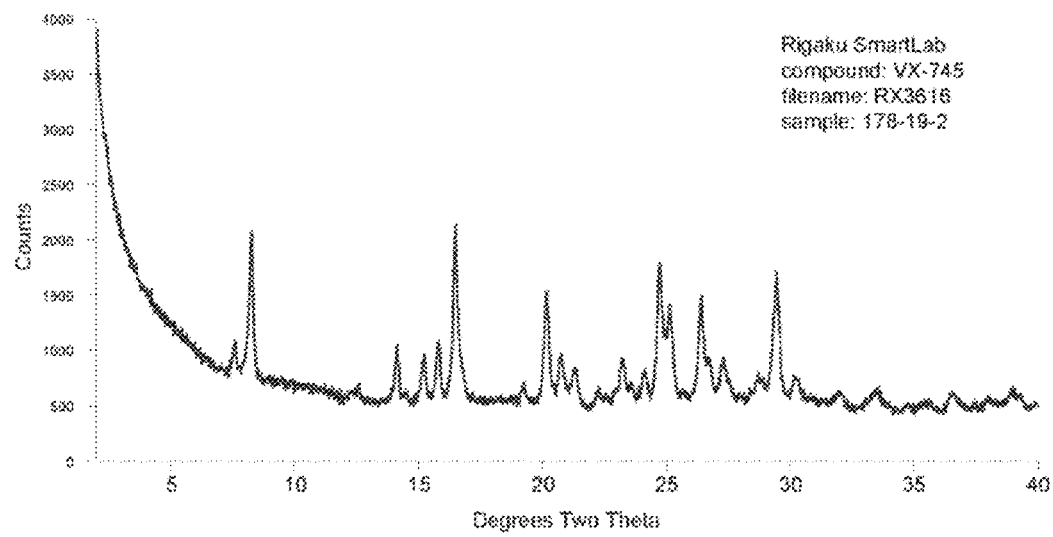

Stoichiometric Wet Milling Experiments. For each experiment, A PEEK grinding cup was charged with about 15 mg of VX-745, an approximately equimolar amount of conformer, about 10 µL of either acetone or water, and one steel grinding ball. The cup was sealed and shaken on a Retsch mill for 20 min. The solid was removed and analyzed by XRPD, which results are shown in FIGS. 216-218. The results are shown in FIG. 241.

Many of the XRPD patterns obtained from experiments using different coformers were similar to each other. It was concluded that VX-745 is polymorphic. Eight unique XRPD patterns of VX-745, designated Forms A through H, were observed during the screening (FIG. 36). In addition to the cocrystal experiments, eight experiments were performed using only VX-7 45 to confirm the observed polymorphism. Six of the eight polymorphs observed during the cocrystal screen were obtained from the polymorph screen experiments (Table 26).

TABLE 26

Samples generated using VX-745

| Method | Solvent | Conditions | Sample ID | XRPD File | Result |
|---|---|---|---|---|---|
| evaporation | acetone | open vial, RT | 178-11-1 | RX3501 | Form E |
| | acetonitrile | | 178-11-2 | RX3497 | Form C |
| | methanol | | 178-11-3 | RX3496 | Form B |
| | tetrahydrofuran | | 178-11-4 | RX3500 | Form E |
| slurry | acetone | RT, 1 day | 178-11-5 | RX3503 | Form G |
| | acetonitrile | | 178-11-6 | RX34B9 | Form A |
| | methanol | | 178-11-7 | RX3498 | Form D |
| | tetrahydrofuran | | 178-11-8 | RX3504 | Form E |

Of 160 samples made using 79 coformers, forty one samples made using thirty five different coformers were found that exhibit XRPD patterns suggestive of new phase formation. Those patterns contain peaks that do not appear to arise from the API or relevant conformer. In many cases, only one or two unique peaks were observed in the XRPD pattern. in those cases the coformers used were not used for further consideration. Materials yielding unique phases in which the XRPD patterns contained a significant number of unique peaks are summarized in Table 27. Plots containing those patterns are shown in FIGS. 37 through 54.

TABLE 27

Exemplary cocrystals exhibiting new phases

| Coformer | Expirement[a] | Sample ID | XRPD Fife | Results[b] | Comments |
|---|---|---|---|---|---|
| acesulfame potassium | SE | 178-7-1 | RX3464 | CF + new | — |
| aconitic acid | slurry | 178-12-3 | RX3609 | CF + new | — |
| calcium chloride | slurry | 178-12-13 | RX3596 | new | — |
| choline chloride | SE | 178-8-1 | RX3495 | API B + new | — |
| gentisic acid | SE | 178-8-13 | RX3520 | new | patterns overlay well |
| | | 178-18-1 | RX3634 | new | |
| glutaric acid | SE | 178-8-16 | RX3582 | new | — |
| 1-hydroxy-2-naphthoic acid | SE | 178-9-2 | RX3540 | CF + new | patterns overlay well |
| | | 178-8-13 | RX3635 | CF + new | |
| | slurry | 178-24-3 | RX3629 | CF + new | |
| ketoglutaric acid | slurry | 178-26-1 | RX3686 | new | — |
| malonic acid | slurry | 178-26-6 | RX3664 | CF + new | — |
| nicotinic acid | SE | 178-9-17 | RX3570 | CF + new | — |
| phenol | SE | 178-9-19 | RX3537 | API E + new | patterns overlay well |
| | slurry | 178-33-2 | RX3833 | new | |
| L-proline | SE | 178-10-1 | RX3863 | CF + new | — |
| salicylic acid | slurry | 178-22-2 | RX3639 | CF + new | — |
| sorbic acid | SE | 178-10-10 | RX3574 | API E + new | — |
| thiamine hydrochloride | SE | 178-10-16 | RX3542 | CF + new | — |
| L-threonene | SE | 178-10-17 | RX3595 | CF + new | — |
| urea | SE | 178-10-19 | RX3605 | CF + new | — |
| zinc chloride | grind | 178-9-2 | RX3616 | new | — |

[a]SE = slow evaporation
[b]CF = coformer

Preparation of Cocrystals at Larger Scales

It was decided to prepare three cocrystals at larger scales for characterization. Those are the gentisic acid, glutaric acid, and zinc chloride cocrystals (Table 28).

Co-crystals were prepared by the methods as described in Table 28.

Figure 219:
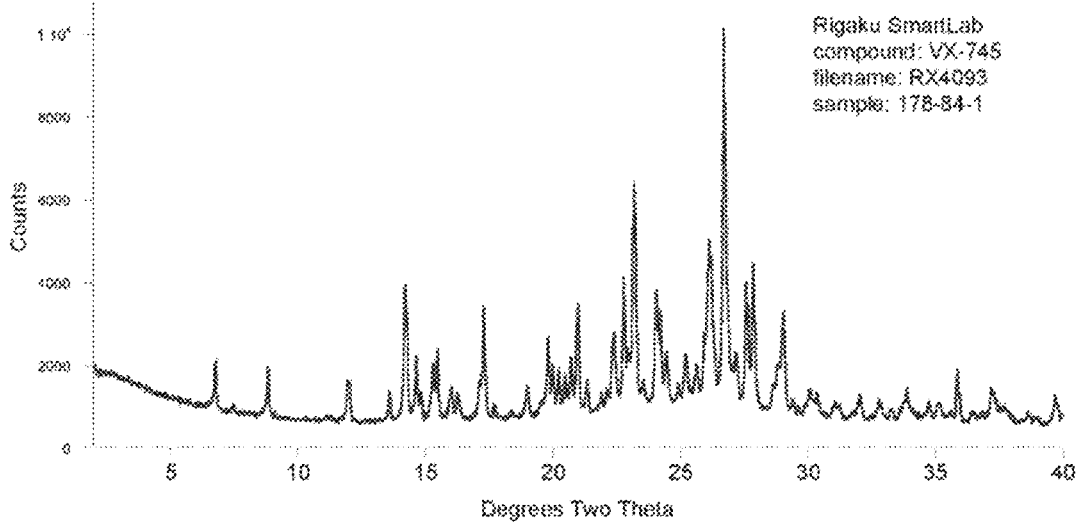
FIG. 219 shows the XRPD result of a co-crystal comprising VX-745 and gentisic acid.
Figure 227:
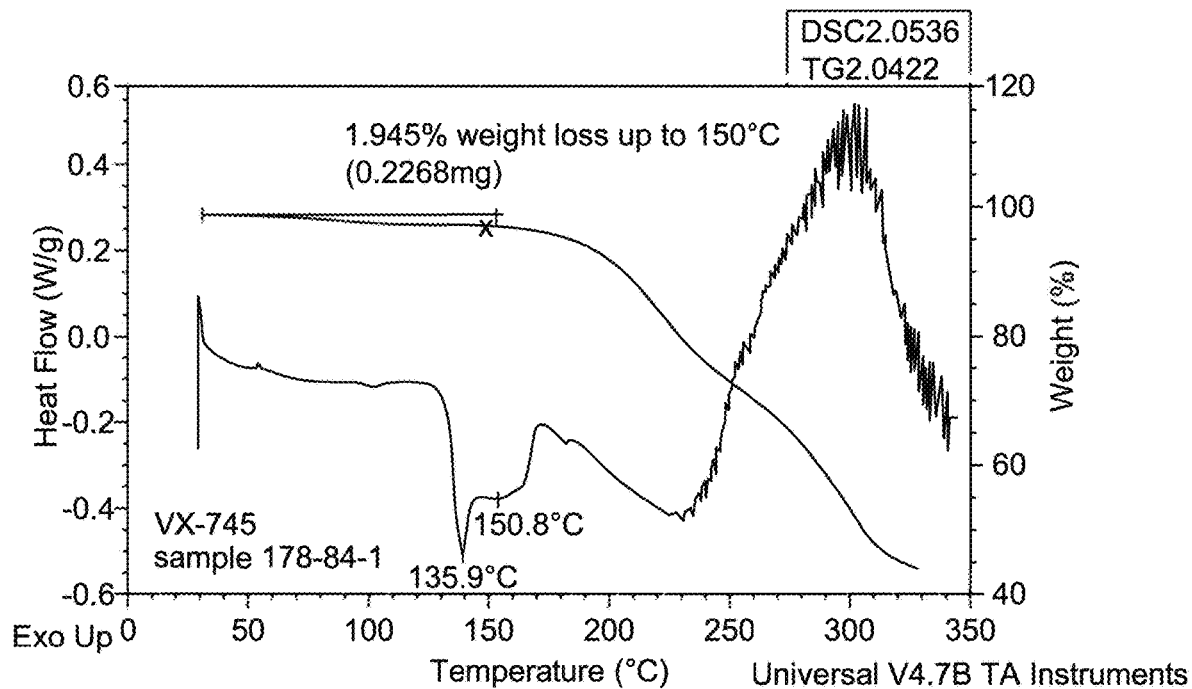
FIG. 227 shows thermogravimetric analysis of a co-crystal comprising VX-745 and gentisic acid.
Figure 230:
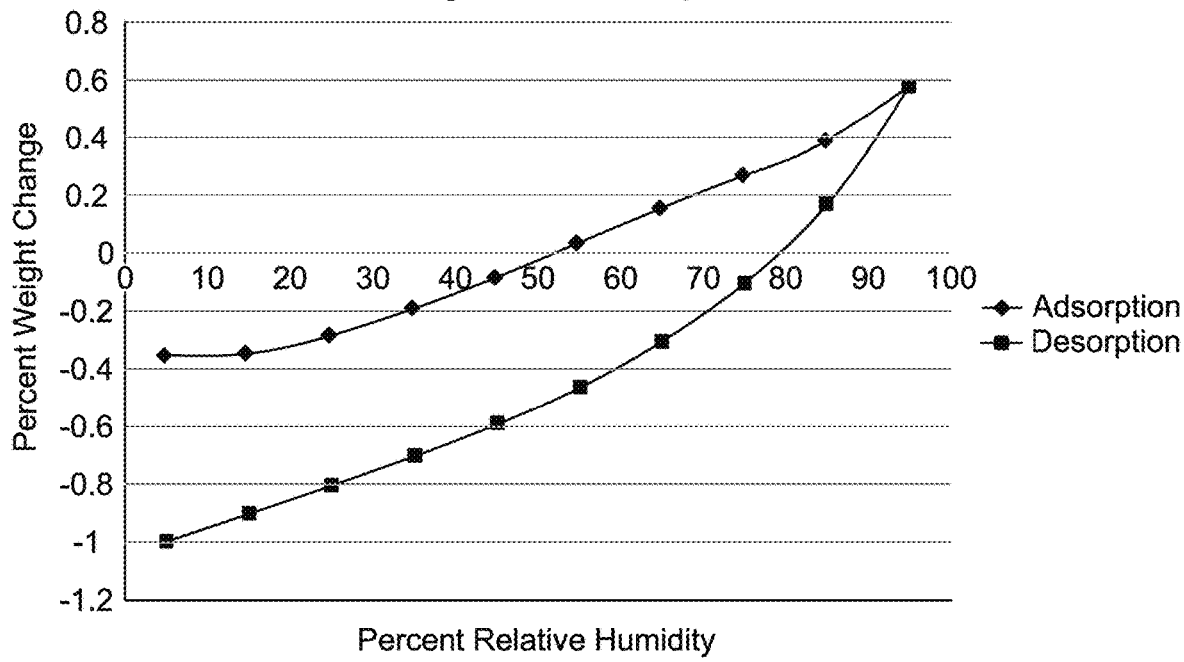
FIG. 230 shows dynamic vapor sorption (DVS) data for a co-crystal comprising VX-745 and gentisic acid.
Figure 233:
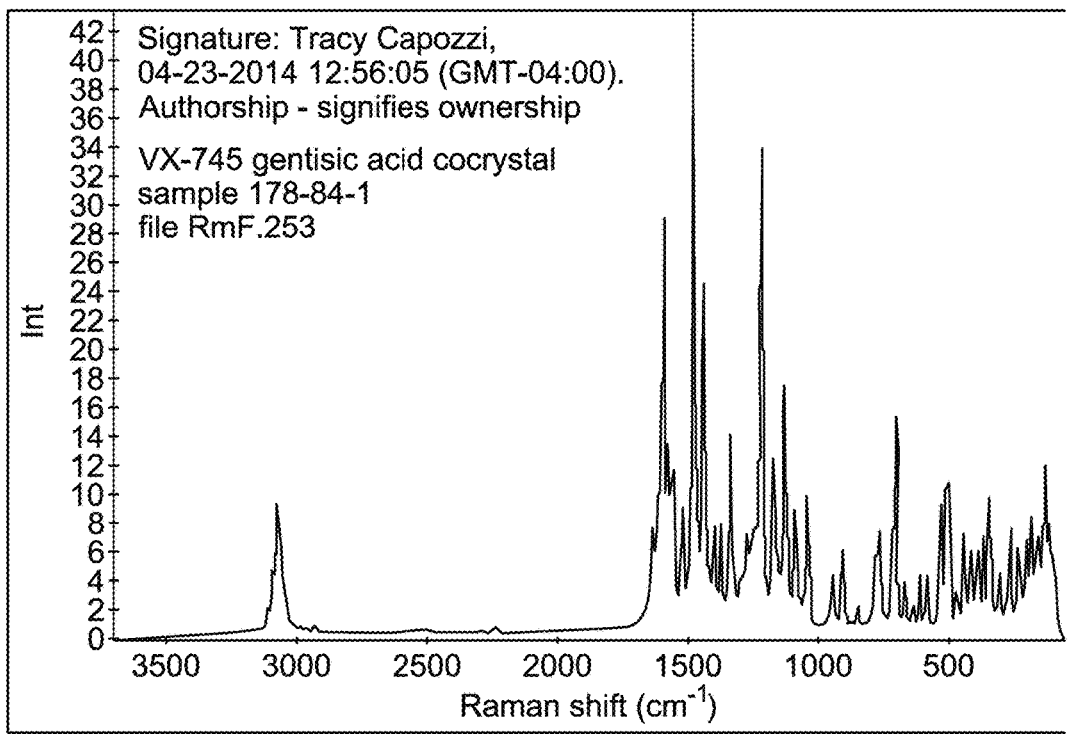
FIG. 233 shows Raman Spectroscopic data for a co-crystal comprising VX-745 and gentisic acid.
Figure 236A:
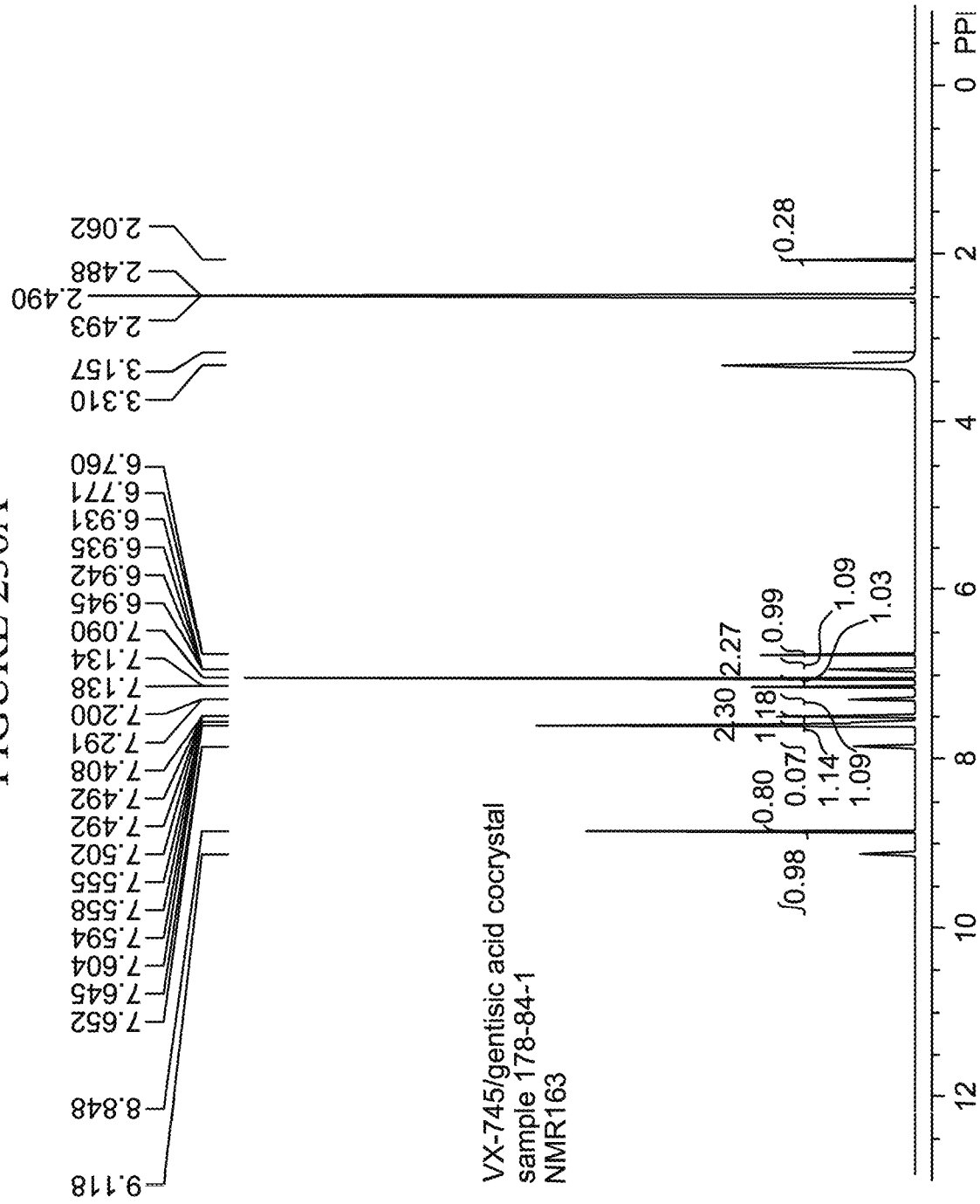
FIG. 236A shows Nuclear Magnetic Resonance (NMR) Spectroscopic data for a co-crystal comprising VX-745 and gentisic acid.
Figure 236B:
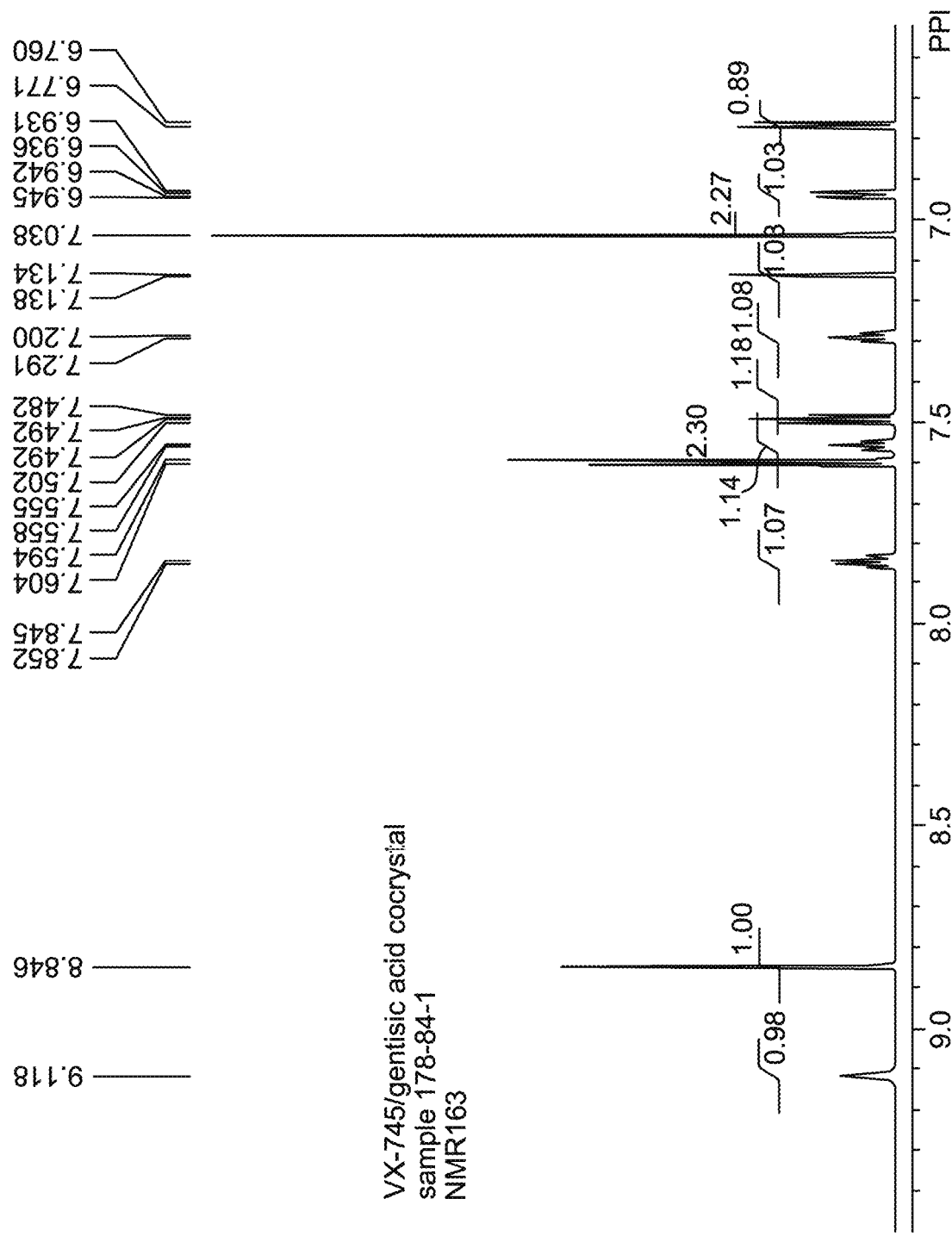
FIG. 236B shows zoom-in NMR spectroscopic data.

Co-crystal comprising VX-745 and gentisic acid: FIG. 219 shows the XRPD result; FIG. 227 shows thermogravimetric analysis; FIG. 230 shows dynamic vapor sorption (DVS) data; FIG. 233 shows Raman Spectroscopic data; FIG. 236A shows Nuclear Magnetic Resonance (NMR) full spectroscopic data and FIG. 236B shows zoom-in NMR spectroscopic data.

Figure 220:
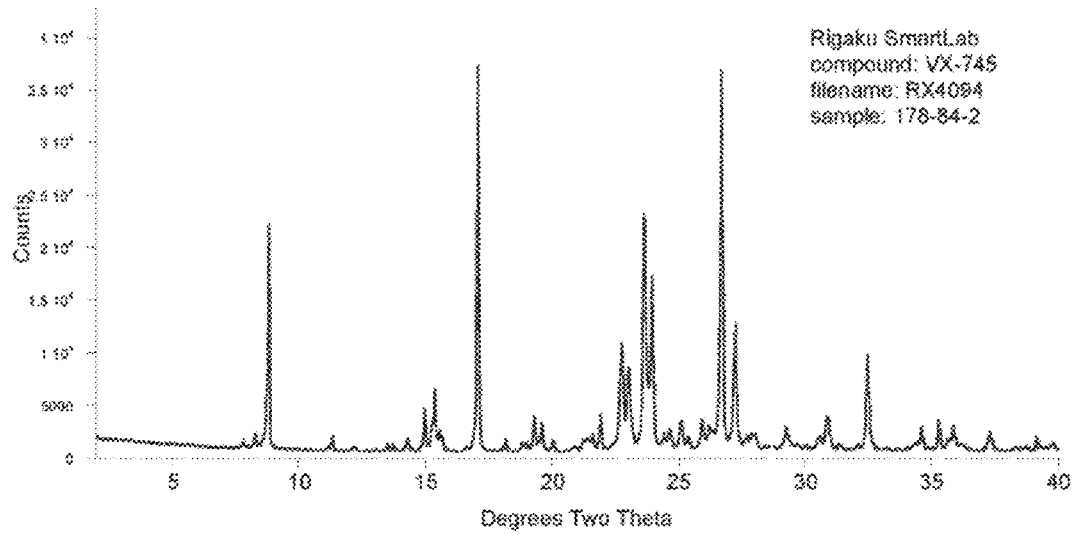
FIGS. 220-221 show the XRPD result of a co-crystal comprising VX-745 and glutaric acid.
Figure 221:
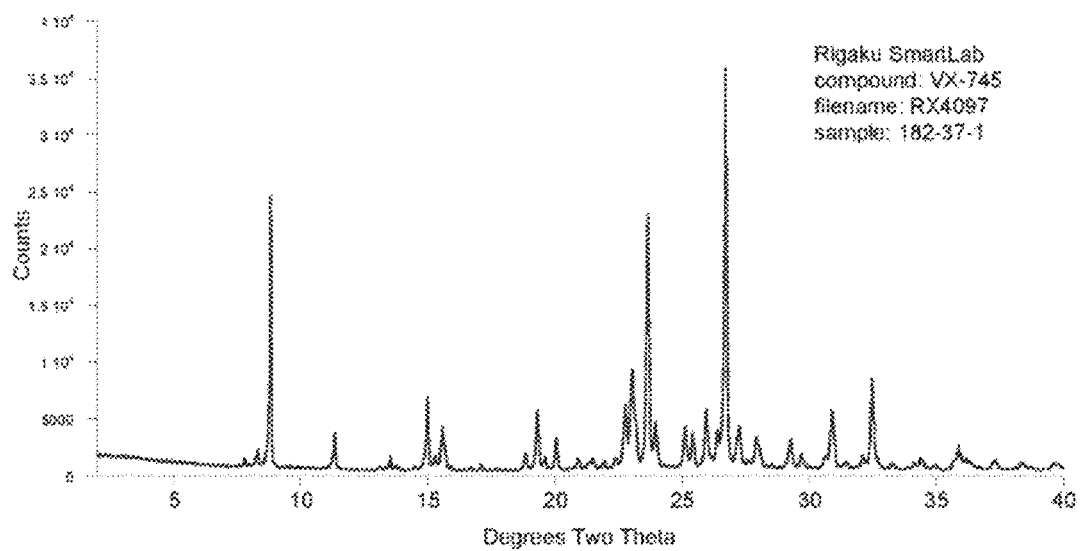
Figure 228:
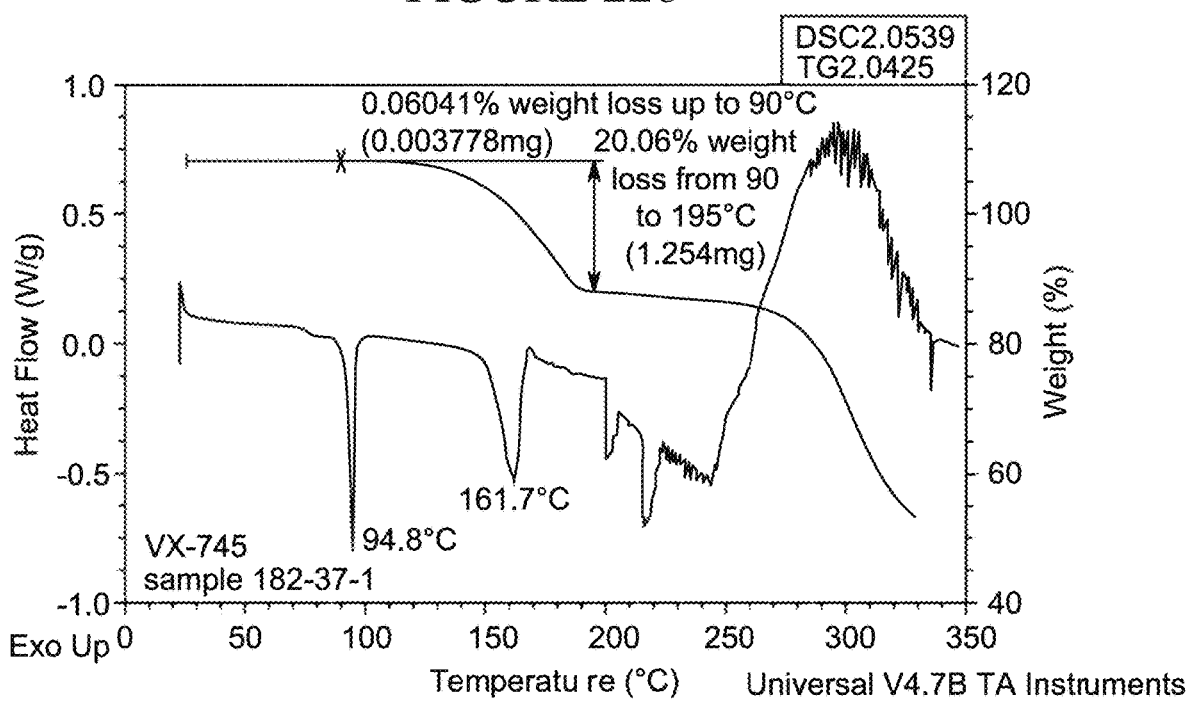
FIG. 228 shows thermogravimetric analysis of a co-crystal comprising VX-745 and glutaric acid.
Figure 231:
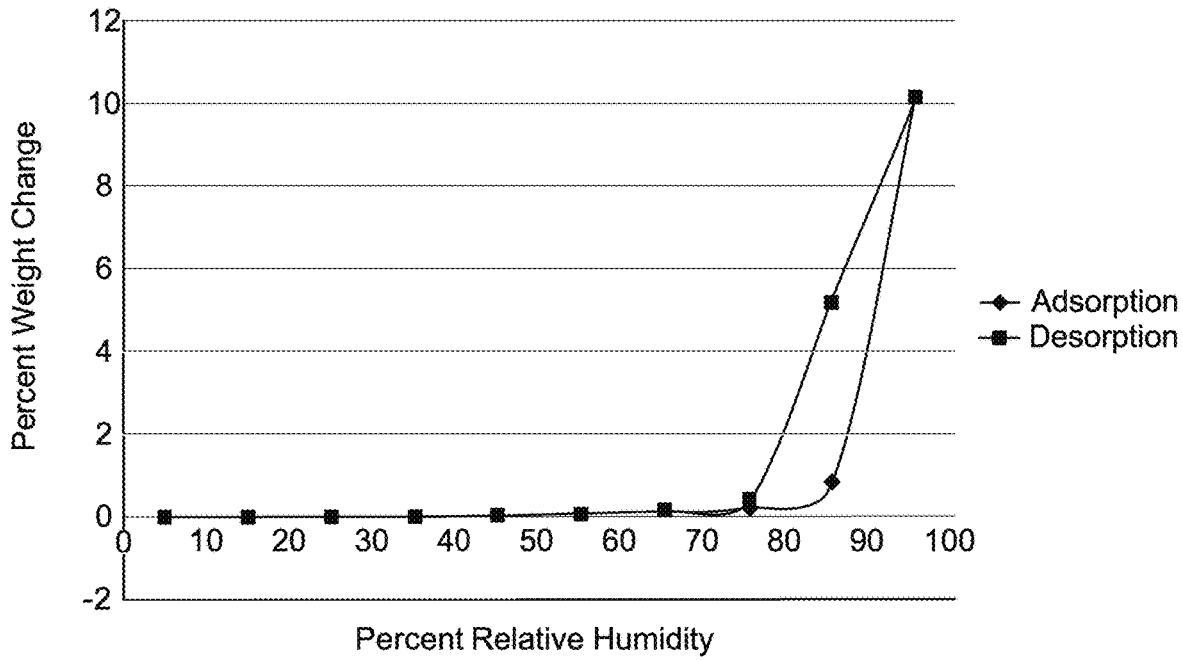
FIG. 231 shows dynamic vapor sorption (DVS) data for a co-crystal comprising VX-745 and glutaric acid.
Figure 234:
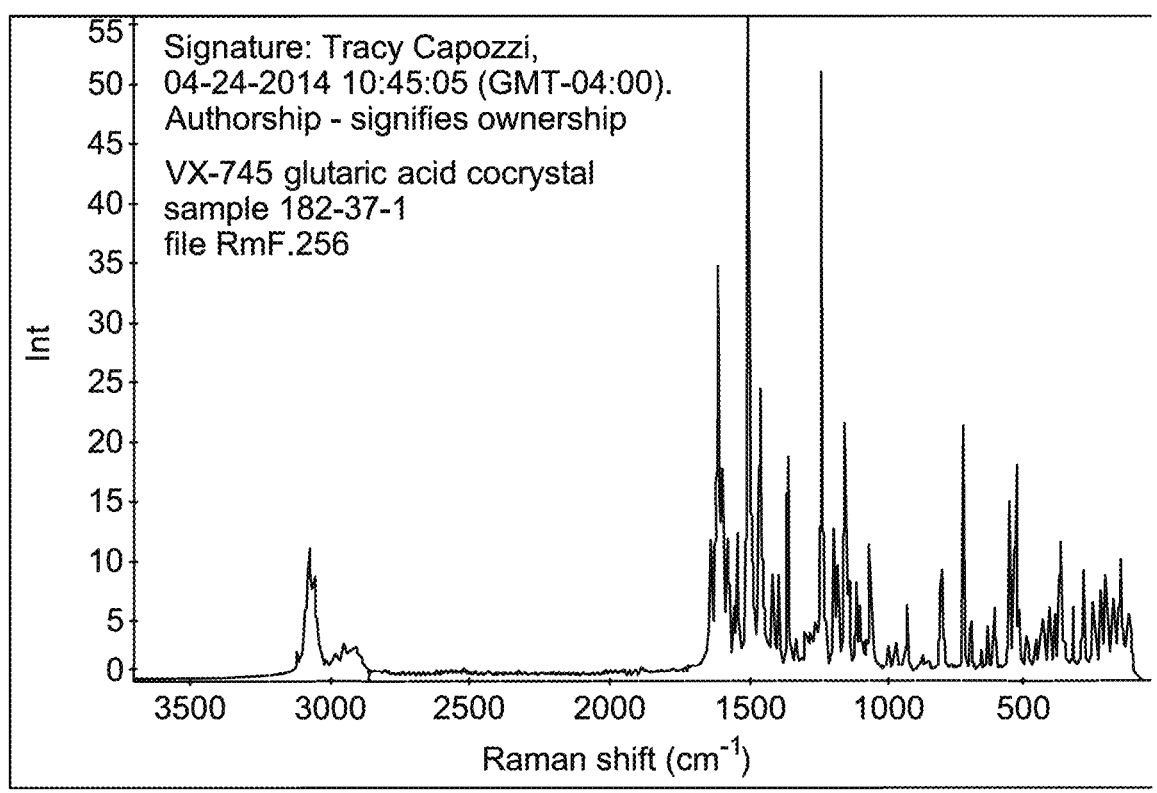
FIG. 234 shows Raman Spectroscopic data for a co-crystal comprising VX-745 and glutaric acid.
Figure 237A:
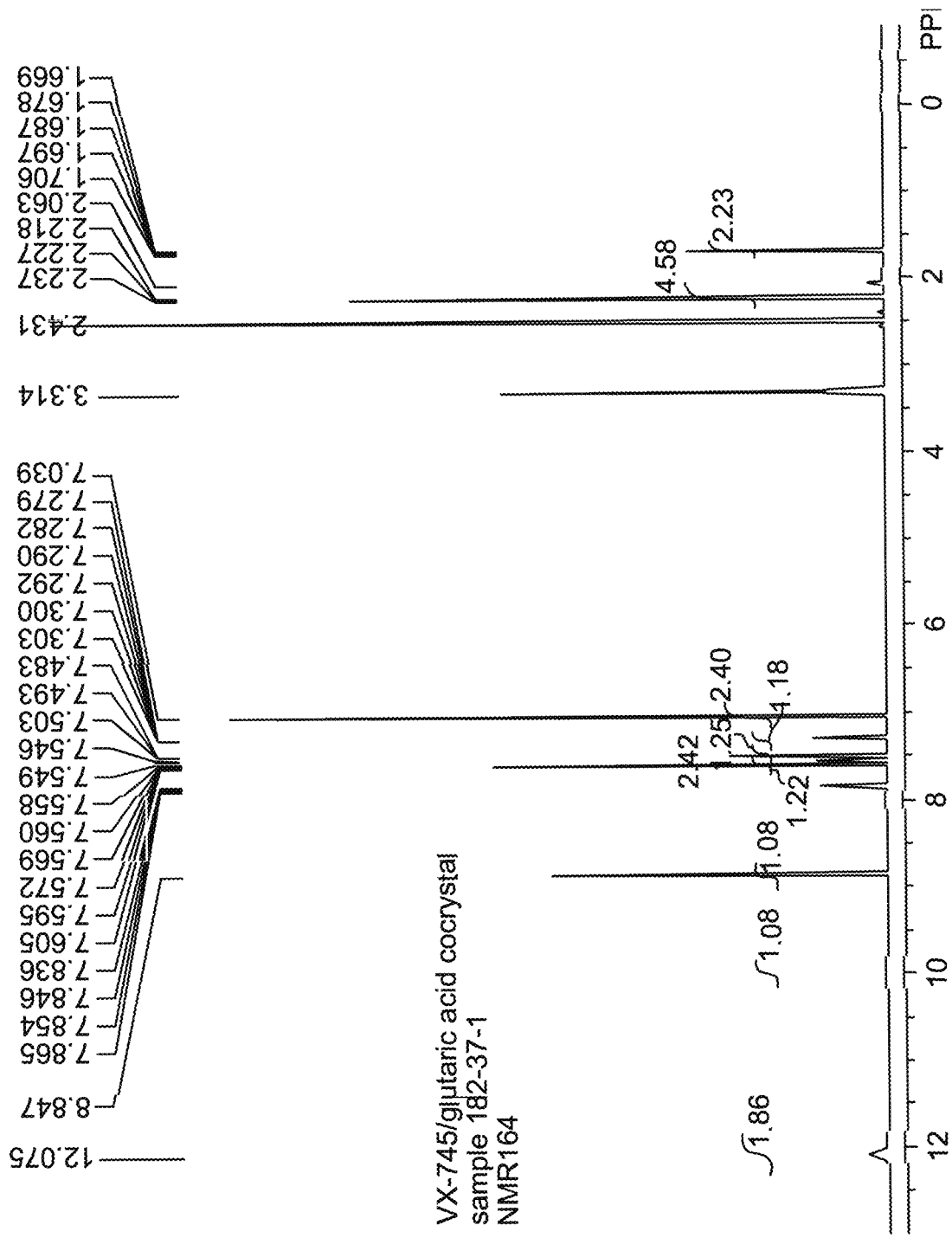
FIG. 237A shows Nuclear Magnetic Resonance (NMR) Spectroscopic data for a co-crystal comprising VX-745 and glutaric acid.
Figure 237B:
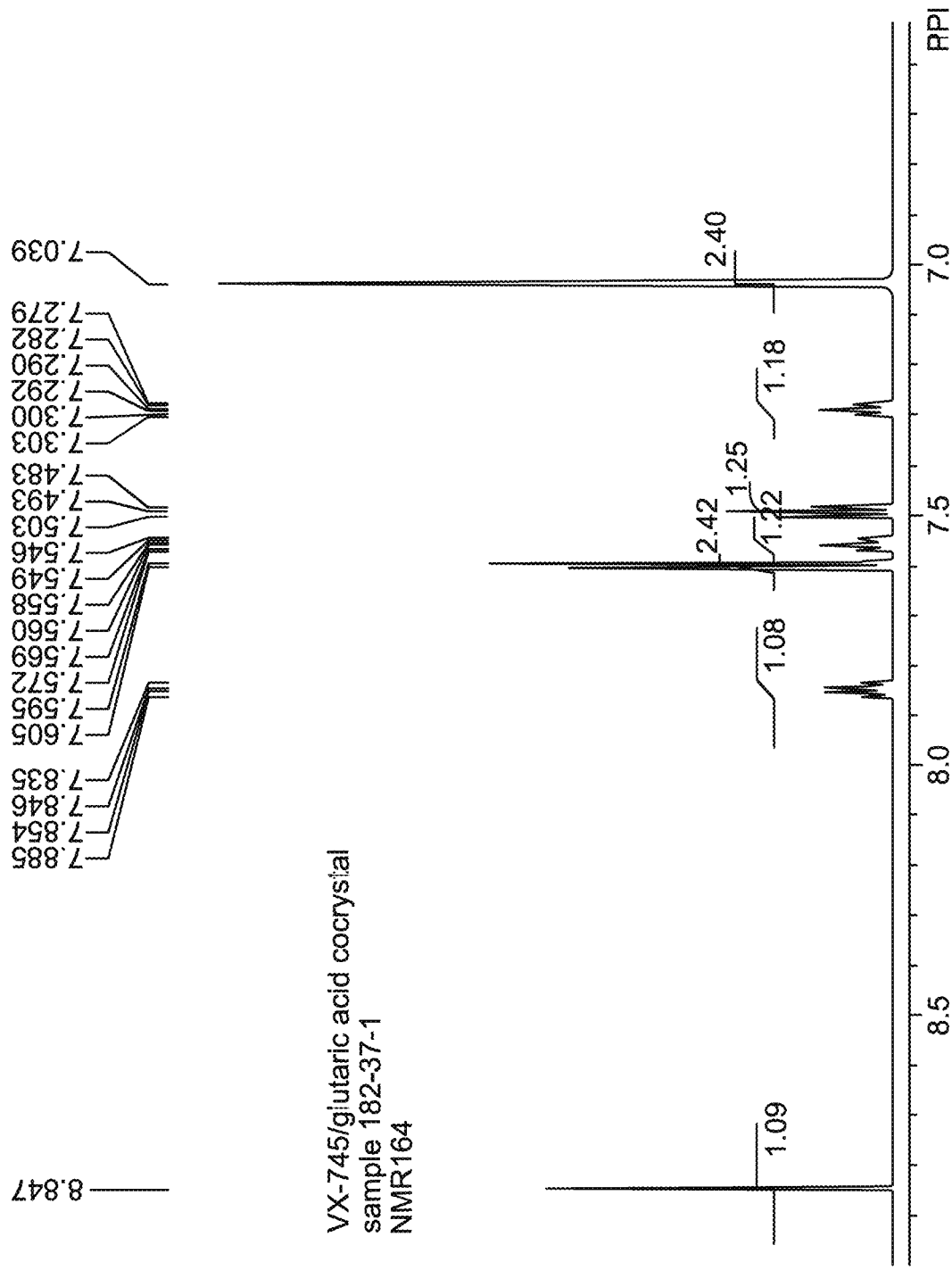
FIG. 237B shows zoom-in NMR spectroscopic data.

Co-crystal comprising VX-745 and glutaric acid: FIGS. 220-221 show the XRPD results; FIG. 228 shows thermogravimetric analysis; FIG. 231 shows dynamic vapor sorption (DVS) data; FIG. 234 shows Raman Spectroscopic data; FIG. 237A shows Nuclear Magnetic Resonance (NMR) full spectroscopic data and FIG. 237B shows zoom-in NMR spectroscopic data.

Figure 222:
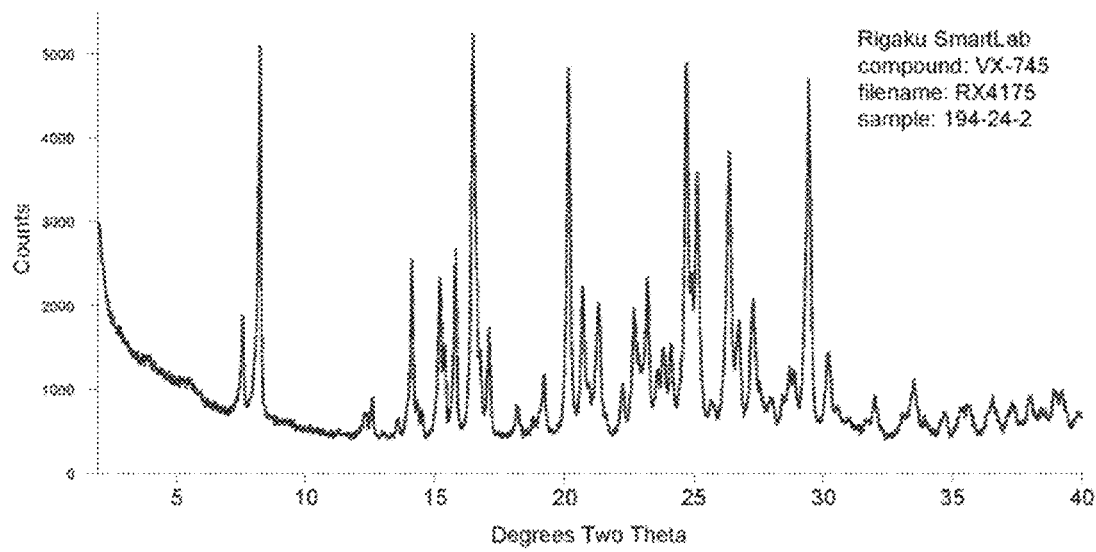
FIG. 222 shows the XRPD result of a co-crystal comprising VX-745 and zinc chloride.
Figure 229:
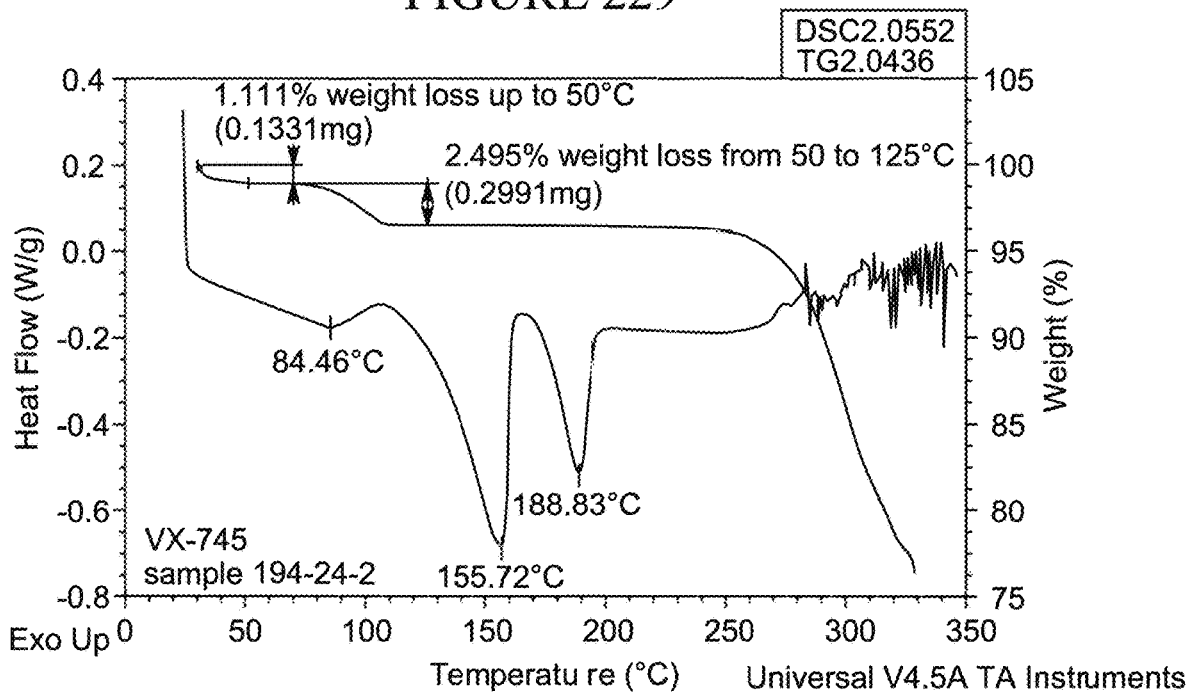
FIG. 229 shows thermogravimetric analysis of a co-crystal comprising VX-745 and zinc chloride.
Figure 232:
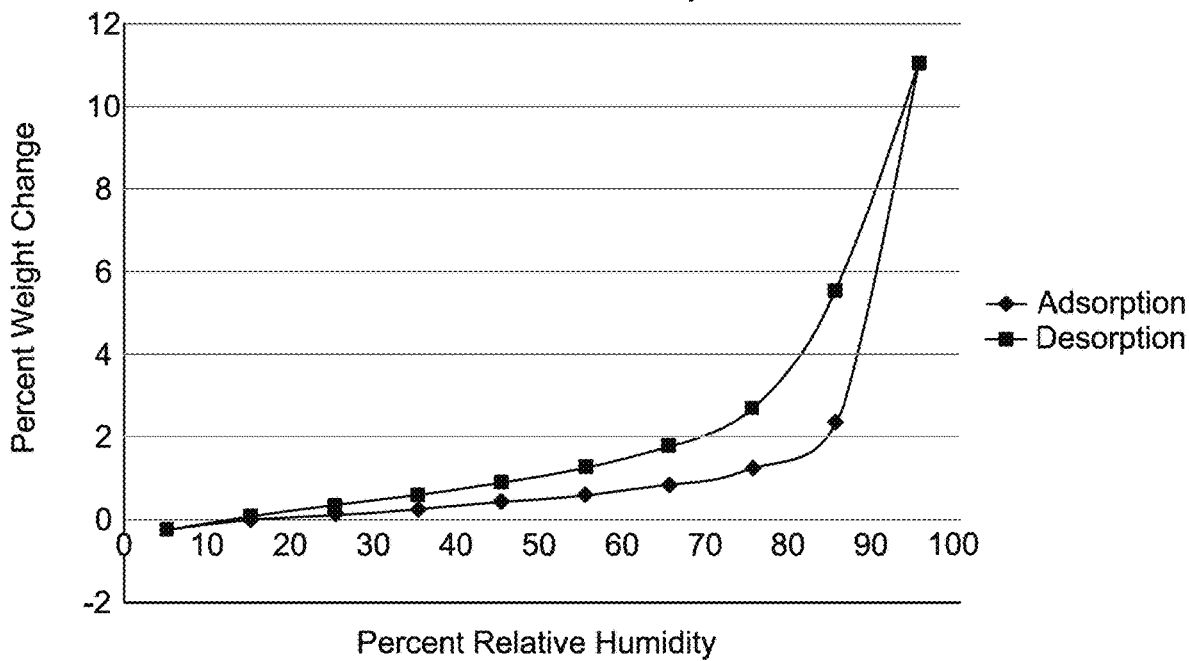
FIG. 232 shows dynamic vapor sorption (DVS) data for a co-crystal comprising VX-745 and zinc chloride.
Figure 238A:
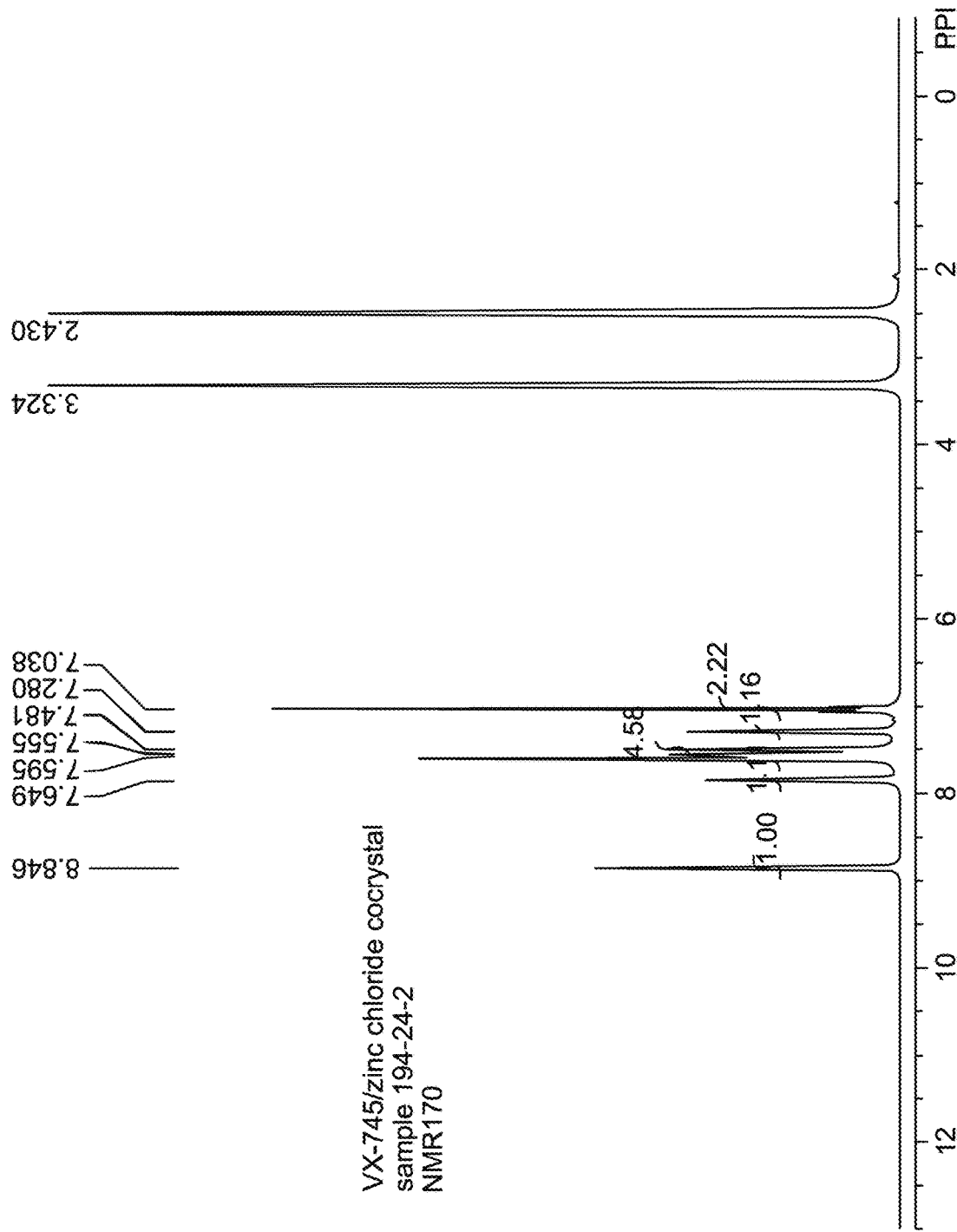
FIG. 238A shows Nuclear Magnetic Resonance (NMR) Spectroscopic data for a co-crystal comprising VX-745 and zinc chloride.
Figure 238B:
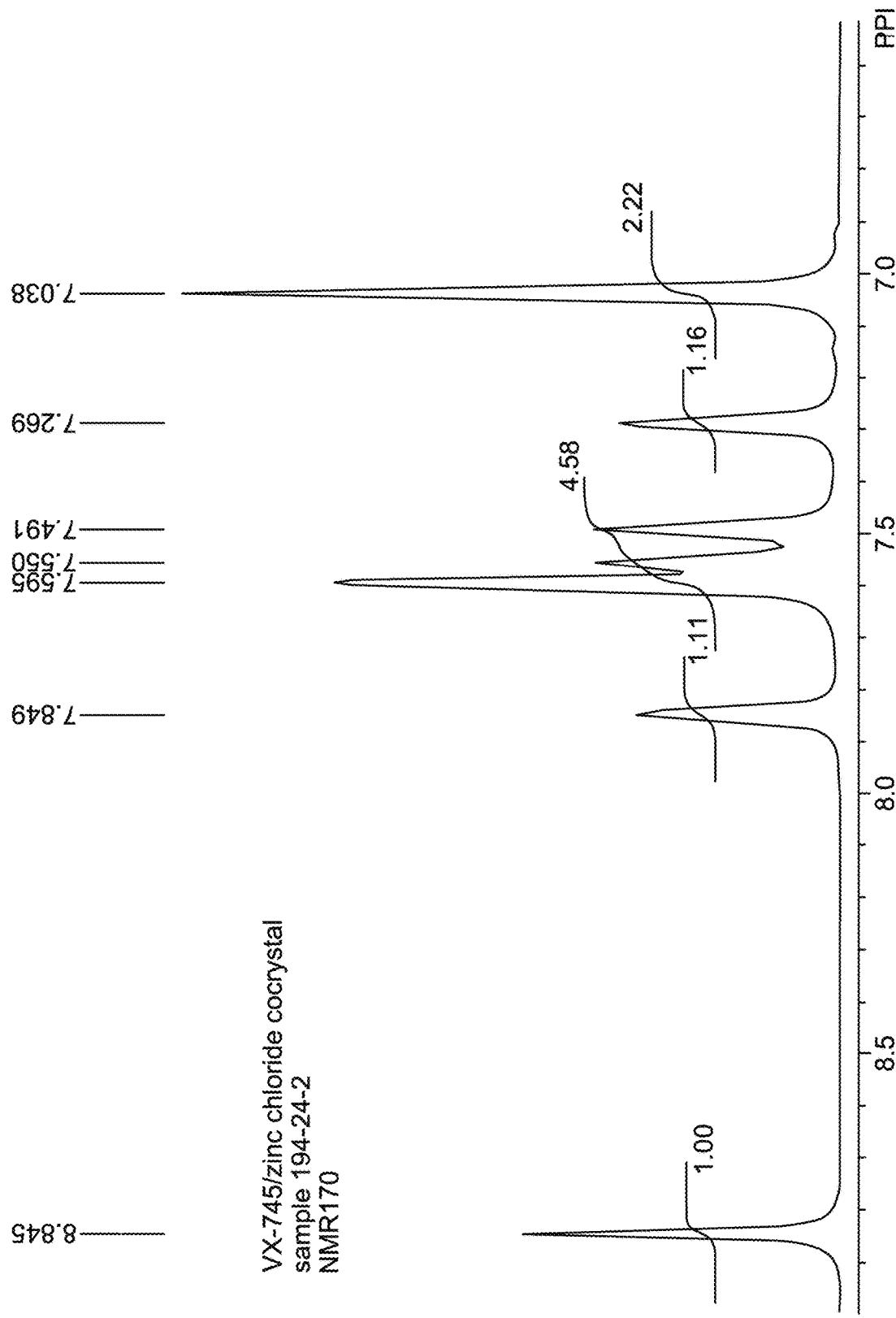
FIG. 238B shows zoom-in NMR spectroscopic data.

Co-crystal comprising VX-745 and zinc chloride: FIG. 222 shows the XRPD result; FIG. 229 shows thermogravimetric analysis; FIG. 232 shows dynamic vapor sorption (DVS) data; FIG. 238A shows Nuclear Magnetic Resonance (NMR) full spectroscopic data and FIG. 238B shows zoom-in NMR spectroscopic data.

TABLE 28

Cocrystals Prepared at Larger Scales

| Cocrystal Guest | Sample No. | Preparation Method[a] | XRPD No. | XRPD Page No. | XRPD Pattern[b] |
|---|---|---|---|---|---|
| gentisic acid | 178-84-1 | evaporation of solvent from an equimolar solution in ACN | RX4093 | 111 | gentisic acid cocrystal A |
| glutaric acid | 178-84-2 | evaporation of solvent from an equimolar solution in ACN | RX4094 | 111 | glutaric acid cocrystal A + API A |
| | 182-37-1 | dissolve 178-84-2 in ACN, evaporate Solvent while stirring[c] | RX4097 | 112 | glutaric acid cocrystal A |
| zinc chloride | 194-24-2 | wet milling (acetone) of an equimolar solid mixture | RX4175 | 112 | zinc chloride cocrystal A |

[a]ACN = acetonitrile
[b]API = VX-745
[c]Procedure carried out to generate phase pure material.

Characterization of the Cocrystals

VX-745 Gentisic Acid Cocrystal

The VX-745 gentisic acid cocrystal has a 1:1 (VX-745: gentisic acid) stoichiometry. It may be a solvate; TG results show 1.95% weight loss below 150° C., corresponding to 0.48 moles of water or 0.21 moles of acetonitrile. Approximately 0.1 moles of acetonitrile are observed in the NMR spectrum (2.06 ppm). It is non-hygroscopic. The endothermic event observed by DSC at 135.8° C. is likely melting. All samples of the gentisic acid cocrystal prepared exhibited the same XRPD pattern, so no polymorphism has yet been identified. Characterization data are shown in Table 29.

TABLE 29

Characterization Data for the Gentisic Acid Cocrystal (sample 178-84-1)

| Technique | Filename or (Notebook Ref) | Page No. | Result |
|---|---|---|---|
| XRPD | RX4093 | 111 | gentisic acid cocrystal A |
| DSC | DSC2.536 | 115 | endo 135.9.150.8° C. |
| TG | TG2.422 | | 1.95% loss up to 150° C. |
| DVS | TGAKIN.143 | 117 | 0.36% loss on drying to 5% RH |
| | | | 0.93% gain from 5 to 95% RH |
| | | | 1.57% loss from 95 to 5% RH |
| Post-DVS XRPD | RX4101 | 112 | unchanged |
| Raman | RmF.253 | 119 | unique spectrum |
| NMR | NMR163 | 122, 123 | 1:1 cocrystal |

Figure 223:
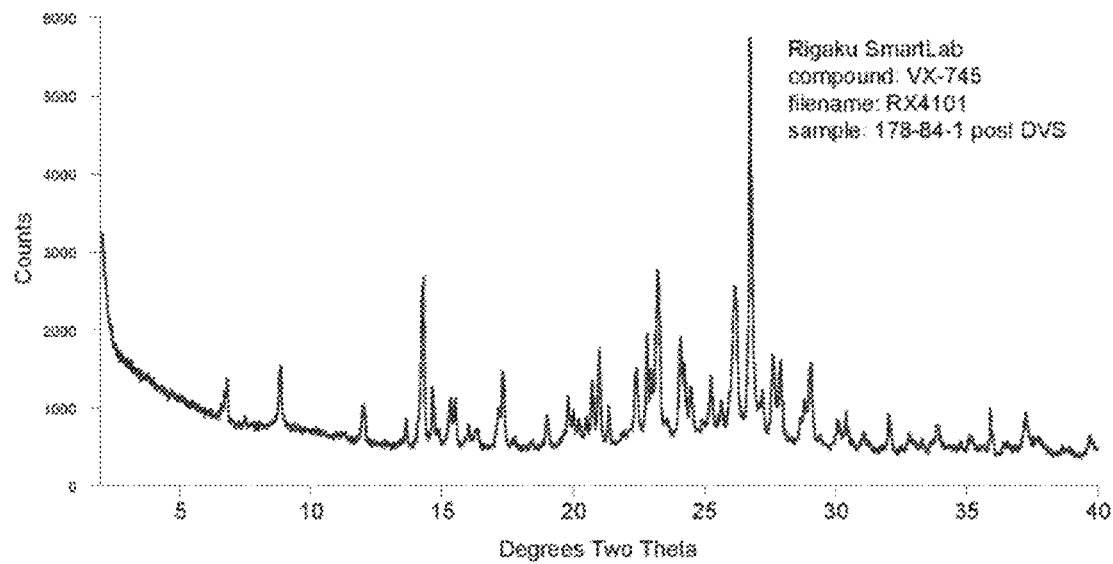
FIG. 223 shows the post-Dynamic Vapor Sorption (DVS) XRPD result of a co-crystal comprising VX-745 and gentisic acid.

FIG. 223 shows the post-Dynamic Vapor Sorption (DVS) XRPD result of a co-crystal comprising VX-745 and gentisic acid.

VX-745 Glutaric Acid Cocrystal

The VX-745 glutaric acid cocrystal has a 1:1 (VX-745: glutaric acid) stoichiometry and appears to be an anhydrate (no solvent of crystallization). It is slightly hygroscopic. The endothermic event observed by DSC at 94.8° C. is likely melting. All samples of the glutaric acid cocrystal prepared exhibited the same XRPD pattern, so no polymorphism has yet been identified. Characterization data are shown in Table 30.

TABLE 30

Characterization Data for the Glutaric Acid Cocrystal (sample 182-37-1)

| Technique | Filename or (Notebook Ref) | Page No. | Result |
|---|---|---|---|
| XRPD | RX4097 | 112 | glutaric acid cocrystal A |
| DSC | DSC2.539 | 116 | endo 94.8, 161.7° C. |
| TG | TG2.425 | | 0.06% loss up to 90°C. |
| | | | 20.06% loss from 90 to 195° C. |
| DVS | TGAKIN.144 | 117 | 0.001% loss on drying to 5% RH |
| | | | 10.16% gain from 5 to 95% RH |
| | | | 10.19% loss from 95 to 5% RH |
| Post-DVS XRPD | RX4102 | 113 | unchanged |
| Raman | RmF.256 | 119 | unique spectrum |
| NMR | NMR164 | 125, 124 | 1:1 cocrystal |

Figure 224:
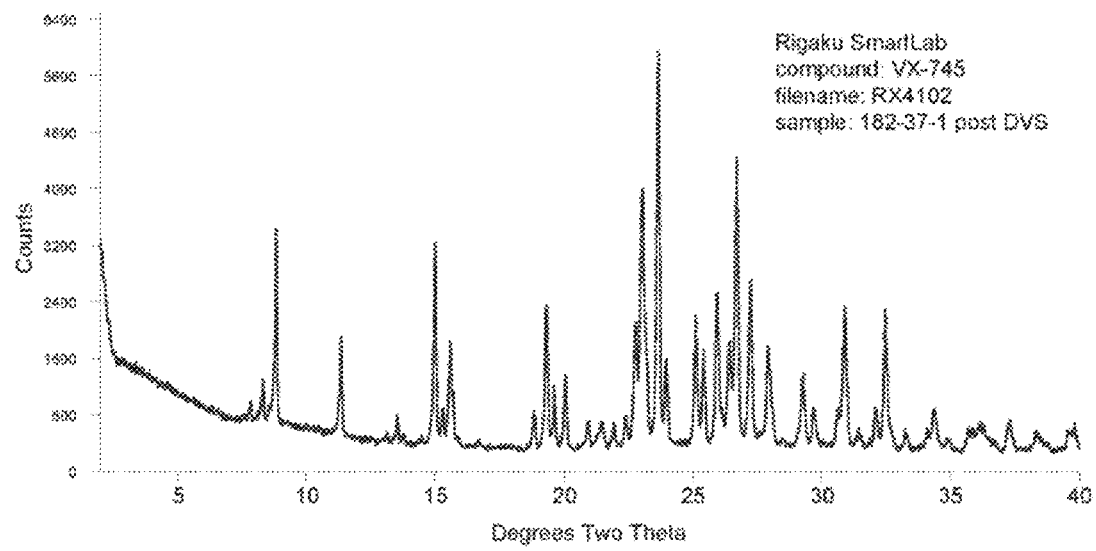
FIG. 224 shows the post-Dynamic Vapor Sorption (DVS) XRPD result of a co-crystal comprising VX-745 and glutaric acid.

FIG. 224 shows the post-Dynamic Vapor Sorption (DVS) XRPD result of a co-crystal comprising VX-745 and glutaric acid.

VX-745 Zinc Chloride Cocrystal

The VX-745 zinc chloride cocrystal has a 1:1 (VX-745: zinc chloride) stoichiometry. It may be a solvate; TG results show 2.5% weight loss between 50 and 120° C., corresponding to 0.62 moles of water or 0.19 moles of acetone. Although no acetone is observed in the NMR spectrum, the initial weight loss observed in the TG results (1.1% up to 50° C.) is likely due to residual acetone. The sample was analyzed by TGA shortly after preparation, but not analyzed by NMR until a day later, giving any residual acetone time to evaporate. It is moderately hygroscopic. The endothermic event observed by DSC at 188.83° C. is likely melting. All samples of the zinc chloride cocrystal prepared exhibited the same XRPD pattern, so no polymorphism has yet been identified. Characterization data are shown in Table 31.

TABLE 31

Characterization Data for the Zinc Chloride Cocrystal (sample 194-24-2)

| Technique | Filename or (Notebook Ref) | Page No. | Result |
|---|---|---|---|
| XRPD | RX4175 | 112 | zinc chloride cocrystal A |
| DSC | DSC2.552 | 116 | endo 84.46, 155.72, 188.83° C. |
| TG | TG2.436 | | 1.11% loss up to 50° C. |
| | | | 2.50% loss from 50 to 125° C. |
| DVS | TGAKIN.152 | 118 | 0.27% loss on drying to 5% RH |
| | | | 11.30% gain from 5 to 95% RH |
| | | | 11.32% loss from 95 to 5% RH |
| Post-DVS XRPD | RX4299 | 114 | unchanged |
| Raman | — | — | not collected, sample burns when exposed to laser |
| NMR | NMR170 | 126, 127 | 1:1 cocrystal |

Figure 225:
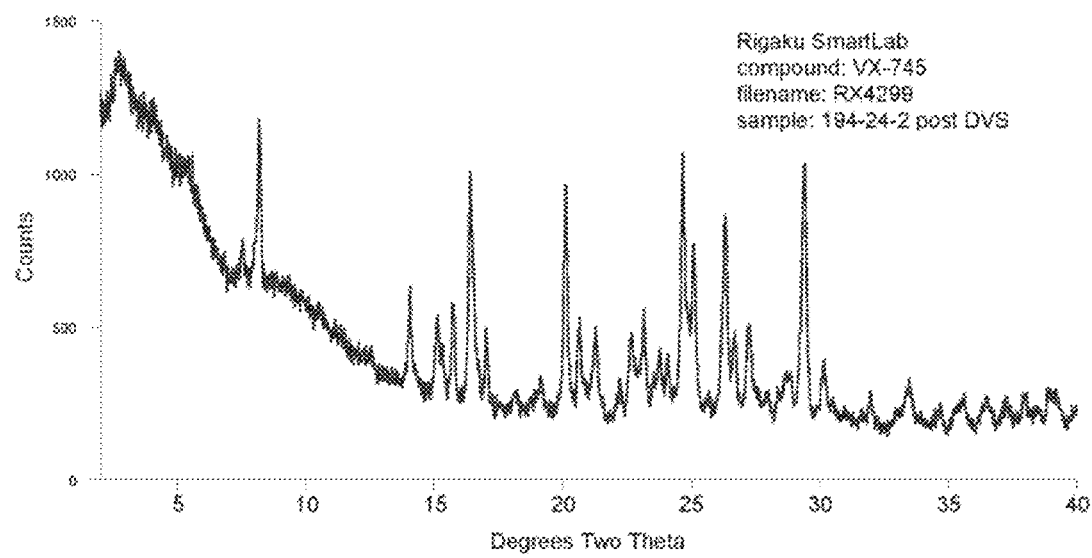
FIG. 225 shows the post-Dynamic Vapor Sorption (DVS) XRPD result of a co-crystal comprising VX-745 and zinc chloride.

FIG. 225 shows the post-Dynamic Vapor Sorption (DVS) XRPD result of a co-crystal comprising VX-745 and zinc chloride.

CONCLUSIONS

A summary of characterization data for the three cocrystals studied in shown in Table 32. Based primarily on salvation state and hygroscopicity, then considering other properties, a rank order was assigned to each cocrystal (1=most desirable). Note that additional considerations (e.g., polymorphism, chemical and physical stability, etc.) could alter those ranks.

TABLE 32

Summary of Cocrystal Data

| Guest | Nature | Melting Point (° C.) | Hygroscopicity | Crystallinity | Polymorphic? | Rank |
|---|---|---|---|---|---|---|
| gentisic acid | solvate | 136 | non | good | not so far | 2 |
| glutaric acid | anhydrate | 95 | slightly | good | not so far | 1 |
| zinc chloride | solvate | 189 | moderately | good | not so far | 3 |

Exemplary Characterization Methods

X-Ray Powder Diffraction (XRPD). The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits were used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. The single-crystal, Si, low-back ground holder has a small circular recess (7 mm diameter and about 1 mm depth) that holds between 5 and 10 mg of powdered material. Each sample was analyzed from 2 to 40° 2θ using a continuous scan of 3° 2θ per minute with an effective step size of 0.02° 2θ.

Differential Scanning calorimetry (DSC). DSC analyses were carried out using a TA Instruments 2920 instrument. The instrument temperature calibration was performed using indium. The DSC cell was kept under a nitrogen purge of ~50 mL per minute during each analysis. Each sample was placed in a standard, crimped, aluminum pan and was heated from 20° C. to 350 at a rate of 10° C. per minute.

Thermogravimetric (TG) Analysis. The TG analysis was carried out using a TA Instruments Q50 instrument. The instrument balance was calibrated using class M weights and the temperature calibration was performed using alurnel. For each analysis, the nitrogen purge at the balance was ~40 mL per minute, while the furnace was purged at ~60 ml per minute. Each sample was placed into a pre-tared platinum pan and heated from 20° C. to 350° C. at a rate of 10° C. per minute.

Dynamic Vapor Sorption (DVS) Analysis. DVS analyses were carried out TA Instruments Q5000 Dynamic Vapor Sorption analyser. The instrument was calibrated with standard weights and a sodium bromide standard for humidity. Samples were analyzed at 25° C. with a maximum equilibration time of 60 minutes in 10% relative humidity (RH) steps from 5 to 95% RH (adsorption cycle) and from 95 to 5% RH (desorption cycle).

Raman Spectroscopy. Fourier transform (FT) Raman spectra were acquired on a Nicolet model 6700 spectrometer interfaced to a Nexus Raman accessory module. This instrument is configured with a Nd:YAG laser operating at 1024 nm, a CaF$_2$ beam splitter, and a indium gallium arsenide detector. OMNIC 8.1 software was used for control of data acquisition and processing of the spectra. Samples were packed into a 3-inch glass NMR tube for analysis.

Nuclear Magnetic Resonance (NMR) Spectroscopy. The $^1$H NMR spectra were acquired on a Bruker DRX-800 spectrometer located at the Chemistry Department of Purdue University. Samples were prepared by dissolving material in MeOH-d$_4$. The solutions were filtered and placed into individual 5-mm NMR tubes for subsequent spectral acquisition. The temperature controlled (296K) $^1$H NMR spectra acquired on the DRX-800 utilized a 5-mm cryoprobe operating at an observing frequency of 800.13 MHz.

Preparation of VX-745/Gentisic Acid Cocrystal (sample 178-84-1). A solution of 100.0 mg of VX-745 (0.229 mmol) and 35.3 mg of gentisic acid (0.229 mmol) in 6 mL of acetonitrile was placed in a vial. The opening was covered with aluminum foil having 3 pinholes and the sample was left at ambient temperature overnight, during which time the solvent evaporated to give VX-745/gentisic acid cocrystal.

Preparation of VX-745/Glutaric Acid Cocrystal (sample 178-84-2). A solution of 100.0 mg of VX-745 (0.229 mmol) and 30.4 mg of glutaric acid (0.230 mmol) in 6 mL of acetonitrile was placed in a vial. The opening was covered with aluminium foil having 3 pinholes and the sample was left at ambient temperature overnight, during which time the solvent evaporated to give VX-7 45/glutaric acid cocrystal.

Preparation of VX-745/Zinc Chloride Cocrystal (sample 194-24-2). A mixture of 100.0 mg of VX-745 (0.229 mmol) and 31.2 mg of zinc chloride (0.229 mmol) was placed in a PEEK grinding cup with 20 µL of acetone and a steel ball. The sample was placed on a Retsch mill and milled at 100% power for 20 minutes to give VX-745/zinc chloride cocrystal.

EQUIVALENTS

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

What is claimed is:

1. A cocrystal comprising a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, and a compound of formula VX-745:

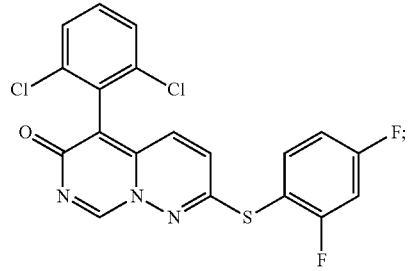

VX-745

(5-(2,6-dichlorophenyl)-2-(2,4-difluorophenylthio)-6H-pyrimido[1,6-b]pyridazin-6-one;
wherein the cocrystal is selected from the group consisting of:

(1) cocrystal 1 (CC-1) comprising VX-745 and acesulfame potassium;
wherein cocrystal 1 is characterized by a powder X-ray diffractogram obtained by irradiation with Cu-Kα radiation comprising at least one characteristic peak at 8.4°±0.2° 2θ, 16.9°±0.2° 2θ 19.1°±0.2° 2θ, 22.3°±0.2° 2θ, 25.0°±0.2° 2θ, 25.4±0.2° 2θ, or 27.4°±0.2° 2θ;

(2) cocrystal 2 (CC-2) comprising VX-745 and trans-aconitic acid;
wherein cocrystal 2 is characterized by a powder X-ray diffractogram obtained by irradiation with Cu-Kα radiation comprising at least one characteristic peak at 13.1°±0.2° 2θ, 14.2°±0.2° 2θ, 15.9°±0.2° 2θ, 21.3°±0.2° 2θ, 23.5±0.2° 2θ, 26.9±0.2° 2θ, or 27.3°±0.2° 2θ;

(3) cocrystal 3 (CC-3) comprising VX-745 and calcium chloride;
wherein cocrystal 3 is characterized by a powder X-ray diffractogram obtained by irradiation with Cu-Kα radiation comprising at least one characteristic peak at 16.9°±0.2° 2θ, 19.3°±0.2° 2θ, 27.0°±0.2° 2θ, 27.7°±0.2° 2θ, 28.5°±0.2° 2θ, 33.0°±0.2° 2θ, or 34.1°±0.2° 2θ;

(4) cocrystal 4 (CC-4) comprising VX-745 and choline chloride;
wherein cocrystal 4 is characterized by a powder X-ray diffractogram obtained by irradiation with Cu-Kα radiation comprising at least one characteristic peak at 8.3°±0.2° 2θ, 16.8°±0.2° 2θ, 17.3°±0.2° 2θ, 18.6°±0.2° 2θ, 20.9°±0.2° 2θ, 22.0°±0.2° 2θ, 22.9°±0.2° 2θ, 24.9°±0.2° 2θ, 26.6°±0.2° 2θ, or 31.7°±0.2° 2θ;

(5) cocrystal 5 (CC-5) comprising VX-745 and gentisic acid;
wherein cocrystal 5 is characterized by a powder X-ray diffractogram obtained by irradiation with Cu-Kα radiation comprising at least one characteristic peak at 8.9°±0.2° 2θ, 14.3°±0.2° 2θ, 17.3°±0.2° 2θ, 21.0°±0.2° 2θ, 22.4°±0.2° 2θ, 23.3°±0.2° 2θ, 26.2°±0.2° 2θ, 26.8°±0.2° 2θ, 27.6°±0.2° 2θ, or 29.1°±0.2° 2θ;

(6) cocrystal 6 (CC-6) comprising VX-745 and glutaric acid;
wherein cocrystal 6 is characterized by a powder X-ray diffractogram obtained by irradiation with Cu-Kα radiation comprising at least one characteristic peak at 8.8°±0.2° 2θ, 15.0°±0.2° 2θ, 19.3°±0.2° 2θ, 23.1°±0.2° 2θ, 23.7°±0.2° 2θ, 26.7°±0.2° 2θ, 30.9°±0.2° 2θ, or 32.5°±0.2° 2θ;

(7) cocrystal 7 (CC-7) comprising VX-745 and 1-hydroxy-2-naphthoic acid;
wherein cocrystal 7 is characterized by a powder X-ray diffractogram obtained by irradiation with Cu-Kα radiation comprising at least one characteristic peak at 7.3°±0.2° 2θ, 8.7°±0.2° 2θ, 14.6°±0.2° 2θ, 15.7°±0.2° 2θ, 21.2°±0.2° 2θ, 22.0°±0.2° 2θ, 24.2°±0.2° 2θ, 28.3°±0.2° 2θ, 25.8°±0.2° 2θ, 27.2°±0.2° 2θ, or 31.1°±0.2° 2θ;

(8) cocrystal 8 (CC-8) comprising VX-745 and ketoglutaric acid;
wherein cocrystal 8 is characterized by a powder X-ray diffractogram obtained by irradiation with Cu-Kα radiation comprising at least one characteristic peak at 7.2°±0.2° 2θ, 9.5°±0.2° 2θ, 15.1°±0.2° 2θ, 16.2°±0.2° 2θ, 21.6°±0.2° 2θ, 22.0°±0.2° 2θ, or 28.0°±0.2° 2θ;

(9) cocrystal 9 (CC-9) comprising VX-745 and malonic acid;
wherein cocrystal 9 is characterized by a powder X-ray diffractogram obtained by irradiation with Cu-Kα radiation comprising at least one characteristic peak at 6.0°±0.2° 2θ, 14.1°±0.2° 2θ, 22.2°±0.2° 2θ, 23.2°±0.2° 2θ, 23.7°±0.2° 2θ, 24.3°±0.2° 2θ, 25.1°±0.2° 2θ, 27.4°±0.2° 2θ, or 28.1°±0.2° 2θ;

(10) cocrystal 10 (CC-10) comprising VX-745 and nicotinic acid;
wherein cocrystal 10 is characterized by a powder X-ray diffractogram obtained by irradiation with Cu-Kα radiation comprising at least one characteristic peak at 7.4°±0.2° 2θ, 15.4°±0.2° 2θ, 20.3°±0.2° 2θ, 23.4°±0.2° 2θ, or 25.1°±0.2° 2θ;

(11) cocrystal 11 (CC-11) comprising VX-745 and phenol;
wherein cocrystal 11 is characterized by a powder X-ray diffractogram obtained by irradiation with Cu-Kα radiation comprising at least one characteristic peak at 6.8°±0.2° 2θ, 13.7°±0.2° 2θ, 16.8°±0.2° 2θ, 18.3°±0.2° 2θ, 20.0°±0.2° 2θ, 21.9°±0.2° 2θ, 23.7°±0.2° 2θ, 24.5°±0.2° 2θ, 24.7°±0.2° 2θ, 26.6°±0.2° 2θ, 27.3°±0.2° 2θ, or 30.2°±0.2° 2θ;

(12) cocrystal 12 (CC-12) comprising VX-745 and L-proline;
wherein cocrystal 12 is characterized by a powder X-ray diffractogram obtained by irradiation with Cu-Kα radiation comprising at least one characteristic peak at 7.4°±0.2° 2θ, 17.6°±0.2° 2θ, 18.0°±0.2° 2θ, 19.5°±0.2° 2θ, 24.7°±0.2° 2θ, or 26.8°±0.2° 2θ;

(13) cocrystal 13 (CC-13) comprising VX-745 and salicylic acid;
wherein cocrystal 13 is characterized by a powder X-ray diffractogram obtained by irradiation with Cu-Kα radiation comprising at least one characteristic peak at 8.9°±0.2° 2θ, 11.0°±0.2° 2θ, 13.8°±0.2° 2θ, 15.3°±0.2° 2θ, 17.3°±0.2° 2θ, 18.8°±0.2° 2θ, 25.3°±0.2° 2θ, 28.1°±0.2° 2θ, 28.8°±0.2° 2θ, or 30.7°±0.2° 2θ;

(14) cocrystal 14 (CC-14) comprising VX-745 and sorbic acid;
wherein cocrystal 14 is characterized by a powder X-ray diffractogram obtained by irradiation with Cu-Kα radiation comprising at least one characteristic peak at 8.5°±0.2° 2θ, 8.9°±0.2° 2θ, 11.4°±0.2° 2θ, 16.7°±0.2° 2θ, 22.8°±0.2° 2θ, 23.0°±0.2° 2θ, 24.2°±0.2° 2θ, 25.7°±0.2° 2θ, or 27.0°±0.2° 2θ;

(15) cocrystal 15 (CC-15) comprising VX-745 and thiamine hydrochloride;
wherein cocrystal 15 is characterized by a powder X-ray diffractogram obtained by irradiation with Cu-Kα radiation comprising at least one characteristic peak at 7.4°±0.2° 2θ, 8.2°±0.2° 2θ, 15.3°±0.2° 2θ, 15.9°±0.2° 2θ, 19.0°±0.2° 2θ, 20.3°±0.2° 2θ, 20.9°±0.2° 2θ, 25.3°±0.2° 2θ, 27.6°±0.2° 2θ, or 28.5°±0.2° 2θ;

(16) cocrystal 16 (CC-16) comprising VX-745 and L-threonine;
wherein cocrystal 16 is characterized by a powder X-ray diffractogram obtained by irradiation with Cu-Kα radiation comprising at least one characteristic peak at 16.9°±0.2° 2θ, 18.4°±0.2° 2θ, 20.6°±0.2° 2θ, 22.7°±0.2° 2θ, 22.9°±0.2° 2θ, 23.9°±0.2° 2θ, or 30.3°±0.2° 2θ;

(17) cocrystal 17 (CC-17) comprising VX-745 and urea;
wherein cocrystal 17 is characterized by a powder X-ray diffractogram obtained by irradiation with Cu-Kα radiation comprising at least one characteristic peak at 5.6°±0.2° 2θ, 14.7°±0.2° 2θ, 16.5°±0.2° 2θ, 16.9°±0.2° 2θ, 22.3°±0.2° 2θ, 24.6°±0.2° 2θ, 24.3°±0.2° 2θ, 27.4°±0.2° 2θ, 34.1°±0.2° 2θ, or 35.5°±0.2° 2θ; and

(18) cocrystal 18 (CC-18) comprising VX-745 and zinc chloride;
wherein cocrystal 18 is characterized by a powder X-ray diffractogram obtained by irradiation with Cu-Kα radiation comprising at least one characteristic peak at 8.2°±0.2° 2θ, 16.5°±0.2° 2θ, 20.1°±0.2° 2θ, 24.7°±0.2° 2θ, 26.4°±0.2° 2θ, or 29.5°±0.2° 2θ.

2. The cocrystal as in claim 1, wherein the cocrystal is selected from the group consisting of:

(1) cocrystal 1 (CC-1) comprising VX-745 and acesulfame potassium;
wherein cocrystal 1 is characterized by a powder X-ray diffractogram obtained by irradiation with Cu-Kα radiation comprising at least two characteristic peaks at 8.4°±0.2° 2θ, 16.9°±0.2° 2θ 19.1°±0.2° 2θ, 22.3°±0.2° 2θ, 25.0°±0.2° 2θ, 25.4±0.2° 2θ, or 27.4°±0.2° 2θ;

(2) cocrystal 2 (CC-2) comprising VX-745 and trans-aconitic acid;
wherein cocrystal 2 is characterized by a powder X-ray diffractogram obtained by irradiation with Cu-Kα radiation comprising at least two characteristic peaks at 13.1±0.2° 2θ, 14.2°±0.2° 2θ, 15.9°±0.2° 2θ, 21.3°±0.2° 2θ, 23.5±0.2° 2θ, 26.9±0.2° 2θ, or 27.3°±0.2° 2θ;

(3) cocrystal 3 (CC-3) comprising VX-745 and calcium chloride;
wherein cocrystal 3 is characterized by a powder X-ray diffractogram obtained by irradiation with Cu-Kα radiation comprising at least two characteristic peaks at 16.9°±0.2° 2θ, 19.3°±0.2° 2θ, 27.0°±0.2° 2θ, 27.7°±0.2° 2θ, 28.5°±0.2° 2θ, 33.0°±0.2° 2θ, or 34.1°±0.2° 2θ;

(4) cocrystal 4 (CC-4) comprising VX-745 and choline chloride;
wherein cocrystal 4 is characterized by a powder X-ray diffractogram obtained by irradiation with Cu-Kα radiation comprising at least two characteristic peaks at 8.3°±0.2° 2θ, 16.8°±0.2° 2θ, 17.3°±0.2° 2θ, 18.6°±0.2° 2θ, 20.9°±0.2° 2θ, 22.0°±0.2° 2θ, 22.9°±0.2° 2θ, 24.9°±0.2° 2θ, 26.6°±0.2° 2θ, or 31.7°±0.2° 2θ;

(5) cocrystal 5 (CC-5) comprising VX-745 and gentisic acid;
wherein cocrystal 5 is characterized by a powder X-ray diffractogram obtained by irradiation with Cu-Kα radiation comprising at least two characteristic peaks at 8.9°±0.2° 2θ, 14.3°±0.2° 2θ, 17.3°±0.2° 2θ, 21.0°±0.2° 2θ, 22.4°±0.2° 2θ, 23.3°±0.2° 2θ, 26.2°±0.2° 2θ, 26.8°±0.2° 2θ, 27.6°±0.2° 2θ, or 29.1°±0.2° 2θ;

(6) cocrystal 6 (CC-6) comprising VX-745 and glutaric acid;
wherein cocrystal 6 is characterized by a powder X-ray diffractogram obtained by irradiation with Cu-Kα radiation comprising at least two characteristic peaks at 8.8°±0.2° 2θ, 15.0°±0.2° 2θ, 19.3°±0.2° 2θ, 23.1°±0.2° 2θ, 23.7°±0.2° 2θ, 26.7°±0.2° 2θ, 30.9°±0.2° 2θ, or 32.5°±0.2° 2θ;

(7) cocrystal 7 (CC-7) comprising VX-745 and 1-hydroxy-2-naphthoic acid;
wherein cocrystal 7 is characterized by a powder X-ray diffractogram obtained by irradiation with Cu-Kα radiation comprising at least two characteristic peaks at 7.3°±0.2° 2θ, 8.7°±0.2° 2θ, 14.6°±0.2° 2θ, 15.7°±0.2° 2θ, 21.2°±0.2° 2θ, 22.0°±0.2° 2θ, 24.2°±0.2° 2θ, 28.3°±0.2° 2θ, 25.8°±0.2° 2θ, 27.2°±0.2° 2θ, or 31.1°±0.2° 2θ;

(8) cocrystal 8 (CC-8) comprising VX-745 and ketoglutaric acid;
wherein cocrystal 8 is characterized by a powder X-ray diffractogram obtained by irradiation with Cu-Kα radiation comprising at least two characteristic peaks at 7.2°±0.2° 2θ, 9.5°±0.2° 2θ, 15.1°±0.2° 2θ, 16.2°±0.2° 2θ, 21.6°±0.2° 2θ, 22.0°±0.2° 2θ, or 28.0°±0.2° 2θ;

(9) cocrystal 9 (CC-9) comprising VX-745 and malonic acid;
wherein cocrystal 9 is characterized by a powder X-ray diffractogram obtained by irradiation with Cu-Kα radiation comprising at least two characteristic peaks at 6.0°±0.2° 2θ, 14.1°±0.2° 2θ, 22.2°±0.2° 2θ, 23.2°±0.2° 2θ, 23.7°±0.2° 2θ, 24.3°±0.2° 2θ, 25.1°±0.2° 2θ, 27.4°±0.2° 2θ, or 28.1°±0.2° 2θ;

(10) cocrystal 10 (CC-10) comprising VX-745 and nicotinic acid;
wherein cocrystal 10 is characterized by a powder X-ray diffractogram obtained by irradiation with Cu-Kα radiation comprising at least two characteristic peaks at 7.4°±0.2° 2θ, 15.4°±0.2° 2θ, 20.3°±0.2° 2θ, 23.4°±0.2° 2θ, or 25.1°±0.2° 2θ;

(11) cocrystal 11 (CC-11) comprising VX-745 and phenol;
wherein cocrystal 11 is characterized by a powder X-ray diffractogram obtained by irradiation with Cu-Kα radiation comprising at least two characteristic peaks at 6.8°±0.2° 2θ, 13.7°±0.2° 2θ, 16.8°±0.2° 2θ, 18.3°±0.2° 2θ, 20.0°±0.2° 2θ, 21.9°±0.2° 2θ, 23.7°±0.2° 2θ, 24.5°±0.2° 2θ, 24.7°±0.2° 2θ, 26.6°±0.2° 2θ, 27.3°±0.2° 2θ, or 30.2°±0.2° 2θ;

(12) cocrystal 12 (CC-12) comprising VX-745 and L-proline;
wherein cocrystal 12 is characterized by a powder X-ray diffractogram obtained by irradiation with Cu-Kα radiation comprising at least two characteristic peaks at 7.4°±0.2° 2θ, 17.6°±0.2° 2θ, 18.0°±0.2° 2θ, 19.5°±0.2° 2θ, 24.7°±0.2° 2θ, or 26.8°±0.2° 2θ;

(13) cocrystal 13 (CC-13) comprising VX-745 and salicylic acid;
wherein cocrystal 13 is characterized by a powder X-ray diffractogram obtained by irradiation with Cu-Kα radiation comprising at least two characteristic peaks at 8.9°±0.2° 2θ, 11.0°±0.2° 2θ, 13.8°±0.2° 2θ, 15.3°±0.2° 2θ, 17.3°±0.2° 2θ, 18.8°±0.2° 2θ, 25.3°±0.2° 2θ, 28.1°±0.2° 2θ, 28.8°±0.2° 2θ, or 30.7°±0.2° 2θ;

(14) cocrystal 14 (CC-14) comprising VX-745 and sorbic acid;
wherein cocrystal 14 is characterized by a powder X-ray diffractogram obtained by irradiation with Cu-Kα radiation comprising at least two characteristic peaks at 8.5°±0.2° 2θ, 8.9°±0.2° 2θ, 11.4°±0.2°

2θ, 16.7°±0.2° 2θ, 22.8°±0.2° 2θ, 23.0°±0.2° 2θ, 24.2°±0.2° 2θ, 25.7°±0.2° 2θ, or 27.0°±0.2° 2θ;

(15) cocrystal 15 (CC-15) comprising VX-745 and thiamine hydrochloride;
wherein cocrystal 15 is characterized by a powder X-ray diffractogram obtained by irradiation with Cu-Kα radiation comprising at least two characteristic peaks at 7.4°±0.2° 2θ, 8.2°±0.2° 2θ, 15.3°±0.2° 2θ, 15.9°±0.2° 2θ, 19.0°±0.2° 2θ, 20.3°±0.2° 2θ, 20.9°±0.2° 2θ, 25.3°±0.2° 2θ, 27.6°±0.2° 2θ, or 28.5°±0.2° 2θ;

(16) cocrystal 16 (CC-16) comprising VX-745 and L-threonine;
wherein cocrystal 16 is characterized by a powder X-ray diffractogram obtained by irradiation with Cu-Kα radiation comprising at least two characteristic peaks at 16.9°±0.2° 2θ, 18.4°±0.2° 2θ, 20.6°±0.2° 2θ, 22.7°±0.2° 2θ, 22.9°±0.2° 2θ, 23.9°±0.2° 2θ, or 30.3°±0.2° 2θ;

(17) cocrystal 17 (CC-17) comprising VX-745 and urea;
wherein cocrystal 17 is characterized by a powder X-ray diffractogram obtained by irradiation with Cu-Kα radiation comprising at least two characteristic peaks at 5.6°±0.2° 2θ, 14.7°±0.2° 2θ, 16.5°±0.2° 2θ, 16.9°±0.2° 2θ, 22.3°±0.2° 2θ, 24.6°±0.2° 2θ, 24.3°±0.2° 2θ, 27.4°±0.2° 2θ, 34.1°±0.2° 2θ, or 35.5°±0.2° 2θ; and

(18) cocrystal 18 (CC-18) comprising VX-745 and zinc chloride;
wherein cocrystal 18 is characterized by a powder X-ray diffractogram obtained by irradiation with Cu-Kα radiation comprising at least two characteristic peaks at 8.2°±0.2° 2θ, 16.5°±0.2° 2θ, 20.1°±0.2° 2θ, 24.7°±0.2° 2θ, 26.4°±0.2° 2θ, or 29.5°±0.2° 2θ.

3. The cocrystal as in claim 1, wherein the cocrystal is selected from the group consisting of:

(1) cocrystal 1 (CC-1) comprising VX-745 and acesulfame potassium;
wherein cocrystal 1 is characterized by a powder X-ray diffractogram obtained by irradiation with Cu-Kα radiation comprising at least three characteristic peaks at 8.4°±0.2° 2θ, 16.9°±0.2° 2θ 19.1°±0.2° 2θ, 22.3°±0.2°, 25.0°±0.2° 2θ, 25.4±0.2° 2θ, or 27.4°±0.2° 2θ;

(2) cocrystal 2 (CC-2) comprising VX-745 and trans-aconitic acid;
wherein cocrystal 2 is characterized by a powder X-ray diffractogram obtained by irradiation with Cu-Kα radiation comprising at least three characteristic peaks at 13.1±0.2° 2θ, 14.2°±0.2° 2θ, 15.9°±0.2° 2θ, 21.3°±0.2° 2θ, 23.5±0.2° 2θ, 26.9±0.2° 2θ, or 27.3°±0.2° 2θ;

(3) cocrystal 3 (CC-3) comprising VX-745 and calcium chloride;
wherein cocrystal 3 is characterized by a powder X-ray diffractogram obtained by irradiation with Cu-Kα radiation comprising at least three characteristic peaks at 16.9°±0.2° 2θ, 19.3°±0.2° 2θ, 27.0°±0.2° 2θ, 27.7°±0.2° 2θ, 28.5°±0.2° 2θ, 33.0°±0.2° 2θ, or 34.1°±0.2° 2θ;

(4) cocrystal 4 (CC-4) comprising VX-745 and choline chloride;
wherein cocrystal 4 is characterized by a powder X-ray diffractogram obtained by irradiation with Cu-Kα radiation comprising at least three characteristic peaks at 8.3°±0.2° 2θ, 16.8°±0.2° 2θ, 17.3°±0.2° 2θ, 18.6°±0.2° 2θ, 20.9°±0.2° 2θ, 22.0°±0.2° 2θ, 22.9°±0.2° 2θ, 24.9°±0.2° 2θ, 26.6°±0.2° 2θ, or 31.7°±0.2° 2θ;

(5) cocrystal 5 (CC-5) comprising VX-745 and gentisic acid;
wherein cocrystal 5 is characterized by a powder X-ray diffractogram obtained by irradiation with Cu-Kα radiation comprising at least three characteristic peaks at 8.9°±0.2° 2θ, 14.3°±0.2° 2θ, 17.3°±0.2° 2θ, 21.0°±0.2° 2θ, 22.4°±0.2° 2θ, 23.3°±0.2° 2θ, 26.2°±0.2° 2θ, 26.8°±0.2° 2θ, 27.6°±0.2° 2θ, or 29.1°±0.2° 2θ;

(6) cocrystal 6 (CC-6) comprising VX-745 and glutaric acid;
wherein cocrystal 6 is characterized by a powder X-ray diffractogram obtained by irradiation with Cu-Kα radiation comprising at least three characteristic peaks at 8.8°±0.2° 2θ, 15.0°±0.2° 2θ, 19.3°±0.2° 2θ, 23.1°±0.2° 2θ, 23.7°±0.2° 2θ, 26.7°±0.2° 2θ, 30.9°±0.2° 2θ, or 32.5°±0.2° 2θ;

(7) cocrystal 7 (CC-7) comprising VX-745 and 1-hydroxy-2-naphthoic acid;
wherein cocrystal 7 is characterized by a powder X-ray diffractogram obtained by irradiation with Cu-Kα radiation comprising at least three characteristic peaks at 7.3°±0.2° 2θ, 8.7°±0.2° 2θ, 14.6°±0.2° 2θ, 15.7°±0.2° 2θ, 21.2°±0.2° 2θ, 22.0°±0.2° 2θ, 24.2°±0.2° 2θ, 28.3°±0.2° 2θ, 25.8°±0.2° 2θ, 27.2°±0.2° 2θ, or 31.1°±0.2° 2θ;

(8) cocrystal 8 (CC-8) comprising VX-745 and ketoglutaric acid;
wherein cocrystal 8 is characterized by a powder X-ray diffractogram obtained by irradiation with Cu-Kα radiation comprising at least three characteristic peaks at 7.2°±0.2° 2θ, 9.5°±0.2° 2θ, 15.1°±0.2° 2θ, 16.2°±0.2° 2θ, 21.6°±0.2° 2θ, 22.0°±0.2° 2θ, or 28.0°±0.2° 2θ;

(9) cocrystal 9 (CC-9) comprising VX-745 and malonic acid;
wherein cocrystal 9 is characterized by a powder X-ray diffractogram obtained by irradiation with Cu-Kα radiation comprising at least three characteristic peaks at 6.0°±0.2° 2θ, 14.1°±0.2° 2θ, 22.2°±0.2° 2θ, 23.2°±0.2° 2θ, 23.7°±0.2° 2θ, 24.3°±0.2° 2θ, 25.1°±0.2° 2θ, 27.4°±0.2° 2θ, or 28.1°±0.2° 2θ;

(10) cocrystal 10 (CC-10) comprising VX-745 and nicotinic acid;
wherein cocrystal 10 is characterized by a powder X-ray diffractogram obtained by irradiation with Cu-Kα radiation comprising at least three characteristic peaks at 7.4°±0.2° 2θ, 15.4°±0.2° 2θ, 20.3°±0.2° 2θ, 23.4°±0.2° 2θ, or 25.1°±0.2° 2θ;

(11) cocrystal 11 (CC-11) comprising VX-745 and phenol;
wherein cocrystal 11 is characterized by a powder X-ray diffractogram obtained by irradiation with Cu-Kα radiation comprising at least three characteristic peaks at 6.8°±0.2° 2θ, 13.7°±0.2° 2θ, 16.8°±0.2° 2θ, 18.3°±0.2° 2θ, 20.0°±0.2° 2θ, 21.9°±0.2° 2θ, 23.7°±0.2° 2θ, 24.5°±0.2° 2θ, 24.7°±0.2° 2θ, 26.6°±0.2° 2θ, 27.3°±0.2° 2θ, or 30.2°±0.2° 2θ;

(12) cocrystal 12 (CC-12) comprising VX-745 and L-proline;
wherein cocrystal 12 is characterized by a powder X-ray diffractogram obtained by irradiation with Cu-Kα radiation comprising at least three characteristic peaks at 7.4°±0.2° 2θ, 17.6°±0.2° 2θ, 18.0°±0.2° 2θ, 19.5°±0.2° 2θ, 24.7°±0.2° 2θ, or 26.8°±0.2° 2θ;

(13) cocrystal 13 (CC-13) comprising VX-745 and salicylic acid;
wherein cocrystal 13 is characterized by a powder X-ray diffractogram obtained by irradiation with Cu-Kα radiation comprising at least three characteristic peaks at 8.9°±0.2° 2θ, 11.0°±0.2° 2θ, 13.8°±0.2° 2θ, 15.3°±0.2° 2θ, 17.3°±0.2° 2θ, 18.8°±0.2° 2θ, 25.3°±0.2° 2θ, 28.1°±0.2° 2θ, 28.8°±0.2° 2θ, or 30.7°±0.2° 2θ;

(14) cocrystal 14 (CC-14) comprising VX-745 and sorbic acid;
wherein cocrystal 14 is characterized by a powder X-ray diffractogram obtained by irradiation with Cu-Kα radiation comprising at least three characteristic peaks at 8.5°±0.2° 2θ, 8.9°±0.2° 2θ, 11.4°±0.2° 2θ, 16.7°±0.2° 2θ, 22.8°±0.2° 2θ, 23.0°±0.2° 2θ, 24.2°±0.2° 2θ, 25.7°±0.2° 2θ, or 27.0°±0.2° 2θ;

(15) cocrystal 15 (CC-15) comprising VX-745 and thiamine hydrochloride;
wherein cocrystal 15 is characterized by a powder X-ray diffractogram obtained by irradiation with Cu-Kα radiation comprising at least three characteristic peaks at 7.4°±0.2° 2θ, 8.2°±0.2° 2θ, 15.3°±0.2° 2θ, 15.9°±0.2° 2θ, 19.0°±0.2° 2θ, 20.3°±0.2° 2θ, 20.9°±0.2° 2θ, 25.3°±0.2° 2θ, 27.6°±0.2° 2θ, or 28.5°±0.2° 2θ;

(16) cocrystal 16 (CC-16) comprising VX-745 and L-threonine;
wherein cocrystal 16 is characterized by a powder X-ray diffractogram obtained by irradiation with Cu-Kα radiation comprising at least three characteristic peaks at 16.9°±0.2° 2θ, 18.4°±0.2° 2θ, 20.6°±0.2° 2θ, 22.7°±0.2° 2θ, 22.9°±0.2° 2θ, 23.9°±0.2° 2θ, or 30.3°±0.2° 2θ;

(17) cocrystal 17 (CC-17) comprising VX-745 and urea;
wherein cocrystal 17 is characterized by a powder X-ray diffractogram obtained by irradiation with Cu-Kα radiation comprising at least three characteristic peaks at 5.6°±0.2° 2θ, 14.7°±0.2° 2θ, 16.5°±0.2° 2θ, 16.9°±0.2° 2θ, 22.3°±0.2° 2θ, 24.6°±0.2° 2θ, 24.3°±0.2° 2θ, 27.4°±0.2° 2θ, 34.1°±0.2° 2θ, or 35.5°±0.2° 2θ; and

(18) cocrystal 18 (CC-18) comprising VX-745 and zinc chloride;
wherein cocrystal 18 is characterized by a powder X-ray diffractogram obtained by irradiation with Cu-Kα radiation comprising at least three characteristic peaks at 8.2°±0.2° 2θ, 16.5°±0.2° 2θ, 20.1°±0.2° 2θ, 24.7°±0.2° 2θ, 26.4°±0.2° 2θ, or 29.5°±0.2° 2θ.

4. The cocrystal as in claim 1, wherein the cocrystal is further characterized by a powder X-ray diffractogram as shown in:
(a) FIG. 37 (cocrystal 1);
(b) FIG. 38 (cocrystal 2);
(c) FIG. 39 (cocrystal 3);
(d) FIG. 40 (cocrystal 4);
(e) FIG. 41 (cocrystal 5);
(f) FIG. 42 (cocrystal 6);
(g) FIG. 43 (cocrystal 7);
(h) FIG. 44 (cocrystal 8);
(i) FIG. 45 (cocrystal 9);
(j) FIG. 46 (cocrystal 10);
(k) FIG. 47 (cocrystal 11);
(l) FIG. 48 (cocrystal 12);
(m) FIG. 49 (cocrystal 13);
(n) FIG. 50 (cocrystal 14);
(o) FIG. 51 (cocrystal 15);
(p) FIG. 52 (cocrystal 16);
(q) FIG. 53 (cocrystal 17); or
(r) FIG. 54 (cocrystal 18).

5. The cocrystal as in claim 1, wherein the coformer is selected from the group consisting of ketoglutaric acid, malonic acid, L-proline, salicylic acid, L-threonine, and urea.

6. The cocrystal as in claim 1, wherein the coformer is selected from the group consisting of acesulfame potassium, trans-aconitic acid, calcium chloride, choline chloride, and 1-hydroxy-2-naphthoic acid.

7. The cocrystal as in claim 1, wherein the co-former is selected from the group consisting of nicotinic acid and phenol.

8. The cocrystal as in claim 1, wherein the coformer is gentisic acid.

9. The cocrystal as in claim 1, wherein the coformer is glutaric acid.

10. The cocrystal as in claim 1, wherein the coformer is sorbic acid.

11. The cocrystal as in claim 1, wherein the coformer is thiamine hydrochloride.

12. The cocrystal as in claim 1, wherein the coformer is zinc chloride.

13. The cocrystal as in claim 1, wherein the molar ratio of the compound of formula VX-745 to the coformer is in the range of 5:1 to 1:5.

14. The cocrystal as in claim 13, wherein the molar ratio of the compound of formula VX-745 to the coformer is 1:1.

15. The cocrystal as in claim 1, wherein the cocrystal contains 3.0 area percent or less of total impurities as determined by high performance liquid chromatography (HPLC).

16. A pharmaceutical composition comprising the cocrystal as in claim 1 and one or more additional components selected from the group consisting of a diluent, a pharmaceutically acceptable carrier, a pharmaceutically acceptable excipient, a solubilizing agent, and a solvent.

17. A method for reducing or inhibiting p38 mitogen activated protein kinase expression or activity in a patient in need thereof, wherein the method comprises administering to the patient a therapeutically effective amount of the cocrystal as in claim 1.

18. The method as in claim 17, wherein the patient has a p38 mitogen activated protein kinase-mediated disease or disorder selected from the group consisting of an allergy, an angiogenic disorder, an autoimmune disease, cardiac hypertrophy, a destructive bone disorder, heart attack, an infectious disease, an inflammatory disease, an ischemia-reperfusion injury in stroke, a neurodegenerative disease, an organ hypoxia, a proliferative disorder, thrombin-induced platelet aggregation, and vascular hyperplasia.

19. A method for reducing or inhibiting p38 mitogen activated protein kinase expression or activity in a patient in need thereof, wherein the method comprises administering to the patient a therapeutically effective amount of the pharmaceutical composition as in claim 16.

20. A process for preparing the cocrystal comprising a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, and a compound of formula VX-745 as in claim 1:

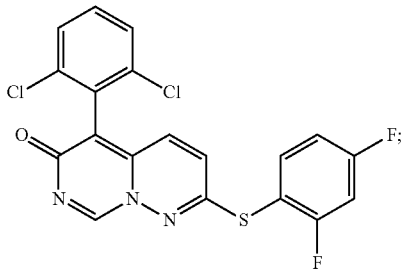

VX-745

(5-(2,6-dichlorophenyl)-2-(2,4-difluorophenylthio)-6H-pyrimido[1,6-b]pyridazin-6-one;
wherein the cocrystal is selected from the group consisting of:
(1) cocrystal 1 (CC-1) comprising VX-745 and acesulfame potassium;
  wherein cocrystal 1 is characterized by a powder X-ray diffractogram obtained by irradiation with Cu-Kα radiation comprising at least one characteristic peak at 8.4°±0.2° 2θ, 16.9°±0.2° 2θ 19.1°±0.2° 2θ, 22.3°±0.2° 2θ, 25.0°±0.2° 2θ, 25.4±0.2° 2θ, or 27.4°±0.2° 2θ;
(2) cocrystal 2 (CC-2) comprising VX-745 and trans-aconitic acid;
  wherein cocrystal 2 is characterized by a powder X-ray diffractogram obtained by irradiation with Cu-Kα radiation comprising at least one characteristic peak at 13.1±0.2° 2θ, 14.2°±0.2° 2θ, 15.9°±0.2° 2θ, 21.3°±0.2° 2θ, 23.5±0.2° 2θ, 26.9±0.2° 2θ, or 27.3°±0.2° 2θ;
(3) cocrystal 3 (CC-3) comprising VX-745 and calcium chloride;
  wherein cocrystal 3 is characterized by a powder X-ray diffractogram obtained by irradiation with Cu-Kα radiation comprising at least one characteristic peak at 16.9°±0.2° 2θ, 19.3°±0.2° 2θ, 27.0°±0.2° 2θ, 27.7°±0.2° 2θ, 28.5°±0.2° 2θ, 33.0°±0.2° 2θ, or 34.1°±0.2° 2θ;
(4) cocrystal 4 (CC-4) comprising VX-745 and choline chloride;
  wherein cocrystal 4 is characterized by a powder X-ray diffractogram obtained by irradiation with Cu-Kα radiation comprising at least one characteristic peak at 8.3°±0.2° 2θ, 16.8°±0.2° 2θ, 17.3°±0.2° 2θ, 18.6°±0.2° 2θ, 20.9°±0.2° 2θ, 22.0°±0.2° 2θ, 22.9°±0.2° 2θ, 24.9°±0.2° 2θ, 26.6°±0.2° 2θ, or 31.7°±0.2° 2θ;
(5) cocrystal 5 (CC-5) comprising VX-745 and gentisic acid;
  wherein cocrystal 5 is characterized by a powder X-ray diffractogram obtained by irradiation with Cu-Kα radiation comprising at least one characteristic peak at 8.9°±0.2° 2θ, 14.3°±0.2° 2θ, 17.3°±0.2° 2θ, 21.0°±0.2° 2θ, 22.4°±0.2° 2θ, 23.3°±0.2° 2θ, 26.2°±0.2° 2θ, 26.8°±0.2° 2θ, 27.6°±0.2° 2θ, or 29.1°±0.2° 2θ;
(6) cocrystal 6 (CC-6) comprising VX-745 and glutaric acid;
  wherein cocrystal 6 is characterized by a powder X-ray diffractogram obtained by irradiation with Cu-Kα radiation comprising at least one characteristic peak at 8.8°±0.2° 2θ, 15.0°±0.2° 2θ, 19.3°±0.2° 2θ, 23.1°±0.2° 2θ, 23.7°±0.2° 2θ, 26.7°±0.2° 2θ, 30.9°±0.2° 2θ, or 32.5°±0.2° 2θ;
(7) cocrystal 7 (CC-7) comprising VX-745 and 1-hydroxy-2-naphthoic acid;
  wherein cocrystal 7 is characterized by a powder X-ray diffractogram obtained by irradiation with Cu-Kα radiation comprising at least one characteristic peak at 7.3°±0.2° 2θ, 8.7°±0.2° 2θ, 14.6°±0.2° 2θ, 15.7°±0.2° 2θ, 21.2°±0.2° 2θ, 22.0°±0.2° 2θ, 24.2°±0.2° 2θ, 28.3°±0.2° 2θ, 25.8°±0.2° 2θ, 27.2°±0.2° 2θ, or 31.1°±0.2° 2θ;
(8) cocrystal 8 (CC-8) comprising VX-745 and ketoglutaric acid;
  wherein cocrystal 8 is characterized by a powder X-ray diffractogram obtained by irradiation with Cu-Kα radiation comprising at least one characteristic peak at 7.2°±0.2° 2θ, 9.5°±0.2° 2θ, 15.1°±0.2° 2θ, 16.2°±0.2° 2θ, 21.6°±0.2° 2θ, 22.0°±0.2° 2θ, or 28.0°±0.2° 2θ;
(9) cocrystal 9 (CC-9) comprising VX-745 and malonic acid;
  wherein cocrystal 9 is characterized by a powder X-ray diffractogram obtained by irradiation with Cu-Kα radiation comprising at least one characteristic peak at 6.0°±0.2° 2θ, 14.1°±0.2° 2θ, 22.2°±0.2° 2θ, 23.2°±0.2° 2θ, 23.7°±0.2° 2θ, 24.3°±0.2° 2θ, 25.1°±0.2° 2θ, 27.4°±0.2° 2θ, or 28.1°±0.2° 2θ;
(10) cocrystal 10 (CC-10) comprising VX-745 and nicotinic acid;
  wherein cocrystal 10 is characterized by a powder X-ray diffractogram obtained by irradiation with Cu-Kα radiation comprising at least one characteristic peak at 7.4°±0.2° 2θ, 15.4°±0.2° 2θ, 20.3°±0.2° 2θ, 23.4°±0.2° 2θ, or 25.1°±0.2° 2θ;
(11) cocrystal 11 (CC-11) comprising VX-745 and phenol;
  wherein cocrystal 11 is characterized by a powder X-ray diffractogram obtained by irradiation with Cu-Kα radiation comprising at least one characteristic peak at 6.8°±0.2° 2θ, 13.7°±0.2° 2θ, 16.8°±0.2° 2θ, 18.3°±0.2° 2θ, 20.0°±0.2° 2θ, 21.9°±0.2° 2θ, 23.7°±0.2° 2θ, 24.5°±0.2° 2θ, 24.7°±0.2° 2θ, 26.6°±0.2° 2θ, 27.3°±0.2° 2θ, or 30.2°±0.2° 2θ;
(12) cocrystal 12 (CC-12) comprising VX-745 and L-proline;
  wherein cocrystal 12 is characterized by a powder X-ray diffractogram obtained by irradiation with Cu-Kα radiation comprising at least one characteristic peak at 7.4°±0.2° 2θ, 17.6°±0.2° 2θ, 18.0°±0.2° 2θ, 19.5°±0.2° 2θ, 24.7°±0.2° 2θ, or 26.8°±0.2° 2θ;
(13) cocrystal 13 (CC-13) comprising VX-745 and salicylic acid;
  wherein cocrystal 13 is characterized by a powder X-ray diffractogram obtained by irradiation with Cu-Kα radiation comprising at least one characteristic peak at 8.9°±0.2° 2θ, 11.0°±0.2° 2θ, 13.8°±0.2° 2θ, 15.3°±0.2° 2θ, 17.3°±0.2° 2θ, 18.8°±0.2° 2θ, 25.3°±0.2° 2θ, 28.1°±0.2° 2θ, 28.8°±0.2° 2θ, or 30.7°±0.2° 2θ;
(14) cocrystal 14 (CC-14) comprising VX-745 and sorbic acid;
  wherein cocrystal 14 is characterized by a powder X-ray diffractogram obtained by irradiation with Cu-Kα radiation comprising at least one characteristic peak at 8.5°±0.2° 2θ, 8.9°±0.2° 2θ, 11.4°±0.2°

2θ, 16.7°±0.2° 2θ, 22.8°±0.2° 2θ, 23.0°±0.2° 2θ, 24.2°±0.2° 2θ, 25.7°±0.2° 2θ, or 27.0°±0.2° 2θ;

(15) cocrystal 15 (CC-15) comprising VX-745 and thiamine hydrochloride;
wherein cocrystal 15 is characterized by a powder X-ray diffractogram obtained by irradiation with Cu-Kα radiation comprising at least one characteristic peak at 7.4°±0.2° 2θ, 8.2°±0.2° 2θ, 15.3°±0.2° 2θ, 15.9°±0.2° 2θ, 19.0°±0.2° 2θ, 20.3°±0.2° 2θ, 20.9°±0.2° 2θ, 25.3°±0.2° 2θ, 27.6°±0.2° 2θ, or 28.5°±0.2° 2θ;

(16) cocrystal 16 (CC-16) comprising VX-745 and L-threonine;
wherein cocrystal 16 is characterized by a powder X-ray diffractogram obtained by irradiation with Cu-Kα radiation comprising at least one characteristic peak at 16.9°±0.2° 2θ, 18.4°±0.2° 2θ, 20.6°±0.2° 2θ, 22.7°±0.2° 2θ, 22.9°±0.2° 2θ, 23.9°±0.2° 2θ, or 30.3°±0.2° 2θ;

(17) cocrystal 17 (CC-17) comprising VX-745 and urea;
wherein cocrystal 17 is characterized by a powder X-ray diffractogram obtained by irradiation with Cu-Kα radiation comprising at least one characteristic peak at 5.6°±0.2° 2θ, 14.7°±0.2° 2θ, 16.5°±0.2° 2θ, 16.9°±0.2° 2θ, 22.3°±0.2° 2θ, 24.6°±0.2° 2θ, 24.3°±0.2° 2θ, 27.4°±0.2° 2θ, 34.1°±0.2° 2θ, or 35.5°±0.2° 2θ; and

(18) cocrystal 18 (CC-18) comprising VX-745 and zinc chloride;
wherein cocrystal 18 is characterized by a powder X-ray diffractogram obtained by irradiation with Cu-Kα radiation comprising at least one characteristic peak at 8.2°±0.2° 2θ, 16.5°±0.2° 2θ, 20.1°±0.2° 2θ, 24.7°±0.2° 2θ, 26.4°±0.2° 2θ, or 29.5°±0.2° 2θ;

wherein the process comprises the following steps:
a) providing the compound of formula VX-745:

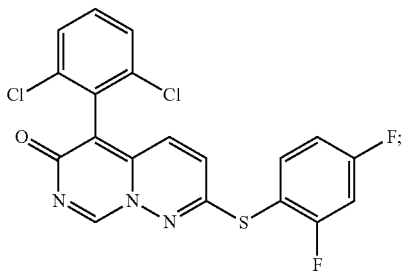

VX-745 b) combining the compound of formula VX-745 above with a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride in the presence of a solvent selected from the group consisting of acetone, acetonitrile, n-butanol, tert-butanol, diglyme, N,N-dimethylformamide, dimethylsulfoxide, ethanol, glyme, heptane, hexane, isopropanol, methanol, methyl tert-butyl ether, tetrahydrofuran, and water, or a combination thereof to produce the cocrystal comprising a conformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, and a compound of formula VX-745 as in claim 1; and c) optionally isolating the cocrystal above comprising a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, and a compound of formula VX-745 as in claim 1.

21. A process for preparing the cocrystal comprising a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, and a compound of formula VX-745 as in claim 1:

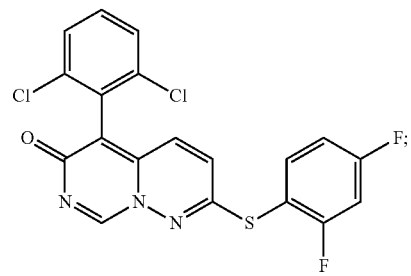

VX-745

(5-(2,6-dichlorophenyl)-2-(2,4-difluorophenylthio)-6H-pyrimido[1,6-b]pyridazin-6-one;

wherein the cocrystal is selected from the group consisting of:

(1) cocrystal 1 (CC-1) comprising VX-745 and acesulfame potassium;
wherein cocrystal 1 is characterized by a powder X-ray diffractogram obtained by irradiation with Cu-Kα radiation comprising at least one characteristic peak at 8.4°±0.2° 2θ, 16.9°±0.2° 2θ 19.1°±0.2° 2θ, 22.3°±0.2° 2θ, 25.0°±0.2° 2θ, 25.4±0.2° 2θ, or 27.4°±0.2° 2θ;

(2) cocrystal 2 (CC-2) comprising VX-745 and trans-aconitic acid;
wherein cocrystal 2 is characterized by a powder X-ray diffractogram obtained by irradiation with Cu-Kα radiation comprising at least one characteristic peak at 13.1±0.2° 2θ, 14.2°±0.2° 2θ, 15.9°±0.2° 2θ, 21.3°±0.2° 2θ, 23.5°±0.2° 2θ, 26.9±0.2° 2θ, or 27.3°±0.2° 2θ;

(3) cocrystal 3 (CC-3) comprising VX-745 and calcium chloride;
wherein cocrystal 3 is characterized by a powder X-ray diffractogram obtained by irradiation with Cu-Kα radiation comprising at least one characteristic peak at 16.9°±0.2° 2θ, 19.3°±0.2° 2θ, 27.0°±0.2° 2θ, 27.7°±0.2° 2θ, 28.5°±0.2° 2θ, 33.0°±0.2° 2θ, or 34.1°±0.2° 2θ;

(4) cocrystal 4 (CC-4) comprising VX-745 and choline chloride;
   wherein cocrystal 4 is characterized by a powder X-ray diffractogram obtained by irradiation with Cu-Kα radiation comprising at least one characteristic peak at 8.3°±0.2° 2θ, 16.8°±0.2° 2θ, 17.3°±0.2° 2θ, 18.6°±0.2° 2θ, 20.9°±0.2° 2θ, 22.0°±0.2° 2θ, 22.9°±0.2° 2θ, 24.9°±0.2° 2θ, 26.6°±0.2° 2θ, or 31.7°±0.2° 2θ;
(5) cocrystal 5 (CC-5) comprising VX-745 and gentisic acid;
   wherein cocrystal 5 is characterized by a powder X-ray diffractogram obtained by irradiation with Cu-Kα radiation comprising at least one characteristic peak at 8.9°±0.2° 2θ, 14.3°±0.2° 2θ, 17.3°±0.2° 2θ, 21.0°±0.2° 2θ, 22.4°±0.2° 2θ, 23.3°±0.2° 2θ, 26.2°±0.2° 2θ, 26.8°±0.2° 2θ, 27.6°±0.2° 2θ, or 29.1°±0.2° 2θ;
(6) cocrystal 6 (CC-6) comprising VX-745 and glutaric acid;
   wherein cocrystal 6 is characterized by a powder X-ray diffractogram obtained by irradiation with Cu-Kα radiation comprising at least one characteristic peak at 8.8°±0.2° 2θ, 15.0°±0.2° 2θ, 19.3°±0.2° 2θ, 23.1°±0.2° 2θ, 23.7°±0.2° 2θ, 26.7°±0.2° 2θ, 30.9°±0.2° 2θ, or 32.5°±0.2° 2θ;
(7) cocrystal 7 (CC-7) comprising VX-745 and 1-hydroxy-2-naphthoic acid;
   wherein cocrystal 7 is characterized by a powder X-ray diffractogram obtained by irradiation with Cu-Kα radiation comprising at least one characteristic peak at 7.3°±0.2° 2θ, 8.7°±0.2° 2θ, 14.6°±0.2° 2θ, 15.7°±0.2° 2θ, 21.2°±0.2° 2θ, 22.0°±0.2° 2θ, 24.2°±0.2° 2θ, 28.3°±0.2° 2θ, 25.8°±0.2° 2θ, 27.2°±0.2° 2θ, or 31.1°±0.2° 2θ;
(8) cocrystal 8 (CC-8) comprising VX-745 and ketoglutaric acid;
   wherein cocrystal 8 is characterized by a powder X-ray diffractogram obtained by irradiation with Cu-Kα radiation comprising at least one characteristic peak at 7.2°±0.2° 2θ, 9.5°±0.2° 2θ, 15.1°±0.2° 2θ, 16.2°±0.2° 2θ, 21.6°±0.2° 2θ, 22.0°±0.2° 2θ, or 28.0°±0.2° 2θ;
(9) cocrystal 9 (CC-9) comprising VX-745 and malonic acid;
   wherein cocrystal 9 is characterized by a powder X-ray diffractogram obtained by irradiation with Cu-Kα radiation comprising at least one characteristic peak at 6.0°±0.2° 2θ, 14.1°±0.2° 2θ, 22.2°±0.2° 2θ, 23.2°±0.2° 2θ, 23.7°±0.2° 2θ, 24.3°±0.2° 2θ, 25.1°±0.2° 2θ, 27.4°±0.2° 2θ, or 28.1°±0.2° 2θ;
(10) cocrystal 10 (CC-10) comprising VX-745 and nicotinic acid;
   wherein cocrystal 10 is characterized by a powder X-ray diffractogram obtained by irradiation with Cu-Kα radiation comprising at least one characteristic peak at 7.4°±0.2° 2θ, 15.4°±0.2° 2θ, 20.3°±0.2° 2θ, 23.4°±0.2° 2θ, or 25.1°±0.2° 2θ;
(11) cocrystal 11 (CC-11) comprising VX-745 and phenol;
   wherein cocrystal 11 is characterized by a powder X-ray diffractogram obtained by irradiation with Cu-Kα radiation comprising at least one characteristic peak at 6.8°±0.2° 2θ, 13.7°±0.2° 2θ, 16.8°±0.2° 2θ, 18.3°±0.2° 2θ, 20.0°±0.2° 2θ, 21.9°±0.2° 2θ, 23.7°±0.2° 2θ, 24.5°±0.2° 2θ, 24.7°±0.2° 2θ, 26.7°±0.2° 2θ, 27.3°±0.2° 2θ, or 30.2°±0.2° 2θ;
(12) cocrystal 12 (CC-12) comprising VX-745 and L-proline;
   wherein cocrystal 12 is characterized by a powder X-ray diffractogram obtained by irradiation with Cu-Kα radiation comprising at least one characteristic peak at 7.4°±0.2° 2θ, 17.6°±0.2° 2θ, 18.0°±0.2° 2θ, 19.5°±0.2° 2θ, 24.7°±0.2° 2θ, or 26.8°±0.2° 2θ;
(13) cocrystal 13 (CC-13) comprising VX-745 and salicylic acid;
   wherein cocrystal 13 is characterized by a powder X-ray diffractogram obtained by irradiation with Cu-Kα radiation comprising at least one characteristic peak at 8.9°±0.2° 2θ, 11.0°±0.2° 2θ, 13.8°±0.2° 2θ, 15.3°±0.2° 2θ, 17.3°±0.2° 2θ, 18.8°±0.2° 2θ, 25.3°±0.2° 2θ, 28.1°±0.2° 2θ, 28.8°±0.2° 2θ, or 30.7°±0.2° 2θ;
(14) cocrystal 14 (CC-14) comprising VX-745 and sorbic acid;
   wherein cocrystal 14 is characterized by a powder X-ray diffractogram obtained by irradiation with Cu-Kα radiation comprising at least one characteristic peak at 8.5°±0.2° 2θ, 8.9°±0.2° 2θ, 11.4°±0.2° 2θ, 16.7°±0.2° 2θ, 22.8°±0.2° 2θ, 23.0°±0.2° 2θ, 24.2°±0.2° 2θ, 25.7°±0.2° 2θ, or 27.0°±0.2° 2θ;
(15) cocrystal 15 (CC-15) comprising VX-745 and thiamine hydrochloride;
   wherein cocrystal 15 is characterized by a powder X-ray diffractogram obtained by irradiation with Cu-Kα radiation comprising at least one characteristic peak at 7.4°±0.2° 2θ, 8.2°±0.2° 2θ, 15.3°±0.2° 2θ, 15.9°±0.2° 2θ, 19.0°±0.2° 2θ, 20.3°±0.2° 2θ, 20.9°±0.2° 2θ, 25.3°±0.2° 2θ, 27.6°±0.2° 2θ, or 28.5°±0.2° 2θ;
(16) cocrystal 16 (CC-16) comprising VX-745 and L-threonine;
   wherein cocrystal 16 is characterized by a powder X-ray diffractogram obtained by irradiation with Cu-Kα radiation comprising at least one characteristic peak at 16.9°±0.2° 2θ, 18.4°±0.2° 2θ, 20.6°±0.2° 2θ, 22.7°±0.2° 2θ, 22.9°±0.2° 2θ, 23.9°±0.2° 2θ, or 30.3°±0.2° 2θ;
(17) cocrystal 17 (CC-17) comprising VX-745 and urea;
   wherein cocrystal 17 is characterized by a powder X-ray diffractogram obtained by irradiation with Cu-Kα radiation comprising at least one characteristic peak at 5.6°±0.2° 2θ, 14.7°±0.2° 2θ, 16.5°±0.2° 2θ, 16.9°±0.2° 2θ, 22.3°±0.2° 2θ, 24.6°±0.2° 2θ, 24.3°±0.2° 2θ, 27.4°±0.2° 2θ, 34.1°±0.2° 2θ, or 35.5°±0.2° 2θ; and
(18) cocrystal 18 (CC-18) comprising VX-745 and zinc chloride;
   wherein cocrystal 18 is characterized by a powder X-ray diffractogram obtained by irradiation with Cu-Kα radiation comprising at least one characteristic peak at 8.2°±0.2° 2θ, 16.5°±0.2° 2θ, 20.1°±0.2° 2θ, 24.7°±0.2° 2θ, 26.4°±0.2° 2θ, or 29.5°±0.2° 2θ;
wherein the process comprises the following steps:
a) combining a solvent selected from the group consisting of acetone, acetonitrile, n-butanol, tert-butanol, diglyme, N,N-dimethylformamide, dimethylsulfoxide, ethanol, glyme, heptane, hexane, isopropanol, methanol, methyl tert-butyl ether, tetrahydrofuran, and water, or a combination thereof, with the compound of formula VX-745:

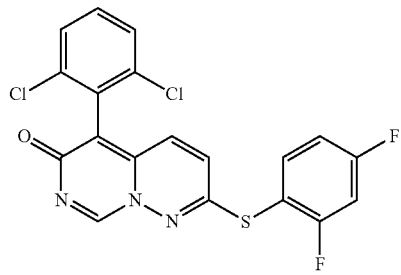 [SMILES: O=c1ncn2nc(Sc3ccc(F)cc3F)ccc2c1-c1c(Cl)cccc1Cl]

VX-745 to produce a mixture comprising the compound of formula VX-745;

b) optionally heating the mixture provided in step a) above to form a solution;

c) adding a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, to the mixture provided in step a) above or the solution formed in step b) above; and d) optionally isolating the cocrystal comprising a coformer selected from the group consisting of acesulfame potassium, trans-aconitic acid, calcium chloride, choline chloride, gentisic acid, glutaric acid, 1-hydroxy-2-naphthoic acid, ketoglutaric acid, malonic acid, nicotinic acid, phenol, L-proline, salicylic acid, sorbic acid, thiamine hydrochloride, L-threonine, urea, and zinc chloride, and a compound of formula VX-745 as in claim 1.

\* \* \* \* \*

UNITED STATES PATENT AND TRADEMARK OFFICE
CERTIFICATE OF CORRECTION

PATENT NO. : 11,466,008 B2
APPLICATION NO. : 16/648267
DATED : October 11, 2022
INVENTOR(S) : John Jahangir Alam et al.

It is certified that error appears in the above-identified patent and that said Letters Patent is hereby corrected as shown below:

In the Claims

In Claim 1, at Column 49, Lines 1-2, the text:
"(5-(2,6-dichlorophenyl)-2-(2,4-difluorophenylthio)-6H-pyrimido[l,6-b]pyridazin-6-one;"
Is replaced with:
-- (5-(2,6-dichlorophenyl)-2-(2,4-difluorophenylthio)-6H-pyrimido[l,6-b]pyridazin-6-one); --.

In Claim 2, at Column 53, Line 35, the text:
"29.5° ± 0.2 °2O."
Is replaced with:
-- 29.5° ± 0.2 °2θ. --.

In Claim 20, at Column 57, Lines 18-19, the text:
"(5-(2,6-dichlorophenyl)-2-(2,4-difluorophenylthio)-6H-pyrimido[l,6-b]pyridazin-6-one;"
Is replaced with:
-- (5-(2,6-dichlorophenyl)-2-(2,4-difluorophenylthio)-6H-pyrimido[l,6-b]pyridazin-6-one); --.

In Claim 21, at Column 60, Lines 38-39, the text:
"(5-(2,6-dichlorophenyl)-2-(2,4-difluorophenylthio)-6H-pyrimido[l,6-b]pyridazin-6-one;"
Is replaced with:
-- (5-(2,6-dichlorophenyl)-2-(2,4-difluorophenylthio)-6H-pyrimido[l,6-b]pyridazin-6-one); --.

Signed and Sealed this
Sixth Day of December, 2022

Katherine Kelly Vidal
*Director of the United States Patent and Trademark Office*